US010562946B2

(12) United States Patent
Lazarus et al.

(10) Patent No.: US 10,562,946 B2
(45) Date of Patent: Feb. 18, 2020

(54) CHAGASIN-BASED SCAFFOLD COMPOSITIONS, METHODS, AND USES

(71) Applicant: Genentech, Inc., South San Francisco, CA (US)

(72) Inventors: Robert A. Lazarus, Millbrae, CA (US); Henry R. Maun, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/320,736

(22) PCT Filed: Jun. 19, 2015

(86) PCT No.: PCT/US2015/036690
§ 371 (c)(1),
(2) Date: Dec. 20, 2016

(87) PCT Pub. No.: WO2015/196070
PCT Pub. Date: Dec. 23, 2015

(65) Prior Publication Data
US 2017/0174733 A1 Jun. 22, 2017

Related U.S. Application Data

(60) Provisional application No. 62/015,296, filed on Jun. 20, 2014.

(51) Int. Cl.
C07K 14/44 (2006.01)
C12N 15/10 (2006.01)
A61K 38/00 (2006.01)

(52) U.S. Cl.
CPC .......... *C07K 14/44* (2013.01); *C12N 15/1037* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. |
| 4,179,337 A | 12/1979 | Davis et al. |
| 4,301,144 A | 11/1981 | Iwashita et al. |
| 4,454,151 A | 6/1984 | Waterbury |
| 4,485,045 A | 11/1984 | Regen |
| 4,496,689 A | 1/1985 | Mitra |
| 4,544,545 A | 10/1985 | Ryan et al. |
| 4,640,835 A | 2/1987 | Shimizu et al. |
| 4,670,417 A | 6/1987 | Iwasaki et al. |
| 4,703,039 A | 10/1987 | Hawiger et al. |
| 4,791,192 A | 12/1988 | Nakagawa et al. |
| 4,933,294 A | 6/1990 | Waterfield et al. |
| 4,994,650 A | 2/1991 | Koontz |
| 5,013,556 A | 5/1991 | Woodle et al. |
| 5,223,409 A | 6/1993 | Ladner et al. |
| 5,274,119 A | 12/1993 | Frazier et al. |
| 5,324,604 A | 6/1994 | Bugner et al. |
| 5,401,638 A | 3/1995 | Carney et al. |
| 5,403,484 A | 4/1995 | Ladner et al. |
| 5,427,908 A | 6/1995 | Dower et al. |
| 5,428,130 A | 6/1995 | Capon et al. |
| 5,428,139 A | 6/1995 | Kiefer et al. |
| 5,432,018 A | 7/1995 | Dower et al. |
| 5,435,990 A | 7/1995 | Cheng et al. |
| 5,476,511 A | 12/1995 | Gwon et al. |
| 5,489,425 A | 2/1996 | Kruper, Jr. et al. |
| 5,498,530 A | 3/1996 | Schatz et al. |
| 5,498,538 A | 3/1996 | Kay et al. |
| 5,501,856 A | 3/1996 | Ohtori et al. |
| 5,505,931 A | 4/1996 | Pribish |
| 5,571,689 A | 11/1996 | Heuckeroth et al. |
| 5,580,717 A | 12/1996 | Dower et al. |
| 5,605,793 A | 2/1997 | Stemmer |
| 5,627,024 A | 5/1997 | Maruyama et al. |
| 5,643,768 A | 7/1997 | Kawasaki |
| 5,652,361 A | 7/1997 | Simon et al. |
| 5,658,754 A | 8/1997 | Kawasaki |
| 5,663,143 A | 9/1997 | Ley et al. |
| 5,696,239 A | 12/1997 | Wilson et al. |
| 5,698,426 A | 12/1997 | Huse |
| 5,714,631 A | 2/1998 | Wilson et al. |
| 5,723,286 A | 3/1998 | Dower et al. |
| 5,723,323 A | 3/1998 | Kauffman et al. |
| 5,734,018 A | 3/1998 | Rutter et al. |
| 5,747,035 A | 5/1998 | Presta et al. |
| 5,756,065 A | 5/1998 | Wilson et al. |

(Continued)

FOREIGN PATENT DOCUMENTS

EP   1 726 643 A1   11/2006
JP   2008541776 A   11/2008

(Continued)

OTHER PUBLICATIONS

Bowie et al (Science, 1990, 257:1306-1310) (Year: 1990).*

(Continued)

*Primary Examiner* — Robert A Zeman
(74) *Attorney, Agent, or Firm* — Morrison & Foerster LLP

(57) ABSTRACT

Provided are novel, non-naturally occurring chagasin scaffold proteins derived from chagasin or chagasin-like protease inhibitor proteins. Also provided are libraries of non-naturally occurring chagasin scaffold proteins and methods of using such libraries to generate non-naturally occurring chagasin scaffold proteins that specifically bind to a target ligand. The present invention further provides methods of using non-naturally occurring chagasin protein scaffold that bind to a target ligand, including diagnostic and therapeutic compositions and methods. The invention also provides novel non-naturally occurring chagasin scaffold proteins that specifically bind low density lipoprotein receptor-related protein 6 (LRP6) and novel non-naturally occurring chagasin scaffold proteins that specifically bind vascular endothelial growth factor (VEGF).

5 Claims, 21 Drawing Sheets
Specification includes a Sequence Listing.

(56) References Cited

U.S. PATENT DOCUMENTS

| | | | |
|---|---|---|---|
| 5,763,192 | A | 6/1998 | Kauffman et al. |
| 5,766,905 | A | 6/1998 | Studier et al. |
| 5,770,434 | A | 6/1998 | Huse |
| 5,808,003 | A | 9/1998 | Subramanian et al. |
| 5,811,238 | A | 9/1998 | Stemmer et al. |
| 5,830,721 | A | 11/1998 | Stemmer et al. |
| 5,834,252 | A | 11/1998 | Stemmer et al. |
| 5,837,458 | A | 11/1998 | Minshull et al. |
| 5,869,046 | A | 2/1999 | Presta et al. |
| 6,258,558 | B1 | 7/2001 | Szostak et al. |
| 6,261,804 | B1 | 7/2001 | Szostak et al. |
| 6,331,313 | B1 | 12/2001 | Wong et al. |
| 6,416,950 | B1 | 7/2002 | Lohse et al. |
| 7,083,784 | B2 | 8/2006 | Dall'Acqua et al. |
| 2003/0181531 | A1 | 9/2003 | Sherris et al. |
| 2004/0058313 | A1 | 3/2004 | Abreu |
| 2011/0256127 | A1 | 10/2011 | Bourhis et al. |
| 2012/0100562 | A1 | 4/2012 | Bourhis et al. |

FOREIGN PATENT DOCUMENTS

| | | |
|---|---|---|
| JP | 2010535859 A | 11/2010 |
| JP | 2011501951 A | 1/2011 |
| JP | 2013527762 A | 7/2013 |
| WO | WO-1991/05264 A1 | 4/1991 |
| WO | WO-1991/14438 A1 | 10/1991 |
| WO | WO-1995/34683 A1 | 12/1995 |
| WO | WO-1996/32478 A1 | 10/1996 |
| WO | WO-1997/04801 A1 | 2/1997 |
| WO | WO-1997/35196 A1 | 9/1997 |
| WO | WO-1997/43316 A1 | 11/1997 |
| WO | WO-1997/46251 A1 | 12/1997 |
| WO | WO-1997/47314 A1 | 12/1997 |
| WO | WO-1998/14277 A1 | 4/1998 |
| WO | WO-1998/15833 A1 | 4/1998 |
| WO | WO-1998/20036 A1 | 5/1998 |
| WO | WO-1998/20159 A1 | 5/1998 |
| WO | WO-1998/20169 A1 | 5/1998 |
| WO | WO-1998/56418 A1 | 12/1998 |
| WO | WO-1999/43713 A1 | 9/1999 |
| WO | WO-2000/09560 A2 | 2/2000 |
| WO | WO-2003/053921 A2 | 7/2003 |
| WO | WO2005012481 A2 | 2/2005 |
| WO | WO2005012481 A3 | 7/2005 |
| WO | WO2006131749 A2 | 12/2006 |
| WO | WO2006131749 A3 | 5/2007 |
| WO | WO-2008/068637 A2 | 6/2008 |
| WO | WO2009023184 A2 | 2/2009 |
| WO | WO2009058379 A2 | 5/2009 |
| WO | WO2009023184 A3 | 7/2009 |
| WO | WO2009058379 A3 | 12/2009 |
| WO | WO2011138392 A1 | 11/2011 |

OTHER PUBLICATIONS

Burgess et al (J. of Cell Bio. 111:2129-2138, 1990) (Year: 1990).*
Lazar et al. (Molecular and Cellular Biology, 1988, 8:1247-1252) (Year: 1988).*
Bork (Genome Research, 2000,10:398-400) (Year: 2000).*
Abou-Nadler, M. et al. (Sep./Oct. 2010). "Rapid Generation of Random Mutant Libraries," *Bioengineered Bugs* 1:337-340.
Ahn, V.E. et al. (Nov. 15, 2011). "Structural Basis of Wnt Signaling Inhibition by Dickkopf Binding to LRP5/6," *Dev. Cell* 21(5):862-873.
Banta, S. et al. (2013, e-pub. Apr. 29, 2013). "Replacing Antibodies: Engineering New Binding Proteins," *Annu. Rev.Biomed. Eng.* 15:93-113.
Binz, H.K. et al (Oct. 2005). "Engineering Novel Binding Proteins From Nonimmunoglobulin Domains," *Nat. Biotechnol.* 23(10):1257-1268.
Binz, H.K. et al. (Aug. 2005, e-pub. Jul. 6, 2005). "Engineered Proteins as Specific Binding Reagents," *Curr. Opin. Biotechnol.* 16(4):459-469.

Boder, E.T. et al. (Jun. 1997). "Yeast Surface Display for Screening Combinatorial Polypeptide Libraries," *Nat. Biotechnol.* 15:553-557.
Bostrom, J. et al. (Mar. 20, 2009). "Variants of the Antibody Herceptin That Interact with HER2 and VEGF at the Antigen Binding Site," *Science* 323:1610-1614.
Bourhis, E. et al. (Mar. 19, 2010). "Reconstitution of a Frizzled8 Wnt3a LRP6 Signaling Complex Reveals Multiple Wnt and Dkk1 Binding Sites on LRP6," *J. Biol. Chem.* 285(12):9172-9179.
Bourhis, E.et al. (Oct. 12, 2011). "Wnt Antagonists Bind Through a Short Peptide to the First β-Propeller Domain of LRP5/6," *Structure* 19:1433-1442.
Brisette, R.et al. (2007). "The Use of Phage Display Peptide Libraries for Basic and Translational Research," Chapter 13 in *Methods Mol. Biol.*, P.B. Fisher ed., Human Press, Inc., Totowa, NJ., 383:203-213.
Caricasole, A. et al. (Jun. 30, 2004). "Induction of Dickkopf-1, a Negative Modulator of the Wnt Pathway, is Associated with Neuronal Degeneration in Alzheimer's Brain," *J Neurosci* 24(26):6021-6027.
Carter, P. et al. (2004). "Identification and Validation of Cell Surface Antigens for Antibody Targeting in Oncology," *Endocr. Relat. Cancer* 11:659-687.
Chen, Y. et al. (1999). "Selection and Analysis of an Optimized Anti-VEGF Antibody: Crystal Structure of an Affinity-Matured Fab in Complex with Antigen," *J. Mol. Biol.* 293:865-881.
Cheng, Z. et al. (2011). "Crystal Structures of the Extracellular Domain of LRP6 and its Complex With DKK1," *Nat Struct Mol Biol* 18(11):1204-1210, 20 pages.
Cirino, P.C. et al. (2003). "Generating Mutant Libraries Using Error-Prone PCR," Chapter 1 in *Methods Mol. Biol.*, F.H. Arnold et al. eds., Humana Press, Inc. Totowa, NJ, 231:3-9.
Clackson, T. et al (Aug. 15, 1991). "Making Antibody Fragments Using Phage Display Libraries," *Nature* 352:624-628.
Clements, J.M. et al. (1994). "Identification of a Key Integrin-Binding Sequence in VCAM-1 Homologous to the LDV Active Site in Fibronectin," *Journal of Cell Science* 107:2127-2135.
Clevers, H. (Nov. 3, 2006). "Wnt/β-Catenin Signaling in Development and Disease," *Cell* 127:469-480.
Creighton, T.E. (1983). "Covalent Modification of Polypeptides," in *Proteins: Structure and Molecular Properties*, W.H. Freeman and Company, New York, pp. 79-86.
Cwirla, S. E. et al. (Aug. 1990). "Peptides on Phage: A Vast Library of Peptides for Identifying Ligands," *Proc. Natl. Acad. Sci. USA*, 87:6378-6382.
Da Silva, F A.A. et al. (2007, e-pub. Aug. 17, 2006). "Crystal Structure of Chagasin, the Endogenous Cysteine-protease Inhibitor from *Trypanosoma cruzi*," *J. Struct. Biol.* 157:416-423.
Database UniProt. (May 14, 2014). "SubName: Full=Cysteine peptidase inhibitor, putative {EC0:00003131 EMBL: EAN97472.1 };", XP00277 4637, retrieved from EBI accession No. UNIPROT:Q4DY71 Database accession No. Q4DY71, one page.
Database Uni Prot. (Oct. 3, 2012). "SubName: Full=Putative inhibitor of cysteine peptidase (Putative icp) {EC0: 000031IEMBL:CCC49998.1};", XP002774638, retrieved from EBI accession No. UNIPROT:GOU1 P1 Database accession No. GOU1 P1, one page.
De Ferrari, G.V. et al. (May 29, 2007, e-pub. May 21, 2007). "Common Genetic Variation Within the Low-Density Lipoprotein Receptor-Related Protein 6 and Late-Onset Alzheimer's Disease," *Proc. Natl. Acad. Sci. USA* 104:9434-9439.
De Nardo, G.L. et al. (Oct. 1998). "Comparison of 1,4,7,10-Tetraazacyclododecane-N,N',N'',N'''-Tetraacetic Acid (DOTA)-:eptide-ChL6, A Novel Immunoconjugate with Catabolizable Linker, to 2-Iminothiolane-2-[p-(bromoacetamido)benzyl]-DOTA-ChL6 in Breast Cancer Xenografts," *Clin. Cancer Res.* 4(10):2483-2490.
Diem, M.D. et al. (2014). "Selection of High-Affinity Centyrin FN3 Domains From a Simple Library Diversified at a Combination of Strand and Loop Positions," *Prot. Engineer. Des. & Sel.* 27(10):419-429.
Dos Reis, F.C.G. et al. (Feb. 2008). "The Role of Conserved Residues of Chagasin in the Inhibition of Cysteine Peptidases," *FEBS Letters* 582:485-490, (13 pages total).
Efimov, V.P. et al. (1995). "Bacteriophage T4 as a Surface Display Vector," *Virus Genes* 10(2):173-177.

(56) References Cited

OTHER PUBLICATIONS

Eppstein, D.A. et al. (Jun. 1985). "Biological Activity of Liposome-Encapsulated Murine Interferon γ is Mediated by a Cell Membrane," *Proc. Natl. Acad. Sci. USA* 82:3688-3692.

Evan, G.I. et al. (Dec. 1985). "Isolation of Monoclonal Antibodies Specific for Human *c-myc* Proto-Oncogene Product," *Mol. Cell. Biol.* 5(12):3610-3616.

Fawell, S. et al. (Jan. 1994). "Tat-Mediated Delivery of Heterologous Proteins into Cells," *Proc. Natl. Acad. Sci. USA* 91:664-668.

Fellouse, F.A. et al. (2007, e-pub. Aug. 1, 2007). "High-Throughput Generation of Synthetic Antibodies from Highly Functional Minimalist Phage-Displaced Libraries," *J. Mol. Biol.* 373:924-940.

Ferrara, N. et al. (Jun. 2003). "The Biology of VEGF and its Receptors," *Nat. Medicine* 9(6):669-676.

Field, J. et al. (May 1988). "Purification of a RAS-Responsive Adenylyl Cyclase Complex from *Saccharomyces cerevisiae* by use of an Epitope Addition Method," *Mol. And Cell. Biol.* 8(5):2159-2165.

Firth, A.E. et al. (2005, e-pub. Jun. 2, 2005). "Statistics of Protein Library Construction" *Bioinformatics* 21(15):3314-3315.

Freudl, R. et al. (Apr. 5, 1986). "Cell Surface Exposure of the Outer Membrane Protein OmpA of *Escherichia coli* K-12," *J. Mol. Biol.* 188(3):491-494.

Fuh, G. et al. (Mar. 10, 2006). "Structure-Function Studies of Two Synthetic Anti-Vascular Endothelial Growth Factor Fabs and Comparison with the Avastin™ Fab,"*J. Biol. Chem.* 281(10):6625-6631.

Gabizon, A. et al. (Oct. 4, 1989). "Pharmacokinetics and Tissue Distribution of Doxorubicin Encapsulated in Stable Liposomes with Long Circulation Times," *J. National Cancer Inst.* 81(19):1484-1488.

Georgiou, G. et al. (Jan. 1997). "Display of Heterologous Proteins on the Surface of Microorganisms: From the Screening of Combinatorial Libraries to Live Recombinant Vaccines" *Nature Biotechnol.* 15:29-34.

Getz, J.A. (2012). "Peptide Discovery Using Bacterial Display and Flow Cytometry," Chapter 4 in *Methods in Enzymology* 503:75-97.

Gille, H. et al. (Feb. 2, 2001). "Analysis of Biological Effects and Signaling Properties of Flt-1 (VEGFR-1) and KDR (VEGFR-2)," *The Journal of Biological Chemistry* 276(5):3222-3230.

Goel, H.L. et al. (Dec. 2013). "VEGF Targets the Tumour Cell," *Nat. Rev. Cancer* 13(12):871-882, 30 pages.

Gong, Y. et al. (Nov. 16, 2001). "LDL Receptor-Related Protein 5 (LRP5) Affects Bone Accrual and Eye Development," *Cell* 107:513-523.

Gong, Y. et al. (Sep. 13, 2010). "Wnt Isoform-Specific Interactions with Coreceptor Specify Inhibition or Potentiation of Signaling by LRP6 Antibodies," *PLoS One* 5(9)e12682:1-17.

Grönwall, C. et al. (Mar. 2009). "Engineered Affinity Proteins-Generation and Applications," *Journal of Biotechnology* 140(3-4):254-269.

Hanes, J. et al. (May 1997). "In Vitro Selection and Evolution of Functional Proteins by Using Ribosome Display," *Proc. Natl. Acad. Sci. USA* 94:4937-4942.

Hansen, G. et al. (Jul. 13, 2011) "Structural Basis for the Regulation of Cysteine-Protease Activity by a New Class of Protease Inhibitors in Plasmodium," *Structure* 19(7):919-929.

Hansson, L.O. et al. (Mar. 26, 1999). "Evolution of Differential Substrate Specificities in Mu Class Glutathione Transferases Probed by DNA Shuffling," *J. Mol. Biol.* 287(2):265-276.

Harayama, S. (Feb. 1, 1998). "Artificial Evolution by DNA Shuffling," *Trends in Biotechnology* 16(2):76-82.

Hope, I.A., et al. (Nov. 1985). "GCN4 Protein, Synthesize in Vitro, Bind H1S3 Regulatory Sequences: Implications for General Control of Amino Acid Biosynthetic Genes in Yeast," *Cell* 43:177-188.

Hope, I.A. et al. (Sep. 12, 1986). "Functional Dissection of a Eukaryotic Transcriptional Activator Protein, GCN4 of Yeast" *Cell* 46(6) 885-894.

Hope, I.A. et al. (1987). "GCN4, a Eukaryotic Transcriptional Activator Protein, Binds as a Dimer to Target DNA," *The EMBO Journal* 6(9)2781-2784.

Hope, I.A. et al. (Jun. 1988). "Structural and Functional Characterization of the Short Acidic Transcriptional Activation Region of Yeast GCN4 Protein" *Nature* 333: 635-640.

Hopp, T.P. et al. (Oct. 1988). "A Short Polypeptide Marker Sequence Useful for Recombinant Protein Identification and Purification," *Nature Biotechnology* 6:1204-1210.

Hwang, K.J. et al. (Jul. 1980). "Hepatic Uptake and Degradation of Unilamellar Sphingomyelin/Cholesterol Liposomes: A Kinetic Study," *Proc. Natl. Acad. Sci. USA* 77(7):4030-4034.

Jalkanen, M. et al. (Sep. 1985). "Heparan Sulfate Proteoglycans from Mouse Mammary Epithelial Cells: Localization on the Cell Surface with a Monoclonal Antibody," *J. Cell. Biol.* 101:976-984.

Jalkanen, M. et al. (Dec. 1987). "Cell Surface Proteoglycan of Mouse Mammary Epithelial Cells is Shed by Cleavage of its Matrix-binding Ectodomain from its Membrane-Associated Domain," *J. Cell. Biol.* 105(6):3087-3096.

Jiang, J. et al. (Nov. 1997). "Display of a PorA Peptide from *Neisseria Meningitidis* on the Bacteriophage T4 Capsid Surface," *Infection & Immunity* 65(11):4770-4777.

Kang, A. S. et al. (May 1991). "Linkage of Recognition and Replication Functions by Assembling Combinatorial Antibody Fab Libraries Along Phage Surfaces," *Proc. Natl. Acad. Sci. USA* 88:4363-4366.

Katoh, M. et al. (Jul. 15, 2007). "WNT Signaling Pathway and Stem Cell Signaling Network," *Clin. Cancer Res.* 13(14):4042-4045.

Kawai, M. et al. (Feb. 2011). "Emerging Therapeutic Opportunities for Skeletal Restoration," *Nat. Rev. Drug Discov.* 10(2):141-156, 32 pages.

Kenrick, S.A. et al. (Jan. 2010). "Bacterial Display Enables Efficient and Quantitative Peptide Affinity Maturation," *Protein Engineering, Design and Selection* 23(1):9-17.

Keyt, B.A. et al. (Mar. 29, 1996). "The Carboxyl-Terminal Domain (111-165) of Vascular Endothelial Growth Factor is Critical for its Mitogenic Potency," *J. Biol. Chem.* 271(13)7788-7795.

Koiwa, H. et al. (Sep. 2001). "Phage Display Selection of Hairpin Loop Soyacystatin Variants That Mediate High Affinity Inhibition of a Cysteine Proteinase," *The Plant Journal: For Cell and Molecular Biology* 27(5):383-391.

Lehmann, M. et al. (Aug. 2001). "Engineering Proteins for Thermostability: The Use of Sequence Alignments Versus Rational Design and Directed Evolution," *Curr. Opin. Biotechnol.* 12(4):371-375.

Leung, D.W. (Dec. 8, 1989). "Vascular Endothelial Growth Factor is a Secreted Angiogenic Mitogen," *Science* 246:1306-1309.

Li, Y. et al. (Jun. 1998). "Filamentous Bacteriophage Display of a Bifunctional Protein A::scFv Fusion," *Mol. Biotech.* 9(3):187-193.

Li, Y. et al. (2004, e-pub. Oct. 25, 2004). "LRP6 Expression Promotes Cancer Cell Proliferation and Tumorigenesis by Altering β-Catenin Subcellular Distribution," *Oncogene* 23:9129-9135.

Liang, W.C. et al. (Jan. 13, 2006). "Cross-Species Vascular Endothelial Growth Factor (VEGF)-Blocking Antibodies Completely Inhibit the Growth of Human Tumor Xenografts and Measure the Contribution of Stromal VEGF," *J. Biol. Chem.* 281(2):951-961.

Lipovsek, D. et al. (2004, e-pub. May 31, 2004). "In-Vitro Protein Evolution by Ribosome Displan and mRNA Display," *J. Immunol. Methods* 290:51-67.

Liu, C-C. et al. (Mar. 16, 2010). "LRP6 Overexpression Defines a Class of Breast Cancer Subtype and is a Target for Therapy," *Proc. Natl. Acad. Sci. USA* 107(11):5136-5141.

Ljunggren, A. et al. (2007). "Crystal Structure of the Parasite Protease Inhibitor Chagasin in complex with a Host Target Cysteine Protease," *J. Mol. Biol.* 371(1):137-153.

Lorenzo, M.M. et al. (Feb. 1998). "PCR-Based Method for the Introduction of Mutations in Genes Cloned and Expressed in Vaccinia Virus," *Biotechniques* 24(2):308-313.

Lowman, H.B. et al. (Nov. 1991). "Selecting High-Affinity Binding Proteins by Monovalent Phage Display," *Biochemistry* 30(45):10832-10838.

Lowman, H.B. et al. (Dec. 1991). "Monovalent Phage Display: A Method for Selecting Variant Proteins from Random Libraries," *Methods* 3(3):205-216.

Lutz-Freyermuth, C. et al. (Aug. 1990). "Quantitative Determination that one of two Potential RNA-Binding Domains of the A Protein Component of the U1 Small Nuclear Ribonucleoprotein Complex Binds with High Affinity to Stemp-Loop II of U1 RNA," *Proc. Natl. Acad. Sci. USA* 87:6393-6397.

(56) References Cited

OTHER PUBLICATIONS

MacDonald, B.T. et al. (Jul. 2009) "Wnt/β-Catenin Signaling: Components, Mechanisms, and Diseases," *Dev. Cell* 17(1):9-26, 33 pages.
Mani, A. et al. (Mar. 2, 2007) "LRP6 Mutation in a Family with Early Coronary Disease and Metabolic Risk Factors," *Science* 315(5816):1278-1282.
Marin-Neto, J.A. et al. (2007) "Pathogenesis of Chronic Chagas Heart Disease," *Circulation* 115:1109-1123.
Marks, J.D. et al. (Dec. 1991) "By-Passing Immunization. Human Antibodies from V-Gene Libraries Displayed on Phage," *J. Mol. Biol.* 222(3):581-597.
Martin, G.A. et al. (Jan. 10, 1992) "GAP Domains Responsible for Ras p21-Dependent Inhibition of Muscarinic Atrial $K^+$ Channel Currents," *Science* 255:192-194.
Mason, J.J. et al. (2010) "SOST and DKK: Antagonists of LRP Family Signaling as Targets for Treating Bone Disease," *J. Osteoporosis*, vol. 2010, Article ID 460120, p. 1-9.
Melton, D.A. et al. (1984) "Efficient In Vitro Synthesis of Biologically Active RNA and RNA Hybridization Probes from Plasmids Containing a Bacteriophage SP6 Promoter," *Nucl. Acids Res.* 12(18):7035-7056.
Merops. (2017). "The Database of Proteolytic Enzymes, their Substrates and Inhibitors," located at-http://www.ebi.ac.uskl/merops, last visited on Sep. 7, 2017, 2 pages.
Miller, O.J. et al. (Jul. 2006). "Directed Evolution by In Vitro Compartmentalization," *Nat Methods* 3(7):561-570.
Molek, P. et al. (2011). "Peptide Phage Display as a Tool for Drug Discovery: Targeting Membrane Receptors," *Molecules* 16:857-887.
Monfardini, C. et al. (Jan. 1995). "A Branched Monomethoxypoly(ethylene glycol) for Protein Modificaiton," *Bioconjugate Chem.* 6(1):62-69.
Monteiro, A.C.S. et al. (2001). "Identification, Characterization and Localization of Chagasin, a Tight-Binding Cysteine Protease inhibitor in *Trypanosoma Cruzi*," *Journal of Cell Science* 114(21):3933-3942.
Muller, Y.A. et al. (Jul. 1997). "Vascular Endothelial Growth Factor: Crystal Structure and Functional Mapping of the Kinase Domain Receptor Binding Site," *Proc. Natl. Acad. Sci. USA* 94:7192-7197.
Nusse, R. (2008, e-pub. Apr. 8, 2008). "Wnt Signaling and Stem Cell Control," *Cell Research* 18:523-527.
Odegrip, R. et al. (Mar. 2, 2004). "CIS Display: In Vitro Selection of Peptides from Libraries of protein-DNA Complexes," *Proc. Natl. Acad. Sci. USA* 101(9):2806-2810.
Ominsky, M.S. et al. (May 2010). "Two Doses of Sclerostin Antibody in Cynomolgus Monkeys Increases bon Formation, Bone Mineral Density, and Bone Strength," *J. Bone Miner. Res.* 25(5):948-959.
Paborsky, L.R. et al. (May 1990). "Mammalian Cell Transient Expression of Tissue Factor for the Production of Antigen," *Protein Eng.* 3(6)547-553.
Padhi, D. et al. (Jan. 2011, e-pub. Jun. 30, 2010). "Single-Dose, Placebo-Controlled, Randomized Study of AMG 785, a Sclerostin Monoclonal Antibody," *J. Bone Miner. Res.* 26(1):19-26.
Patten, P.A. et al. (1997) "Applications of DNA Shuffling to Pharmaceuticals and Vaccines," *Curr. Opinion Biotechnol.* 8:724-733.
Peterson, J.J. et al. (Jul./Aug. 1999, e-pub. May 20, 1999). "Enzymatic Cleavage of Peptide-Linked Radiolabels from Immunoconjugates," *Bioconjug. Chem.* 10(4):553-557.
Pinson, K.I. et al. (Sep. 28, 2000). "An LDL-Receptor-Related protein Mediates Wnt Signaling in Mice," *Nature* 407:535-538.
Pirakitikulr, N. et al. (Dec. 2010, e-pub. Jan. 20, 2010). "PCRless Library Mutagenesis Via Oligonucleotide Recombination in Yeast," *Protein Sci* 19(12):2336-2346.
Polakis, P. (Feb. 2007). "The Many Ways of Wnt in Cancer," *Current Opinion in Genetics & Development* 17(1):45-51.
Pooga, M. et al. (Jan. 1998). "Cell Penetration by Transportan," *The FASEB Journal* 12:67-77.

Raghava, S. et al. (Nov. 2004, e-pub. Feb. 23, 2005). "Periocular Routes for Retinal Drug Delivery," *Expert Opin. Drug Deliv.* 1(1):99-114.
Rassi, A. et al. (Mar. 6, 2007). "Predictors of Mortality in Chronic Chagas Disease A Systematic Review of Observational Studies," *Circulation* 115:1101-1109.
Redzynia, I. et al. (Aug. 15, 2008). "Displacement of the Occluding Loop by the Parasite Protein, Chagasin, Results in Efficient Inhibition of Human Cathepsin B," *J. Biol. Chem.* 283(33):22815-22825.
Redzynia, I. et al. (2009). "Crystal Structure of the Parasite Inhibitor Chagasin in Complex with Papain Allows Identification of Structural Requirements for Broad Reactivity and Specificity Determinants for Target Proteases," *The FEBS Journal* 276(3)793-806.
Ren, Z.J. et al. (Jul. 1998) "Phage T4 SOC and HOC Display of Biologically Active, Full-Length Proteins on the Viral Capsid," *Gene* 215:439-444.
Ren, Z.J. et al. (Aug. 1997). "Cloning of Linear DNAs in Vivo by Overexpressed T4 DNA Ligase: Construction of a T4 Phage Hoc Gene Display Vector," *Gene* 195(2):303-311.
Ren, Z.J. et al. (1996). "Phage Display of Intact Domains at High Copy Number: A System Based on SOC, the Small Outer Capsid Protein of Bacteriophage T4," *Protein Science* 5:1833-1843.
Rigden, D.J. et al. (2001, e-pub. Aug. 6, 2001). "The Protease Inhibitor Chagasin of *Trypanosoma cruzi* Adopts an Immunoglobulin-Type Fold and may have Arisen by Horizontal Gene Transfer," *FEBS Letters* 504:41-44.
Rigden, D.J. et al. (2002). "Sequence Conservation in the Chagasin Family Suggests a Common Trend in Cysteine Proteinase Binding by Unrelated Protein Inhibitors," *Protein Science* 11:1971-1977.
Sadick, M.D. (1999). "Kinase Receptor Activation (KIRA): A Rapid and Accurate Alternative to Endpoint Bioassays," *J. Pharm. Biomed. Anal.* 19(6):883-891.
Salmon, D. et al. (2006). "Solution Structure and Backbone Dynamics of the *Trypanosoma cruzi* Cysteine Protease inhibitor Chagasin," *J. Mol. Biol.* 357:1511-1521.
Sanderson, S.J. et al. (2003, e-pub. Apr. 8, 2003) "Functional Conservation of a Natural Cysteine Peptidase Inhibitor in Protozoan and Bacterial Pathogens," *FEBS Lett.* 542:12-16.
Schmidt, T.G. et al. (2007, e-pub. Jun. 14, 2007). "The Strep-Tag System for One-Step Purification and High-Affinity Detection or Capturing of Proteins," *Nat. Protoc.* 2(6):1528-1535.
Schwarze, S.R. et al. (Sep. 3, 1999) "In Vivo Protein Transduction: Delivery of a Biologically Active Protein into the Mouse," *Science* 285(5433):1569-1572.
Scott, J.K. et al. (Jul. 27, 1990). "Searching for Peptide Ligands with an Epitope Library," *Science* 249(4967):386-390.
Sergeeva, A. et al. (Dec. 2006, e-pub. Oct. 6, 2006). "Display Technologies: Application for the Discovery of Drug and Gene Delivery Agents," *Adv. Drug Deliv. Rev.* 58(15):1622-1654, 42 pages.
Shih, H.H. (2012). "Discovery Process for Antibody-Based Therapeutics," Chapter 2 in *Development of Antibody-Based Therapeutics*, M.A. Tabrizi et al. eds., Springer Science & Business Media, New York, pp. 9-32.
Sias, P.E. et al. (Aug. 1990). "ELISA for Quantitation of the Extracellular Domain of p185$^{HER2}$ in Biological Fluids," *J. Immunol. Methods* 132:73-80.
Sidhu, S.S. et al. (Aug. 2007, e-pub. Sep. 2007). "Phage Display for Engineering and Analyzing Protein Interaction Interfaces," *Curr. Opin. Struct. Biol.* 17(4):481-487.
Sidhu, S.S. et al. (2000) "Phage Display for Selection of Novel Binding Peptides," Chapter 21 in *Methods in Enzymology*, W. B. Saunders, Philadelphia, PA, 328:333-363.
Skelton, N.J. et al. (Feb. 28, 2003). "Origins of PDZ Domain Ligand Specificity," *J. Biol. Chem.* 278(9):7645-7654.
Skerra, A. (2007, e-pub. Jul. 20, 2007). "Alternative Non-Antibody Scaffolds for Molecular Recongnition," *Curr. Opin. in Biotechnol.* 18:295-304.
Skinner, R.H. et al. (Aug. 5, 1991). "Use of the Glu-Glu-Phe C-Terminal Epitope for Rapid Purification of the Catalytic Domain of Normal and Mutant ras GTPase-Activating Proteins," *J. Biol. Chem.* 266(22):14163-14166.

(56) References Cited

OTHER PUBLICATIONS

Smith, G.P. (Jun. 14, 1985). "Filamentous Fusion Phage: Novel Expression Vectors that Display Cloned Antigens on the Virion Surface," *Science* 228(4705)1315-1317.
Smith, G. P. (Oct. 1991). "Surface Presentation of Protein Epitopes Using Backteriophage Expression Systems," *Current Opin. Biotechnol.* 2(5):668-673.
Smith, G.P. (1993) "Libraries of Peptides and Proteins Displayed on Filamentous Phage," Chapter 15 in *Methods Enzymology*, Academic Press, Inc. 217:228-257.
Smith, B.O. et al. (Mar. 3, 2006) "The Structure of *Leishmania Mexicana* ICP Provides Evidence for Convergent Evolution of Cysteine Peptidase Inhibitors," *J. Biol. Chem.* 281(9):5821-5828.
Smith, E.S. et al. (Mar. 2014). "Antibody Library Display on a Mammalian Virus Vector: Combining the Advantages of Both Phage and yeast Display into One Technology," *Curr. Drug Discov. Technol.* 11:48-55.
Steffens, D.L. et al. (Jul. 2007). "Efficient Site-Directed Saturation Mutagenesis Using Degenerate Oligonucleotides," *J. Biomol. Tech.* 18(3):147-149.
Tamai, K. et al. (Sep. 28, 2000). "LDL-Receptor-Related Proteins in Wnt Signal Transduction," *Nature* 407(6803):530-535.
Theodore, L. et al. (Nov. 1995). "Intraneuronal Delivery of Protein Kinase C Pseudosubstrate Leads to Growth Cone Collapse," *The Journal of Neuroscience* 15(11):7158-7167.
Thorpe, P.E. (1985) "Antibody Carriers of Cytotoxic Agents in Cancer Therapy: A Review", *Monoclonal Antibodies '84: Biological and Clinical Applications* pp. 475-506.
Thorpe, P.E. et al. (Feb. 1982) "The Preparation and Cytotoxic Properties of Antibody-Toxin Conjugates," *Immunol. Rev.* 62(1):119-158.
Tonikian, R. et al. (2007, e-pub. May 24, 2007) "Identifying Specificity Profiles for Peptide Recognition Modules from Phage-Displayed Peptide Libraries," *Nat. Protoc.* 2(6):1368-1386.
Tung, E.K.K. et al. (May 3, 2012) "Upregulation of the Wnt Co-Receptor LRP6 Promotes Hepatocarcinogenesis and Enhances Cell Invasion," *PLoS ONE* 7(5):e36565:1-10.
Ullman, C.G. et al. (May 2011). "In Vitro Methods for Peptide Display and their Applications," *Brief. Funct. Genomics* 10(3):125-134.
Van Beijnum, J.R. et al. (2002). "Target Validation for Genomics Using Peptide-Specific Phage Antibodies: A Study of Five Gene Products Overexpressed in Colorectal Cancer," *International Journal of Cancer* 101(2):118-127.
Van Den Berg, A. et al (Dec. 2011, e-pub. Apr. 12, 2011). "Protein Transduction Domain Delivery of Therapeutic Macromolecules," *Curr. Opin. Biotechnol.* 22(6):888-893.
Verheesen, P. et al. (Aug. 2006, e-pub Jun. 10, 2006). "Reliable and Controllable Antibody Fragment Selections from Camelid Non-Immune Libraries for Target Validation," *Biochim. Biophys. Acta* 1764(8):1307-1319.
Vitetta, E.S. et al. (Nov. 20, 1987) "Redesigning Nature's Poisons to Create Anti-Tumor Reagents," *Science* 238(4830):1098-1104.
Wang, S.X. et al. (May 2007). "The Structure of Chagasin in Complex with a Cysteine Protease Clarifies the Binding Mode and Evolution of an Inhibitor Family," *Structure* 15:535-543.
Weiss, G.A. et al. (Aug. 1, 2000). "Rapid Mapping of Protein Functional Epitopes by Combinatorial Alanine Scanning," *Proc. Natl. Acad. Sci. USA* 97(16):8950-8954.
Wells, J.A. et al. (1992). "Rapid Evolution of Peptide and Protein binding Properties in vitro," *Curr. Opin. Struct. Biol.* 3:355-362.
Welsch, M.E. et al. (2010). "Privileged Scaffolds for Library Design and Drug Discovery," *Curr. Opin. Chem. Biol.* 14:1-15.
Wiesmann, C. et al. (Nov. 28, 1997). "Crystal Structure at 1.7 Å Resolution of VEGF in Complex with Domain 2 of the Flt-1 Receptor," *Cell* 91(5):695-704.
Wilson, D.H. et al. (Mar. 27, 2001, e-pub. Mar. 13, 2001). "The Use of mRNA Display to Select High-Affinity Protein-Binding Peptides," *Proc. Natl. Acad. Sci. USA* 98(7):3750-3755.
Wise, A. et al. (Feb. 2002). "Target Validation of G-Protein Coupled Receptors," *Drug Disc. Today* 7(4):235-246.
Wu, H. et al. (May 1998) "Stepwise in vitro Affinity Maturation of Vitaxin, an $\alpha v\beta 3$-Specific Humanized mAb," *Proc. Natl. Acad. Sci. U.S.A.* vol. 95:6037-6042.
Wurch, T. et al. (Nov. 2012). "Novel Protein Scaffolds as Emerging Therapeutic Proteins: From Discovery to Clinical Proof-of-Concept," *Trends Biotechnol.* 30(11):575-582.
Zhang, Y. et al. (Apr. 2009, e-pub. Mar. 1, 2009). "Inhibition of Wnt Signaling by Dishevelled PDZ Peptides," *Nat. Chem. Biol.* 5(4):217-219.
Zhang, Y. et al. (Jan. 10, 2014, e-pub. Nov. 13, 2013). "Identification of a Small Peptide That Inhibits PCSK9 Protein Binding to the Low Density Lipoprotein Receptor," *J. Biol. Chem.* 289(2):942-955.
Zhu, Z. et al. (Aug. 1, 1998) "Inhibition of Vascular Endothelial Growth Factor-Induced Receptor Activation With Anti-Kinase Insert Domain-Containing Receptor Single-Chain Antibodies From a Phage Display Library," *Cancer Research* 58(15):3209-3214.
Zimmermann, K. et al. (1999). "A Triglycine Linker Improves Tumor Uptake and Biodistributions of 67-Cu-Labeled Anti-Neuroblastoma MAb chCE7 F(ab')$_2$ Fragments," *Nucl. Med. Biol.* 26:943-950.
Zingales, B. et al. (1997). "*Trypanosoma cruzi* Genome Project: Biological Characteristics and Molecular Typing of Clone CL Brener," *Acta Tropica* 68:159-173.
Extended European Search Report and Search Opinion dated Oct. 25, 2017, for European Patent Application No. 15809994.5, filed on Dec. 23, 2015, 14 pages.
International Search Report dated Nov. 2, 2015, for PCT Application No. PCT/US15/36690, filed on Jun. 19, 2015, 4 pages.
Written Opinion dated Nov. 2, 2015, for PCT Application No. PCT/US15/36690, filed on Jun. 19, 2015, 6 pages.
Arnon, R. et al. (1985). "Monoclonal Antibodies for Immunotargeting of Drugs in Cancer Therapy", Monoclonal Antibodies and Cancer Therapy, Reisfeld, R.A. et al. eds., Alan R. Liss, Inc., New York, New York, pp. 243-256.
Costa, T. F.R. et al. (2016, e-pub. Nov. 4, 2015). "Natural Cysteine Protease Inhibitors in Protozoa: Fifteen Years of the Chagasin Family," Biochimie 122:197-207.
Davenport, A.P. et al. (1996). "Radioligand Binding Assays: Theory and Practice," Chapter 11 in Current Directions in Radiopharmaceutical Research and Development, Mather, S.J. ed., Kluwer Academic Publishers, Dordrecht, The Netherlands, pp. 169-179.
Hellstrom, K.E. et al. (1987). "Antibodies for Drug Delivery", Controlled Drug Delivery, Robinson, J.R. et al. eds., Marcel Dekker, Inc., New York, New York, pp. 623-653.
Order, S.E. (1985). "Analysis, Results, and Future Prospective of the Therapeutic Use of Radiolabeled Antibody in Cancer Therapy", Chapter 15 in Monoclonal Antibodies for Cancer Detection and Therapy, Baldwin, R.W. et al. eds., Academic Press, Inc., Orlando, Florida, pp. 303-316.
Bruning, M. et al. (2012). "The Intracellular Ig Fold: A Robust Protein Scaffold for the Engineering of Molecular Recognition," Protein Engineering, Design & Selection 25(5):205-212.
Casados-Vazquez, L.E. et al. (Jan. 2011, e-pub. Oct. 15, 2010). "Crystal Structure of the Cysteine Protease Inhibitor 2 From Entamoeba Histolytica: Functional Convergence of a Common Protein Fold," Gene 471(1-2):45-52.
Guy, P.A. et al. (Mar. 1997). "Crystal Structure of the Type-I Interleukin-1 Receptor Complexed With Interleukin-1$\beta$," Nature 386:190-194.
Hashiguchi. S. et al. (2010). "Beyond Antibody Using Phage Display: Molecular Targeting by Novel Designed Molecule," Seikagaku Journal of Japanese Biochemical Society 82(8):710-726. (English Abstract Only).
Petrovskaya, L.E. et al. (2012). "Construction of TNF-Binding Proteins by Grafting Hypervariable Regions of F10 Antibody on Human Fibronectin Domain Scaffold," Biochemistry (Moscow) 77(1):62-70.
Schreuder, H. et al. (Mar. 13, 1997). "A New Cytokine-Receptor Binding Mode Revealed by the Crystal Structure of the IL-1 Receptor with an Antagonist," Nature 386:194-200.

(56) References Cited

OTHER PUBLICATIONS

Sundararaj, S. et al. (Apr. 3, 2014). "Cross-Talk between Malarial Cysteine Proteases and Falstatin: The BC Loop as a Hot-Spot Target," PLOS One 9(4):39003, 1-9.

* cited by examiner

A

L4-NNIRGLPGF (SEQ ID NO:81)

B

| L2-SNPSC | L4-DSNEIWYC | L6-SPYYGPTKVE |
| (SEQ ID NO:79) | (SEQ ID NO:82) | (SEQ ID NO:85) |

FIG. 12

CHAGASIN-BASED SCAFFOLD COMPOSITIONS, METHODS, AND USES

CROSS REFERENCE TO RELATED APPLICATIONS

This application is the national stage of International Application No. PCT/US2015/036690, filed internationally Jun. 19, 2015, which claims priority benefit of U.S. Provisional Application Ser. No. 62/015,296, filed Jun. 20, 2014, the disclosures of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392026600SUBSEQLIST.txt, date recorded: Jun. 8, 2018, size: 94 KB).

BACKGROUND OF THE INVENTION

The design and engineering of novel proteins from alternative protein scaffolds has been an emerging field in the last decade with a broad spectrum of applications ranging from structure biology and imaging tools to therapeutic reagents that are currently being tested in the clinic (H K Binz et al., *Nat Biotechnol* 23, 1257-1268, 2005; H K Binz and A Pluckthun, *Curr Opin Biotechnol* 16, 459-469, 2005; S S Sidhu and S Koide, *Curr Opin Struct Biol* 17, 481-487, 2007; A Skerra, *Curr Opin Biotechnol* 18, 295-304, 2007; C Gronwall and S Stahl, *J Biotechnol* 140, 254-269, 2009; T Wurch et al., *Trends Biotechnol* 30, 575-582, 2012; S Banta et al., *Annu Rev Biomed Eng* 15, 93-113, 2013).

Desirable physical properties of potential alternative scaffold molecules include high thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase α-helix propensity, engineering of salt bridges, alteration of the surface charge of the protein, directed evolution, and composition of consensus sequences (Lehmann and Wyss, *Curr Opin Biotechnol* 12, 371-375, 2001).

Chagasin is an endogenous protein from the parasite *Trypanosoma cruzi*, which is the causative pathogen of Chagas disease (ACS Monteiro et al., *J Cell Sci* 114, 3933-3942, 2001). Chagasin is the signature member of the I42 family of cysteine protease inhibitors and was originally discovered in protozoan parasites; proteins homologous to chagasin have been found to be widely distributed in prokaryotes and eukaryotes as well (D J Rigden et al., *FEBS Lett* 504, 41-44, 2001; S J Sanderson et al., *FEBS Lett* 542, 12-16, 2003). Chagasin was isolated as a heat-stable protein that binds to the major lysosomal cysteine protease cruzipain that is essential for the parasite to invade and multiply in mammalian host cells. Besides cruzipain, chagasin also inhibits other cysteine proteases such as Falcipain 2, Falcipain 3, Cathepsins B, L, K and H (S X Wang et al., *Structure* 15, 535-543, 2007). To date, several homologs of chagasin have been described (D Salmon et al., *J Mol Biol* 357, 1511-1521, 2006; B O Smith et al., *J Biol Chem* 281, 5821-5828, 2006; G Hansen et al., *Structure* 19, 919-929, 2011). Crystal structures of chagasin alone and in complex with the cysteine proteases papain, cathepsin B, cathepsin L and Falcipain2 have shown that three loops (designated L2, L4 and L6 or BC, DE and FG, respectively) protruding out from the β-sandwich protein scaffold are essential for binding to the active site cleft of these proteases in order to inhibit enzymatic activity (A A Figueiredo da Silva et al., *J Struct Biol* 157, 416-423, 2007; A Ljunggren et al., *J Mol Biol* 371, 137-153, 2007; S X Wang et al., *Structure* 15, 535-543, 2007; I Redzynia et al., *J Biol Chem* 283, 22815-22825, 2008; I Redzynia et al., *FEBS J* 276, 793-806, 2009). Chagasin has a unique immunoglobulin-like fold with homology to human CD8α (DJ Rigden et al., *FEBS Lett* 504, 41-44, 2001; S X Wang et al., *Structure* 15, 535-543, 2007).

Thus, there is a need to develop small, stable, artificial antibody-like molecules for a variety of therapeutic and diagnostic applications. The present invention meets this and other needs.

SUMMARY OF THE INVENTION

Provided herein is a non-naturally occurring chagasin scaffold protein comprising at least one amino acid alteration in Loop 2 (L2), Loop 4 (L4), and/or Loop 6 (L6), with reference to a wild-type chagasin-like cysteine protease inhibitor. In certain embodiments, the wild type chagasin-like cysteine protease inhibitor is from *T. cruzi* (Dm28c clone), *T. cruzi* (CL Brenner strain, isoform 1), *T. cruzi* (CL Brenner strain, isoform 2), *T. brucei, L. mexicana, L. major, E. hystolytica,* or *P. aeruginosa*. In certain embodiments, the wild type chagasin-like cysteine protease inhibitor is from human CD8 T-cell surface glycoprotein, human interleukine-1 type 1 receptor (IL-1 R1), or human vascular cell adhesion molecule-1 (Vcam-1). In certain embodiments, the wild type chagasin-like cysteine protease inhibitor is *T. cruzi* (CL Brenner strain, isoform 1) having the amino acid sequence set forth in SEQ ID NO: 1. In certain embodiments, L2 comprises the amino acid sequence $X_{5-8}$-GF (SEQ ID NO: 151), wherein X represents any amino acid. In certain embodiments, L2 comprises the amino acid sequence $SNX_{3-6}$-GF (SEQ ID NO: 152), wherein X represents any amino acid. In certain embodiments, L4 comprises the amino acid sequence $X_{7-15}$-GAGG (SEQ ID NO: 153) wherein X represents any amino acid. In certain embodiments, L6 comprises the amino acid sequence $X_{3-12}$ (SEQ ID NO: 154), wherein X represents any amino acid. In certain embodiments, L6 comprises the amino acid sequence $X_{10}$ (SEQ ID NO: 106) wherein X represents any amino acid. In certain embodiments, non-naturally occurring chagasin scaffold protein of any of the embodiments above comprises the amino acid sequence set forth in SEQ ID NO: 2.

In certain embodiments, the non-naturally occurring chagasin scaffold protein specifically binds a target ligand. In certain embodiments, the target ligand is a protein, a nucleic acid, a polysaccharide, a lipopolysaccharide, a lipid, or a phospholipid. In certain embodiments, the target ligand is a protein. In certain embodiments, the protein is a cell surface protein, a soluble protein, a viral protein, a bacterial protein, a protein associated with ocular disease, a protein associated with cancer, a protein associated with bone disease, a protein associated with inflammation, or a therapeutic protein. In certain embodiments, the protein is LRP6. In certain embodiments, the protein is VEGF.

In certain embodiments, the non-naturally occurring chagasin scaffold protein of any one of the embodiments above is conjugated to a therapeutic agent. In certain embodiments, the non-naturally occurring chagasin scaffold protein of any one of the embodiments above is conjugated to a label. In certain embodiments, the label is selected from the group consisting of a radioisotope, a fluorescent dye, and an enzyme.

Also provided herein is an isolated nucleic acid encoding the non-naturally occurring chagasin scaffold protein according to any one of the embodiments above. An expression vector encoding a nucleic acid molecule according to any one of the embodiments above is also provided herein. Further provided herein is a cell comprising an expression vector according to any one of the embodiments above.

Provided herein is a method of producing the non-naturally occurring chagasin scaffold protein according to any one of the embodiments above. The methods can include culturing a cell comprising an expression vector according to any one of the embodiments above, and recovering the non-naturally occurring chagasin scaffold protein from the cell culture. Also provided is a method of producing the non-naturally occurring chagasin scaffold protein according to any one of the embodiments above. The methods can include chemically synthesizing the non-naturally occurring chagasin scaffold protein.

Also provided herein is a composition containing the non-naturally occurring chagasin scaffold protein according to any one of the embodiments above and a pharmaceutically acceptable carrier.

Also encompassed herein is a polypeptide display library. The display library can include a plurality of the non-naturally occurring chagasin scaffold proteins according to any one of the embodiments above. In certain embodiments, the non-naturally occurring chagasin scaffold proteins are displayed on the surfaces of ribosomes, bacteriophage, viruses, bacteria, or yeast cells. In certain embodiments, the non-naturally occurring chagasin scaffold proteins are displayed on bacteriophage. In certain embodiments, the bacteriophage is a filamentous bacteriophage. In certain embodiments, the filamentous bacteriophage is an M13 phage. In certain embodiments, the polypeptide library has a sequence diversity of between about $10^8$ and about $10^{14}$. Also provided herein are nucleic acid molecules encoding the polypeptide display library according to any one of the embodiments above. Also provided herein is an expression vector operably linked to the nucleic acid molecules according to any one of the embodiments above.

Also encompassed herein is a method of obtaining a non-naturally occurring chagasin scaffold protein that specifically binds to a target ligand. The methods can include: (a) contacting a target ligand with the library according to any one of the embodiments above under conditions that allow a non-naturally occurring chagasin scaffold protein: target ligand complex to form; (b) detecting the formation of the non-naturally occurring chagasin scaffold protein: target ligand complex; and (c) obtaining from the complex the non-naturally occurring chagasin scaffold protein that specifically binds the target ligand. In certain embodiments, the method can further include randomizing L2, L4, and/or L6 of the non-naturally occurring chagasin scaffold protein obtained in step (c) to generate a further randomized non-naturally occurring chagasin scaffold protein and repeating steps (a) and (b) using said further randomized non-naturally occurring chagasin scaffold protein.

In some embodiments, provided herein is a non-naturally occurring chagasin scaffold protein that specifically binds to the same epitope as a second non-naturally occurring chagasin scaffold protein that binds human low density lipoprotein receptor-related protein 6 (LRP6), wherein the second non-naturally occurring chagasin scaffold protein that binds human LRP6 comprises an L2 that comprises the amino acid sequence SNP-T/S/A/Q-T/C/D (SEQ ID NO: 150) or SN-V/A-D (155), an L4 that comprises the amino acid sequence Y/S-N-N/K-I/V-R/K-G-L/V/I-PGF (SEQ ID NO: 156) or SN-Y/S-TK-H/R (SEQ ID NO: 157), or DSNEIWYC (SEQ ID NO: 77); and an L6 that comprises the amino acid sequence R/S/P/G-P/R-W/Y/E/S/V-T/Y/K/T-G-P/S/A-S/T/Y-H/K/L/Q/D-D/V/E-S/E/M/P/V (SEQ ID NO: 148), with reference to SEQ ID NO: 2. Also provided herein is an antibody that specifically binds to the same epitope as a non-naturally occurring chagasin scaffold protein that binds human low density lipoprotein receptor-related protein 6 (LRP6), wherein the non-naturally occurring chagasin scaffold protein that binds human LRP6 comprises an L2 that comprises the amino acid sequence SNP-T/S/A/Q-T/C/D (SEQ ID NO: 150) or SN-V/A-D (155), an L4 that comprises the amino acid sequence Y/S-N-N/K-I/V-R/K-G-L/V/I-PGF (SEQ ID NO: 156) or SN-Y/S-TK-H/R (SEQ ID NO: 157), or DSNEIWYC (SEQ ID NO: 77); and an L6 that comprises the amino acid sequence R/S/P/G-P/R-W/Y/E/S/V-T/Y/K/T-G-P/S/A-S/T/Y-H/K/L/Q/D-D/V/E-S/E/M/P/V (SEQ ID NO: 148), with reference to SEQ ID NO: 2.

The invention provides a non-naturally occurring chagasin scaffold protein that specifically binds human low density lipoprotein receptor-related protein 6 (LRP6), wherein the non-naturally occurring chagasin scaffold protein competes for binding with a second non-naturally occurring chagasin scaffold protein that binds human LRP6, wherein the second non-naturally occurring chagasin scaffold protein that binds human LRP6 comprises an L2 that comprises the amino acid sequence SNP-T/S/A/Q-T/C/D (SEQ ID NO: 150) or SN-V/A-D (155), an L4 that comprises the amino acid sequence Y/S-N-N/K-I/V-R/K-G-L/V/I-PGF (SEQ ID NO: 156) or SN-Y/S-TK-H/R (SEQ ID NO: 157), or DSNEIWYC (SEQ ID NO: 77); and an L6 that comprises the amino acid sequence R/S/P/G-P/R-W/Y/E/S/V-T/Y/K/T-G-P/S/A-S/T/Y-H/K/L/Q/D-D/V/E-S/E/M/P/V (SEQ ID NO: 148), with reference to SEQ ID NO: 2.

In certain embodiment of (or as applied to) any of the embodiments above the non-naturally occurring chagasin scaffold protein that specifically binds human LRP6 comprises an L2 that comprises the amino acid sequence SNP-T/S/A/Q-T/C/D (SEQ ID NO: 150) or SN-V/A-D (155), an L4 that comprises the amino acid sequence Y/S-N-N/K-I/V-R/K-G-L/V/I-PGF (SEQ ID NO: 156) or SN-Y/S-TK-H/R (SEQ ID NO: 157), or DSNEIWYC (SEQ ID NO: 77); and an L6 that comprises the amino acid sequence R/S/P/G-P/R-W/Y/E/S/V-T/Y/K/T-G-P/S/A-S/T/Y-H/K/L/Q/D-D/V/E-S/E/M/P/V (SEQ ID NO: 148), with reference to SEQ ID NO: 2

In some embodiments, provided herein is a non-naturally occurring chagasin scaffold protein that specifically binds to the same epitope as a second non-naturally occurring chagasin scaffold protein that binds human low density lipoprotein receptor-related protein 6 (LRP6), wherein the second non-naturally occurring chagasin scaffold protein that binds human LRP6 comprises an L2 that comprises the amino acid sequence S-N/S-P/N-Q/T/V/S/A-T/D/C-GF (SEQ ID NO: 6), an L4 that comprises the amino acid sequence P-S/Y-N-N/K-V/I-K/R-G-V/I/L-PGFGAGG (SEQ ID NO: 10), PSN-S/Y-TK-H/R-GAGG (SEQ ID NO: 90), or DSNEIWYC (SEQ ID NO: 77); and an L6 that comprises the amino acid sequence G/R/P/S-P/R-W/S/V/Y/E-T/K/Y-G-A/P/S-S/Y/T-Q/D/L/H/K-E/D/V-P/S/M/E (SEQ ID NO: 14), with reference to SEQ ID NO: 2. Also provided herein is an antibody that specifically binds to the same epitope as a non-naturally occurring chagasin scaffold protein that binds human low density lipoprotein receptor-related protein 6 (LRP6), wherein the non-naturally occurring chagasin scaffold protein that binds human LRP6 comprises an L2 that comprises the amino acid sequence S-N/S-P/N-Q/T/V/S/A-T/D/C-GF (SEQ ID NO: 6), an L4 that comprises the amino acid sequence P-S/Y-N-N/K-V/I-K/R-G-V/I/L-PGFGAGG (SEQ ID NO: 10), PSN-S/Y-TK-H/R-GAGG (SEQ ID NO: 90), or DSNEIWYC (SEQ ID NO: 77); and an L6 that comprises the amino acid sequence G/R/P/S-P/R-W/S/V/Y/E-T/K/Y-G-A/P/S-S/Y/T-Q/D/L/H/K-E/D/V-P/S/M/E (SEQ ID NO: 14), with reference to SEQ ID NO: 2.

The invention provides a non-naturally occurring chagasin scaffold protein that specifically binds human low density lipoprotein receptor-related protein 6 (LRP6), wherein the non-naturally occurring chagasin scaffold protein competes for binding with a second non-naturally occurring chagasin scaffold protein that binds human LRP6, wherein the second non-naturally occurring chagasin scaffold protein that binds human LRP6 comprises an L2 that comprises the amino acid sequence S-N/S-P/N-Q/T/V/S/A-T/D/C-GF (SEQ ID NO: 6), an L4 that comprises the amino acid sequence P-S/Y-N-N/K-V/I-K/R-G-V/I/L-PGFGAGG (SEQ ID NO: 10), PSN-S/Y-TK-H/R-GAGG (SEQ ID NO: 90), or DSNEIWYC (SEQ ID NO: 77); and an L6 that comprises the amino acid sequence G/R/P/S-P/R-W/S/V/Y/E-T/K/Y-G-A/P/S-S/Y/T-Q/D/L/H/K-E/D/V-P/S/M/E (SEQ ID NO: 14), with reference to SEQ ID NO: 2.

In certain embodiment of (or as applied to) any of the embodiments above the non-naturally occurring chagasin scaffold protein that specifically binds human LRP6 comprises an L2 that comprises the amino acid sequence S-N/S-P/N-Q/T/V/S/A-T/D/C-GF (SEQ ID NO: 6), an L4 that the amino acid sequence P-S/Y-N-N/K-V/I-K/R-G-V/I/L-PGFGAGG (SEQ ID NO: 10), PSN-S/Y-TK-H/R-GAGG (SEQ ID NO: 90), or DSNEIWYC (SEQ ID NO: 77); and an L6 that comprises the amino acid sequence G/R/P/S-P/R-W/S/V/Y/E-T/K/Y-G-A/P/S-S/Y/T-Q/D/L/H/K-E/D/V-P/S/M/E (SEQ ID NO: 14), with reference to SEQ ID NO: 2.

In certain embodiments, provided herein is a non-naturally occurring chagasin scaffold protein that specifically binds human low density lipoprotein receptor-related protein 6 (LRP6) and comprises: an L2 that comprises an amino acid sequence set forth in any one of SEQ ID NOs: 3-5, 78-80, and 146, an L4 that comprises an amino acid sequence set forth in any one of SEQ ID NOs: 7-9, 77, and 81-83; and an L6 that comprises an amino acid sequence set forth in any one of SEQ ID NOs: 11-13, 84-86, and 147, with reference to SEQ ID NO: 2.

In certain embodiments, provided herein is a non-naturally occurring chagasin scaffold protein that specifically binds human low density lipoprotein receptor-related protein 6 (LRP6) and comprises: an L2 that comprises an amino acid sequence set forth in any one of SEQ ID NOs: 3-5, an L4 that comprises an amino acid sequence set forth in any one of SEQ ID NOs: 7-9; and an L6 that comprises an amino acid sequence set forth in any one of SEQ ID NOs: 11-13, with reference to SEQ ID NO: 2. In certain embodiments, L2 comprises the amino acid sequence SNPQT (SEQ ID NO: 3), L4 comprises the amino acid sequence SNKVKGVPGF (SEQ ID NO: 7); and L6 comprises the amino acid sequence GPWTGASQEP (SEQ ID NO: 11). In certain embodiments, L2 comprises the amino acid sequence SNPTT (SEQ ID NO: 4), L4 comprises the amino acid sequence SNKIKGIPGF (SEQ ID NO: 8); and L6 comprises the amino acid sequence RPSTGPSDDS (SEQ ID NO: 12). In certain embodiments, L2 comprises the amino acid sequence SNVD (SEQ ID NO: 5), L4 comprises the amino acid sequence SNSTKR (SEQ ID NO: 9); and L6 comprises the amino acid sequence PRVKGAYLVM (SEQ ID NO: 13).

In certain embodiments, the non-naturally occurring chagasin scaffold protein that specifically binds human LRP6 comprises an L2 that comprises the amino acid sequence SNPTT (SEQ ID NO: 4), an L4 that comprises the amino acid sequence YNNIRGLPGF (SEQ ID NO: 81); and an L6 that comprises the amino acid sequence RPWTGPSHDS (SEQ ID NO: 84), with reference to SEQ ID NO: 2.

In certain embodiments, the non-naturally occurring chagasin scaffold protein that specifically binds human LRP6 comprises an L2 that comprises the amino acid sequence SNPSC (SEQ ID NO: 79), an L4 that comprises the amino acid sequence DSNEIWYC (SEQ ID NO: 82); and an L6 that comprises the amino acid sequence SPYYGPTKVE (SEQ ID NO: 85), with reference to SEQ ID NO: 2.

In certain embodiments, the non-naturally occurring chagasin scaffold protein that specifically binds human LRP6 comprises an L2 that comprises the amino acid sequence SNPAD (SEQ ID NO: 80), an L4 that comprises the amino acid sequence SNYTKH (SEQ ID NO: 83); and an L6 that comprises the amino acid sequence PREKGSSLVM (SEQ ID NO: 86), with reference to SEQ ID NO: 2.

In certain embodiments, the non-naturally occurring chagasin scaffold protein that specifically binds human LRP6 comprises an L2 that comprises the amino acid sequence SNAD (SEQ ID NO: 146), an L4 that comprises the amino acid sequence SNSTKR (SEQ ID NO: 9); and an L6 that comprises the amino acid sequence RREKGSTLVV (SEQ ID NO: 147), with reference to SEQ ID NO: 2.

In certain embodiments, the non-naturally occurring chagasin scaffold protein comprises the amino acid sequence set forth in SEQ ID NO: 15. In certain embodiments, the non-naturally occurring chagasin scaffold protein comprises the amino acid sequence set forth in SEQ ID NO: 16. In certain embodiments, the non-naturally occurring chagasin scaffold protein comprises the amino acid sequence set forth in SEQ ID NO: 17.

In certain embodiments, the non-naturally occurring chagasin scaffold protein that specifically binds human LRP6 comprises the amino acid sequence set forth in SEQ ID NO: 87. In certain embodiments, the non-naturally occurring chagasin scaffold protein that specifically binds human LRP6 comprises the amino acid sequence set forth in SEQ ID NO: 88. In certain embodiments, the non-naturally occurring chagasin scaffold protein that specifically binds human LRP6 comprises the amino acid sequence set forth in SEQ ID NO: 89. In certain embodiments, the non-naturally occurring chagasin scaffold protein that specifically binds human LRP6 comprises the amino acid sequence set forth in SEQ ID NO: 149.

In certain embodiments, the non-naturally occurring chagasin scaffold protein according to any of the embodiments above binds a human LRP6 with a Kd between 500 nM and 1 pM. In certain embodiments, the non-naturally occurring chagasin scaffold protein according to any of the embodiments above specifically binds LRP6 and inhibits Wnt1 signaling.

In another embodiment, provided herein is a non-naturally occurring chagasin scaffold protein that specifically binds to the same epitope as a second non-naturally occurring chagasin scaffold protein that binds human vascular endothelial growth factor (VEGF), wherein the second non-naturally occurring chagasin scaffold protein that binds human VEGF comprises an L2 that comprises the amino acid sequence SN-L/Y-R/F/Q-S/Y/N/D-M/D/A/S (SEQ ID NO: 23), an L4 that comprises the amino acid sequence A/N/L/S/V-G/D/S/R-P/L/T/A-S/G/Y/T-A/S/G/Q-V/R/S/K/A-P/L/E/S/N-L/S/T/N/E (SEQ ID NO: 29); and an L6 that comprises the amino acid sequence A/N/F/S-P/K-W/N/S/V-R/L/W-G-P/L-A/S/D/M/R-N/R/Y/V/F-V/W/P-I/L (SEQ ID NO: 35), with reference to SEQ ID NO: 2. Also encompassed herein is an antibody that specifically binds to the same epitope as a non-naturally occurring chagasin scaffold protein that binds human vascular endothelial growth factor (VEGF), wherein the non-naturally occurring chagasin scaffold protein that binds human VEGF comprises an L2 that comprises the amino acid sequence SN-L/Y-R/F/Q-S/Y/N/D-M/D/A/S (SEQ ID NO: 23), an L4 that comprises the amino acid sequence A/N/L/S/V-G/D/S/R-P/L/T/A-S/G/Y/T-A/S/G/Q-V/R/S/K/A-P/L/E/S/N-L/S/T/N/E (SEQ ID NO: 29); and an L6 that comprises the amino acid sequence A/N/F/S-P/K-W/N/S/V-R/L/W-G-P/L-A/S/D/M/R-N/R/Y/V/F-V/W/P-I/L (SEQ ID NO: 35), with reference to SEQ ID NO: 2.

In another embodiment, provided herein is a non-naturally occurring chagasin scaffold protein that specifically binds human vascular endothelial growth factor (VEGF), wherein the non-naturally occurring chagasin scaffold protein competes for binding with a second non-naturally occurring chagasin scaffold protein that binds human VEGF, wherein the second non-naturally occurring chagasin scaffold protein that binds human VEGF comprises an L2 that comprises the amino acid sequence SN-L/Y-R/F/Q-S/Y/N/D-M/D/A/S (SEQ ID NO: 23), an L4 that comprises the amino acid sequence A/N/L/S/V-G/D/S/R-P/L/T/A-S/G/Y/T-A/S/G/Q-V/R/S/K/A-P/L/E/S/N-L/S/T/N/E (SEQ ID NO: 29); and an L6 that comprises the amino acid sequence A/N/F/S-P/K-W/N/S/V-R/L/W-G-P/L-A/S/D/M/R-N/R/Y/V/F-V/W/P-I/L (SEQ ID NO: 35), with reference to SEQ ID NO: 2.

In certain embodiment of (or as applied to) any of the embodiments above, the non-naturally occurring chagasin scaffold protein that binds VEGF comprises an L2 that comprises the amino acid sequence SN-L/Y-R/F/Q-S/Y/N/D-M/D/A/S (SEQ ID NO: 23), an L4 that comprises the amino acid sequence A/N/L/S/V-G/D/S/R-P/L/T/A-S/G/Y/T-A/S/G/Q-V/R/S/K/A-P/L/E/S/N-L/S/T/N/E (SEQ ID NO: 29); and an L6 that comprises the amino acid sequence A/N/F/S-P/K-W/N/S/V-R/L/W-G-P/L-A/S/D/M/R-N/R/Y/V/F-V/W/P-I/L (SEQ ID NO: 35). In certain embodiment of (or as applied to) any of the embodiments above, the non-naturally occurring chagasin scaffold protein that binds VEGF comprises an L2 comprising an amino acid sequence set forth in any one of SEQ ID NOs: 18-22, an L4 comprising an amino acid sequence set forth in any one of SEQ ID NOs: 24-28; and an L6 comprising an amino acid sequence set forth in any one of SEQ ID NOs: 30-34. In certain embodiments, L2 comprises the amino acid sequence SNLRSM (SEQ ID NO: 18), L4 comprises the amino acid sequence AGPSAVPL (SEQ ID NO: 24) and L6 comprises the amino acid sequence APWRGPANVI (SEQ ID NO: 30). In certain embodiments, L2 comprises the amino acid sequence SNYFYD (SEQ ID NO: 19), L4 comprises the amino acid sequence NDPGSRLS (SEQ ID NO: 25) and L6 comprises the amino acid sequence APWLGPSRVL (SEQ ID NO: 31). In certain embodiments, L2 comprises the amino acid sequence SNLQNA (SEQ ID NO: 20), L4 comprises the amino acid sequence LSLYASET (SEQ ID NO: 26) and L6 comprises the amino acid sequence NPNWGPDYWI (SEQ ID NO: 32). In certain embodiments, L2 comprises the amino acid sequence SNLQDS (SEQ ID NO: 21), L4 comprises the amino acid sequence SGTTGKSN (SEQ ID NO: 27) and L6 comprises the amino acid sequence FKSRGLMVPL (SEQ ID NO: 33). In certain embodiments, L2 comprises the amino acid sequence SNYRDS (SEQ ID NO: 22), L4 comprises the amino acid sequence VRAGQANE (SEQ ID NO: 28) and L6 comprises the amino acid sequence SPVLGPRFWL (SEQ ID NO: 34). In certain embodiments, the non-naturally occurring chagasin scaffold protein comprises the amino acid sequence set forth in SEQ ID NO: 36. In certain embodiments, the non-naturally occurring chagasin scaffold protein comprises the amino acid sequence set forth in SEQ ID NO: 37. In certain embodiments, the non-naturally occurring chagasin scaffold protein comprises the amino acid sequence set forth in SEQ ID NO: 38. In certain embodiments, the non-naturally occurring chagasin scaffold protein comprises the amino acid sequence set forth in SEQ ID NO: 39. In certain embodiments, the non-naturally occurring chagasin scaffold protein comprises the amino acid sequence set forth in SEQ ID NO: 40.

Also provided herein is a non-naturally occurring chagasin scaffold protein that specifically binds to the same epitope as a second non-naturally occurring chagasin scaffold protein that binds human vascular endothelial growth factor (VEGF), wherein the second non-naturally occurring chagasin scaffold protein that binds human VEGF comprises an L2 that comprises the amino acid sequence SNY-F/Y-Y/C/N/R-D/E (SEQ ID NO: 49), an L4 that comprises the amino acid sequence HYYNLGGRYT (SEQ ID NO: 57), D/N/S-D/G/V/Y-P/N/S-G/Y-S/L/M-G/H/S-L/V/A/Y-W/Y/L/S (SEQ ID NO: 58), or G/H-S/V-S/Q-Y/W-W/G-G/W (SEQ ID NO: 68), and an L6 that comprises the amino acid sequence A/G-PW-S/Q/F/A/L/V-GPSR-Y/E/F/V/D-L (SEQ ID NO: 67), with reference to SEQ ID NO: 2. Also encompassed herein is an antibody that specifically binds to the same epitope as a non-naturally occurring chagasin scaffold protein that binds human vascular endothelial growth factor (VEGF), wherein the non-naturally occurring chagasin scaffold protein that binds human VEGF comprises an L2 that comprises the amino acid sequence SNY-F/Y-Y/C/N/R-D/E (SEQ ID NO: 49), an L4 that comprises the amino acid sequence HYYNLGGRYT (SEQ ID NO: 57), D/N/S-D/G/V/Y-P/N/S-G/Y-S/L/M-G/H/S-L/V/A/Y-W/Y/L/S (SEQ ID NO: 58), or G/H-S/V-S/Q-Y/W-W/G-G/W (SEQ ID NO: 68), and an L6 that comprises the amino acid sequence A/G-PW-S/Q/F/A/L/V-GPSR-Y/E/F/V/D-L (SEQ ID NO: 67), with reference to SEQ ID NO: 2.

Also encompassed herein is a non-naturally occurring chagasin scaffold protein that specifically binds human vascular endothelial growth factor (VEGF), wherein the non-naturally occurring chagasin scaffold protein competes for binding with a second non-naturally occurring chagasin scaffold protein that binds human VEGF, wherein the second non-naturally occurring chagasin scaffold protein that binds human VEGF comprises an L2 that comprises the amino acid sequence SNY-F/Y-Y/C/N/R-D/E (SEQ ID NO: 49), an L4 that comprises the amino acid sequence HYYNLGGRYT (SEQ ID NO: 57), D/N/S-D/G/V/Y-P/N/S-G/Y-S/L/M-G/H/S-L/V/A/Y-W/Y/L/S (SEQ ID NO: 58), or G/H-S/V-S/Q-Y/W-W/G-G/W (SEQ ID NO: 68), and an L6 that comprises the amino acid sequence A/G-PW-S/Q/F/A/L/V-GPSR-Y/E/F/V/D-L (SEQ ID NO: 67), with reference to SEQ ID NO: 2. In certain embodiments, the non-naturally occurring chagasin scaffold protein comprises an L2 that comprises the amino acid sequence SNY-F/Y-Y/C/N/R-D/E (SEQ ID NO: 49), an L4 that comprises the amino acid sequence HYYNLGGRYT (SEQ ID NO: 57), D/N/S-D/G/V/Y-P/N/S-G/Y-

S/L/M-G/H/S-L/V/A/Y-W/Y/L/S (SEQ ID NO: 58), or G/H-S/V-S/Q-Y/W-W/G-G/W (SEQ ID NO: 68), and an L6 that comprises the amino acid sequence A/G-PW-S/Q/F/A/L/V-GPSR-Y/E/F/V/D-L (SEQ ID NO: 67), with reference to SEQ ID NO: 2. In certain embodiments, the non-naturally occurring chagasin scaffold protein comprises an L2 that comprises an amino acid sequence set forth in any one of SEQ ID NOs: 19 and 42-48, an L4 that comprises an amino acid sequence set forth in any one of SEQ ID NOs: 50-57; and an L6 that comprises an amino acid sequence set forth in any one of SEQ ID NOs: 59-66. In certain embodiments, L2 comprises the amino acid sequence SNYFYD (SEQ ID NO: 19), L4 comprises the amino acid sequence DDPGS-GLW (SEQ ID NO: 50) and L6 comprises the amino acid sequence APWSGPSRYL (SEQ ID NO: 59). In certain embodiments, L2 comprises the amino acid sequence SNYFYE (SEQ ID NO: 42), L4 comprises the amino acid sequence NGPGLGVY (SEQ ID NO: 51) and L6 comprises the amino acid sequence APWQGPSREL (SEQ ID NO: 60). In certain embodiments, L2 comprises the amino acid sequence SNYYYD (SEQ ID NO: 48), L4 comprises the amino acid sequence NVNGSHAW (SEQ ID NO: 52) and L6 comprises the amino acid sequence APWSGPSRFL (SEQ ID NO: 61). In certain embodiments, L2 comprises the amino acid sequence SNYFCD (SEQ ID NO: 44), L4 comprises the amino acid sequence NYPGSGVL (SEQ ID NO: 53) and L6 comprises the amino acid sequence APWFGPSRVL (SEQ ID NO: 62). In certain embodiments, L2 comprises the amino acid sequence SNYFND (SEQ ID NO: 45), L4 comprises the amino acid sequence GSSYWG (SEQ ID NO: 54) and L6 comprises the amino acid sequence APWAGPSRVL (SEQ ID NO: 63). In certain embodiments, L2 comprises the amino acid sequence SNYFYD (SEQ ID NO: 19), L4 comprises the amino acid sequence SGSYMSYS (SEQ ID NO: 55) and L6 comprises the amino acid sequence APWLGPSRDL (SEQ ID NO: 64). In certain embodiments, L2 comprises the amino acid sequence SNYFRE (SEQ ID NO: 47), L4 comprises the amino acid sequence HVQWGW (SEQ ID NO: 56) and L6 comprises the amino acid sequence APWVGPSREL (SEQ ID NO: 65). In certain embodiments, L2 comprises the amino acid sequence SNYYYD (SEQ ID NO: 48), L4 comprises the amino acid sequence HYYNLGGRYT (SEQ ID NO: 57) and L6 comprises the amino acid sequence GPWLGPSRVL (SEQ ID NO: 66). In certain embodiments, the non-naturally occurring chagasin scaffold protein comprises the amino acid sequence set forth in SEQ ID NO: 69. In certain embodiments, the non-naturally occurring chagasin scaffold protein comprises the amino acid sequence set forth in EQ ID NO: 70. In certain embodiments, the non-naturally occurring chagasin scaffold protein comprises the amino acid sequence set forth in SEQ ID NO: 71. In certain embodiments, the non-naturally occurring chagasin scaffold protein comprises the amino acid sequence set forth in SEQ ID NO: 72. In certain embodiments, the non-naturally occurring chagasin scaffold protein comprises the amino acid sequence set forth in SEQ ID NO: 73. In certain embodiments, the non-naturally occurring chagasin scaffold protein comprises the amino acid sequence set forth in SEQ ID NO: 74. In certain embodiments, the non-naturally occurring chagasin scaffold protein comprises the amino acid sequence set forth in SEQ ID NO: 75. In certain embodiments, the non-naturally occurring chagasin scaffold protein comprises the amino acid sequence set forth in SEQ ID NO: 76.

Also provided herein is a non-naturally occurring chagasin scaffold protein that specifically binds to the same epitope as a second non-naturally occurring chagasin scaffold protein that binds human vascular endothelial growth factor (VEGF), wherein the second non-naturally occurring chagasin scaffold protein that binds human VEGF comprises an L2 that comprises the amino acid sequence SNYY-Y/K-D (SEQ ID NO: 114), an L4 that comprises the amino acid sequence HY-Y/Q/S/T-NLGGRYT (SEQ ID NO: 115); and an L6 that comprises the amino acid sequence GPWL-GPSRVL (SEQ ID NO: 66), with reference to SEQ ID NO: 2. Also provided herein is a non-naturally occurring chagasin scaffold protein that specifically binds human vascular endothelial growth factor (VEGF), wherein the non-naturally occurring chagasin scaffold protein competes for binding with a second non-naturally occurring chagasin scaffold protein that binds human VEGF, wherein the second non-naturally occurring chagasin scaffold protein that binds human VEGF comprises an L2 that comprises the amino acid sequence SNYY-Y/K-D (SEQ ID NO: 114), an L4 that comprises the amino acid sequence HY-Y/Q/S/T-NLG-GRYT (SEQ ID NO: 115); and an L6 that comprises the amino acid sequence GPWLGPSRVL (SEQ ID NO: 66), with reference to SEQ ID NO: 2. In certain embodiments, the non-naturally occurring chagasin scaffold protein comprises an L2 that comprises the amino acid sequence SNYY-Y/K-D (SEQ ID NO: 114), an L4 that comprises the amino acid sequence HY-Y/Q/S/T-NLGGRYT (SEQ ID NO: 115); and an L6 that comprises the amino acid sequence GPWL-GPSRVL (SEQ ID NO: 66), with reference to SEQ ID NO: 2. In certain embodiments, L2 comprises an amino acid sequence set forth in any one of SEQ ID NOs: 48 and 110, L4 comprises an amino acid sequence set forth in any one of SEQ ID NOs: 57 and 111-113; and L6 that comprises an amino acid sequence set forth in SEQ ID NO: 66, with reference to SEQ ID NO: 2.

In certain embodiments, L2 comprises the amino acid sequence SNYYKD (SEQ ID NO: 110), L4 comprises the amino acid sequence HYYNLGGRYT (SEQ ID NO: 57); and L6 comprises the amino acid sequence GPWLGPSRVL (SEQ ID NO: 66), with reference to SEQ ID NO: 2. In certain embodiments, L2 comprises the amino acid sequence SNYYYD (SEQ ID NO: 48), L4 comprises the amino acid sequence HYQNLGGRYT (SEQ ID NO: 111); and L6 comprises the amino acid sequence GPWLGPSRVL (SEQ ID NO: 66), with reference to SEQ ID NO: 2. In certain embodiments, L2 comprises the amino acid sequence SNYYYD (SEQ ID NO: 48), L4 comprises the amino acid sequence HYSNLGGRYT (SEQ ID NO: 112); and L6 comprises the amino acid sequence GPWLGPSRVL (SEQ ID NO: 66), with reference to SEQ ID NO: 2. In certain embodiments, L2 comprises the amino acid sequence SNYYYD (SEQ ID NO: 48), L4 comprises the amino acid sequence HYTNLGGRYT (SEQ ID NO: 113); and L6 comprises the amino acid sequence GPWLGPSRVL (SEQ ID NO: 66), with reference to SEQ ID NO: 2.

In certain embodiments, the non-naturally occurring chagasin scaffold protein comprises the amino acid sequence set forth in SEQ ID NO: 116. In certain embodiments, the non-naturally occurring chagasin scaffold protein comprises the amino acid sequence set forth in SEQ ID NO: 117. In certain embodiments, the non-naturally occurring chagasin scaffold protein comprises the amino acid sequence set forth in SEQ ID NO: 118. In certain embodiments, the non-naturally occurring chagasin scaffold protein comprises the amino acid sequence set forth in SEQ ID NO: 119.

In certain embodiments, the non-naturally occurring chagasin scaffold protein according to any of the embodiments above binds a human VEGF with a Kd between 500 nM and 1 pM. In certain embodiments, the non-naturally occurring chagasin scaffold protein forms a homodimer.

In certain embodiments, the non-naturally occurring chagasin scaffold protein that binds LRP6 according to any one of the embodiments above and/or the non-naturally occurring chagasin scaffold protein that binds VEGF according to any one of the embodiments above is conjugated to a therapeutic agent. In certain embodiments, the non-naturally occurring chagasin scaffold protein that binds LRP6 according to any one of the embodiments above and/or the non-naturally occurring chagasin scaffold protein that binds VEGF according to any one of the embodiments above is conjugated to a label. In certain embodiments, the label is selected from the group consisting of a radioisotope, a fluorescent dye, and an enzyme.

The invention also provides an isolated nucleic acid molecule that encodes the non-naturally occurring chagasin scaffold protein that binds LRP6 according to any one of the embodiments above or the non-naturally occurring chagasin scaffold protein that binds VEGF according to any one of the embodiments above. The invention also provides an expression vector encoding the nucleic acid molecule according to any of the embodiments above. Also provided herein is a cell comprising the expression vector according to any of the embodiments above.

The invention provides a method of producing the non-naturally occurring chagasin scaffold protein that binds LRP6 according to any one of the embodiments above and/or the non-naturally occurring chagasin scaffold protein that binds VEGF according to any one of the embodiments above, comprising culturing the cell according to any of the embodiments above and recovering the non-naturally occurring chagasin scaffold protein that binds LRP6 according to any one of the embodiments above or the non-naturally occurring chagasin scaffold protein that binds VEGF according to any one of the embodiments above from the cell culture. The invention also provides a method of producing the non-naturally occurring chagasin scaffold protein that binds LRP6 according to any one of the embodiments above or the non-naturally occurring chagasin scaffold protein that binds VEGF according to any one of the embodiments above, comprising chemically synthesizing the non-naturally occurring chagasin scaffold protein that binds LRP6 or the non-naturally occurring chagasin scaffold protein that binds VEGF.

The invention provides a method of detecting an LRP6 protein in sample from a patient by contacting the non-naturally occurring chagasin scaffold protein that binds LRP6 according to any of the embodiments above to the sample and detecting the non-naturally occurring chagasin scaffold protein bound to the LRP6 protein. The invention also provides a method of detecting a VEGF protein in sample from a patient by contacting the non-naturally occurring chagasin scaffold protein that binds VEGF according to any of the embodiments above to the sample and detecting the non-naturally occurring chagasin scaffold protein bound to the VEGF protein. In certain embodiments, the non-naturally occurring chagasin scaffold protein is used an immunohistochemistry assay (IHC) or in an ELISA assay.

Provided by the invention is a composition comprising the non-naturally occurring chagasin scaffold protein that binds LRP6 according to any of the embodiments above and a pharmaceutically acceptable carrier. Also provided is a method of treating cancer, metastatic disease, osteoporosis, bone metabolism disease, neuronal disease, neurodegenerative disease, rheumatoid arthritis, or other inflammatory disease in a subject, comprising administering an effective amount of said composition to the subject. Also provided is composition comprising the non-naturally occurring chagasin scaffold protein that binds LRP6 according to any of the embodiments above for use in treating cancer, metastatic disease, osteoporosis, bone metabolism disease, neuronal disease, neurodegenerative disease, rheumatoid arthritis, or other inflammatory disease. Also provided is the use of the non-naturally occurring chagasin scaffold protein that binds LRP6 according to any of the embodiments above in the manufacture of a medicament for treating cancer, metastatic disease, osteoporosis, bone metabolism disease, neuronal disease, neurodegenerative disease, rheumatoid arthritis, or other inflammatory disease.

Also provided by the invention is a composition comprising a non-naturally occurring chagasin scaffold protein that binds VEGF according to any of the embodiments above and a pharmaceutically acceptable carrier. The invention provides a method of inhibiting angiogenesis and/or vascular permeability or leakage in a subject, comprising administering an effective amount of said composition to the subject. Provided is a method of treating a disease characterized by angiogenesis and/or vascular permeability or leakage in a subject, comprising administering an effective amount of said composition to the subject. In certain embodiments, the disease is cancer, ocular disease, or an inflammatory disease. The invention provides a composition comprising the non-naturally occurring chagasin scaffold protein that binds VEGF according to any of the embodiments above for use in treating a disease characterized by angiogenesis and/or vascular permeability or leakage in a subject. The invention also provides use of the non-naturally occurring chagasin scaffold protein that binds VEGF according to any of the embodiments above in the manufacture of a medicament for treating a disease characterized by angiogenesis and/or vascular permeability or leakage in a subject.

BRIEF DESCRIPTION OF THE DRAWINGS

Figure 12:
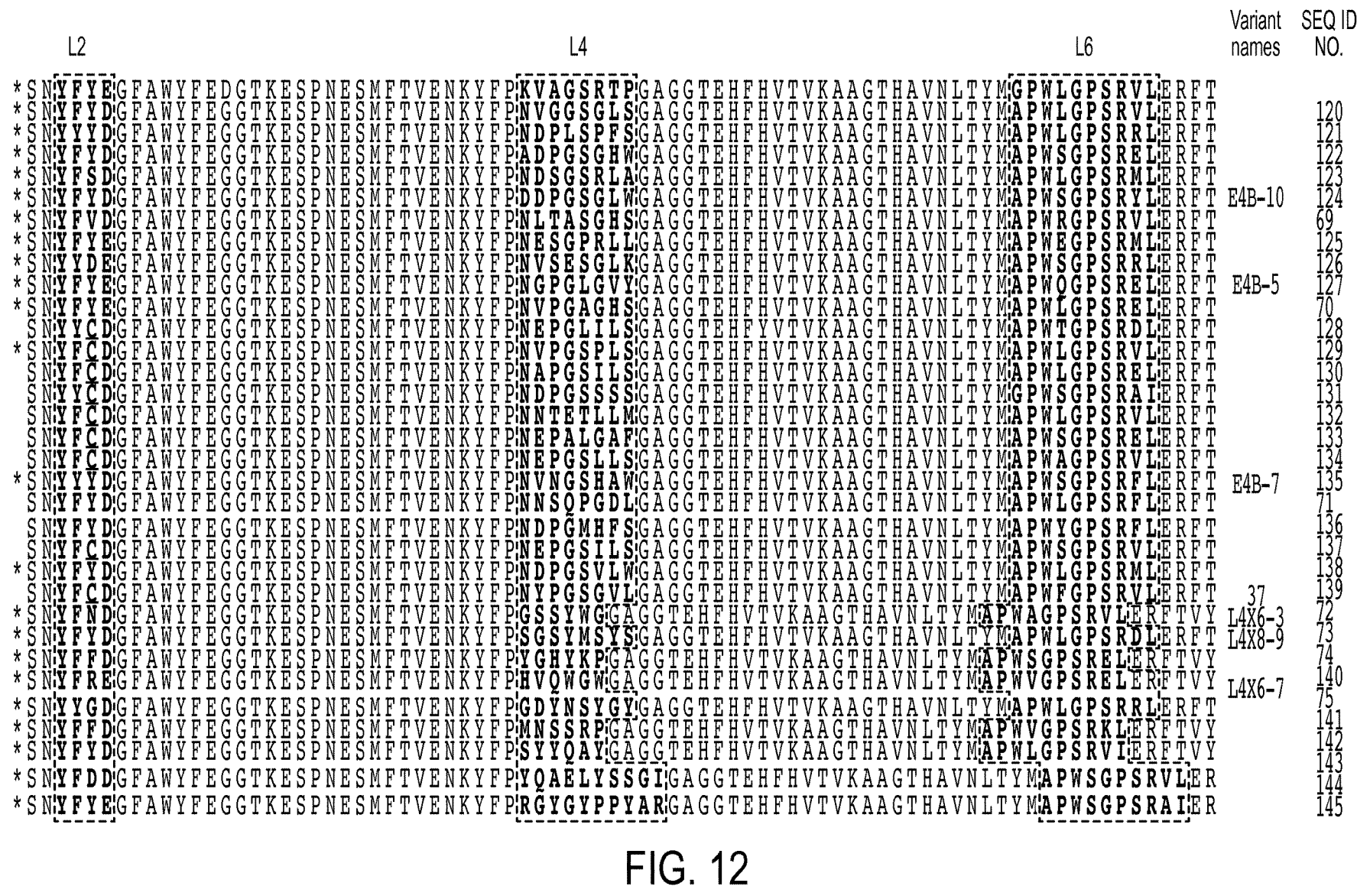

FIG. 12 shows partial sequence of 33 phage clones with high target affinity and specificity to VEGF determined by phage spot ELISA.

DETAILED DESCRIPTION OF THE INVENTION

Figure 1:
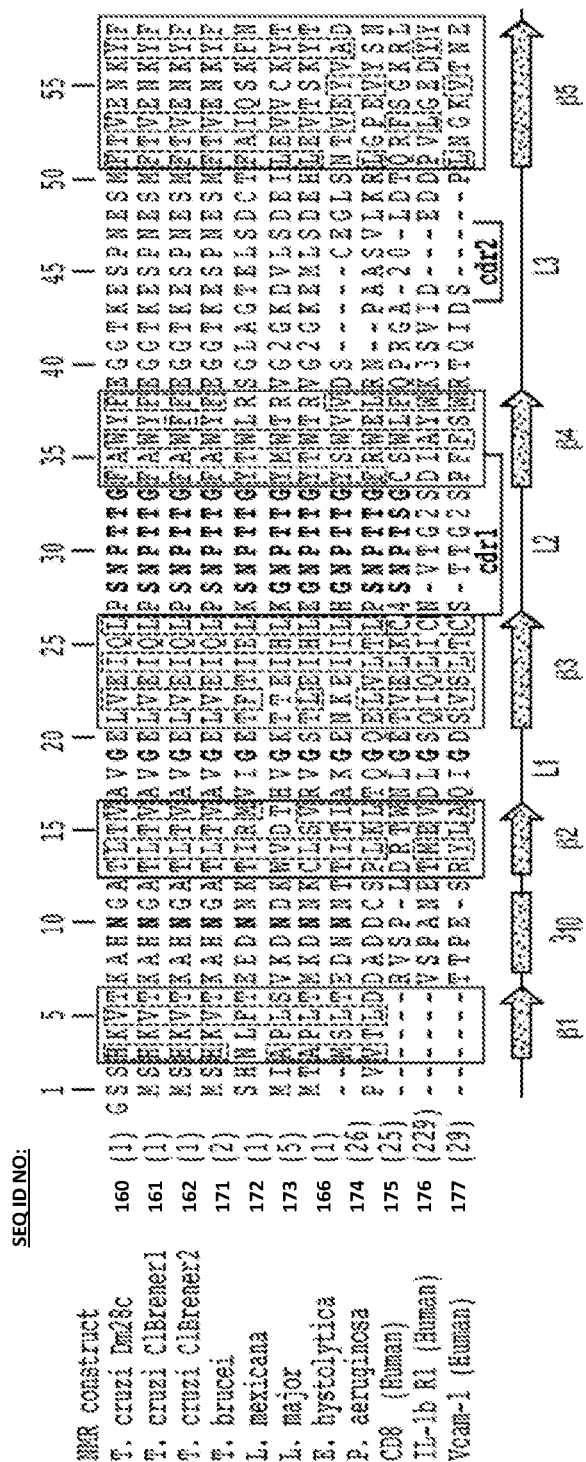
FIG. 1 shows a sequence alignment of chagasin-like protease inhibitors from different organisms.
Figure 1:
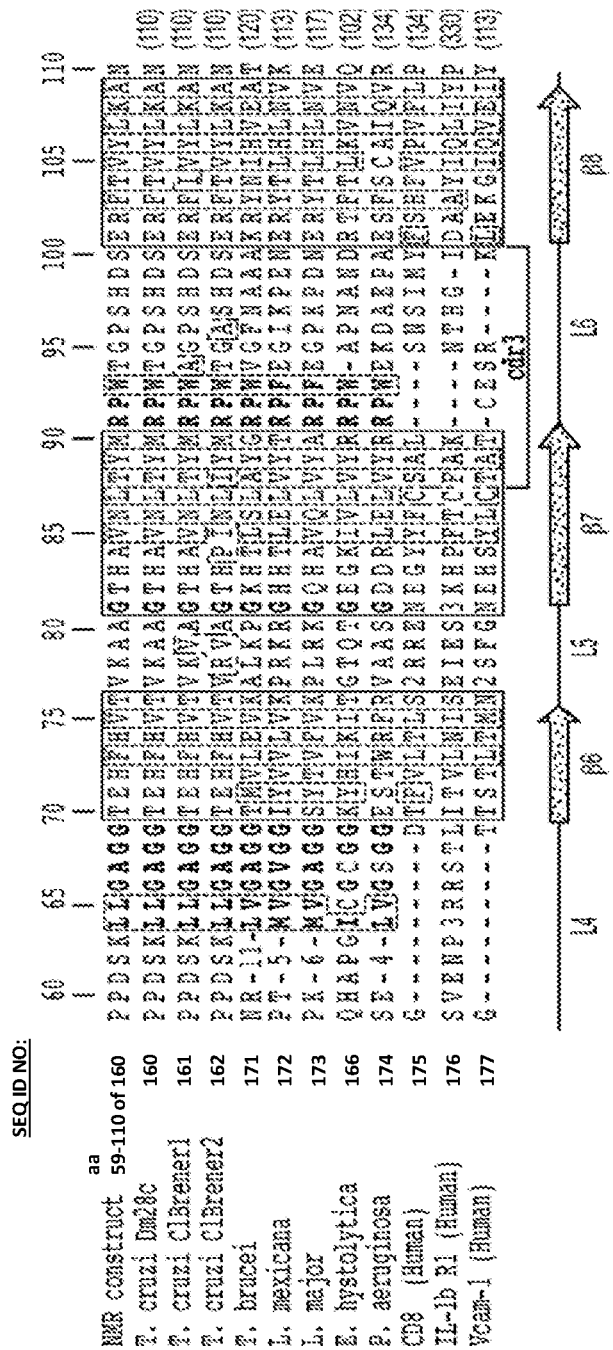

The present invention provides novel, non-naturally occurring chagasin scaffold proteins derived from chagasin or chagasin-like protease inhibitor proteins. The chagasin scaffold proteins provided herein are highly thermostable, which in turn can increase yield of recombinant protein obtained, improve solubility of the purified molecule, improve activity of intracellular scaffolds, decrease immunogenicity, and minimize the need of a cold chain in manufacturing.

The overall fold of a non-naturally occurring chagasin scaffold proteins makes it possible to display three of its loops (L2, L4, and L6) in an analogous fashion to antibody CDRs in relative orientations. Because of this structure, the scaffolds of the invention possess antigen binding properties that are similar in nature and affinity to those of antibodies. Accordingly, a non-naturally occurring chagasin scaffold protein provided herein binds to epitopes (i.e., determinants) on target ligands much like an antibody binds to an epitope of an antigen.

Provided herein are libraries of non-naturally occurring chagasin scaffold proteins and methods of using such libraries to generate non-naturally occurring chagasin scaffold proteins that specifically bind to a target ligand. Also provided are methods of using a non-naturally occurring chagasin protein scaffold that bind to a target ligand, as disclosed herein. The methods can include but are not limited to diagnostic and therapeutic methods. Also encompassed herein are diagnostic and therapeutic compositions.

In a related aspect, the invention provides novel non-naturally occurring chagasin scaffold proteins that specifically bind low density lipoprotein receptor-related protein 6 (LRP6) and novel non-naturally occurring chagasin scaffold proteins that specifically bind vascular endothelial growth factor (VEGF).

Also provided are chimeric molecules and conjugates comprising non-naturally occurring chagasin scaffold proteins described herein, nucleic acids encoding the non-naturally occurring chagasin scaffold proteins described herein, and compositions (such as pharmaceutical compositions). The invention also provides methods of using non-naturally occurring chagasin scaffold proteins described herein to detect LRP6 or VEGF or another target in a sample (such as an in vivo or ex vivo sample), compositions comprising such non-naturally occurring chagasin scaffold proteins described herein for use in treating diseases and disorders resulting from abnormal LRP6 activity or expression or from abnormal VEGF activity or expression, and uses of such non-naturally occurring chagasin scaffold proteins in the manufacture of a medicament for the treatment of cancer.

Practice of the present disclosure employs, unless otherwise indicated, standard methods and conventional techniques in the fields of cell biology, toxicology, molecular biology, biochemistry, cell culture, immunology, oncology, recombinant DNA and related fields as are within the skill of the art. Such techniques are described in the literature and thereby available to those of skill in the art. See, for example, Alberts, B. et al., "Molecular Biology of the Cell," 5$^{th}$ edition, Garland Science, New York, N.Y., 2008; Voet, D. et al. "Fundamentals of Biochemistry: Life at the Molecular Level," 3rd edition, John Wiley & Sons, Hoboken, N.J., 2008; Sambrook, J. et al., "Molecular Cloning: A Laboratory Manual," 3rd edition, Cold Spring Harbor Laboratory Press, 2001; Ausubel, F. et al., "Current Protocols in Molecular Biology," John Wiley & Sons, New York, 1987 and periodic updates; Freshney, R. I., "Culture of Animal Cells: A Manual of Basic Technique," 4th edition, John Wiley & Sons, Somerset, N J, 2000; and the series "Methods in Enzymology," Academic Press, San Diego, Calif.

Definitions

As used herein "non-naturally occurring" means a polypeptide or nucleic acid that is not found in nature. The non-naturally occurring chagasin scaffold protein (or nucleic acid encoding the same) can be produced by genetic engineering methods or by chemical synthesis methods. Thus, a non-naturally occurring chagasin scaffold protein described herein may be recombinant, i.e., produced by a cell, or nucleic acid, or vector, that has been modified by the introduction of a heterologous nucleic acid or the alteration of a native nucleic acid to a form not native to that cell, or that the cell is derived from a cell so modified. Alternatively, a non-naturally occurring chagasin scaffold protein described herein can be produced via chemical peptide synthesis.

As used herein, an "amino acid alteration" refers to the addition, deletion, or substitution of at least one amino acid from a corresponding sequence in a naturally occurring protein sequence (such as a naturally occurring chagasin protein sequence or chagasin-like protease inhibitor protein sequence).

An "isolated" non-naturally occurring chagasin scaffold protein or composition is one which has been identified and separated and/or recovered from a component of its natural environment. Contaminant components of its natural environment are materials which would interfere with diagnostic or therapeutic uses for the non-naturally occurring chagasin scaffold protein, and can include enzymes, hormones, and other proteinaceous or nonproteinaceous solutes. In preferred embodiments, the non-naturally occurring chagasin scaffold protein or composition will be purified (1) to greater than 95% by weight of non-naturally occurring chagasin scaffold protein as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated non-naturally occurring chagasin scaffold protein includes the chagasin scaffold protein in situ within recombinant cells since at least one component of the chagasin scaffold protein's natural environment will not be present. Ordinarily, however, isolated non-naturally occurring chagasin scaffold protein will be prepared by at least one purification step.

"Percent (%) amino acid sequence identity" or "homology" with respect to the polypeptide sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST®, BLAST-2®, ALIGN or Megalign (DNASTAR®) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2™. The ALIGN-2™ sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2™ program is publicly available through Genentech, Inc., South San Francisco, Calif. The ALIGN-2™ program should be compiled for use on a UNIX® operating system, preferably digital UNIX® V4.0D. All sequence comparison parameters are set by the ALIGN-2™ program and do not vary.

An "effective amount" of a non-naturally occurring chagasin scaffold protein or composition as disclosed herein is an amount sufficient to carry out a specifically stated purpose. An "effective amount" can be determined empirically and by known methods relating to the stated purpose.

The term "therapeutically effective amount" refers to an amount of a non-naturally occurring chagasin scaffold protein or composition as disclosed herein, effective to "treat" a disease or disorder in a mammal (aka patient). In the case of cancer, the therapeutically effective amount of a non-naturally occurring chagasin scaffold protein or composition as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent that a non-naturally occurring chagasin scaffold protein or composition as disclosed herein can prevent growth and/or kill existing cancer cells, it can be cytostatic and/or cytotoxic. In one embodiment, the therapeutically effective amount is a growth inhibitory amount. In another embodiment, the therapeutically effective amount is an amount that extends the survival of a patient. In another embodiment, the therapeutically effective amount is an amount that improves progression free survival of a patient.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods of the invention contemplate any one or more of these aspects of treatment.

A "disorder" is any condition that would benefit from treatment with a non-naturally occurring chagasin scaffold protein described herein. For example, mammals who suffer from or need prophylaxis against abnormal LRP6 expression or activity or against abnormal VEGF expression or activity. This includes chronic and acute disorders or diseases including those pathological conditions which predispose the mammal to the disorder in question. Non-limiting examples of LRP6-related disorders to be treated herein include cancer and metastatic disease, osteoporosis and other bone metabolism and disease, neuronal and neurodegenerative disease, rheumatoid arthritis and other inflammatory disease, as described elsewhere herein. Non-limiting examples of VEGF-related disorders to be treated herein include cancer, ocular disease, inflammatory disease, as described elsewhere herein.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The term "detecting" is intended to include determining the presence or absence of a substance or quantifying the amount of a substance (such as a target ligand). The term thus refers to the use of the materials, compositions, and methods of the present invention for qualitative and quantitative determinations. In general, the particular technique used for detection is not critical for practice of the invention.

For example, "detecting" according to the invention may include: observing the presence or absence of a target ligand (including, but not limited to, a human low density lipoprotein receptor-related protein 6 (LRP6) polypeptide or a human vascular endothelial growth factor (VEGF) polypeptide); a change in the levels of a target ligand; and/or a change in biological function/activity of a target ligand. In certain embodiments, "detecting" may include detecting levels of a target ligand (e.g., polypeptide levels of a human LRP6 or human VEGF). Detecting may include quantifying a change (increase or decrease) of any value between 10% and 90%, or of any value between 30% and 60%, or over 100%, when compared to a control. Detecting may include quantifying a change of any value between 2-fold to 10-fold, inclusive, or more e.g., 100-fold.

The word "label" when used herein refers to a detectable compound or composition which is conjugated directly or indirectly to the non-naturally occurring chagasin scaffold protein. The label may itself be detectable by itself (e.g., radioisotope labels or fluorescent labels) or, in the case of an enzymatic label, may catalyze chemical alteration of a substrate compound or composition which is detectable.

With regard to the binding of a non-naturally occurring chagasin scaffold protein to a target ligand, the term "specific binding" or "specifically binds to" or is "specific for" a particular target ligand means that binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. In certain embodiments, the extent of binding of the non-naturally occurring chagasin scaffold protein to a "non-target" ligand will be less than about 10% of the binding of the non-naturally occurring chagasin scaffold protein to its target ligand as determined by, e.g., fluorescence activated cell sorting (FACS) analysis or radioimmunoprecipitation (RIA). In certain embodiments, a non-naturally occurring chagasin scaffold protein of the present disclosure specifically binds to a target ligand (including, but not limited to, a human low density lipoprotein receptor-related protein 6 (LRP6) or a human vascular endothelial growth factor (VEGF)) with a dissociation constant (Kd) equal to or lower than 100 nM, optionally lower than 10 nM, optionally lower than 1 nM, optionally lower than 0.5 nM, optionally lower than 0.1 nM, optionally lower than 0.01 nM, or optionally lower than 0.005 nM; measured at a temperature of about 4° C., 25° C., 37° C., or 45° C.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

It is understood that aspects and embodiments of the invention described herein include "comprising," "consisting," and "consisting essentially of" aspects and embodiments.

All references cited herein, including patent applications and publications, are hereby incorporated by reference in their entirety.

Non-Naturally Occurring Chagasin Scaffold Proteins

Chagasin is a natural inhibitor of Clan CA, Family C1 cysteine peptidases (CP), which was identified in the protozoan *Trypanosoma cruzi*, the causative agent of human Chagas disease (Monteiro et al. (2001) *J. Cell Sci.* 114:3933-3942; Marin-Neto et al. (2007) *Circulation*. 115:1101-1108). It is a single 110-residue polypeptide chain with no sequence similarity to other known groups of CP inhibitors and potently inactivates papain-like enzymes through the formation of 1:1 tight-binding complexes. Chagasin-like inhibitors which occur in other protozoa and bacteria have been designated as ICP (Inhibitor of Cysteine Peptidases), and together comprise the chagasin family (Family 142 of Clan JL) (Rigden et al. (2002) *Protein Sci.* 11, 1971-1977; Sanderson et al. (2003) *FEBS Lett* 542:12-16; MEROPS database (world wide web at-merops.sanger.ac.uk/).

Chagasin homologs are typically 110-130 amino acids long and do not contain any additional domains. The conserved core structure includes seven predicted β-strands (FIG. 1) with one or two more potential β-strands on the flanks. Previous fold recognition and modeling experiments convincingly favored an Ig-type domain over other β-sandwich structures. Furthermore, comparison of the chagasin sequence with an antibody light-chain variable domain consensus sequence revealed conservation of key residues, including an invariant tryptophan and several neighbors, suggestive of a distant evolutionary relationship.

The solution structures of chagasin and of *Leishmania mexicana* ICP determined by NMR showed that the molecule has an Ig-like fold and three exposed loop regions (i.e., Loop 2 (L2), Loop 4 (L4), and Loop 6 (L6)), which bear evolutionarily conserved residues, located at one end of the molecule (Salmon D et al. (2006) *J. Mol. Biol.* 357:1511-1521; Smith et al. (2006) *J. Biol. Chem.* 281:5821-5828. These three key loops, L2 (residues 28-34), L4 (residues 59-69) and L6 (residues 91-100) contain, respectively: (i)

the NPTTG motif; (ii) a conserved region bearing two hydrophobic residues followed by GXGG; and (iii) the RPW/F motif (Salmon D et al. (2006) *J. Mol. Biol.* 357: 1511-1521). Studies of chemical shift perturbations upon chagasin contact with cruzipain identified residues in L2, L4 and L6 as candidates to comprise chagasin's binding-site to target enzymes (Salmon D et al. (2006) *J. Mol. Biol.* 357:1511-1521). This hypothesis was reinforced by docking of a high resolution crystal structure of chagasin to the high-resolution structure of cruzain (truncated recombinant cruzipain) (Figueiredo da Silva et al. (2006) *J. Struct. Biol.* 157:416-423).

A sequence alignment of chagasin-like protease inhibitors from different pathogenic bacteria and protozoa is shown in FIG. 1. Residue numbers refer to *T. cruzi* chagasin. β-Strands and $3_{10}$-helix are displayed by arrows and cylinders, respectively, as found in the *T. cruzi* chagasin NMR structure, and the sequences relative to the β-strands are boxed. The positions of the most conserved residues in loops are highlighted in bold and conserved hydrophobic (aromatic and aliphatic) residues are colored yellow. *T. cruzi* non-conserved residues are highlighted in blue. Complementarity-determining regions (CDR 1-3) in CD8 are indicated. Swiss-Prot accession codes are as follows: chagasin-like ICPs from *T. cruzi* (Dm28c clone), Q966X9; CL Brenner strain, isoform 1, Q4DH32; CL Brenner strain, isoform 2, Q4DY71); *T. brucei* (Q868H0), *L. mexicana* (Q868H1), *L. major* (Q868G9), *E. hystolytica* (Q6KCA4), *P. aeruginosa* (Q9I5G0) and human structural homologue proteins CD8 T-cell surface glycoprotein (P01732), IL-1 R1, interleukine-1 type1 receptor (P14778); Vcam-1, vascular cell adhesion molecule-1 (P19320). Adapted from D Salmon et al., J Mol Biol, 357, 1511-1521, 2006).

Such sequence alignment reveals a high degree of conservation for residues that constitute Loop 2, whereas Loop 4 and Loop 6, which bind more on the edges of the protease active site cleft are only partially conserved (A Ljunggren et al., *J Mol Biol* 371, 137-153, 2007; S X Wang et al., *Structure* 15, 535-543, 2007; I Redzynia et al., *J Biol Chem* 283, 22815-22825, 2008; I Redzynia et al., *FEBS J* 276, 793-806, 2009). Loop 4 can vary in length from 10 to 21 residues between different organisms and has been found to be quite flexible based on NMR analysis (D Salmon et al., *J Mol Biol* 357, 1511-1521, 2006; BO Smith et al., *J Biol Chem* 281, 5821-5828, 2006).

In one aspect, the invention provides a non-naturally occurring chagasin scaffold protein comprising at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin or wild-type chagasin-like cysteine protease inhibitor. The term "scaffold" refers to the minimal polypeptide "framework" or "sequence motif" that is used as the conserved, common sequence in the construction of protein libraries. In between the fixed or conserved residues/positions of the scaffold lie variable and hypervariable positions, e.g., L2, L4, and/or L6. A large diversity of amino acids is provided in the variable regions between the fixed scaffold residues to provide specific binding to a target ligand. A scaffold is typically defined by the conserved residues that are observed in an alignment of a family of sequence-related proteins. Fixed residues may be required for folding or structure, especially if the functions of the aligned proteins are different.

In certain embodiments, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 2 (L2), Loop 4 (L4), and/or Loop 6 (L6), with reference to a wild-type chagasin from *T. cruzi* (Dm28c clone). Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin from *T. cruzi* (Dm28c clone). In certain embodiments, amino acid alterations are introduced into L1, L3, and/or L5, e.g., to create a bispecific molecule or to add a linker. In certain embodiments L1, L3, and/or L5 are engineered to bind to a different epitope on same target ligand bound by L2, L4, and/or L6. In certain embodiments, L1, L3, and/or L5 are engineered to bind a different target ligand than the target ligand bound by L2, L4, and/or L6.

In certain embodiments, the non-naturally occurring chagasin scaffold protein comprises at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin from *T. cruzi* (CL Brenner strain, isoform 1). Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin from *T. cruzi* (CL Brenner strain, isoform 1). In certain embodiments, amino acid alterations are introduced into L1, L3, and/or L5, e.g., to create a bispecific molecule or to add a linker. In certain embodiments L1, L3, and/or L5 are engineered to bind to a different epitope on same target ligand bound by L2, L4, and/or L6. In certain embodiments, L1, L3, and/or L5 are engineered to bind a different target ligand than the target ligand bound by L2, L4, and/or L6.

In certain embodiments, the non-naturally occurring chagasin scaffold protein comprises at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin from *T. cruzi* (CL Brenner strain, isoform 2). Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin from *T. cruzi* (CL Brenner strain, isoform 2). In certain embodiments, amino acid alterations are introduced into L1, L3, and/or L5, e.g., to create a bispecific molecule or to add a linker. In certain embodiments L1, L3, and/or L5 are engineered to bind to a different epitope on same target ligand bound by L2, L4, and/or L6. In certain embodiments, L1, L3, and/or L5 are engineered to bind a different target ligand than the target ligand bound by L2, L4, and/or L6.

In certain embodiments, the non-naturally occurring chagasin scaffold protein comprises at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin-like inhibitor from *T. brucei*. Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin-like inhibitor from *T. brucei*. In certain embodiments, amino acid alterations are introduced into L1, L3, and/or L5, e.g., to create a bispecific molecule or to add a linker. In certain embodiments L1, L3, and/or L5 are engineered to bind to a different epitope on same target ligand bound by L2, L4, and/or L6. In certain embodiments, L1, L3, and/or L5 are engineered to bind a different target ligand than the target ligand bound by L2, L4, and/or L6.

In certain embodiments, the non-naturally occurring chagasin scaffold protein comprises at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin-like inhibitor from *L. mexicana*. Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin-like inhibitor from *L. mexicana*. In certain embodiments, amino acid alterations are introduced into L1, L3, and/or L5, e.g., to create a bispecific molecule or to add a linker. In certain embodiments L1, L3, and/or L5 are engineered to bind to a different epitope on same target ligand bound by L2, L4, and/or L6. In certain embodiments, L1, L3, and/or L5 are engineered to bind a different target ligand than the target ligand bound by L2, L4, and/or L6.

In certain embodiments, the non-naturally occurring chagasin scaffold protein comprises at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin-like inhibitor from *L. major*. Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin-like inhibitor from *L. major*. In certain embodiments, amino acid alterations are introduced into L1, L3, and/or L5, e.g., to create a bispecific molecule or to add a linker. In certain embodiments L1, L3, and/or L5 are engineered to bind to a different epitope on same target bound by L2, L4, and/or L6. In certain embodiments, L1, L3, and/or L5 are engineered to bind a different target than the target bound by L2, L4, and/or L6.

In certain embodiments, the non-naturally occurring chagasin scaffold protein comprises at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin-like inhibitor from *E. hystolytica*. Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin-like inhibitor from *E. hystolytica*. In certain embodiments, amino acid alterations are introduced into L1, L3, and/or L5, e.g., to create a bispecific molecule or to add a linker. In certain embodiments L1, L3, and/or L5 are engineered to bind to a different epitope on same target bound by L2, L4, and/or L6. In certain embodiments, L1, L3, and/or L5 are engineered to bind a different target than the target bound by L2, L4, and/or L6.

In certain embodiments, the non-naturally occurring chagasin scaffold protein comprises at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin-like inhibitor from *P. aeruginosa*. Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin-like inhibitor from *P. aeruginosa*. In certain embodiments, amino acid alterations are introduced into L1, L3, and/or L5, e.g., to create a bispecific molecule or to add a linker. In certain embodiments L1, L3, and/or L5 are engineered to bind to a different epitope on same target bound by L2, L4, and/or L6. In certain embodiments, L1, L3, and/or L5 are engineered to bind a different target than the target bound by L2, L4, and/or L6.

In certain embodiments, the non-naturally occurring chagasin scaffold protein comprises at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type human CD8 T-cell surface glycoprotein. Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type human CD8 T-cell surface glycoprotein. In certain embodiments, amino acid alterations are introduced into L1, L3, and/or L5, e.g., to create a bispecific molecule or to add a linker. In certain embodiments L1, L3, and/or L5 are engineered to bind to a different epitope on same target bound by L2, L4, and/or L6. In certain embodiments, L1, L3, and/or L5 are engineered to bind a different target than the target bound by L2, L4, and/or L6.

In certain embodiments, the non-naturally occurring chagasin scaffold protein comprises at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin-like inhibitor from human interleukine-1 type 1 receptor (IL-1 R1). Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin-like inhibitor from human interleukine-1 type 1 receptor (IL-1 R1). In certain embodiments, amino acid alterations are introduced into L1, L3, and/or L5, e.g., to create a bispecific molecule or to add a linker. In certain embodiments L1, L3, and/or L5 are engineered to bind to a different epitope on same target bound by L2, L4, and/or L6. In certain embodiments, L1, L3, and/or L5 are engineered to bind a different target than the target bound by L2, L4, and/or L6.

In certain embodiments, the non-naturally occurring chagasin scaffold protein comprises at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin-like inhibitor from human vascular cell adhesion molecule-1 (Vcam-1). Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin-like inhibitor from human vascular cell adhesion molecule-1 (Vcam-1). In certain embodiments, amino acid alterations are introduced into L1, L3, and/or L5, e.g., to create a bispecific molecule or to add a linker. In certain embodiments L1, L3, and/or L5 are engineered to bind to a different epitope on same target bound by L2, L4, and/or L6. In certain embodiments, L1, L3, and/or L5 are engineered to bind a different target than the target bound by L2, L4, and/or L6.

In certain embodiments, amino acid alterations (such as additions, deletions or substitutions) are introduced into one or more of the beta strands of a non-naturally occurring chagasin scaffold protein to, e.g., improve binding to a target ligand, to bind a different epitope on the same target ligand, or to bind a different target ligand than the target ligand bound by L2, L4, and/or L6. (See, e.g., Diem et al. (2014) *Prot Engineer Des & Sel* 27, 419-429.)

In certain embodiments, the non-naturally occurring chagasin scaffold protein comprises at least at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin from *T. cruzi* (CL Brenner strain, isoform 1) having the amino acid sequence set forth in SEQ ID NO: 1:

```
                                           (SEQ ID NO: 1)
MSHKVTKAHN GATLTVAVGE LVEIQLPSNP TTGFAWYFEG

GTKESPNESM FTVENKYFPP DSKLLGAGGT EHFHVTVKAA

GTHAVNLTYM RPWTGPSHDS ERFTVYLKAN
```

Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a with reference to a wild-type chagasin from *T. cruzi* (CL Brenner strain, isoform 1) having the amino acid sequence set forth in SEQ ID NO: 1. In certain embodiments, amino acid alterations are introduced into L1, L3, and/or L5, e.g., to create a bispecific molecule or to add a linker. In certain embodiments L1, L3, and/or L5 are engineered to bind to a different epitope on same target bound by L2, L4, and/or L6. In certain embodiments, L1, L3, and/or L5 are engineered to bind a different target than the target bound by L2, L4, and/or L6.

In certain embodiments, L1 of SEQ ID NO: 1 corresponds to amino acids 17-20 of SEQ ID NO: 1. In certain embodiments, L2 of SEQ ID NO: 1 corresponds to amino acids 28-34 of SEQ ID NO: 1. In certain embodiments, L3 of SEQ ID NO: 1 corresponds to amino acids 39-50 of SEQ ID NO: 1. In certain embodiments, L4 of SEQ ID NO: 1 corresponds to amino acids 59-69 of SEQ ID NO: 1. In certain embodiments, L5 of SEQ ID NO: 1 corresponds to amino acids 77-80 of SEQ ID NO: 1. In certain embodiments, L6 of SEQ ID NO: 1 corresponds to amino acids 91-100 of SEQ ID NO: 1.

In certain embodiments, amino acid alterations (such as additions, deletions or substitutions) are introduced into one or more of the beta strands 1-8 of SEQ ID NO: 1 in order to, e.g., improve binding to a target ligand, to bind a different epitope on the same target ligand, or to bind a different target ligand than the target ligand bound by L2, L4, and/or L6. (See, e.g., Diem et al. (2014) *Prot Engineer Des & Sel* 27, 419-429.) In certain embodiments, beta strand 1 of SEQ ID NO: 1 corresponds to amino acids 3-6 of SEQ ID NO: 1. In certain embodiments, beta strand 2 of SEQ ID NO: 1 corresponds to amino acids 13-16 of SEQ ID NO: 1. In certain embodiments, beta strand 3 of SEQ ID NO: 1 corresponds to amino acids 21-26 of SEQ ID NO: 1. In certain embodiments, beta strand 4 of SEQ ID NO: 1 corresponds to amino acids 34-38 of SEQ ID NO: 1. In certain embodiments, beta strand 5 of SEQ ID NO: 1 corresponds to amino acids 51-58 of SEQ ID NO: 1. In certain embodiments, beta strand 6 of SEQ ID NO: 1 corresponds to amino acids 70-76 of SEQ ID NO: 1. In certain embodiments, beta strand 7 of SEQ ID NO: 1 corresponds to amino acids 81-90 of SEQ ID NO: 1. In certain embodiments, beta strand 8 of SEQ ID NO: 1 corresponds to amino acids 101-109 of SEQ ID NO: 1.

In certain embodiments, Loop 2 (L2) of SEQ ID NO: 1 is at least 7, at least 8, at least 9, at least 10, at least 11, at least 12, at least 13 or at least 14 amino acids in length. In certain embodiments, L2 of SEQ ID NO: 1 comprises the amino acid sequence $X_{5-8}$-GF (SEQ ID NO: 151), wherein X represents any amino acid. In certain embodiments, L2 of SEQ ID NO: 1 comprises the amino acid sequence SNX$_{3-6}$-GF (SEQ ID NO: 152), wherein X represents any amino acid. In certain embodiments, Loop 4 (L4) of SEQ ID NO: 1 is at least 11, at least 12, at least 13, at least 14, at least 15, at least 16, at least 17, at least 18, or at least 19 amino acids in length. In certain embodiments, L4 of SEQ ID NO: 1 comprises the amino acid sequence X$_{7-15}$-GAGG (SEQ ID NO: 153), wherein X represents any amino acid. In certain embodiments, Loop 6 (L6) of SEQ ID NO: 1 is at least 8, at least 9, or at least 10 amino acids in length. In certain embodiments, Loop 6 (L6) of SEQ ID NO: 1 comprises the amino acid sequence X$_{3-12}$ (SEQ ID NO: 154), wherein X represents any amino acid. In certain embodiments, Loop 6 (L6) of SEQ ID NO: 1 comprises the amino acid sequence X$_{10}$ (SEQ ID NO: 106), wherein X represents any amino acid.

In certain embodiments, the non-naturally occurring chagasin scaffold protein comprises an amino acid sequence set forth in SEQ ID NO: 2:

```
                                            (SEQ ID NO: 2)
MSHKVTKAHN GATLTVAVGE LVEIQLP-X5-8-GF AWYFEGGTKE

SPNESMFTVE NKYFP-X7-15-GAGG TEHFHVTVKA AGTHAVNLTY

MX10ERFTVYLK AN
```

In certain embodiments, the non-naturally occurring chagasin scaffold protein specifically binds to a target ligand. In certain embodiments, the target ligand is a protein, a nucleic acid, a polysaccharide, a lipopolysaccharide, a lipid, a phospholipid. In certain embodiments, the non-naturally occurring chagasin scaffold protein binds to a cell surface protein, a soluble protein, a mammalian protein, a viral protein, a bacterial protein, a protein associated with ocular disease, a protein associated with cancer, a protein associated with inflammation, a protein associated with bone disease, a protein associated with neurodegenerative disease, or a therapeutic protein. In certain embodiments, the non-naturally occurring chagasin scaffold protein specifically binds low-density lipoprotein receptor-related protein 6 (LRP6), such as a human LRP6. In certain embodiments, the non-naturally occurring chagasin scaffold protein specifically binds vascular endothelial growth factor (VEGF), such as a human VEGF. In certain embodiments, the VEGF is a VEGF-A.

As described elsewhere herein, a non-naturally occurring chagasin scaffold protein can be generated via genetic engineering. Accordingly, provided by the invention is a non-naturally occurring chagasin scaffold protein obtained by genetically engineering any one of the wild-type chagasins or wild-type chagasin-like cysteine protease inhibitors described herein. Alternatively, a non-naturally occurring chagasin scaffold protein can be generated via chemical peptide synthesis, as described elsewhere herein. Thus, in certain embodiments, the invention provides a non-naturally occurring chagasin scaffold protein obtained via synthesis, e.g., solid phase peptide syntheses, liquid phase peptide synthesis, etc.

In certain embodiments, the invention provides a nucleic acid molecule encoding a non-naturally occurring chagasin scaffold protein. Such a nucleic acid molecule can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include, but are not limited to, those encoding a chagasin scaffold protein or a fragment thereof. In some embodiments, the isolated nucleic acids comprise additional, non-coding sequences, including but not limited to, noncoding 5' and 3' sequences, such as the transcribed, non-translated sequences that play a role in transcription, mRNA processing, including splicing and polyadenylation signals (for example, ribosome binding and stability of mRNA). In some embodiments, the isolated nucleic acids comprise an additional coding sequence that codes for additional amino acids, such as those that provide additional functionalities. Thus, the sequence encoding a protein scaffold can be fused to a marker sequence, such as a sequence encoding a peptide that facilitates purification of the fused chagasin scaffold protein, a sequence encoding a peptide that facilitates entry into the cell (i.e., a cell-permeability peptide), a peptide that facilitates the secretion of a non-naturally occurring chagasin scaffold protein from a cell and/or a peptide that facilitates the localization of a non-naturally occurring chagasin scaffold protein to, e.g., the endoplasmic reticulum, the golgi apparatus, to endosomes, etc.

In certain embodiments, a nucleic acid encoding a non-naturally occurring chagasin scaffold protein provided herein is transiently transfected in a cell under conditions that allow expression of the non-naturally occurring chagasin scaffold protein and binding of the non-naturally occurring chagasin scaffold protein to a target ligand in the cell.

In certain embodiments, provided is an expression vector comprising an isolated nucleic acid described herein. In certain embodiments, provided is a host cell comprising an expression vector comprising an isolated nucleic acid described herein. In certain embodiments, a host cell is cultured under conditions that allow the expression of the non-naturally occurring chagasin scaffold protein. In certain embodiments, the non-naturally occurring chagasin scaffold protein is expressed in order to identify the intracellular target ligand to which the non-naturally occurring chagasin scaffold protein binds.

The non-naturally occurring chagasin scaffold proteins provided herein can be used as monospecific in monomeric form or as bi- or multi-specific (for different target ligands or different epitopes on the same target ligand) in multimer form. The attachments may be covalent or non-covalent. In certain embodiments, a dimeric bispecific non-naturally occurring chagasin scaffold protein has one subunit with specificity for a first target ligand or epitope and a second subunit with specificity for a second target ligand or epitope. Non-naturally occurring chagasin scaffold protein subunits can be joined in a variety of conformations that can increase the valency and thus the avidity of binding to a target ligand.

Non-Naturally Occurring Chagasin Scaffold Protein Libraries

Provided herein are polypeptide display libraries comprising a plurality of non-naturally occurring chagasin scaffold proteins described herein. Such polypeptide display libraries can be screened to select and/or evolve binding proteins with desired properties for a wide variety of utilities, including but not limited to therapeutic, prophylactic, veterinary, diagnostic, reagent or material applications.

In certain embodiments, the non-naturally occurring chagasin scaffold proteins in the polypeptide display library have at least 30%, at least 35%, at least 40%, at least 45%, at least 50%, at least 55%, at least 60%, at least 65%, at least 70%, at least 75%, at least 80%, at least 85%, at least 90%, at least 95% or at least 99% amino acid homology to the sequence of a naturally occurring chagasin or chagasin-like protease inhibitor described herein.

In certain embodiments, the polypeptide display library comprises non-naturally occurring chagasin scaffold proteins that comprise randomized L2, L4, and/or L6 loop region sequences that vary by deletion, substitution or addition by at least one amino acid from the corresponding loop sequences in a naturally occurring chagasin or chagasin-like protease inhibitor.

In certain embodiments, the polypeptide display library comprises non-naturally occurring chagasin scaffold proteins that each comprise at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin or wild-type chagasin-like cysteine protease inhibitor. Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin or wild-type chagasin-like cysteine protease inhibitor.

In certain embodiments, the polypeptide display library comprises non-naturally occurring chagasin scaffold proteins that each comprise at least one, at least two, at least three, at least four, at least five, at least six, at least seven, at least eight, at least nine, at least ten, or more than ten (e.g., at least 11, at least 12, at least 13, at least 14, or at least 15) in Loop 2 (L2), Loop 4 (L4), and/or Loop 6 (L6), with reference to a wild-type chagasin from *T. cruzi* (Dm28c clone). Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin from *T. cruzi* (Dm28c clone).

In certain embodiments, the polypeptide display library comprises non-naturally occurring chagasin scaffold proteins that each comprise at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin from *T. cruzi* (CL Brenner strain, isoform 1). Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin from *T. cruzi* (CL Brenner strain, isoform 1).

In certain embodiments, the polypeptide display library comprises non-naturally occurring chagasin scaffold proteins that each comprise at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin from *T. cruzi* (CL Brenner strain, isoform 2). Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin from *T. cruzi* (CL Brenner strain, isoform 2).

In certain embodiments, the polypeptide display library comprises non-naturally occurring chagasin scaffold proteins that each comprise at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin-like inhibitor from *T. brucei*. Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin-like inhibitor from *T. brucei*.

In certain embodiments, the polypeptide display library comprises non-naturally occurring chagasin scaffold proteins that each comprise at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin-like inhibitor from *L. mexicana*. Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin-like inhibitor from *L. mexicana*.

In certain embodiments, the polypeptide display library comprises non-naturally occurring chagasin scaffold proteins that each comprise at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin-like inhibitor from *L. major*. Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin-like inhibitor from *L. major*.

In certain embodiments, the polypeptide display library comprises non-naturally occurring chagasin scaffold proteins that each comprise at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin-like inhibitor from *E. hystolytica*. Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin-like inhibitor from *E. hystolytica.*

In certain embodiments, the polypeptide display library comprises non-naturally occurring chagasin scaffold proteins that each comprise at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin-like inhibitor from *P. aeruginosa*. Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin-like inhibitor from *P. aeruginosa.*

In certain embodiments, the polypeptide display library comprises non-naturally occurring chagasin scaffold proteins that each comprise at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type human CD8 T-cell surface glycoprotein. Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type human CD8 T-cell surface glycoprotein.

In certain embodiments, the polypeptide display library comprises non-naturally occurring chagasin scaffold proteins that each comprise at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin-like inhibitor from human interleukine-1 type 1 receptor (IL-1 R1). Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin-like inhibitor from human interleukine-1 type 1 receptor (IL-1 R1).

In certain embodiments, the polypeptide display library comprises non-naturally occurring chagasin scaffold proteins that each comprise at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin-like inhibitor from human vascular cell adhesion molecule-1 (Vcam-1). Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a wild-type chagasin-like inhibitor from human vascular cell adhesion molecule-1 (Vcam-1).

In certain embodiments, amino acid alterations (such as additions, deletions or substitutions) are introduced into one or more of the beta strands of a non-naturally occurring chagasin scaffold protein to, e.g., improve binding to a target ligand, to bind a different epitope on the same target ligand, or to bind a different target ligand than the target ligand bound by L2, L4, and/or L6. (See, e.g., Diem et al. (2014) *Prot Engineer Des & Sel* 27, 419-429.)

In certain embodiments, the polypeptide display library comprises non-naturally occurring chagasin scaffold proteins that each comprise at least at least one, at least two, at least three, at least four, at least five, at least six, at least seven, at least eight, at least nine, at least ten, or more than 10 (e.g., at least 11, at least 12, at least 13, at least 14, or at least 15) amino acid alterations in Loop 2 (L2), Loop 4 (L4), and/or Loop 6 (L6), with reference to a wild-type chagasin from *T. cruzi* (CL Brenner strain, isoform 1) having the amino acid sequence set forth in SEQ ID NO: 1:

```
                                          (SEQ ID NO: 1)
MSHKVTKAHN GATLTVAVGE LVEIQLPSNP TTGFAWYFEG

GTKESPNESM FTVENKYFPP DSKLLGAGGT EHFHVTVKAA

GTHAVNLTYM RPWTGPSHDS ERFTVYLKAN
```

Alternatively or additionally, the non-naturally occurring chagasin scaffold protein comprises at least one, at least two, at least three, at least four, at least five, at least six, at least seven, at least eight, at least nine, at least ten, or more than ten (e.g., at least 11, at least 12, at least 13, at least 14, or at least 15) amino acid alterations in Loop 1 (L1), Loop3 (L3), and/or Loop 5 (L5), with reference to a with reference to a wild-type chagasin from *T. cruzi* (CL Brenner strain, isoform 1) having the amino acid sequence set forth in SEQ ID NO: 1. In certain embodiments, amino acid alterations are introduced into L1, L3, and/or L5, e.g., to create a bispecific molecule or to add a linker. In certain embodiments L1, L3, and/or L5 are engineered to bind to a different epitope on same target bound by L2, L4, and/or L6. In certain embodiments, L1, L3, and/or L5 are engineered to bind a different target than the target bound by L2, L4, and/or L6.

In certain embodiments, L1 of SEQ ID NO: 1 corresponds to amino acids 17-20 of SEQ ID NO: 1. In certain embodiments, L2 of SEQ ID NO: 1 corresponds to amino acids 28-34 of SEQ ID NO: 1. In certain embodiments, L3 of SEQ ID NO: 1 corresponds to amino acids 39-50 of SEQ ID NO: 1. In certain embodiments, L4 of SEQ ID NO: 1 corresponds to amino acids 59-69 of SEQ ID NO: 1. In certain embodiments, L5 of SEQ ID NO: 1 corresponds to amino acids 77-80 of SEQ ID NO: 1. In certain embodiments, L6 of SEQ ID NO: 1 corresponds to amino acids 91-100 of SEQ ID NO: 1.

In certain embodiments, amino acid alterations (such as additions, deletions or substitutions) are introduced into one or more of the beta strands 1-8 of SEQ ID NO: 1 in order to, e.g., improve binding to a target ligand, to bind a different epitope on the same target ligand, or to bind a different target ligand than the target ligand bound by L2, L4, and/or L6. (See, e.g., Diem et al. (2014) *Prot Engineer Des & Sel* 27, 419-429.) In certain embodiments, beta strand 1 of SEQ ID NO: 1 corresponds to amino acids 3-6 of SEQ ID NO: 1. In certain embodiments, beta strand 2 of SEQ ID NO: 1 corresponds to amino acids 13-16 of SEQ ID NO: 1. In certain embodiments, beta strand 3 of SEQ ID NO: 1 corresponds to amino acids 21-26 of SEQ ID NO: 1. In certain embodiments, beta strand 4 of SEQ ID NO: 1 corresponds to amino acids 34-38 of SEQ ID NO: 1. In certain embodiments, beta strand 5 of SEQ ID NO: 1 corresponds to amino acids 51-58 of SEQ ID NO: 1. In certain embodiments, beta strand 6 of SEQ ID NO: 1 corresponds to amino acids 70-76 of SEQ ID NO: 1. In certain embodiments, beta strand 7 of SEQ ID NO: 1 corresponds to amino acids 81-90 of SEQ ID NO: 1. In certain embodiments, beta strand 8 of SEQ ID NO: 1 corresponds to amino acids 101-109 of SEQ ID NO: 1.

In certain embodiments, Loop 2 (L2) of SEQ ID NO: 1 is at least 7, at least 8, at least 9, at least 10, at least 11, at least 12, at least 13 or at least 14 amino acids in length. In certain embodiments, L2 of SEQ ID NO: 1 comprises the amino acid sequence $X_{5-8}$-GF (SEQ ID NO: 151), wherein X represents any amino acid. In certain embodiments, Loop 4 (L4) of SEQ ID NO: 1 is at least 11, at least 12, at least 13, at least 14, at least 15, at least 16, at least 17, at least 18, or at least 19 amino acids in length. In certain embodiments, L4 of SEQ ID NO: 1 comprises the amino acid sequence $X_{7-15}$-GAGG (SEQ ID NO: 153), wherein X represents any amino acid. In certain embodiments, Loop 6 (L6) of SEQ ID NO: 1 is at least 8, at least 9, or at least 10 amino acids in length. In certain embodiments, Loop 6 (L6) of SEQ ID NO: 1 comprises the amino acid sequence $X_{10}$ (SEQ ID NO: 106), wherein X represents any amino acid.

In certain embodiments, the polypeptide display library comprises non-naturally occurring chagasin scaffold proteins that each comprise an amino acid sequence set forth in SEQ ID NO: 2:

```
                                          (SEQ ID NO: 2)
MSHKVTKAHN GATLTVAVGE LVEIQLP-X5-8-GF AWYFEGGTKE

SPNESMFTVE NKYFP-X7-15-GAGG TEHFHVTVKA AGTHAVNLTY

MX10ERFTVYLK AN
```

In one embodiment, provided herein are non-naturally occurring chagasin scaffold protein libraries comprising at least 2, 3, 4, 5, 10, 30, 100, 250, 500, 750, 1000, 2500, 5000, 7500, 10000, 25000, 50000, 75000, 100000, 250000, 500000, 750000, 1000000, 2500000, 5000000, 7500000, 10000000, or more than 10000000 chagasin scaffold proteins with unique amino acid sequences, including any range in between these values. In certain embodiments, the non-naturally occurring chagasin scaffold library has a sequence diversity of about 2, about 5, about 10, about 50, about 100, about 250, about 500, about 750, about $10^3$, about $10^4$, about $10^5$, about $10^6$, about $10^7$, about $10^8$, about $10^9$, about $10^{10}$, about $10^{11}$, about $10^{12}$, about $10^{13}$, about $10^{14}$, or more than about $10^{14}$ (such as about $10^{15}$ or about $10^{16}$), including any range in between these values.

In certain embodiments, a non-naturally occurring chagasin scaffold protein library is generated via genetic engineering. A variety of methods for mutagenesis and subsequent library construction have been previously described (along with appropriate methods for screening or selection). Such mutagenesis methods include, but are not limited to, e.g., error-prone PCR, loop shuffling, or oligonucleotide-directed mutagenesis, random nucleotide insertion or other methods prior to recombination. Further details regarding these methods are described in, e.g., Abou-Nadler et al. (2010) *Bioengineered Bugs* 1, 337-340; Firth et al. (2005) *Bioinformatics* 21, 3314-3315; Cirino et al. (2003) *Methods Mol Biol* 231, 3-9; Pirakitikulr (2010) *Protein Sci* 19, 2336-2346; Steffens et al. (2007) *J. Biomol Tech* 18, 147-149; and others. Accordingly, in certain embodiments, provided is a non-naturally occurring chagasin scaffold protein library generated via genetic engineering techniques.

In certain embodiments, a non-naturally occurring chagasin scaffold protein library is generated via in vitro translation. Briefly, in vitro translation entails cloning the protein-coding sequence(s) into a vector containing a promoter, producing mRNA by transcribing the cloned sequence(s) with an RNA polymerase, and synthesizing the protein by translation of this mRNA in vitro, e.g., using a cell-free extract. A desired mutant protein can be generated simply by altering the cloned protein-coding sequence. Many mRNAs can be translated efficiently in wheat germ extracts or in rabbit reticulocyte lysates. Further details regarding in vitro translation are described in, e.g., Hope et al. (1985) *Cell* 43, 177-188; Hope et al. (1986) *Cell* 46, 885-894; Hope et al. (1987) *EMBO J.* 6, 2781-2784; Hope et al. (1988) *Nature* 333, 635-640; and Melton et al. (1984) *Nucl. Acids Res.* 12, 7057-7070.

Accordingly, provided are a plurality of nucleic acid molecules encoding a polypeptide display library described herein. An expression vector operably linked to the plurality of nucleic acid molecules is also provided by the invention.

In certain embodiments, a non-naturally occurring chagasin scaffold protein library is generated via chemical synthesis. In certain embodiments, chemically synthesized L2, L4, and/or L6 peptides onto a chagasin framework to generate a non-naturally occurring chagasin scaffold protein library. Methods of solid phase and liquid phase peptide synthesis are well known in the art and described in detail in, e.g., Methods of Molecular Biology, 35, Peptide Synthesis Protocols, (M. W. Pennington and B. M. Dunn Eds), Springer, 1994; Welsch et al. (2010) *Curr Opin Chem Biol* 14, 1-15; Methods of Enzymology, 289, Solid Phase Peptide Synthesis, (G. B. Fields Ed.), Academic Press, 1997; Chemical Approaches to the Synthesis of Peptides and Proteins, (P. Lloyd-Williams, F. Albericio, and E. Giralt Eds), CRC Press, 1997; Fmoc Solid Phase Peptide Synthesis, A Practical Approach, (W. C. Chan, P. D. White Eds), Oxford University Press, 2000; Solid Phase Synthesis, A Practical Guide, (S. F. Kates, F Albericio Eds), Marcel Dekker, 2000; P. Seneci, Solid-Phase Synthesis and Combinatorial Technologies, John Wiley & Sons, 2000; Synthesis of Peptides and Peptidomimetics (M. Goodman, Editor-in-chief, A. Felix, L. Moroder, C. Tmiolo Eds), Thieme, 2002; N. L. Benoiton, Chemistry of Peptide Synthesis, CRC Press, 2005; Methods in Molecular Biology, 298, Peptide Synthesis and Applications, (J. Howl Ed) Humana Press, 2005; and Amino Acids, Peptides and Proteins in Organic Chemistry, Volume 3, Building Blocks, Catalysts and Coupling Chemistry, (A. B. Hughs, Ed.) Wiley-VCH, 2011. Accordingly, in certain embodiments, provided is a non-naturally occurring chagasin scaffold protein library generated via chemical synthesis techniques.

In certain embodiments, the non-naturally occurring chagasin scaffold protein library comprises a display library. In certain embodiments, the display library is a phage display library, a phagemid display library, a virus display library, a bacterial display library, yeast display library, a λgt11 library, a CIS display library, and in vitro compartmentalization library, or a ribosome display library. Methods of making and screening such display libraries are well known to those of skill in the art and described in, e.g., Molek et al. (2011) *Molecules* 16, 857-887; Boder et al., (1997) *Nat Biotechnol* 15, 553-557; Scott et al. (1990) *Science* 249, 386-390; Brisette et al. (2007) *Methods Mol Biol* 383, 203-213; Kenrick et al. (2010) *Protein Eng Des Sel* 23, 9-17; Freudl et al. (1986) *J Mol Biol* 188, 491-494; Getz et al. (2012) *Methods Enzymol* 503, 75-97; Smith et al. (2014) *Curr Drug Discov Technol* 11, 48-55; Hanes, et al. (1997) *Proc Natl Acad Sci USA* 94, 4937-4942; Lipovsek et al., (2004) *J Imm Methods* 290, 51-67; Ullman et al. (2011) Brief. Funct. Genomics, 10, 125-134; Odegrip et al. (2004) *Proc Natl Acad Sci* USA 101, 2806-2810; and Miller et al. (2006) Nat Methods 3, 561-570.

In certain embodiments, the non-naturally occurring chagasin scaffold protein library comprises an RNA-protein fusion library generated, for example, by the techniques described in Szostak et al., U.S. Pat. Nos. 6,258,558, 6,261,804, 5,643,768, and 5,658,754. In certain embodiments, the non-naturally occurring chagasin scaffold protein library comprises a DNA-protein library, as described, for example, in U.S. Pat. No. 6,416,950.

Directed Evolution of Non-Naturally Occurring Chagasin Scaffold Proteins

Also provided herein is a method of obtaining a non-naturally occurring chagasin scaffold protein that specifically binds a target ligand (such as a polypeptide, a nucleic acid, a polysaccharide, a lipid, a phospholipid, a lipopolysaccharide, a small molecule, or any target ligand that can be bound by an antibody). In certain embodiments, the method comprises a) contacting a target ligand with a library of non-naturally occurring chagasin scaffold proteins (such as a library described herein) under conditions that allow a non-naturally occurring chagasin scaffold protein: target ligand complex to form, (b) detecting the formation of the non-naturally occurring chagasin scaffold protein: target ligand complex, and (c) obtaining from the complex the non-naturally occurring chagasin scaffold protein that specifically binds the target ligand.

In certain embodiments, provide is a complex comprising a non-naturally occurring chagasin scaffold protein and a target ligand (i.e., a non-naturally occurring chagasin scaffold protein: target ligand complex). In certain embodiments, provided is a non-naturally occurring chagasin scaffold protein capable of binding to a target ligand. In certain embodiments, the method further comprises (d) determining the nucleic acid sequence of the non-naturally occurring chagasin scaffold protein that specifically binds the target ligand.

In certain embodiments, a non-naturally occurring chagasin scaffold protein that specifically binds a target ligand is subject to affinity maturation. In this process, a specific binding protein is subject to a scheme that selects for increased affinity for a specific target (see Wu et al. (1998) *Proc Natl Acad Sci USA*. 95, 6037-42). In certain embodiments, a non-naturally occurring chagasin scaffold protein that specifically binds a target ligand is further randomized after identification from a library screen. For example, in certain embodiments, the method of obtaining a non-naturally occurring chagasin scaffold protein that specifically binds a target ligand further comprises (e) randomizing L2, L4, and/or L6 of the non-naturally occurring chagasin scaffold protein obtained from the non-naturally occurring chagasin scaffold protein: target ligand complex identified previously to generate further randomized non-naturally occurring chagasin scaffold proteins, (f) contacting the target ligand with the further randomized non-naturally occurring chagasin scaffold proteins, (g) detecting the formation of the further randomized non-naturally occurring chagasin scaffold protein: target ligand complex, and (h) obtaining from the complex the further randomized non-naturally occurring chagasin scaffold protein that specifically binds the target ligand. In certain embodiments, the method further comprises (i) determining the nucleic acid sequence of the non-naturally occurring chagasin scaffold protein that specifically binds the target ligand.

In certain embodiments, the further randomized non-naturally occurring chagasin scaffold proteins comprise at least one or at least two randomized loops which were not previously randomized in the first library. Multiple rounds of randomization, screening and selection can be performed until non-naturally occurring chagasin scaffold protein(s) having sufficient affinity for the target ligand are obtained. Thus, in certain embodiments, steps (e)-(h) or steps (e)-(i) are repeated one, two, three, four, five, six, seven, eight, nine, ten, or more than ten times in order to identify the non-naturally occurring chagasin scaffold protein that specifically binds a target ligand.

In certain embodiments, the non-naturally occurring chagasin scaffold protein that has undergone at least two, three, four, five, six, seven, eight, nine, ten, or more than ten rounds of randomization, screening and selection binds the target ligand with an affinity that is at least as high as that of the non-naturally occurring chagasin scaffold protein that has undergone one round of randomization, screening, and selection. In certain embodiments, the non-naturally occurring chagasin scaffold protein that has undergone at least two, three, four, five, six, seven, eight, nine, ten, or more than ten rounds of randomization, screening and selection binds the target ligand with an affinity that is higher than that of the non-naturally occurring chagasin scaffold protein that has undergone one round of randomization, screening, and selection.

A library of non-naturally occurring chagasin scaffold proteins described herein may be screened by any technique known in the art for evolving new or improved binding proteins that specifically bind a target ligand. In certain embodiments, the target ligand is immobilized on a solid support (such as a column resin or microtiter plate well), and the target ligand is contacted with a library of candidate non-naturally occurring chagasin scaffold proteins (such as any library described herein). Selection techniques can be, for example, phage display (Smith (1985) *Science* 228, 1315-1317), mRNA display (Wilson et al. (2001) *Proc Natl Acad Sci USA* 98: 3750-3755) bacterial display (Georgiou, et al. (1997) *Nat Biotechnol* 15:29-34.), yeast display (Boder and Wittrup (1997) *Nat. Biotechnol.* 15:553-5577) or ribosome display (Hanes and Pluckthun (1997) *Proc Natl Acad Sci USA* 94:4937-4942 and WO2008/068637).

In certain embodiments, the library of non-naturally occurring chagasin scaffold proteins is a phage display library. In certain embodiments, provided is a phage particle displaying a non-naturally occurring chagasin scaffold protein described herein. In certain embodiments, provided is a phage particle displaying a non-naturally occurring chagasin scaffold protein described herein capable of binding to a target ligand.

Phage display is a technique by which a plurality non-naturally occurring chagasin scaffold protein variants are displayed as fusion proteins to the coat protein on the surface of bacteriophage particles (Smith, G. P. (1985) *Science.* 228:1315-7; Scott, J. K. and Smith, G. P. (1990) *Science* 249: 386; Sergeeva, A., et al. (2006) *Adv. Drug Deliv. Rev.* 58:1622-54). The utility of phage display lies in the fact that large libraries of selectively randomized protein variants (or randomly cloned cDNAs) can be rapidly and efficiently sorted for those sequences that bind to a target ligand with high affinity.

Display of peptides (Cwirla, S. E. et al. (1990) *Proc. Natl. Acad. Sci. USA,* 87:6378) or protein (Lowman, H. B. et al. (1991) *Biochemistry,* 30:10832; Clackson, T. et al. (1991) *Nature,* 352:624; Marks, J. D. et al. (1991), *J. Mol. Biol.,* 222:581; Kang, A. S. et al. (1991) *Proc. Natl. Acad. Sci. USA,* 88:8363) libraries on phage have been used for screening millions of polypeptides or oligopeptides for ones with specific binding properties (Smith, G. P. (1991) *Current Opin. Biotechnol.,* 2:668; Wu et al. (1998) *Proc Natl Acad Sci USA.* May 95, 6037-42). Polyvalent phage display methods have been used for displaying small random peptides and small proteins through fusions to either gene III or gene VIII of filamentous phage. (Wells and Lowman, *Curr. Opin. Struct. Biol.,* 3:355-362 (1992), and references cited therein.) In a monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. (Lowman and Wells, *Methods: A companion to Methods in Enzymology,* 3:205-0216 (1991).)

Sorting phage libraries of non-naturally occurring chagasin scaffold proteins entails the construction and propagation of a large number of variants, a procedure for affinity purification using the target ligand, and a means of evaluating the results of binding enrichments (see for example, U.S. Pat. Nos. 5,223,409, 5,403,484, 5,571,689, and 5,663, 143).

Most phage display methods use filamentous phage (such as M13 phage). Lambdoid phage display systems (see WO1995/34683, U.S. Pat. No. 5,627,024), T4 phage display systems (Ren et al. (1998) *Gene* 215:439; Zhu et al. (1998) *Cancer Research,* 58:3209-3214; Jiang et al., (1997) *Infection & Immunity,* 65:4770-4777; Ren et al. (1997) *Gene,* 195:303-311; Ren (1996) *Protein Sci.,* 5:1833; Efimov et al. (1995) *Virus Genes,* 10:173) and T7 phage display systems (Smith and Scott (1993) *Methods in Enzymology,* 217:228-257; U.S. Pat. No. 5,766,905) are also known.

Many other improvements and variations of the basic phage display concept have now been developed. These improvements enhance the ability of display systems to screen peptide libraries for binding to selected target ligands and to display functional proteins with the potential of screening these proteins for desired properties. Combinatorial reaction devices for phage display reactions have been developed (WO 1998/14277) and phage display libraries have been used to analyze and control bimolecular interactions (WO 1998/20169; WO 1998/20159) and properties of constrained helical peptides (WO 1998/20036). WO 1997/35196 describes a method of isolating an affinity ligand in which a phage display library is contacted with one solution in which the ligand will bind to a target ligand and a second solution in which the affinity ligand will not bind to the target ligand, to selectively isolate binding ligands. WO 1997/46251 describes a method of biopanning a random phage display library with an affinity purified antibody and then isolating binding phage, followed by a micropanning process using microplate wells to isolate high affinity binding phage. Such method can be applied to the non-naturally occurring chagasin scaffold proteins disclosed herein. The use of *Staphylococcus aureus* protein A as an affinity tag has also been reported (Li et al. (1998) *Mol Biotech.* 9:187). WO 1997/47314 describes the use of substrate subtraction libraries to distinguish enzyme specificities using a combinatorial library which may be a phage display library. Additional methods of selecting specific binding proteins are described in U.S. Pat. Nos. 5,498,538, 5,432,018, and WO 1998/15833. Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

In certain embodiments, non-naturally occurring chagasin scaffold proteins produced via directed evolution can be used in the identification and/or validation of disease-causing targets (such as target proteins) or lead therapeutic candidates. For example, a non-naturally occurring chagasin scaffold protein engineered to bind a target ligand of interest can be used to inhibit the expression of the target in vitro (such as in cell culture) or in vivo (such as in an animal model) so that, e.g., the physiological role of the target ligand can be characterized or confirmed, or, e.g., the disease association and therapeutic potential of the target ligand can be investigated and/or validated. In certain embodiments, the engineered non-naturally occurring chagasin scaffold protein is screened for binding to a human target ligand. In certain embodiments, the engineered non-naturally occurring chagasin scaffold protein is screened for cross-reactivity to a mouse target ligand. In certain embodiments, the engineered non-naturally occurring chagasin scaffold protein is screened for effects on in vitro functions (e.g., inhibition of ligand/receptor binding). In certain embodiments, the function and binding of the engineered non-naturally occurring chagasin scaffold protein is investigated in cell-based assays. In certain embodiments, the binding affinity of the engineered non-naturally occurring chagasin scaffold protein is determined. In certain embodiments, the epitope of the target ligand to which the engineered non-naturally occurring chagasin scaffold protein binds is mapped. In certain embodiments, the engineered non-naturally occurring chagasin scaffold protein is used to determine the distribution of the target ligand in the body. In certain embodiments, the engineered non-naturally occurring chagasin scaffold protein is used to determine the subcellular localization of the target ligand. In certain embodiments, the engineered non-naturally occurring chagasin scaffold protein is used to profile the expression of the target ligand in diseased tissue and non-diseased tissue and/or to verify the expression of the target ligand in diseased tissue. In certain embodiments, the engineered non-naturally occurring chagasin scaffold protein is used to perform pre-clinical efficacy studies. In certain embodiments, the engineered non-naturally occurring chagasin scaffold protein is used to perform toxicity studies. In certain embodiments, the engineered non-naturally occurring chagasin scaffold protein is used to perform pharmacokinetic and/or pharmacodynamic studies. Further details regarding target validation are described in, e.g., Carter et al. (2004) *Endocr Relat Cancer* 11, 659-687; van Beijnum et al. (2002) *Int J Cancer* 101, 118-127; Verheesen et al. (2006) Biochim et Biophys Acta 1764, 1307-1319; Shih (2012) "Development of Antibody-Based Therapeutics" Springer, pp. 9-32; and Wise et al. (2002) Drug Disc Today 7, 235-246.

Non-Naturally Occurring Chagasin Scaffold Proteins that Specifically Bind Human Low Density Lipoprotein Receptor (LDL)-Related Protein 6 (LRP6)

LDL receptors are transmembrane cell surface proteins involved in receptor-mediated endocytosis of lipoprotein and protein ligands. Human LDL receptor-related protein 6 (LRP6) (Accession Nos: NM_002336 (mRNA) and NP_002327 (protein); UniProtKB: O75581) functions as a receptor or, with Frizzled, a co-receptor for Wnt and thereby transmits the canonical Wnt/beta-catenin signaling cascade (Katoh et al. (2007) *Clin Cancer Res* 13:4042-4045). Through its interaction with the Wnt/beta-catenin signaling cascade, LRP6 plays a role in the regulation of cell differentiation, proliferation, and migration, and in the development of many cancer types (Li et al. (2004) *Oncogene* 23:9129-9135; Tung et al. (2012) PLoS ONE 7(5): e36565. doi:10.1371/journal.pone.0036565; Liu et al. (2010) *Proc Natl Acad Sci USA* 107:5136-5141).

Wnt signaling is involved in many biological pathways. With respect to diseases it is involved with cancer and metastatic disease, osteoporosis and other bone metabolism and disease, neuronal and neurodegenerative disease, rheumatoid arthritis and other inflammatory disease. This inhibition of Wnt signaling by blockade of LRP6 may have a wide range of therapeutic utility. Bone loss is a serious medical problem, not only during postmenopausal osteoporosis, but also in rheumatoid arthritis. Bone is degraded in multiple myeloma and in bone metastases. Therapeutic strategies aimed at strengthening bone, fracture prevention, or restoration of damaged bone are therefore of very high interest (Kawai et al. (2011) *Nat. Rev. Drug Discov.* 10, 141-156; Mason and Williams (2010) *J. Osteoporosis, vol.* 2010, Article ID 460120, 9 pages; doi:10.4061/2010/460120). The Wnt pathway inhibitors DKK1 and SOST, because of their roles in suppressing new bone formation, are considered highly promising therapeutic targets; antibodies with neutralizing the function of SOST show significant preclinical activity (Ominsky et al. (2010) *J. Bone Miner. Res.* 25, 948-959) and are now in human clinical trials (Padhi et al. (2011) *J. Bone Miner. Res.* 26, 19-26.

Misregulated Wnt signaling is implicated in diseases ranging from osteoporosis to cancer (Clevers (2006) *Cell* 127:469-80; MacDonald et al. 2009. *Dev Cell* 17: 9-26; Nusse (2008) *Cell Res* 18:523-7; Polakis (2007) *Curr Opin Genet Dev* 17:45-51). This list has expanded to include metabolic disorders (Mani et al. (2007) *Science* 315:1278-82 and neurodegeneration (Caricasole et al. (2004) *J Neurosci* 24:6021-7; De Ferrari et al. (2007) *Proc Natl Acad Sci USA* 104: 9434-9). An especially clear link exists between mutations of the protein adenomatous polyposis coli (APC), which prevent effective regulation of β-catenin levels, and colorectal cancers (Polakis (2007) *Curr Opin Genet Dev* 17:45-51). Also of particular note is the strong genetic relationship between LRP5 and bone homeostasis. Loss-of-function mutations in LRP5 cause the autosomal recessive disorder osteoporosispseudoglioma syndrome (OPPG), characterized by low bone mass, ocular defects and a predisposition to fractures (Gong et al. (2001) *Cell* 107: 513-23.

A non-naturally occurring chagasin scaffold protein specific for human LRP6 described herein binds human LRP6 with sufficient affinity and specificity. Preferably, such non-naturally occurring chagasin scaffold protein can be used as a therapeutic agent in targeting and interfering with diseases or conditions wherein LRP6 activity is involved. A non-naturally occurring chagasin scaffold protein that specifically binds human LRP6 will usually not bind to other LRP proteins, such as LRP1, LRP1B, LRP2, LRP3, LRP4, LRP5, LRP8, LRP10, LRP11, and LRP12.

In some embodiments, provided herein is a non-naturally occurring chagasin scaffold protein that specifically binds to the same epitope as a second non-naturally occurring chagasin scaffold protein that binds human low density lipoprotein receptor-related protein 6 (LRP6), wherein the second non-naturally occurring chagasin scaffold protein that binds human LRP6 comprises an L2 that comprises the amino acid sequence comprises an L2 that comprises the amino acid sequence SNP-T/S/A/Q-T/C/D (SEQ ID NO: 150) or SN-V/A-D (155), an L4 that comprises the amino acid sequence Y/S-N-N/K-I/V-R/K-G-L/V/I-PGF (SEQ ID NO: 156) or SN-Y/S-TK-H/R (SEQ ID NO: 157), or DSNEIWYC (SEQ ID NO: 77); and an L6 that comprises the amino acid sequence R/S/P/G-P/R-W/Y/E/S/V-T/Y/K/T-G-P/S/A-S/T/Y-H/K/L/Q/D-D/V/E-S/E/M/P/V (SEQ ID NO: 148), with reference to SEQ ID NO: 2. Also provided herein is an antibody that specifically binds to the same epitope as a non-naturally occurring chagasin scaffold protein that binds human low density lipoprotein receptor-related protein 6 (LRP6), wherein the non-naturally occurring chagasin scaffold protein that binds human LRP6 comprises an comprises an L2 that comprises the amino acid sequence SNP-T/S/A/Q-T/C/D (SEQ ID NO: 150) or SN-V/A-D (155), an L4 that comprises the amino acid sequence Y/S-N-N/K-I/V-R/K-G-L/V/I-PGF (SEQ ID NO: 156) or SN-Y/S-TK-H/R (SEQ ID NO: 157), or DSNEIWYC (SEQ ID NO: 77); and an L6 that comprises the amino acid sequence R/S/P/G-P/R-W/Y/E/S/V-T/Y/K/T-G-P/S/A-S/T/Y-H/K/L/Q/D-D/V/E-S/E/M/P/V (SEQ ID NO: 148), with reference to SEQ ID NO: 2.

Provided is a non-naturally occurring chagasin scaffold protein that specifically binds human low density lipoprotein receptor-related protein 6 (LRP6), wherein the non-naturally occurring chagasin scaffold protein competes for binding with a second non-naturally occurring chagasin scaffold protein that binds human LRP6, wherein the second non-naturally occurring chagasin scaffold protein that binds human LRP6 comprises an L2 that comprises the amino acid sequence SNP-T/S/A/Q-T/C/D (SEQ ID NO: 150) or SN-V/A-D (155), an L4 that comprises the amino acid sequence Y/S-N-N/K-I/V-R/K-G-L/V/I-PGF (SEQ ID NO: 156) or SN-Y/S-TK-H/R (SEQ ID NO: 157), or DSNEIWYC (SEQ ID NO: 77); and an L6 that comprises the amino acid sequence R/S/P/G-P/R-W/Y/E/S/V-T/Y/K/T-G-P/S/A-S/T/Y-H/K/L/Q/D-D/V/E-S/E/M/P/V (SEQ ID NO: 148), with reference to SEQ ID NO: 2.

In certain embodiment of (or as applied to) any of the embodiments above the non-naturally occurring chagasin scaffold protein that specifically binds human LRP6 comprises an L2 that comprises the amino acid sequence SNP-T/S/A/Q-T/C/D (SEQ ID NO: 150) or SN-V/A-D (155), an L4 that comprises the amino acid sequence Y/S-N-N/K-I/V-R/K-G-L/V/I-PGF (SEQ ID NO: 156) or SN-Y/S-TK-H/R (SEQ ID NO: 157), or DSNEIWYC (SEQ ID NO: 77); and an L6 that comprises the amino acid sequence R/S/P/G-P/R-W/Y/E/S/V-T/Y/K/T-G-P/S/A-S/T/Y-H/K/L/Q/D-D/V/E-S/E/M/P/V (SEQ ID NO: 148), with reference to SEQ ID NO: 2.

In certain embodiments, the non-naturally occurring chagasin scaffold protein that specifically binds human LRP6 binds the same epitope of human LRP6 bound by a second non-naturally occurring chagasin scaffold protein comprising an L2 that comprises the amino acid sequence S-N/S-P/N-Q/T/V/S/A-T/D/C-GF (SEQ ID NO: 6), an L4 that comprises the amino acid sequence P-S/Y-N-N/K-V/I-K/R-

G-V/I/L-PGFGAGG (SEQ ID NO: 10), PSN-S/Y-TK-H/R-GAGG (SEQ ID NO: 90), or DSNEIWYC (SEQ ID NO: 77); and an L6 that comprises the amino acid sequence G/R/P/S-P/R-W/S/V/Y/E-T/K/Y-G-A/P/S-S/Y/T-Q/D/L/H/K-E/D/V-P/S/M/E (SEQ ID NO: 14), with reference to SEQ ID NO: 2.

In certain embodiments, the non-naturally occurring chagasin scaffold protein that specifically binds human LRP6 competitively inhibits the binding of a competing molecule to human LRP6. In certain embodiments, the competing molecule is an anti-LRP6 antibody. In certain embodiments, the competing molecule is a second non-naturally occurring chagasin scaffold protein that binds to human LRP6.

In certain embodiments, the non-naturally occurring chagasin scaffold protein that specifically binds human LRP6 competitively inhibits the binding of a second non-naturally occurring chagasin scaffold protein to human LRP6, wherein the second non-naturally occurring chagasin scaffold protein comprises an L2 that comprises the amino acid sequence S-N/S-P/N-Q/T/V/S/A-T/D/C-GF (SEQ ID NO: 6), an L4 that comprises the amino acid sequence P-S/Y-N-N/K-V/I-K/R-G-V/I/L-PGFGAGG (SEQ ID NO: 10), PSN-S/Y-TK-H/R-GAGG (SEQ ID NO: 90), or DSNEIWYC (SEQ ID NO: 77); and an L6 that comprises the amino acid sequence G/R/P/S-P/R-W/S/V/Y/E-T/K/Y-G-A/P/S-S/Y/T-Q/D/L/H/K-E/D/V-P/S/M/E (SEQ ID NO: 14), with reference to SEQ ID NO: 2. In certain embodiments, the non-naturally occurring chagasin scaffold protein that specifically binds human LRP6 and competitively inhibits the binding of a second non-naturally occurring chagasin scaffold protein to human LRP6 comprises an L2 that comprises the amino acid sequence S-N/S-P/N-Q/T/V/S/A-T/D/C-GF (SEQ ID NO: 6), an L4 that comprises the amino acid sequence P-S/Y-N-N/K-V/I-K/R-G-V/I/L-PGFGAGG (SEQ ID NO: 10), PSN-S/Y-TK-H/R-GAGG (SEQ ID NO: 90), or DSNEIWYC (SEQ ID NO: 77); and an L6 that comprises the amino acid sequence G/R/P/S-P/R-W/S/V/Y/E-T/K/Y-G-A/P/S-S/Y/T-Q/D/L/H/K-E/D/V-P/S/M/E (SEQ ID NO: 14), with reference to SEQ ID NO: 2.

Non-naturally occurring chagasin scaffold proteins characterized by binding to overlapping or similar areas on a target can be identified by competitive inhibition/binding assays. Such assays are well known in the art and are described in, e.g., S. J. Mather (ed.) 1996. *Current Directions in Radiopharmaceutical Research and Development*, 169-179, Kluwer Academic Publishers; Zenner (1973) *Clin. Chem.* 19, 699-705; Gao (2012) *Analytical Methods* 4, 3718-3723.

In certain embodiments, the non-naturally occurring chagasin scaffold protein specific for human LRP6 comprises an L2, L4, and/or L6 of any one of the non-naturally occurring chagasin scaffold protein specific for human LRP6 disclosed herein. In certain embodiments, provided herein is a non-naturally occurring chagasin scaffold protein that specifically binds human low density lipoprotein receptor-related protein 6 (LRP6) and comprises: an L2 that comprises an amino acid sequence set forth in any one of SEQ ID NOs: 3-5, 78-80, and 146, an L4 that comprises an amino acid sequence set forth in any one of SEQ ID NOs: 7-9, 77, and 81-83; and an L6 that comprises an amino acid sequence set forth in any one of SEQ ID NOs: 11-13, 84-86, and 147, with reference to SEQ ID NO: 2. The L2, L4, and L6 amino acid sequences described above are provided in Table 1 below:

TABLE 1

L2, L4, and L6 Amino Acid Sequences of Non-Naturally Occurring Chagasin Scaffold Proteins that Specifically Bind LRP6

| | | |
|---|---|---|
| SNPQT (SEQ ID NO: 3) | SNKVKGVPGF (SEQ ID NO: 7) | GPWTGASQEP (SEQ ID NO: 11) |
| SNPTT (SEQ ID NO: 4) | SNKIKGIPGF (SEQ ID NO: 8) | RPSTGPSDDS (SEQ ID NO: 12) |
| SNVD (SEQ ID NO: 5) | SNSTKR (SEQ ID NO: 9) | PRVKGAYLVM (SEQ ID NO: 13) |
| SNPTT (SEQ ID NO: 78) | YNNIRGLPGF (SEQ ID NO: 81) | RPWTGPSHDS (SEQ ID NO: 84) |
| SNPSC (SEQ ID NO: 79) | DSNEIWYC (SEQ ID NO: 82) | SPYYGP

In certain embodiments, the non-naturally occurring chagasin scaffold protein that specifically binds human LRP6 comprises an L2 that comprises the amino acid s TABLE 2-continued Conservative Substitutions

| Original Residue | Exemplary Substitutions | Preferred Substitutions |
|---|---|---|
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Non-conservative substitutions will entail exchanging a member of one of these classes for another class. An exemplary substitutional variant is an affinity matured chagasin scaffold protein that specifically binds LRP6, which may be conveniently generated, e.g., using phage display based affinity maturation techniques such as those described herein. Briefly, one or more residues in L2, L4, and/or L6 altered (i.e., added, deleted, or substituted) and the variant chagasin scaffold protein displayed on phage and screened for LRP6 binding affinity. In certain embodiments of affinity maturation, diversity is introduced into the variable genes chosen for maturation by any of a variety of methods (e.g., error-prone PCR, loop shuffling, or oligonucleotide-directed mutagenesis). A secondary library is then created. The library is then screened to identify any chagasin scaffold protein variants with the desired affinity for LRP6. In certain embodiments, introducing diversity involves loop-directed approaches, in which several residues in L2, L4, and/or L6 (e.g., 4-6 residues at a time) are randomized. L2, L4, and/or L6 residues involved in binding a target ligand may be specifically identified, e.g., using alanine scanning mutagenesis or modeling.

In certain embodiments, the non-naturally occurring chagasin scaffold protein that specifically binds human LRP6 has a stronger binding affinity for a LRP6 than it has for LRP proteins or LRP6 homologues, such as LRP1, LRP1B, LRP2, LRP3, LRP4, LRP5, LRP8, LRP10, LRP11, and LRP12.

Normally, the non-naturally occurring chagasin scaffold protein that "specifically binds" human LRP6 (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for another LRP protein which is at least about 50-fold, or at least about 500-fold, or at least about 1000-fold, weaker than its binding affinity for LRP6.

In certain embodiments, the extent of binding of the non-naturally occurring chagasin scaffold protein that specifically binds human LRP6 to a non-target ligand (such as LRP 1, LRP1B, LRP2, LRP3, LRP4, LRP5, LRP8, LRP10, LRP11, and LRP12) is less than about 10% of the binding of the non-naturally occurring chagasin scaffold protein to human LRP6 as determined by methods known in the art, such as ELISA, fluorescence activated cell sorting (FACS) analysis, or radioimmunoprecipitation (RIA). Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

In certain embodiments, the non-naturally occurring chagasin scaffold protein that specifically binds LRP6 binds a human LRP6 with a Kd between about 1 pM to about 500 nM. In certain embodiments, the non-naturally occurring chagasin scaffold protein that specifically binds LRP6 binds a human LRP6 with a Kd between about 1 pM to about 50 pM, between about 50 pM to about 250 pM, between about 250 pM to about 500 pM, between about 500 pM to 750 pM, between about 750 pM to about 1 nM, between about 1 nM to about 25 nM, between about 25 nM to about 50 nM, between 50 nM to about 100 nM, between about 100 nM to about 250 nM, or between about 250 nM to about 500 nM.

In certain embodiments, the non-naturally occurring chagasin scaffold protein specifically binds LRP6 inhibits Wnt1 signaling, e.g., as determined using methods described in the Examples below.

Nucleic acid molecules encoding the non-naturally occurring chagasin scaffold proteins described herein that specifically bind LRP6, expression vectors comprising nucleic acid molecules encoding the non-naturally occurring chagasin scaffold proteins described herein that specifically bind LRP6, and cells comprising the nucleic acid molecules are also contemplated. Also provided herein are methods of producing a non-naturally chagasin scaffold protein described herein that specifically binds LRP6 by culturing such cells, expressing the non-naturally occurring chagasin scaffold protein, and recovering the non-naturally occurring chagasin scaffold protein from the cell culture.

In certain embodiments, a non-naturally occurring chagasin scaffold protein that specifically binds LRP6 can be produced via in vitro translation, as described elsewhere herein.

As described elsewhere herein, a non-naturally occurring chagasin scaffold protein that specifically binds LRP6 can also be generated via chemical peptide synthesis, e.g., by grafting chemically synthesized L2, L4, and/or L6 peptides onto a chagasin framework.

Non-Naturally Occurring Chagasin Scaffold Proteins that Specifically Bind Human Vascular Endothelial Growth Factor (VEGF)

Vascular endothelial growth factor (VEGF or VEGFA) is a highly specific mitogen for vascular endothelial cells. The expression of VEGF is potentiated in response to hypoxia, by activated oncogenes, and by a variety of cytokines. VEGF induces endothelial cell proliferation, promotes cell migration, and inhibits apoptosis. In vivo VEGF induces angiogenesis as well as permeabilization of blood vessels, and plays a central role in the regulation of vasculogenesis. VEGF has multiple isoforms that can bind various receptors. For example, VEGF-A can bind to VEGFR1 (Flt-1), VEGFR2 (KDR) as well as neuropilin (NRP-1) (Ferarra et al. (2003) *Nat Medicine* 9, 669-676; Goel et al. *Nat Rev Cancer* (2013) 12, 871-882).

Deregulated VEGF expression contributes to the development of solid tumors by promoting tumor angiogenesis and to the etiology of several additional diseases that are characterized by abnormal angiogenesis, such as diseases caused by ocular neovascularisation, including, but not limited to, e.g., diabetic blindness, retinopathies, primarily diabetic retinopathy or age-related macular degeneration, choroidal neovascularization (CNV), diabetic macular edema, pathological myopia, von Rippel-Lindau disease, histoplasmosis of the eye, retinal vein occlusion (both branched retinal vein occlusion (BRVO) and central retinal vein occlusion (CRVO), corneal neovascularization, retinal neovascularization and rubeosis; psoriasis, psoriatic arthritis, haemangioblastoma such as haemangioma; inflammatory renal diseases, such as glomerulonephritis, especially mesangioproliferative glomerulonephritis, haemolytic uremic syndrome, diabetic nephropathy or hypertensive nephrosclerosis. Other diseases characterized by deregulated VEGF expression include various inflammatory diseases, such as arthritis, especially rheumatoid arthritis, inflammatory bowel disease, psorsasis, sarcoidosis, arterial arteriosclerosis and diseases occurring after transplants, endometriosis or chronic asthma. Excessive, inappropriate or uncontrolled angiogenesis also occurs when there is new blood vessel growth that contributes to the worsening of the diseased state or cause of a diseased state, such as in cancer, especially vascularized solid tumors and metastatic tumors (including colon, lung cancer (especially small-cell lung cancer), or prostate cancer). The new blood vessels can feed the diseased tissues, destroy normal tissues, and in the case of cancer, the new vessels can allow tumor cells to escape into the circulation and lodge in other organs (tumor metastases). Consequently, inhibition of VEGF signaling abrogates the development of a wide variety of tumors.

A non-naturally occurring chagasin scaffold protein specific for human VEGF described herein binds human VEGF with sufficient affinity and specificity. In certain embodiments, the VEGF is a VEGF-A. Preferably, such non-naturally occurring chagasin scaffold protein can be used as a therapeutic agent in targeting and interfering with diseases or conditions wherein VEGF activity is involved. A non-naturally occurring chagasin scaffold protein that specifically binds human VEGF will usually not bind to other VEGF homologues such as VEGF-B or VEGF-C, or other growth factors such as P1GF, PDGF or bFGF.

In certain embodiments, the non-naturally occurring chagasin scaffold protein that specifically binds human VEGF binds an epitope of human VEGF bound by a second non-naturally occurring chagasin scaffold protein comprising an L2 that comprises the amino acid sequence SN-L/Y-R/F/Q-S/Y/N/D-M/D/A/S (SEQ ID NO: 23), an L4 that comprises the amino acid sequence A/N/L/S/V-G/D/S/R-P/L/T/A-S/G/Y/T-A/S/G/Q-V/R/S/K/A-P/L/E/S/N-L/S/T/N/E (SEQ ID NO: 29); and an L6 that comprises the amino acid sequence A/N/F/S-P/K-W/N/S/V-R/L/W-G-P/L-A/S/D/M/R-N/R/Y/V/F-V/W/P-I/L (SEQ ID NO: 35), with reference to SEQ ID NO: 2.

In certain embodiments, the non-naturally occurring chagasin scaffold protein that specifically binds human VEGF binds an epitope of human VEGF bound by a second non-naturally occurring chagasin scaffold protein comprising an L2 that comprises the amino acid sequence SNY-F/Y-Y/C/N/R-D/E (SEQ ID NO: 49), an L4 that comprises the amino acid sequence HYYNLGGRYT (SEQ ID NO: 57), D/N/S-D/G/V/Y-P/N/S-G/Y-S/L/M-G/H/S-L/V/A/Y-W/Y/L/S (SEQ ID NO: 58), or G/H-S/V-S/Q-Y/W-W/G-G/W (SEQ ID NO: 68); and an L6 that comprises the amino acid sequence A/G-PW-S/Q/F/A/L/V-GPSR-Y/E/F/V/D-L (SEQ ID NO: 67), with reference to SEQ ID NO: 2.

In certain embodiments, the non-naturally occurring chagasin scaffold protein that specifically binds human VEGF competitively inhibits the binding of a competing molecule to human VEGF. In certain embodiments, the competing molecule is an anti-VEGF antibody. In certain embodiments, the competing molecule is a second non-naturally occurring chagasin scaffold protein that binds to human VEGF.

In certain embodiments, the non-naturally occurring chagasin scaffold protein that specifically binds human VEGF competitively inhibits the binding of a second non-naturally occurring chagasin scaffold protein to human VEGF, wherein the second non-naturally occurring chagasin scaffold protein comprises an comprises an L2 that comprises the amino acid sequence SN-L/Y-R/F/Q-S/Y/N/D-M/D/A/S (SEQ ID NO: 23), an L4 that comprises the amino acid sequence A/N/L/S/V-G/D/S/R-P/L/T/A-S/G/Y/T-A/S/G/Q-V/R/S/K/A-P/L/E/S/N-L/S/T/N/E (SEQ ID NO: 29); and an L6 that comprises the amino acid sequence A/N/F/S-P/K-W/N/S/V-R/L/W-G-P/L-A/S/D/M/R-N/R/Y/V/F-V/W/P-I/L (SEQ ID NO: 35), with reference to SEQ ID NO: 2. In certain embodiments, the non-naturally occurring chagasin scaffold protein that specifically binds human VEGF and competitively inhibits the binding of a second non-naturally occurring chagasin scaffold protein to human VEGF comprises an comprises an L2 that comprises the amino acid sequence SN-L/Y-R/F/Q-S/Y/N/D-M/D/A/S (SEQ ID NO: 23), an L4 that comprises the amino acid sequence A/N/L/S/V-G/D/S/R-P/L/T/A-S/G/Y/T-A/S/G/Q-V/R/S/K/A-P/L/E/S/N-L/S/T/N/E (SEQ ID NO: 29); and an L6 that comprises the amino acid sequence A/N/F/S-P/K-W/N/S/V-R/L/W-G-P/L-A/S/D/M/R-N/R/Y/V/F-V/W/P-I/L (SEQ ID NO: 35), with reference to SEQ ID NO: 2.

In certain embodiments, the non-naturally occurring chagasin scaffold protein that specifically binds human VEGF competitively inhibits the binding of a second non-naturally occurring chagasin scaffold protein to human VEGF, wherein the second non-naturally occurring chagasin scaffold protein comprises an comprises an L2 that comprises the amino acid sequence SNY-F/Y-Y/C/N/R-D/E (SEQ ID NO: 49), an L4 that comprises the amino acid sequence HYYNLGGRYT (SEQ ID NO: 57), D/N/S-D/G/V/Y-P/N/S-G/Y-S/L/M-G/H/S-L/V/A/Y-W/Y/L/S (SEQ ID NO: 58), or G/H-S/V-S/Q-Y/W-W/G-G/W (SEQ ID NO: 68); and an L6 that comprises the amino acid sequence A/G-PW-S/Q/F/A/L/V-GPSR-Y/E/F/V/D-L (SEQ ID NO: 67), with reference to SEQ ID NO: 2.

As noted elsewhere herein, non-naturally occurring chagasin scaffold proteins characterized by binding to overlapping or similar areas on a target can be identified by competitive inhibition/binding assays.

In certain embodiments, the non-naturally occurring chagasin scaffold protein specific for human VEGF comprises an L2, L4, and/or L6 of any one of the non-naturally occurring chagasin scaffold protein specific for human VEGF disclosed herein. Thus, in certain embodiments, the non-naturally occurring chagasin scaffold protein that specifically binds human VEGF comprises an L2 that comprises an amino acid sequence set forth in any one of SEQ ID NOs: 18-22 and 41-48, an L4 that comprises an amino acid sequence set forth in any one of SEQ ID NOs: 24-28 and 50-57; and an L6 that comprises an amino acid sequence set forth in any one of SEQ ID NOs: 30-34 and 59-66, with reference to SEQ ID NO: 2.

The L2, L4, and L6 amino acid sequences described above are provided in Table 3 below:

TABLE 3

| L2, L4, and L6 Amino Acid Sequences of Non-Naturally Occurring Chagasin Scaffold Proteins that Specifically Bind VEGF | | |
|---|---|---|
| SNLRSM (SEQ ID NO: 18) | AGPSAVPL (SEQ ID NO: 24) | APWRGPANVI (SEQ ID NO: 30) |
| SNYFYD (SEQ ID NO: 19) | NDPGSRLS (SEQ ID NO: 25) | APWLGPSRVL (SEQ ID NO: 31) |
| SNLQNA (SEQ ID NO: 20) | LSLYASET (SEQ ID NO: 26) | NPNWGPDYWI (SEQ ID NO: 32) |
| SNLQDS (SEQ ID NO: 21) | SGTTGKSN (SEQ ID NO: 27) | FKSRGLMVPL (SEQ ID NO: 33) |
| SNYRDS (SEQ ID NO: 22) | VRAGQANE (SEQ ID NO: 28) | SPVLGPRFWL (SEQ ID NO: 34) |
| A/N/L/S/V-G/D/S/R-P/L/T/A-S/G/Y/T-A/S/G/Q-V/R/S/K/A-P/L/E/S/N-L/S/T/N/E (SEQ ID NO: 23) | A/N/F/S-P/K-W/N/S/V-R/L/W-G-P/L-A/S/D/M/R-N/R/Y/V/F-V/W/P-I/L (SEQ ID NO: 29) | SN-L/Y-R/F/Q-S/Y/N/D-M/D/A/S (SEQ ID NO: 35) |
| SNYFYD (SEQ ID NO: 41) | DDPGSGLW (SEQ ID NO: 50) | APWSGPSRYL (SEQ ID NO: 59) |
| SNYFYE (SEQ ID NO: 42) | NGPGLGVY (SEQ ID NO: 51) | APWQGPSREL (SEQ ID NO: 60) |
| SNYYYD (SEQ ID NO: 43) | NVNGSHAW (SEQ ID NO: 52) | APWSGPSRFL (SEQ ID NO: 61) |
| SNYFCD (SEQ ID NO: 44) | NYPGSGVL (SEQ ID NO: 53) | APWFGPSRVL (SEQ ID NO: 62) |
| SNYFND (SEQ ID NO: 45) | GSSYWG (SEQ ID NO: 54) | APWAGPSRVL (SEQ ID NO: 3) |
| SNYFYD (SEQ ID NO: 46) | SGSYMSYS (SEQ ID NO: 55) | APWLGPSRDL (SEQ ID NO: 4) |
| SNYFRE (SEQ ID NO: 47) | HVQWGW (SEQ ID NO: 56) | APWVGPSREL (SEQ ID NO: 5) |
| SNYYYD (SEQ ID NO: 48) | HYYNLGGRYT (SEQ ID NO: 57) | GPWLGPSRVL (SEQ ID NO: 66) |
| SNY-F/Y-Y/C/N/R-D/E (SEQ ID NO: 49) | D/N/S-D/G/V/Y-P/N/S-G/Y-S/L/M-G/H/S-L/V/A/Y-W/Y/L/S (SEQ ID NO: 58) | A/G-PW-S/Q/F/A/L/V-GPSR-Y/E/F/V/D-L (SEQ ID NO: 67) |
| G/H-S/V-S/Q-Y/W-W/G-G/W (SEQ ID NO: 68) | | |

In certain embodiments, the non-naturally occurring chagasin scaffold protein that specifically binds human VEGF comprises an L2 that comprises the amino acid sequence SNLRSM (SEQ ID NO: 18), an L4 that comprises the amino acid sequence AGPSAVPL (SEQ ID NO: 24), and an L6 that comprises the amino acid sequence APWRGPANVI (SEQ ID NO: 30), with reference to SEQ ID NO: 2.

In certain embodiments, the non-naturally occurring chagasin scaffold protein that specifically binds human VEGF comprises an L2 that comprises the amino acid sequence SNYFYD (SEQ ID NO: 19), an L4 that comprises the amino acid sequence NDPGSRLS (SEQ ID NO: 25), and an L6 that comprises the amino acid sequence APWLGPSRVL (SEQ ID NO: 31), with reference to SEQ ID NO: 2.

In certain embodiments, the non-naturally occurring chagasin scaffold protein that specifically binds human VEGF comprises an L2 that comprises the amino acid sequence SNLQNA (SEQ ID NO: 20), an L4 that comprises the amino acid sequence LSLYASET (SEQ ID NO: 26), and an L6 that comprises the amino acid sequence NPNWGPDYWI (SEQ ID NO: 32), with reference to SEQ ID NO: 2.

In certain embodiments, the non-naturally occurring chagasin scaffold protein that specifically binds human VEGF comprises an L2 that comprises the amino acid sequence SNLQDS (SEQ ID NO: 21), an L4 that comprises the amino acid sequence SGTTGKSN (SEQ ID NO: 27); and an L6 that comprises the amino acid sequence FKSRGLMVPL (SEQ ID NO: 33), with reference to SEQ ID NO: 2.

In certain embodiments, the non-naturally occurring chagasin scaffold protein that specifically binds human VEGF comprises an L2 that comprises the amino acid sequence SNYRDS (SEQ ID NO: 22), an L4 that comprises the amino acid sequence VRAGQANE (SEQ ID NO: 28); and an L6 that comprises the amino acid sequence SPVLGPRFWL (SEQ ID NO: 34), with reference to SEQ ID NO: 2.

In certain embodiments, the non-naturally occurring chagasin scaffold protein that specifically binds human VEGF comprises an L2 that comprises the amino acid sequence SNYFYD (SEQ ID NO: 19), an L4 that comprises the amino acid sequence DDPGSGLW (SEQ ID NO: 50), and an L6 that comprises the amino acid sequence APWSGPSRYL (SEQ ID NO: 59), with reference to SEQ ID NO: 2.

In certain embodiments, the non-naturally occurring chagasin scaffold protein that specifically binds human VEGF comprises an L2 that comprises the amino acid sequence SNYFYE (SEQ ID NO: 42), an L4 that comprises the amino acid sequence NGPGLGVY (SEQ ID NO: 51); and an L6 that comprises the amino acid sequence APWQGPSREL (SEQ ID NO: 60), with reference to SEQ ID NO: 2.

In certain embodiments, the non-naturally occurring chagasin scaffold protein that specifically binds human VEGF comprises an L2 that comprises the amino acid sequence SNYYYD (SEQ ID NO: 48), an L4 that comprises the amino acid sequence NVNGSHAW (SEQ ID NO: 52); and an L6 that comprises the amino acid sequence APWSGPSRFL (SEQ ID NO: 61), with reference to SEQ ID NO: 2.

In certain embodiments, the non-naturally occurring chagasin scaffold protein that specifically binds human VEGF comprises an L2 that comprises the amino acid sequence SNYFCD (SEQ ID NO: 44), an L4 that comprises the amino acid sequence NYPGSGVL (SEQ ID NO: 53); and an L6 that comprises the amino acid sequence APWFGPSRVL (SEQ ID NO: 62), with reference to SEQ ID NO: 2.

In certain embodiments, the non-naturally occurring chagasin scaffold protein that specifically binds human VEGF that comprises an L2 that comprises the amino acid sequence SNYFCD (SEQ ID NO: 44), an L4 that comprises the amino acid sequence NYPGSGVL (SEQ ID NO: 53); and an L6 that comprises the amino acid sequence APWFGPSRVL (SEQ ID NO: 62), with reference to SEQ ID NO: 2 forms homodimers.

In certain embodiments, the non-naturally occurring chagasin scaffold protein that specifically binds human VEGF comprises an L2 that comprises the amino acid sequence SNYFND (SEQ ID NO: 45), an L4 that comprises the amino acid sequence GSSYWG (SEQ ID NO: 54), and an L6 that comprises the amino acid sequence APWAGPSRVL (SEQ ID NO: 63), with reference to SEQ ID NO: 2.

In certain embodiments, the non-naturally occurring chagasin scaffold protein that specifically binds human VEGF comprises an L2 that comprises the amino acid sequence SNYFYD (SEQ ID NO: 19), an L4 that comprises the amino acid sequence SGSYMSYS (SEQ ID NO: 55); and an L6 that comprises the amino acid sequence APWLGPSRDL (SEQ ID NO: 64), with reference to SEQ ID NO: 2.

In certain embodiments, the non-naturally occurring chagasin scaffold protein that specifically binds human VEGF comprises an L2 that comprises the amino acid sequence SNYFRE (SEQ ID NO: 47), an L4 that comprises the amino acid sequence HVQWGW (SEQ ID NO: 56); and an L6 that comprises the amino acid sequence APWVGPSREL (SEQ ID NO: 65), with reference to SEQ ID NO: 2.

In certain embodiments, the non-naturally occurring chagasin scaffold protein that specifically binds human VEGF comprises an L2 that comprises the amino acid sequence SNYYYD (SEQ ID NO: 48), an L4 that comprises the amino acid sequence HYYNLGGRYT (SEQ ID NO: 57); and an L6 that comprises the amino acid sequence GPWLGPSRVL (SEQ ID NO: 66), with reference to SEQ ID NO: 2.

In certain embodiments, the non-naturally occurring chagasin scaffold protein that specifically binds human VEGF comprises the amino acid sequence set forth in SEQ ID NO: 36. In certain embodiments, the non-naturally occurring chagasin scaffold protein that specifically binds human VEGF comprises the amino acid sequence set forth in SEQ ID NO: 37. In certain embodiments, the non-naturally occurring chagasin scaffold protein that specifically binds human VEGF comprises the amino acid sequence set forth in SEQ ID NO: 38. In certain embodiments, the non-naturally occurring chagasin scaffold protein that specifically binds human VEGF comprises the amino acid sequence set forth in SEQ ID NO: 39. In certain embodiments, the non-naturally occurring chagasin scaffold protein that specifically binds human VEGF comprises the amino acid sequence set forth in SEQ ID NO: 40. The sequences of SEQ ID NOs: 36-40 are provided below:

(SEQ ID NO: 36)
MSHKVTKAHN GATLTVAVGE LVEIQLPSNL RSMGFAWYFE

GGTKESPNES MFTVENKYFP AGPSAVPLGA GGTEHFHVTV

KAAGTHAVNL TYMAPWRGPA NVIERFTVYL KAN (SEQ ID NO: 37)
MSHKVTKAHN GATLTVAVGE LVEIQLPSNY FYDGFAWYFE

GGTKESPNES MFTVENKYFP NDPGSRLSGA GGTEHFHVTV

KAAGTHAVNL TYMAPWLGPS RVLERFTVYL KAN (SEQ ID NO: 38)
MSHKVTKAHN GATLTVAVGE LVEIQLPSNL QNAGFAWYFE

GGTKESPNES MFTVENKYFP LSLYASETGA GGTEHFHVTV

KAAGTHAVNL TYMNPNWGPD YWIERFTVYL KAN (SEQ ID NO: 39)
MSHKVTKAHN GATLTVAVGE LVEIQLPSNL QDSGFAWYFE

GGTKESPNES MFTVENKYFP SGTTGKSNGA GGTEHFHVTV

KAAGTHAVNL TYMFKSRGLM VPLERFTVYL KAN (SEQ ID NO: 40)
MSHKVTKAHN GATLTVAVGE LVEIQLPSNY RDSGFAWYFE

GGTKESPNES MFTVENKYFP VRAGQANEGA GGTEHFHVTV

KAAGTHAVNL TYMSPVLGPR FWLERFTVYL KAN

In certain embodiments, the non-naturally occurring chagasin scaffold protein that specifically binds human VEGF comprises the amino acid sequence set forth in SEQ ID NO: 69. In certain embodiments, the non-naturally occurring chagasin scaffold protein that specifically binds human VEGF comprises the amino acid sequence set forth in SEQ ID NO: 70. In certain embodiments, the non-naturally occurring chagasin scaffold protein that specifically binds human VEGF comprises the amino acid sequence set forth in SEQ ID NO: 71. In certain embodiments, the non-naturally occurring chagasin scaffold protein that specifically binds human VEGF comprises the amino acid sequence set forth in SEQ ID NO: 72. In certain embodiments, the non-naturally occurring chagasin scaffold protein that specifically binds human VEGF comprises the amino acid sequence set forth in SEQ ID NO: 73. In certain embodiments, the non-naturally occurring chagasin scaffold protein that specifically binds human VEGF comprises the amino acid sequence set forth in SEQ ID NO: 74. In certain embodiments, the non-naturally occurring chagasin scaffold protein that specifically binds human VEGF comprises the amino acid sequence set forth in SEQ ID NO: 75. In certain embodiments, the non-naturally occurring chagasin scaffold protein that specifically binds human VEGF comprises the amino acid sequence set forth in SEQ ID NO: 76. The sequences of SEQ ID NOs: 69-76 are provided below:

(SEQ ID NO: 69)
MSHKVTKAHN GATLTVAVGE LVEIQLPSNY FYDGFAWYFE

GGTKESPNES MFTVENKYFP DDPGSGLWGA GGTEHFHVTV

KAAGTHAVNL TYMAPWSGPS RYLERFTVYL KAN (SEQ ID NO: 70)
MSHKVTKAHN GATLTVAVGE LVEIQLPSNY FYEGFAWYFE

GGTKESPNES MFTVENKYFP NGPGLGVYGA GGTEHFHVTV

KAAGTHAVNL TYMAPWQGPS RELERFTVYL KAN (SEQ ID NO: 71)
MSHKVTKAHN GATLTVAVGE LVEIQLPSNY YYDGFAWYFE

GGTKESPNES MFTVENKYFP NVNGSHAWGA GGTEHFHVTV

KAAGTHAVNL TYMAPWSGPS RFLERFTVYL KAN (SEQ ID NO: 72)
MSHKVTKAHN GATLTVAVGE LVEIQLPSNY FCDGFAWYFE

GGTKESPNES MFTVENKYFP NYPGSGVLGA GGTEHFHVTV

KAAGTHAVNL TYMAPWFGPS RVLERFTVYL KAN (SEQ ID NO: 73)
MSHKVTKAHN GATLTVAVGE LVEIQLPSNY FNDGFAWYFE

GGTKESPNES MFTVENKYFP GSSYWGGAGG TEHFHVTVKA

AGTHAVNLTY MAPWAGPSRV LERFTVYLKA N (SEQ ID NO: 74)
MSHKVTKAHN GATLTVAVGE LVEIQLPSNY FYDGFAWYFE

GGTKESPNES MFTVENKYFP SGSYMSYSGA GGTEHFHVTV

KAAGTHAVNL TYMAPWLGPS RDLERFTVYL KAN (SEQ ID NO: 75)
MSHKVTKAHN GATLTVAVGE LVEIQLPSNY FREGFAWYFE

GGTKESPNES MFTVENKYFP HVQWGWGAGG TEHFHVTVKA

AGTHAVNLTY MAPWVGPSRE LERFTVYLKA N (SEQ ID NO: 76)
MSHKVTKAHN GATLTVAVGE LVEIQLPSNY YYDGFAWYFE

GGTKESPNES MFTVENKYFP HYYNLGGRYT GAGGTEHFHV

TVKAAGTHAV NLTYMGPWLG PSRVLERFTV YLKAN

In certain embodiments, the non-naturally occurring chagasin scaffold protein that specifically binds human VEGF competitively inhibits the binding of a second non-naturally occurring chagasin scaffold protein to human VEGF, wherein the second non-naturally occurring chagasin scaffold protein comprises an comprises an L2 that comprises the amino acid sequence SNYY-Y/K-D (SEQ ID NO: 114), an L4 that comprises the amino acid sequence HY-Y/Q/S/T-NLGGRYT (SEQ ID NO: 115); and an L6 that comprises the amino acid sequence GPWLGPSRVL (SEQ ID NO: 66), with reference to SEQ ID NO: 2. In certain embodiments, the non-naturally occurring chagasin scaffold protein that specifically binds human VEGF and competitively inhibits the binding of a second non-naturally occurring chagasin scaffold protein to human VEGF comprises an comprises an L2 that comprises the amino acid sequence SNYY-Y/K-D (SEQ ID NO: 114), an L4 that comprises the amino acid sequence HY-Y/Q/S/T-NLGGRYT (SEQ ID NO: 115); and an L6 that comprises the amino acid sequence GPWLGPSRVL (SEQ ID NO: 66), with reference to SEQ ID NO: 2.

In certain embodiments, the non-naturally occurring chagasin scaffold protein that specifically binds human VEGF competitively inhibits the binding of a second non-naturally occurring chagasin scaffold protein to human VEGF, wherein the second non-naturally occurring chagasin scaffold protein comprises an comprises an n L2 that comprises the amino acid sequence SNYY-Y/K-D (SEQ ID NO: 114), an L4 that comprises the amino acid sequence HY-Y/Q/S/T-NLGGRYT (SEQ ID NO: 115); and an L6 that comprises the amino acid sequence GPWLGPSRVL (SEQ ID NO: 66), with reference to SEQ ID NO: 2.

As noted elsewhere herein, non-naturally occurring chagasin scaffold proteins characterized by binding to overlapping or similar areas on a target can be identified by competitive inhibition/binding assays.

In certain embodiments, the non-naturally occurring chagasin scaffold protein specific for human VEGF comprises an L2, L4, and/or L6 of any one of the non-naturally occurring chagasin scaffold protein specific for human VEGF disclosed herein. Thus, in certain embodiments, the non-naturally occurring chagasin scaffold protein that specifically binds human VEGF comprises an L2 that comprises an amino acid sequence set forth in any one of SEQ ID NOs: 48 and 110, an L4 that comprises an amino acid sequence set forth in any one of SEQ ID NOs: 57 and 111-113; and an L6 that comprises an amino acid sequence set forth in SEQ ID NO: 66, with reference to SEQ ID NO: 2.

The L2, L4, and L6 amino acid sequences described above are provided in Table 4 below:

TABLE 4

| | |
|---|---|
| SNYYYD<br>SEQ ID NO: 48 | HYSNLGGRYT<br>SEQ ID NO: 112 |
| SNYYKD<br>SEQ ID NO: 110 | HYTNLGGRYT<br>SEQ ID NO: 113 |
| HYYNLGGRYT<br>SEQ ID NO: 57 | SNYY-Y/K-D<br>SEQ ID NO: 114 |
| HYQNLGGRYT<br>SEQ ID NO: 111 | HY-Y/Q/S/T-NLGGRYT<br>SEQ ID NO: 115 |

In certain embodiments, the non-naturally occurring chagasin scaffold protein that specifically binds human VEGF comprises an L2 that comprises the amino acid sequence SNYYKD (SEQ ID NO: 110), an L4 that comprises the amino acid sequence HYYNLGGRYT (SEQ ID NO: 57); and an L6 that comprises the amino acid sequence GPWLGPSRVL (SEQ ID NO: 66), with reference to SEQ ID NO: 2.

In certain embodiments, the non-naturally occurring chagasin scaffold protein that specifically binds human VEGF comprises an L2 that comprises the amino acid sequence SNYYYD (SEQ ID NO: 48), an L4 that comprises the amino acid sequence HYQNLGGRYT (SEQ ID NO: 111); and an L6 that comprises the amino acid sequence GPWLGPSRVL (SEQ ID NO: 66), with reference to SEQ ID NO: 2.

In certain embodiments, the non-naturally occurring chagasin scaffold protein that specifically binds human VEGF comprises an L2 that comprises the amino acid sequence SNYYYD (SEQ ID NO: 48), an L4 that comprises the amino acid sequence HYSNLGGRYT (SEQ ID NO: 112); and an L6 that comprises the amino acid sequence GPWLGPSRVL (SEQ ID NO: 66), with reference to SEQ ID NO: 2.

In certain embodiments, the non-naturally occurring chagasin scaffold protein that specifically binds human VEGF comprises an L2 that comprises the amino acid sequence SNYYYD (SEQ ID NO: 48), an L4 that comprises the amino acid sequence HYTNLGGRYT (SEQ ID NO: 113); and an L6 that comprises the amino acid sequence GPWLGPSRVL (SEQ ID NO: 66), with reference to SEQ ID NO: 2.

In certain embodiments, the non-naturally occurring chagasin scaffold protein that specifically binds human VEGF comprises the amino acid sequence set forth in SEQ ID NO: 116. In certain embodiments, the non-naturally occurring chagasin scaffold protein that specifically binds human VEGF comprises the amino acid sequence set forth in SEQ ID NO: 117. In certain embodiments, the non-naturally occurring chagasin scaffold protein that specifically binds human VEGF comprises the amino acid sequence set forth in SEQ ID NO: 118. In certain embodiments, the non-naturally occurring chagasin scaffold protein that specifically binds human VEGF comprises the amino acid sequence set forth in SEQ ID NO: 119. The sequences of SEQ ID NOs: 116-119 are provided below:

(SEQ ID NO: 116)
MSHKVTKAHN GATLTVAVGE LVEIQLPSNY YKDGFAWYFE

GGTKESPNES MFTVENKYFP HYYNLGGRYT GAGGTEHFHV

TVKAAGTHAV NLTYMGPWLG PSRVLERFTV YLKAN (SEQ ID NO: 117)
MSHKVTKAHN GATLTVAVGE LVEIQLPSNY YYDGFAWYFE

GGTKESPNES MFTVENKYFP HYQNLGGRYT GAGGTEHFHV

TVKAAGTHAV NLTYMGPWLG PSRVLERFTV YLKAN (SEQ ID NO: 118)
MSHKVTKAHN GATLTVAVGE LVEIQLPSNY YYDGFAWYFE

GGTKESPNES MFTVENKYFP HYSNLGGRYT GGAGTEHFHV

TVKAAGTHAV NLTYMGPWLG PSRVLERFTV YLKAN (SEQ ID NO: 119)
MSHKVTKAHN GATLTVAVGE LVEIQLPSNY YYDGFAWYFE

GGTKESPNES MFTVENKYFP HYTNLGGRYT GGAGTEHFHV

TVKAAGTHAV NLTYMGPWLG PSRVLERFTV YLKAN

In certain embodiments, the non-naturally occurring chagasin scaffold protein that specifically binds human VEGF is a variant of any one of the non-naturally occurring chagasin scaffold proteins that specifically bind human VEGF described herein. In certain embodiments, such a variant chagasin scaffold protein comprises at least 1, at least 2, at least 3, at least 4, at least 5, at least 6, at least 7, at least 8, at least 9, or at least 10 amino acid substitutions in one or more of SEQ ID NOs: 3, 4, 5, 7, 8, 9, 11, 12, 13, 19, 25, 31, 48, 57, and/or 66. In certain embodiments, the amino acid substitution(s) are conservative amino acid substitution(s). In certain embodiments, the amino acid substitutions do not substantially reduce the ability of the non-naturally occurring chagasin scaffold protein to specifically bind human VEGF. For example, conservative alterations (e.g., conservative substitutions as provided herein) that do not substantially reduce VEGF binding affinity may be made. The binding affinity of a variant chagasin scaffold protein that specifically binds human VEGF can be assessed using a method described in the Examples below.

As noted elsewhere herein, conservative substitutions are shown in Table 2 under the heading of "conservative substitutions." More substantial changes are provided in Table 2 under the heading of "exemplary substitutions," and as further described below in reference to amino acid side chain classes. Amino acid substitutions may be introduced into a variant chagasin scaffold protein and the products screened for a desired activity, e.g., retained/improved VEGF binding.

Non-conservative substitutions will entail exchanging a member of one of these classes for another class. An exemplary substitutional variant is an affinity matured chagasin scaffold protein that specifically binds VEGF, which may be conveniently generated, e.g., using phage display based affinity maturation techniques such as those described herein. Briefly, one or more residues in L2, L4, and/or L6 are altered (i.e., added, deleted, or substituted) and the variant chagasin scaffold protein displayed on phage and screened for VEGF binding affinity. In certain embodiments of affinity maturation, diversity is introduced into the variable genes chosen for maturation by any of a variety of methods (e.g., error-prone PCR, loop shuffling, or oligonucleotide-directed mutagenesis). A secondary library is then created. The library is then screened to identify any chagasin scaffold protein variants with the desired affinity for VEGF. In certain embodiments, introducing diversity involves loop-directed approaches, in which several residues in L2, L4, and/or L6 (e.g., 4-6 residues at a time) are randomized. L2, L4, and/or L6 residues involved in binding a target ligand may be specifically identified, e.g., using alanine scanning mutagenesis or modeling. In certain embodiments, that non-naturally occurring chagasin scaffold protein that specifically binds VEGF in which one or more residues in L2, L4, and/or L6 is altered for the purpose of generating affinity matured chagasin scaffold proteins that specifically bind VEGF comprises the amino acid sequence set forth in SEQ ID NO: 37. In certain embodiments, that non-naturally occurring chagasin scaffold protein that specifically binds VEGF in which one or more residues in L2, L4, and/or L6 is altered for the purpose of generating affinity matured chagasin scaffold proteins that specifically bind VEGF comprises the amino acid sequence set forth in SEQ ID NO: 76.

In certain embodiments, non-naturally occurring chagasin scaffold protein that specifically binds human VEGF has a stronger binding affinity for a VEGF than it has for a homologue of that VEGF, such as VEGF-B or VEGF-C, or other growth factors such as P1GF, PDGF or bFGF. Normally, non-naturally occurring chagasin scaffold protein that "specifically binds" human VEGF, i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a homologue of that VEGF or other growth factor which is at least about 50-fold, or at least about 500-fold, or at least about 1000-fold, weaker than its binding affinity for VEGF.

In certain embodiments, the extent of binding of the non-naturally occurring chagasin scaffold protein that specifically binds human VEGF to a non-target ligand (such as such as VEGF-B or VEGF-C, or other growth factors such as P1GF, PDGF or bFGF) is less than about 10% of the binding of the non-naturally occurring chagasin scaffold protein to human VEGF as determined by methods known in the art, such as ELISA, fluorescence activated cell sorting (FACS) analysis, or radioimmunoprecipitation (RIA). Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

In certain embodiments, the non-naturally occurring chagasin scaffold protein that specifically binds VEGF binds a human VEGF with a Kd between about 1 pM to about 500 nM. In certain embodiments, the non-naturally occurring chagasin scaffold protein that specifically binds VEGF binds a human VEGF with a Kd between about 1 pM to about 50 pM, between about 50 pM to about 250 pM, between about 250 pM to about 500 pM, between about 500 pM to 750 pM, between about 750 pM to about 1 nM, between about 1 nM to about 25 nM, between about 25 nM to about 50 nM, between 50 nM to about 100 nM, between about 100 nM to about 250 nM, or between about 250 nM to about 500 nM.

Nucleic acid molecules encoding the non-naturally occurring chagasin scaffold proteins described herein that specifically bind VEGF, expression vectors comprising nucleic acid molecules encoding the non-naturally occurring chagasin scaffold proteins described herein that specifically bind VEGF, and cells comprising the nucleic acid molecules are also contemplated. Also provided herein are methods of producing a non-naturally occurring chagasin scaffold protein described herein that specifically binds VEGF by culturing such cells, expressing the non-naturally occurring chagasin scaffold protein, and recovering the non-naturally occurring chagasin scaffold protein from the cell culture.

In certain embodiments, a non-naturally occurring chagasin scaffold protein that specifically binds VEGF can be produced via in vitro translation, as described elsewhere herein.

As described elsewhere herein, a non-naturally occurring chagasin scaffold protein that specifically binds VEGF can also be generated via chemical peptide synthesis, e.g., by grafting chemically synthesized L2, L4, and/or L6 peptides onto a chagasin framework.

Chimeric Molecules Comprising a Non-Naturally Occurring Chagasin Scaffold Protein A non-naturally occurring chagasin scaffold protein described herein (such as a chagasin scaffold protein that specifically binds LRP6 and/or a chagasin scaffold protein specifically binds VEGF) can also be modified if advantageous in a way to form a chimeric molecule comprising the chagasin scaffold protein fused (e.g., recombinantly fused) to another, heterologous polypeptide or amino acid sequence. In certain embodiments, such a chimeric molecule comprises a fusion of a non-naturally occurring chagasin scaffold protein described herein with an antibody to form, e.g., a divalent molecule or a bispecific molecule. In certain embodiments, such a chimeric molecule comprises a fusion of a non-naturally occurring chagasin scaffold protein described herein with a protein transduction domain which targets the polypeptide for delivery to various tissues and more particularly across the brain blood barrier, using, for example, the protein transduction domain of human immunodeficiency virus TAT protein (Schwarze et al., 1999, *Science* 285:1569-72).

In certain embodiments, a chimeric molecule comprises a fusion of a non-naturally occurring chagasin scaffold protein described herein with a cell-penetrating peptide (CPP) to facilitate delivery of the non-naturally occurring chagasin scaffold protein into the cytosol, the nucleus or other cellular compartments. CPPs (also referred to as protein transduction domains (PTDs), membrane translocating sequences (MTSs), or Trojan peptides) are a class of peptides with the ability to convey various, otherwise impermeable, macromolecules across the plasma membrane of cells in a relatively non-toxic fashion. The CPP peptides are typically between 5 and about 30 amino acids (aa) in length with a cationic, amphipathic, or hydrophobic nature. Notable examples of cell-penetrating peptides that can be fused to a non-naturally occurring chagasin scaffold protein provided herein include, e.g., Tat from HIV-1, Penetratin, and Transportan. (Fawell, S. et al. Proc. Natl. Acad. Sci. 1994, pp 664-668; Theodore, L. et al. J. Neurosci. 1995, pp 7158-7167; Pooga, M. et al. FASEB J. 1998, pp 67-77). Other examples of CPPs include, but are not limited to, e.g., antennapedia, poly-cationic peptides, etc. or derivatives of such peptides as described in, e.g., van den Berg et al, *Curr Opin Biotechnol* 22, 1-6, 2011). In certain embodiments, the CPP is recombinantly fused to the N-terminus of a non-naturally occurring chagasin scaffold protein provided herein. In certain embodiments, the CPP is recombinantly fused to the C-terminus of a non-naturally occurring chagasin scaffold protein provided herein.

In certain embodiments, a chimeric molecule comprises a fusion of a non-naturally occurring chagasin scaffold protein described herein with a signal sequence to facilitate the localization of the non-naturally occurring chagasin scaffold protein to, e.g., the endoplasmic reticulum, the golgi apparatus, endosomes, etc. In certain embodiments, a chimeric molecule comprises a fusion of a non-naturally occurring chagasin scaffold protein described herein with a signal sequence to facilitate the secretion of the non-naturally occurring chagasin scaffold protein.

In certain embodiments, the non-naturally occurring chagasin scaffold proteins provided herein can be used as bi- or multi-specific (for different target ligands or different epitopes on the same target ligand) in multimer form. For example, a dimeric bispecific non-naturally occurring chagasin scaffold protein has one subunit with specificity for a first target ligand or epitope and a second subunit with specificity for a second target ligand or epitope. Non-naturally occurring chagasin scaffold protein subunits can be joined in a variety of conformations that can increase the valency and thus the avidity of binding to a target ligand.

In certain embodiments a chimeric molecule provided herein comprises two or more (such as three, four, five, six, seven, eight, nine, ten, or more than ten) non-naturally occurring chagasin scaffold proteins. In certain embodiments, a nucleic acid can be engineered to encode two or more copies of a single non-naturally occurring chagasin scaffold protein, which copies are transcribed and translated in tandem to produce a covalently linked multimer of identical scaffold subunits. In certain embodiments, the nucleic acid can be engineered to encode two or more different non-naturally occurring chagasin scaffold proteins, which copies are transcribed and translated in tandem to produce a covalently linked multimer of different scaffold subunits that bind, e.g., different epitopes of a single target ligand, or, e.g., different target ligands. In another embodiment, such a chimeric molecule comprises a fusion of a non-naturally occurring chagasin scaffold protein described herein (such as a chagasin scaffold protein that specifically binds LRP6 and/or a chagasin scaffold protein specifically binds VEGF) with a tag polypeptide which provides an epitope to which an anti-tag antibody can selectively bind. The epitope tag is generally placed at the amino- or carboxyl-terminus of the chagasin scaffold protein. The presence of such epitope-tagged forms of the non-naturally occurring chagasin scaffold protein can be detected using an antibody against the tag polypeptide. Also, provision of the epitope tag enables the chagasin scaffold protein to be readily purified by affinity purification using an anti-tag antibody or another type of affinity matrix that binds to the epitope tag. Various tag polypeptides and their respective antibodies are known in the art. Examples include poly-histidine (poly-His) or poly-histidine-glycine (poly-His-Gly) tags; the flu HA tag polypeptide and its antibody 12CA5 (Field et al. (1988) *Mol. Cell. Biol.* 8, 2159-2165); the c-myc tag and the 8F9, 3C7, 6E10, G4, B7 and 9E10 antibodies thereto (Evan et al. (1985) *Mol. Cell. Biol.* 5, 3610-3616]; and the Herpes Simplex virus glycoprotein D (gD) tag and its antibody (Paborsky et al. (1990) *Protein Eng.,* 3, 547-553). Other tag polypeptides include the Flag-peptide (Hopp et al. (1988) *BioTechnology,* 6, 1204-1210); the KT3 epitope peptide (Martin et al. (1992) *Science,* 255, 192-194]; an α-tubulin epitope peptide (Skinner et al. (1991) *J. Biol. Chem.* 266, 15163-15166); and the T7 gene 10 protein peptide tag (Lutz-Freyermuth et al. (1990) *Proc. Natl. Acad. Sci. USA* 87, 6393-6397].

In certain embodiments, the chimeric molecule can comprise a fusion of a non-naturally occurring chagasin scaffold protein described herein (such as a chagasin scaffold protein that specifically binds LRP6 and/or a chagasin scaffold protein specifically binds VEGF) with an immunoglobulin or a particular region of an immunoglobulin. For a bivalent form of the chimeric molecule (e.g., an "immunoadhesin"), such a fusion could be to the Fc region of an IgG molecule. Ig fusions provided herein include polypeptides that comprise approximately or only residues 94-243, residues 33-53 or residues 33-52 of human in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also, U.S. Pat. No. 5,428,130 issued Jun. 27, 1995. In certain embodiments, a non-naturally occurring chagasin scaffold protein described herein (such as a chagasin scaffold protein that specifically binds LRP6 and/or a chagasin scaffold protein specifically binds VEGF) is fused, e.g., at the N or C terminus, to the constant region of an IgG (Fc). In certain embodiments, the chagasin scaffold protein/Fc fusion molecule activates the complement component of the immune response. In certain embodiments, the chagasin scaffold protein/Fc fusion protein increases the therapeutic value of the chagasin scaffold protein. In certain embodiments, a non-naturally occurring chagasin scaffold protein described herein (such as a chagasin scaffold protein that specifically binds LRP6 and/or a chagasin scaffold protein that specifically binds VEGF) is fused (such as recombinantly fused), e.g., at the N or C terminus, to a complement protein, such as C1q. Various publications describe methods for obtaining non-naturally occurring chagasin scaffold proteins whose half-lives are modified either by introducing an FcRn-binding polypeptide into the molecules (WO 1997/43316, U.S. Pat. Nos. 5,869,046, 5,747,035, WO 1996/32478, WO 1991/14438) or by fusing the non-naturally occurring chagasin scaffold proteins with antibodies whose FcRn-binding affinities are preserved but affinities for other Fc receptors have been greatly reduced (WO 1999/43713) or fusing with FcRn binding domains of antibodies (WO 2000/09560, U.S. Pat. No. 4,703,039). Specific techniques and methods of increasing half-life of physiologically active molecules (e.g., non-naturally occurring chagasin scaffold proteins) can also be found in U.S. Pat. No. 7,083,784. In certain embodiments, a non-naturally occurring chagasin scaffold protein described herein (such as a chagasin scaffold protein that specifically binds LRP6 and/or a chagasin scaffold protein specifically binds VEGF) is fused to an Fc region from an IgG that comprises an amino acid residue mutations (as numbered by the EU index in Kabat): M252Y/S254T/T256E or H433KJN434F/Y436H.

In certain embodiments, non-naturally occurring chagasin scaffold proteins described herein (such as those that specifically bind LRP6 and/or those that specifically bind VEGF) are fused with molecules that increase or extend in vivo or serum half-life. In certain embodiments, a non-naturally occurring chagasin scaffold protein described herein (such as a non-naturally occurring chagasin scaffold protein that specifically binds LRP6 and/or a non-naturally occurring chagasin scaffold protein that specifically binds VEGF) is fused with albumin, such as human serum albumin (HSA), polyethylene glycol (PEG), polysaccharides, immunoglobulin molecules (IgG), complement, hemoglobin, a binding peptide, lipoproteins or other factors to increase its half-life in the bloodstream and/or its tissue penetration.

Additional chimeric molecules comprising chagasin scaffold proteins may be generated through the techniques of gene-shuffling, motif-shuffling, exon-shuffling, and/or codon-shuffling (collectively referred to as "DNA shuffling"). DNA shuffling may be employed to alter the activities of scaffolds provided herein (e.g., scaffolds with higher affinities and lower dissociation rates). See, generally, U.S. Pat. Nos. 5,605,793, 5,811,238, 5,830,721, 5,834,252, 5,837,458, Patten et al. (1997) Curr. Opinion Biotechnol. 8, 724-33; Harayama (1998) Trends Biotechnol. 16, 76-82; Hansson, et al., (1999) J. Mol. Biol. 287, 265-76; and Lorenzo and Blasco, (1998) Biotechniques 24, 308-313

In certain embodiments, a non-naturally occurring chagasin scaffold protein encompassed herein is altered by being subjected to random mutagenesis by error-prone PCR, random nucleotide insertion or other methods prior to recombination. One or more portions of a polynucleotide encoding a scaffold that binds to a specific target may be recombined with one or more components, motifs, sections, parts, domains, fragments, etc. of one or more heterologous molecules.

Any of these fusions can generated by standard techniques, for example, by expression of the fusion protein from a recombinant fusion gene constructed using publicly available gene sequences.

Conjugates Comprising a Non-Naturally Occurring Chagasin Scaffold Protein

Also provided herein are immunoconjugates comprising a non-naturally occurring chagasin scaffold protein described herein (such as a chagasin scaffold protein that specifically binds LRP6 and/or a chagasin scaffold protein that specifically binds VEGF) conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes. Other toxins include maytansine and maytansinoids, calicheamicin and other cytotoxic agents. A variety of radionuclides are available for the production of radioconjugated chagasin scaffold proteins. Examples include $^{212}$Bi, $^{131}$I, $^{131}$In, $^{90}$Y, and $^{186}$Re.

Conjugates of a non-naturally occurring chagasin scaffold protein described herein (such as a chagasin scaffold protein that specifically binds LRP6 and/or a chagasin scaffold protein that specifically binds VEGF) and, e.g., cytotoxic agent, are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bisdiazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionuclide to the non-naturally occurring chagasin scaffold protein. See, WO94/11026.

In another embodiment, the non-naturally occurring chagasin scaffold protein described herein (such as a chagasin scaffold protein that specifically binds LRP6 and/or a chagasin scaffold protein that specifically binds VEGF) can be conjugated to a "receptor" (such as streptavidin) for utilization in tumor pre-targeting wherein the non-naturally occurring chagasin scaffold protein-receptor conjugate is administered to the patient, followed by removal of unbound conjugate from the circulation using a clearing agent and then administration of a "ligand" (e.g., avidin) that is conjugated to a cytotoxic agent (e.g., a radionuclide).

In certain embodiments, the non-naturally occurring chagasin scaffold proteins provided herein can be used as bi- or multi-specific (for different target ligands or different epitopes on the same target ligand) in multimer form. The attachments may be covalent or non-covalent. For example, a dimeric bispecific non-naturally occurring chagasin scaffold protein has one subunit with specificity for a first target ligand or epitope and a second subunit with specificity for a second target ligand or epitope. Non-naturally occurring chagasin scaffold protein subunits can be joined, e.g., via conjugation, in a variety of conformations that can increase the valency and thus the avidity of binding to a target ligand or to bind multiple target ligands. For example, amino acid alterations (e.g., additions, deletions, and/or substitutions) can be introduced into L1, L3, and/or L5 of a non-naturally occurring chagasin scaffold protein, e.g., to create a bispecific molecule or to add a linker. In certain embodiments L1, L3, and/or L5 are engineered to bind to a different epitope on the same target bound by L2, L4, and/or L6. In certain embodiments, L1, L3, and/or L5 are engineered to bind a different target ligand than the target ligand bound by L2, L4, and/or L6.

In certain embodiments, non-naturally occurring chagasin scaffold proteins provided herein are engineered to provide reactive groups for conjugation. In certain embodiments, the N-terminus and/or C-terminus may also serve to provide reactive groups for conjugation. In certain embodiments, the N-terminus is conjugated to one moiety (such as, but not limited to PEG) while the C-terminus is conjugated to another moiety (such as, but not limited to biotin), or vice versa.

Provided herein is the use of a non-naturally occurring chagasin scaffold protein described herein (such as a chagasin scaffold protein that specifically binds LRP6 and/or a chagasin scaffold protein that specifically binds VEGF) conjugated to one or more moieties, including but not limited to, peptides, polypeptides, proteins, fusion proteins, nucleic acid molecules, small molecules, mimetic agents, synthetic drugs, inorganic molecules, and organic molecules. Also provided herein is the use of a non-naturally occurring chagasin scaffold protein described herein (such as a chagasin scaffold protein that specifically binds LRP6 and/or a chagasin scaffold protein that specifically binds VEGF) chemically conjugated (including both covalent and non-covalent conjugations) to a heterologous protein or polypeptide (or fragment thereof, to a polypeptide of at least 10, at least 20, at least 30, at least 40, at least 50, at least 60, at least 70, at least 80, at least 90 or at least 100 amino acids). The fusion does not necessarily need to be direct, but may occur through linker sequences described herein.

In certain embodiments, a non-naturally occurring chagasin scaffold protein described herein (such as a chagasin scaffold protein that specifically binds LRP6 and/or a chagasin scaffold protein that specifically binds VEGF), or analogs or derivatives thereof may be conjugated to a diagnostic or detectable agent. Such chagasin scaffold proteins can be useful for monitoring or prognosing the development or progression of a disease as part of a clinical testing procedure, such as determining the efficacy of a particular therapy. Such diagnosis and detection can be accomplished by coupling the scaffold to detectable substances including, but not limited to various enzymes, such as but not limited to horseradish peroxidase, alkaline phosphatase, beta-galactosidase, or acetylcholinesterase; prosthetic groups, such as but not limited to streptavidinIbiotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I) carbon ($^{14}$C), sulfur ($^{35}$S), tritium ($^{3}$H), indium ($^{115}$In, $^{113}$In, $^{112}$In, $^{111}$In,), and technetium ($^{99}$Tc), thallium ($^{201}$Ti), gallium ($^{68}$Ga, $^{67}$Ga), palladium ($^{103}$Fa) molybdenum ($^{99}$Mo), xenon ($^{133}$Xe), fluorine ($^{18}$F), $^{1535}$M, $^{177}$Lu, $^{159}$Gd, $^{149}$Pm, $^{140}$La, $^{175}$Yb, $^{166}$Ho, $^{90}$Y, $^{47}$Sc $^{186}$Re, $^{188}$Re, $^{142}$Pr $^{105}$Rh, $^{97}$Ru, $^{68}$Ge $^{57}$Co, $^{65}$Zn, $^{855}$R, $^{32}$P, $^{153}$Gd, $^{169}$Yb, $^{51}$Cr, $^{54}$Mn, $^{75}$Se, $^{113}$Sn, and $^{117}$Tn; positron emitting metals using various positron emission tomographies, non-radioactive paramagnetic metal ions, and molecules that are radiolabelled or conjugated to specific radioisotopes.

Further, provided herein are uses of a non-naturally occurring chagasin scaffold protein described herein (such as a chagasin scaffold protein that specifically binds LRP6 and/or a chagasin scaffold protein that specifically binds VEGF) conjugated to a therapeutic moiety. In certain embodiments, a chagasin scaffold protein may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

In certain embodiments, a non-naturally occurring chagasin scaffold protein described herein (such as a chagasin scaffold protein that specifically binds LRP6 and/or a chagasin scaffold protein that specifically binds VEGF) is conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$Lu, $^{131}$Y, $^{131}$Ho, $^{131}$Sm, to polypeptides. In certain embodiments, the macrocyclic chelator is 1, 4, 7, 10-tetraazacyclododecane-N,N', N",N'''-tetra-acetic acid (DOTA) which can be attached to the chagasin scaffold protein via a linker molecule. Such linker molecules are commonly known in the art and described in, e.g., Denardo et al. (1998) Clin Cancer Res. 4, 2483-90; Peterson et al. (1999) Bioconjug. Chem. 10, 553-557; and Zimmerman et al. (1999) Nucl. Med. Biol. 26, 943-50.

Techniques for conjugating therapeutic moieties to antibodies are well known and can be applied to the non-naturally occurring chagasin scaffold proteins disclosed herein, see, e.g., Amon et al., "Monoclonal Antibodies For Immunotargeting Of Drugs In Cancer Therapy," in Monoclonal Antibodies And Cancer Therapy, Reisfeld et al. (eds.), pp. 243-56. (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radio labeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58. Similar approaches may be adapted for use with chagasin scaffold proteins of the invention.

The therapeutic moiety or drug conjugated to a non-naturally occurring chagasin scaffold protein described herein (such as a chagasin scaffold protein that specifically binds LRP6 and/or a chagasin scaffold protein that specifically binds VEGF) should be chosen to achieve the desired prophylactic or therapeutic effect(s) for a particular disorder in a subject. A clinician or other medical personnel should consider the following when deciding on which therapeutic moiety or drug to conjugate to a scaffold: the nature of the disease, the severity of the disease, and the condition of the subject.

In certain embodiments, non-naturally occurring chagasin scaffold proteins described herein (such as a chagasin scaffold proteins that specifically bind LRP6 and/or a chagasin scaffold proteins that specifically bind VEGF) can also be attached to solid supports, which are particularly useful for immunoassays or purification of the target ligand. Such solid supports include, but are not limited to, glass, cellulose, polyacrylamide, nylon, polystyrene, polyvinyl chloride or polypropylene.

Covalent Modifications

Covalent modifications of non-naturally occurring chagasin scaffold proteins described herein (such as a chagasin scaffold proteins that specifically bind LRP6 and/or a chagasin scaffold proteins that specifically bind VEGF) are included within the scope of this invention. One type of covalent modification includes reacting targeted amino acid residues of a non-naturally occurring chagasin scaffold protein with an organic derivatizing agent that is capable of reacting with selected side chains or the N- or C-terminal residues of the chagasin scaffold protein. Derivatization with bifunctional agents is useful, for instance, for crosslinking the non-naturally occurring chagasin scaffold protein to a water-insoluble support matrix or surface for use in the method for purifying target ligand, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), bifunctional maleimides such as bis-N-maleimido-1,8-octane and agents such as methyl-3-[(p-azidophenyl)-dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification of a chagasin scaffold protein comprises linking the chagasin scaffold protein to one of a variety of nonproteinaceous polymers, e.g., polyethylene glycol (PEG), polypropylene glycol, or polyoxyalkylenes, in the manner set forth in U.S. Pat. Nos. 4,640,835, 4,496,689, 4,301,144, 4,670,417, 4,791,192 or U.S. Pat. No. 4,179,337

The term "polyethylene glycol" or "PEG" means a polyethylene glycol compound or a derivative thereof, with or without coupling agents, coupling or activating moieties (e.g., with thiol, triflate, tresylate, azirdine, oxirane, N-hydroxysuccinimide or a maleimide moiety). The term "PEG" is intended to indicate polyethylene glycol of a molecular weight between 500 and 150,000 Da, including analogues thereof, wherein for instance the terminal OR-group has been replaced by a methoxy group (referred to as mPEG).

In certain embodiments, non-naturally occurring chagasin scaffold proteins described herein (such as those that specifically bind LRP6 and/or those that specifically bind VEGF) are derivatized with polyethylene glycol (PEG). PEG is a linear, water-soluble polymer of ethylene oxide repeating units with two terminal hydroxyl groups. PEGs are classified by their molecular weights which typically range from about 500 daltons to about 40,000 daltons. In a presently preferred embodiment, the PEGs employed have molecular weights ranging from 5,000 daltons to about 20,000 daltons. PEGs coupled to the scaffolds provided herein can be either branched or unbranched (for example, Monfardini, C. et al. 1995 Bioconjugate Chem 6:62-69). PEGs are commercially available from Nektar Inc., Sigma Chemical Co. and other companies. Such PEGs include, but are not limited to, monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), and monomethoxypolyethylene glycol-imidazolyl-carbonyl (MePEG-IM).

In certain embodiments, the hydrophilic polymer which is employed, for example, PEG, is capped at one end by an unreactive group such as a methoxy or ethoxy group. Thereafter, the polymer is activated at the other end by reaction with a suitable activating agent, such as cyanuric halides (for example, cyanuric chloride, bromide or fluoride), diimadozle, an anhydride reagent (for example, a dihalosuccinic anhydride, such as dibromosuccinic anhydride), acyl azide, p-diazoiumbenzyl ether, 3-(p-diazoniumphenoxy)-2-hydroxypropylether) and the like. The activated polymer is then reacted with a non-naturally occurring chagasin scaffold proteins described herein (such as those that specifically bind LRP6 and/or those that specifically bind VEGF) to produce a chagasin scaffold protein derivatized with a polymer. Alternatively, a functional group in the non-naturally occurring chagasin scaffold proteins provided herein can be activated for reaction with the polymer, or the two groups can be joined in a concerted coupling reaction using known coupling methods. It will be readily appreciated that the non-naturally occurring chagasin scaffold proteins provided herein can be derivatized with PEG using a myriad of other reaction schemes known to and used by those of skill in the art.

Immunoliposomes

Non-naturally occurring chagasin scaffold proteins disclosed herein (such as those that specifically bind LRP6 or those that specifically bind VEGF) can also be formulated as immunoliposomes. Liposomes containing a non-naturally occurring chagasin scaffold protein described herein are prepared by methods known in the art, such as described in Epstein et al., Proc Natl Acad Sci USA, 82: 3688 (1985); Hwang et al., Proc Natl Acad Sci USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. An anti-neoplastic agent, a growth inhibitory agent, or a chemotherapeutic agent (such as doxorubicin) is optionally also contained within the liposome. See, Gabizon et al., *J. National Cancer Inst.*, 81(19):1484 (1989).

Methods of Treatment

Diseases and Disorders Associated with LRP6

Non-naturally occurring chagasin scaffold proteins that specifically bind LRP6 and/or compositions provided herein comprising such chagasin scaffold proteins can be administered to subjects (e.g., mammals such as humans) to treat diseases and disorders involving abnormal LRP6 activity, including, for example, cancer and metastatic disease, osteoporosis and other bone metabolism and disease, neuronal and neurodegenerative disease, rheumatoid arthritis and other inflammatory disease, as described elsewhere herein. In certain embodiments, provided are non-naturally occurring chagasin scaffold proteins that specifically bind LRP6 for use in the manufacture of a medicament for the treatment of cancer and metastatic disease, osteoporosis and other bone metabolism and disease, neuronal and neurodegenerative disease, rheumatoid arthritis and other inflammatory disease in a subject. In certain embodiments, provided are non-naturally occurring chagasin scaffold proteins that specifically bind LRP6 for use in treating cancer and metastatic disease, osteoporosis and other bone metabolism and disease, neuronal and neurodegenerative disease, rheumatoid arthritis and other inflammatory disease in a subject. In certain embodiments, the subject to be treated is a mammal (e.g., human, non-human primate, rat, mouse, cow, horse, pig, sheep, goat, dog, cat, etc.). In certain embodiments, the subject is a human. In certain embodiments, the subject is a clinical patient, a clinical trial volunteer, an experimental animal, etc. In certain embodiments, the subject is suspected of having or at risk for having cancer, metastatic disease, osteoporosis, a bone metabolism disease, a neuronal disease, a neurodegenerative disease, rheumatoid arthritis or other inflammatory disease, or be diagnosed with a cancer, metastatic disease, osteoporosis, a bone metabolism disease, a neuronal disease, a neurodegenerative disease, rheumatoid arthritis or other inflammatory disease or any other disease having abnormal LRP6 expression or activity.

Diseases and Disorders Associated with VEGF

Non-naturally occurring chagasin scaffold proteins that specifically bind VEGF and/or compositions provided herein comprising such chagasin scaffold proteins can be administered to subjects (e.g., mammals such as humans) to treat diseases and disorders involving abnormal VEGF activity, including, for example diseases and disorders involving abnormal angiogenesis and/or abnormal vascular permeability. Excessive, inappropriate or uncontrolled angiogenesis occurs when there is new blood vessel growth that contributes to the worsening of the diseased state or cause of a diseased state, such as in cancer, especially vascularized solid tumors and metastatic tumors (including colon, lung cancer (especially small-cell lung cancer), or prostate cancer), diseases caused by ocular neovascularisation, especially diabetic blindness, retinopathies, primarily diabetic retinopathy or age-induced macular degeneration, choroidal neovascularization (CNV), diabetic macular edema, pathological myopia, von Rippel-Lindau disease, histoplasmosis of the eye, retinal vein occlusion (both branched retinal vein occlusion (BRVO) and central retinal vein occlusion (CRVO)), corneal neovascularization, retinal neovascularization and rubeosis; psoriasis, psoriatic arthritis, haemangioblastoma such as haemangioma; inflammatory renal diseases, such as glomerulonephritis, especially mesangioproliferative glomerulonephritis, haemolytic uremic syndrome, diabetic nephropathy or hypertensive nephrosclerosis; various inflammatory diseases, such as arthritis, especially rheumatoid arthritis, inflammatory bowel disease, psorsasis, sarcoidosis, arterial arteriosclerosis and diseases occurring after transplants, endometriosis or chronic asthma. The new blood vessels can feed the diseased tissues, destroy normal tissues, and in the case of cancer, the new vessels can allow tumor cells to escape into the circulation and lodge in other organs (tumor metastases). Undesirable vascular permeability is associated with, e.g., edema associated with brain tumors, ascites associated with malignancies, Meigs' syndrome, lung inflammation, nephrotic syndrome, pericardial effusion, pleural effusion, permeability associated with cardiovascular diseases such as the condition following myocardial infarctions and strokes and the like.

In certain embodiments, provided are non-naturally occurring chagasin scaffold proteins that specifically bind VEGF for use in the manufacture of a medicament for the treatment of a disease or disorder characterized by abnormal angiogenesis and/or abnormal vascular permeability in a subject. In certain embodiments, provided are non-naturally occurring chagasin scaffold proteins that specifically bind VEGF for use in treating disease or disorder characterized by abnormal angiogenesis and/or abnormal vascular permeability in a subject. In certain embodiments, the subject to be treated is a mammal (e.g., human, non-human primate, rat, mouse, cow, horse, pig, sheep, goat, dog, cat, etc.). In certain embodiments, the subject is a human. In certain embodiments, the subject is a clinical patient, a clinical trial volunteer, an experimental animal, etc. In certain embodiments, the subject is suspected of having or at risk for having a disease or disorder associated with abnormal angiogenesis and/or abnormal vascular permeability (such as those described herein) or be diagnosed with a disease or disorder associated with abnormal angiogenesis and/or abnormal vascular permeability (such as those described herein), or any other disease having abnormal VEGF expression or activity.

Administration and Dosing

Administration of a non-naturally occurring chagasin scaffold protein described herein (such as a non-naturally occurring chagasin scaffold protein that specifically binds LRP6 and/or a non-naturally occurring chagasin scaffold protein that specifically binds VEGF) or a composition comprising such a chagasin scaffold protein can be by any suitable route including, e.g., intravenous, intramuscular, or subcutaneous. In certain embodiments, the non-naturally occurring chagasin scaffold protein described herein (such as a non-naturally occurring chagasin scaffold protein that specifically binds LRP6 and/or a non-naturally occurring chagasin scaffold protein that specifically binds VEGF) and/or compositions provided herein are administered in combination with a second, third, or fourth agent (including, e.g., an antineoplastic agent, a growth inhibitory agent, a cytotoxic agent, or a chemotherapeutic agent) to treat the diseases or disorders involving, e.g., abnormal LRP6 activity or abnormal VEGF activity. For diseases involving abnormal LRP6 activity, such agents include those described in, e.g., US 2012/0100562 and US 2011/0256127. In certain embodiments, the non-naturally occurring chagasin scaffold that specifically binds LRP6 is conjugated to the additional agent. For diseases involving abnormal VEGF activity, such agents include, e.g., chemotherapeutic agents or other anti-angiogenic molecules. In certain embodiments, the non-naturally occurring chagasin scaffold that specifically binds VEGF is conjugated to the additional agent.

A non-naturally occurring chagasin scaffold protein described herein (such as a non-naturally occurring chagasin scaffold protein that specifically binds LRP6 and/or a non-naturally occurring chagasin scaffold protein that specifically binds VEGF) and/or a composition described herein can be administered to an individual via any route, including, but not limited to, intravenous (e.g., by infusion pumps), intraperitoneal, intraocular, intra-arterial, intrapulmonary, oral, inhalation, intravesicular, intramuscular, intra-tracheal, subcutaneous, intraocular, intrathecal, transdermal, transpleural, intraarterial, topical, inhalational (e.g., as mists of sprays), mucosal (such as via nasal mucosa), subcutaneous, transdermal, gastrointestinal, intraarticular, intracisternal, intraventricular, rectal (i.e., via suppository), vaginal (i.e., via pessary), intracranial, intraurethral, intrahepatic, and intratumoral. In some embodiments, a non-naturally occurring chagasin scaffold protein described herein (such as a non-naturally occurring chagasin scaffold protein that specifically binds LRP6 and/or a non-naturally occurring chagasin scaffold protein that specifically binds VEGF) is administered systemically (for example by intravenous injection). In some embodiments, the chagasin scaffold proteins or compositions provided herein are administered locally (for example by intraarterial or intraocular injection).

In some embodiments, a non-naturally occurring chagasin scaffold protein described herein (such as a non-naturally occurring chagasin scaffold protein that specifically binds LRP6 and/or a non-naturally occurring chagasin scaffold protein that specifically binds VEGF) and/or a composition described herein is administered directly to the eye or the eye tissue. In some embodiments, the a non-naturally occurring chagasin scaffold protein described herein (such as a non-naturally occurring chagasin scaffold protein that specifically binds LRP6 and/or a non-naturally occurring chagasin scaffold protein that specifically binds VEGF) and/or a composition described herein is administered topically to the eye, for example, in eye drops. In some embodiments, the chagasin scaffold proteins and/or compositions provided herein are administered by injection to the eye (intraocular injection) or to the tissues associated with the eye. A non-naturally occurring chagasin scaffold protein described herein (such as a non-naturally occurring chagasin scaffold protein that specifically binds LRP6 and/or a non-naturally occurring chagasin scaffold protein that specifically binds VEGF) and/or a composition described herein can be administered, for example, by intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. These methods are known in the art. For example, for a description of exemplary periocular routes for retinal drug delivery, see Periocular routes for retinal drug delivery, Raghava et al. (2004), *Expert Opin. Drug Deliv.* 1(1):99-114. A non-naturally occurring chagasin scaffold protein described herein (such as a non-naturally occurring chagasin scaffold protein that specifically binds LRP6 and/or a non-naturally occurring chagasin scaffold protein that specifically binds VEGF) and/or a composition described herein can be administered, for example, to the vitreous, aqueous humor, sclera, conjunctiva, the area between the sclera and conjunctiva, the retina choroids tissues, macula, or other area in or proximate to the eye of an individual. The compositions can also be administered to the individual as an implant. Preferred implants are biocompatible and/or biodegradable sustained release formulations which gradually release the compounds over a period of time. Ocular implants for drug delivery are well-known in the art. See, e.g., U.S. Pat. Nos. 5,501,856, 5,476,511, and 6,331,313. The compositions can also be administered to the individual using iontophoresis, including, but are not limited to, the ionophoretic methods described in U.S. Pat. No. 4,454,151 and U.S. Pat. App. Pub. No. 2003/0181531 and 2004/0058313.

Depending on the indication to be treated and factors relevant to the dosing that a physician of skill in the field would be familiar with, the non-naturally occurring chagasin scaffold proteins described herein (such as non-naturally occurring chagasin scaffold proteins that specifically binds LRP6 and/or non-naturally occurring chagasin scaffold proteins that specifically bind VEGF) provided herein will be administered at a dosage that is efficacious for the treatment of that indication while minimizing toxicity and side effects. A typical dose can be, for example, in the rage of 0.001 to 1000 µg; however, doses below or above this exemplary range are within the scope of the invention. The daily dose can be about 0.1 µg/kg to about 100 mg/kg of total body weight (e.g., about 5 µg/kg, about 10 µg/kg, about 100 µg/kg, about 500 µg/kg, about 1 mg/kg, about 50 mg/kg, or a range defined by any two of the foregoing values), preferably from about 0.3 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values), more preferably from about 1 µg/kg to 1 mg/kg of total body weight (e.g., about 3 µg/kg, about 15 µg/kg, about 75 µg/kg, about 300 µg/kg, about 900 µg/kg, or a range defined by any two of the foregoing values), and even more preferably from about 0.5 to 10 mg/kg body weight per day (e.g., about 2 mg/kg, about 4 mg/kg, about 7 mg/kg, about 9 mg/kg, or a range defined by any two of the foregoing values). As noted above, therapeutic or prophylactic efficacy can be monitored by periodic assessment of treated patients. For repeated administrations over several days or longer, depending on the condition, the treatment is repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

A pharmaceutical composition comprising a non-naturally occurring chagasin scaffold protein described herein (such as a non-naturally occurring chagasin scaffold protein that specifically binds LRP6 and/or a non-naturally occurring chagasin scaffold protein that specifically binds VEGF) can be administered one, two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection A non-naturally occurring chagasin scaffold protein described herein (such as a non-naturally occurring chagasin scaffold protein that specifically binds LRP6 and/or a non-naturally occurring chagasin scaffold protein that specifically binds VEGF) may be administered in a single daily dose, or the total daily dose may be administered in divided dosages of two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection or surgically implanted in various locations.

Pharmaceutical Formulations

The non-naturally occurring chagasin scaffold proteins disclosed herein (such as those that specifically bind LRP6 or those that specifically bind VEGF) can be formulated with suitable carriers or excipients so that they are suitable for administration. Suitable formulations of the non-naturally occurring chagasin scaffold proteins disclosed herein are obtained by mixing non-naturally occurring chagasin scaffold proteins disclosed herein having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary antibody formulations, which can be applied to the non-naturally chagasin scaffold proteins provided herein, are described in WO98/56418, expressly incorporated herein by reference. Lyophilized formulations adapted for subcutaneous administration are described in W097/04801. Such lyophilized formulations may be reconstituted with a suitable diluent to a high protein concentration and the reconstituted formulation may be administered subcutaneously to the mammal to be treated herein.

The formulation herein may also contain more than one active compound as necessary for the particular indication being treated, preferably those with complementary activities that do not adversely affect each other. For example, it may be desirable to further provide an anti-neoplastic agent, a growth inhibitory agent, a cytotoxic agent, or a chemotherapeutic agent. Such molecules are suitably present in combination in amounts that are effective for the purpose intended. The effective amount of such other agents depends on the amount of non-naturally occurring chagasin scaffold protein present in the formulation, the type of disease or disorder or treatment, and other factors discussed above. These are generally used in the same dosages and with administration routes as described herein or about from 1 to 99% of the heretofore employed dosages. The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980). Sustained-release preparations may be prepared. Suitable examples of sustained release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and. ethyl-L-glutamate, non-degradable ethylene-vinyl, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

Lipofectins or liposomes can be used to deliver the non-naturally occurring chagasin scaffold proteins disclosed herein (such as those that specifically bind LRP6 or those that specifically bind VEGF) or compositions provided herein into cells.

The active ingredients can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's PHARMACEUTICAL SCIENCES, supra.

Sustained-release preparations can be prepared. Suitable examples of sustained-release preparations include semipermeable matrices of solid hydrophobic polymers containing a non-naturally occurring chagasin scaffold protein disclosed herein, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydro gels release proteins for shorter time periods. When encapsulated chagasin scaffold proteins remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

The formulations to be used for in vivo administration must be sterile. This is readily accomplished by, e.g., filtration through sterile filtration membranes.

Diagnosis and Imaging Using Non-Naturally Occurring Chagasin Scaffold Proteins

Non-naturally occurring chagasin scaffold proteins described herein (such as those that specifically bind LRP6 and/or those that specifically bind VEGF) can be used to detect, e.g., LRP6 protein or VEGF protein, in patient samples (e.g., via FACS, immunohistochemistry (IHC), ELISA assays) or in patients. Labeled non-naturally occurring chagasin scaffold proteins (such as those that that specifically bind human LRP6 or that specifically bind human VEGF) can be used for diagnostic purposes to detect, diagnose, or monitor diseases and/or disorders associated with the expression, aberrant expression and/or activity a target ligand (such as LRP6 or VEGF). For example, the non-naturally occurring chagasin scaffold proteins provided herein can be used in in situ, in vivo, ex vivo, and in vitro diagnostic assays or imaging assays.

Provided are methods for detecting expression of a human LRP6 comprising (a) assaying the expression of the polypeptide in cells (e.g., tissue) or body fluid of an individual using one or more non-naturally occurring chagasin scaffold proteins that specifically bind human LRP6 and (b) comparing the level of LRP6 expression with a standard LRP6 expression level, whereby an increase or decrease in the assayed LRP6 expression level compared to the standard expression level is indicative of aberrant expression. Also provided are methods for detecting expression of a human VEGF comprising (a) assaying the expression of the polypeptide in cells (e.g., tissue) or body fluid of an individual using one or more non-naturally occurring chagasin scaffold proteins that specifically bind human VEGF and (b) comparing the level of VEGF expression with a standard VEGF expression level, whereby an increase or decrease in the assayed VEGF expression level compared to the standard expression level is indicative of aberrant expression.

Additional embodiments include methods of diagnosing a disease or disorder associated with expression or aberrant expression of LRP6 in an animal (e.g., a mammal such as a human). The methods comprise detecting LRP6 molecules in the mammal. In certain embodiments, diagnosis comprises: (a) administering an effective amount of a labeled non-naturally occurring chagasin scaffold protein that specifically binds human LRP6 to a mammal (b) waiting for a time interval following the administering for permitting the labeled chagasin scaffold protein to preferentially concentrate at sites in the subject where the LRP6 molecule is expressed (and for unbound labeled molecule to be cleared to background level); (c) determining background level; and (d) detecting the labeled molecule in the subject, such that detection of labeled molecule above the background level indicates that the subject has a particular disease or disorder associated with expression or aberrant expression of LRP6. In certain embodiments, diagnosis comprises: (a) administering an effective amount of a labeled non-naturally occurring chagasin scaffold protein that specifically binds human VEGF to a mammal (b) waiting for a time interval following the administering for permitting the labeled chagasin scaffold protein to preferentially concentrate at sites in the subject where the VEGF molecule is expressed (and for unbound labeled molecule to be cleared to background level); (c) determining background level; and (d) detecting the labeled molecule in the subject, such that detection of labeled molecule above the background level indicates that the subject has a particular disease or disorder associated with expression or aberrant expression of VEGF. Background level can be determined by various methods including, comparing the amount of labeled molecule detected to a standard value previously determined for a particular system.

Labeled chagasin scaffold proteins described herein (such as labeled chagasin scaffold proteins that specifically bind human LRP6 or labeled chagasin scaffold proteins described herein that specifically bind human VEGF) can be used to assay protein levels in a biological sample using classical immunohistological methods known to those of skill in the art (e.g., see Jalkanen, et al., *J. Cell. Biol.* 101:976-985 (1985); Jalkanen, et al., *J. Cell. Biol.* 105:3087-3096 (1987)). Other methods useful for detecting protein expression include immunoassays, such as the enzyme linked immunosorbent assay (ELISA) and the radioimmunoassay (RIA). Suitable protein assay labels are known in the art and include enzyme labels, such as, glucose oxidase; radioisotopes, such as iodine ($^{131}$I, $^{125}$I, $^{123}$I, $^{121}$I) carbon ($^{14}$C), sulfur $^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd) molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminol; and fluorescent labels, such as fluorescein and rhodamine, and biotin.

Techniques known in the art may be applied to labeled non-naturally occurring chagasin scaffold proteins provided herein (e.g., such as labeled non-naturally occurring chagasin scaffold proteins that specifically bind human LRP6 or labeled non-naturally occurring chagasin scaffold proteins that specifically bind human VEGF). Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003). One can also study LRP6 or VEGF overexpression by measuring shed antigen in a biological fluid such as serum, e.g., using labeled chagasin scaffold-based assays (see also, e.g., U.S. Pat. No. 4,933,294 issued Jun. 12, 1990; WO91/05264 published Apr. 18, 1991; U.S. Pat. No. 5,401, 638 issued Mar. 28, 1995; and Sias et al., J. Immunol. Methods 132:73-80 (1990)). Aside from the above assays, various in vivo and ex vivo assays are available to the skilled practitioner. For example, one can expose cells within the body of the mammal to an chagasin scaffold protein which is optionally labeled with a detectable label, e.g., a radioactive isotope, and binding of the chagasin scaffold protein to the target ligand (e.g., LRP6 or VEGF) can be evaluated, e.g., by external scanning for radioactivity or by analyzing a sample (e.g., a biopsy or other biological sample) taken from a mammal previously exposed to the chagasin scaffold protein.

Articles of Manufacture and Kits

In certain embodiments, provided herein is an article of manufacture containing a non-naturally occurring chagasin scaffold protein described herein that specifically binds LRP6 and materials useful for the treatment of, e.g., cancer and metastatic disease, osteoporosis and other bone metabolism and disease, neuronal and neurodegenerative disease, rheumatoid arthritis and other inflammatory disease. In certain embodiments, provided herein is an article of manufacture containing a non-naturally occurring chagasin scaffold protein described herein that specifically binds VEGF and materials useful for the treatment of a disease or disorder characterized by abnormal angiogenesis and/or abnormal vascular permeability, or any other disease characterized by abnormal VEGF activity or expression (such as those described elsewhere herein).

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating the condition and may have a sterile access port (for example the container may be an intravenous solution bag or a vial having a stopper pierceable by a hypodermic injection needle). At least one active agent in the composition is a non-naturally occurring chagasin scaffold protein described herein that specifically binds LRP6 or a non-naturally occurring chagasin scaffold protein described herein that specifically binds VEGF. The label or package insert indicates that the composition is used for treating the particular condition. The label or package insert will further comprise instructions for administering the chagasin scaffold composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In certain embodiments, the package insert indicates that the composition comprising the non-naturally occurring chagasin scaffold protein that specifically binds LRP6 is used for treating cancer and metastatic disease, osteoporosis and other bone metabolism and disease, neuronal and neurodegenerative disease, rheumatoid arthritis and other inflammatory disease. In certain embodiments, the package insert indicates that the composition comprising the non-naturally occurring chagasin scaffold protein that specifically binds VEGF is used for treating a disease or disorder characterized by abnormal angiogenesis and/or abnormal vascular permeability, or any other disease characterized by abnormal VEGF activity or expression (such as those described elsewhere herein). Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for isolation or detection of LRP6 or VEGF in patients, optionally in combination with the articles of manufacture. For isolation and purification of LRP6, the kit can contain a non-naturally occurring chagasin scaffold protein that specifically binds LRP6 described herein coupled to beads (e.g., sepharose beads). For isolation and purification of VEGF, the kit can contain a non-naturally occurring chagasin scaffold protein that specifically binds VEGF described herein coupled to beads. Kits can be provided which contain the non-naturally occurring chagasin scaffold proteins described herein for detection and quantitation of LRP6 or VEGF in vitro, e.g. in an ELISA or blot. As with the article of manufacture, the kit comprises a container and a label or package insert on or associated with the container. For example, the container holds a composition comprising at least one non-naturally occurring chagasin scaffold protein described herein that specifically binds LRP6 or at least one non-naturally occurring chagasin scaffold protein described herein that specifically binds VEGF. Additional containers may be included that contain, e.g., diluents and buffers, control antibodies, etc. The label or package insert may provide a description of the composition as well as instructions for the intended in vitro or diagnostic use.

EXAMPLES

Example 1: Materials and Methods

Chagasin Cloning and Phagemid Construct Design

The chagasin gene was synthesized with an optimized codon usage with the following sequence:

(SEQ ID NO: 91)
ATGTCCCACAAGGTGACGAAAGCCCATAACGGTGCGACCTTGACGGTGG

CCGTCGGCGAGCTGGTGGAGATTCAGCTTCCGAGCAATCCGACCACTGG

GTTCGCGTGGTATTTTGAAGGTGGTACCAAAGAAAGTCCGAATGAATCC

ATGTTCACCGTCGAGAATAAGTACTTTCCGCCGGACAGTAAACTGTTGG

GTGCTGGCGGGACGGAGCACTTTCATGTGACAGTGAAGGCGGCGGGTAC

GCACGCAGTAAATCTCACTTACATGCGCCCGTGGACAGGCCCGTCGCAC

GATTCCGAGCGTTTCACTGTATATCTCAAGGCAAAC

The chagasin gene was amplified by PCR with an N-terminal epitope tag (gD-tag) MADPNRFRGKDLGSLE (SEQ ID NO: 92) (N J Skelton et al., *J Biol Chem* 278, 7645-7654, 2003) and cloned into the phagemid vector (S S Sidhu et al., *Methods Enzymol* 328, 333-363, 2000; R Tonikian et al., *Nat Protoc* 2, 1368-1386, 2007) between a MalE signal peptide and phage coat proteins g3 or g8 including a $(GGS)_3$ linker before the coat protein. Chagasin containing phagemid vectors were modified using Kunkel mutagenesis (R Tonikian et al., *Nat Protoc* 2, 1368-1386, 2007) by replacing the three loop regions of chagasin with two stop codons. Alternatively, a TAG amber stop codon was introduced after the chagasin gene for some libraries to reduce the display level. These constructs were used as Kunkel templates for library production using oligonucleotides synthesized with either NNK codons or from trinucleotide at positions selected for randomization (R Tonikian et al., *Nat Protoc* 2, 1368-1386, 2007).

Determination of Chagasin Display on Phage

Phage displaying gD-tagged chagasin fused to either coat protein p3 or p8 were produced as described (SS Sidhu et al., *Methods Enzymol* 328, 333-363, 2000; R Tonikian et al., *Nat Protoc* 2, 1368-1386, 2007). Binding of purified phage against an anti-gD antibody (Genentech, Inc.) or papain was measured by phage ELISA with serial 2-fold dilution of phage solution starting at $2.5 \times 10^{12}$ phage per ml and detected using an anti-M13 HRP-conjugated antibody (NEB).

Alanine Scanning of Chagasin Loops

Three alanine scanning libraries were made each containing two randomized loops simultaneously (L2 and L4, L2 and L6, L4 and L6) for analysis. The following positions in loops 2, 4 and 6 (Ser28 to Phe34, Pro59 to Gly69 and Arg91 to Ser100, respectively) were randomized using alanine shotgun scanning codons (GA Weiss et al., *Proc Natl Acad Sci USA* 97, 8950-8954, 2000). Two rounds of affinity selection were performed using anti-gD antibody coated MAXISPORP™ immunoplates (Nunc) and selected phage clones were analyzed by phage spot ELISA and DNA sequencing using methods previously described (R Tonikian et al., *Nat Protoc* 2, 1368-1386, 2007).

Naive Chagasin Phage Library Design

Chagasin libraries were made using methods essentially as described (R Tonikian et al., *Nat Protoc* 2, 1368-1386, 2007). Chagasin phagemid constructs, in which DNA encoding for residue positions in L2, L4 and L6 (28-34, 59-69 and 91-100, respectively) were replaced with two stop codons, served as Kunkel templates.

TABLE 5

Residue Positions Chosen For Randomization

| | | |
|---|---|---|
| L2: | SNPX$_2$GF | SEQ ID NO: 93 |
| L2: | SNX$_4$GF | SEQ ID NO: 94 |
| L4: | PX$_{6-14}$GAGG | SEQ ID NO: 95 |
| L6: | RPWTGPSHDS | SEQ ID NO: 84 |

Amino acid residue positions in bold type were chosen for randomization in chagasin loops L2, L4, and L6 based on alanine scanning results (Example 2) and extra residue insertions in L2 (Example 3). The underlined positions were fixed in conservative libraries. Seven oligonucleotides were designed based on selected positions for randomization (X) shown in Table 5 above using NNK codons:

L2-X2:
(SEQ ID NO: 96)
GGA GAT TCA GCT TCC GAG CAA TCC GNN KNN KGG GTT

CGC GTG GTA TTT TGA AGG

L2-X4:
(SEQ ID NO: 97)
GGA GAT TCA GCT TCC GAG CAA TNN KNN KNN KGG

GTT CGC GTG GTA TTT TGA AGG

L4-X6:
(SEQ ID NO: 98)
GTC GAG AAT AAG TAC TTT CCG NNK NNK NNK NNK NNK

NNK GGT GCT GGC GGG ACG GAG CAC TTT CAT GTG

L4-X8:
(SEQ ID NO: 99)
GTC GAG AAT AAG TAC TTT CCG NNK NNK NNK NNK NNK

NNK NNK NNK GGT GCT GGC GGG ACG GAG CAC TTT CAT

GTG

L4-X10:
(SEQ ID NO: 100)
GTC GAG AAT AAG TAC TTT CCG NNK NNK NNK NNK NNK

NNK NNK NNK NNK NNK GGT GCT GGC GGG ACG GAG CAC

TTT CAT GTG

L6-X4GX5:
(SEQ ID NO: 101)
GTA AAT CTC ACT TAC ATG NNK NNK NNK NNK GGT NNK

NNK NNK NNK NNK GAG CGT TTC ACT GTA TAT C

L6-XPX2GPX4:
(SEQ ID NO: 102)
GTA AAT CTC ACT TAC ATG NNK CCA NNK NNK GGT CCG

NNK NNK NNK NNK GAG CGT TTC ACT GTA TAT C

A total of 8 naive individual libraries were made with these oligonucleotides where either L4 alone, L4 and L2 or all 3 loops contained randomized positions. (See Table 6 below.) Between 8 and 21 residues were randomized simultaneously.

TABLE 6

Naïve Chagasin Libraries

| Chagasin Library | L2 Loop | L4 Loop | L6 Loop | Pool |
|---|---|---|---|---|
| g3-display | X$_2$ | X$_6$ (SEQ ID NO: 104) | WT | B |
| g3-display | X$_4$ (SEQ ID NO: 103) | X$_8$ (SEQ ID NO: 105) | WT | |
| g3-display | X$_2$ | X$_6$ (SEQ ID NO: 104) | X$_4$GX$_5$ (SEQ ID NO: 107) | C |
| g3-display | X$_2$ | X$_8$ (SEQ ID NO: 105) | XPX$_2$GPX$_4$ (SEQ ID NO: 108) | |
| g3-display | X$_4$ (SEQ ID NO: 103) | X$_8$ (SEQ ID NO: 105) | X$_4$GX$_5$ (SEQ ID NO: 107) | |
| g3-display | X$_4$ (SEQ ID NO: 103) | X$_8$ (SEQ ID NO: 105) | X$_4$GX$_5$ (SEQ ID NO: 107) | |
| g8-display | WT | X$_8$ (SEQ ID NO: 105) | WT | A |
| g8-display | WT | X$_{10}$ (SEQ ID NO: 106) | WT | |

Phage Panning

Phage panning in solution or on coated plates was carried out essentially as described (R Tonikian et al., *Nat Protoc* 2, 1368-1386, 2007; Y Zhang et al., *J Biol Chem* 289, 942-955, 2014). Four rounds of phage panning were performed to enrich for target specific binders. Library panning for LRP6 was always done in solution, while initial naive library panning against VEGF109 was done on plates and then switched to solution sorting during affinity maturation. After the fourth round of panning, 96 clones from each library or library pool were individually produced and analyzed by phage ELISA and DNA sequencing. During solution phage panning, the target protein concentration was adjusted from round to round (ranging from 500 nM to 0.5 nM).

Affinity Maturation of Target Specific Chagasin Binders

Target specific chagasin binders to LRP6 or VEGF109 were affinity matured by soft randomization of the selected new sequences in the loops. Soft randomized libraries were constructed using degenerate oligonucleotides synthesized with 70-10-10-10 mixtures of nucleotide bases, in which the wild-type base is in excess. This results in the wild-type amino acids occurring at approximately 50% in frequency at the targeted position and approximately 50% for all other amino acids. Phage panning of these new libraries was carried out as described above, and WebLogo plots were generated using the online software WebLogo 3.3.

Expression and Purification of LRP6

LRP6 E1E2 with a C-terminal Avi-tag and His$_6$-tag was produced as previously described (E Bourhis et al., *J Biol Chem* 285, 9172-9179, 2010). Biotinylation was carried out using a kit (GeneCopoeia) according to manufacturer's protocol.

Expression and Purification of Chagasin Variants

Chagasin variants were cloned into pET52b vector backbone with N-terminal $His_6$-GST-tag, separating the chagasin variant by a TEV cleavage site. Constructs were transformed into BL21 STAR™ *E. coli* cells (Invitrogen) and expressed in TB auto media at 16° C. for 72 hours at 200 rpm. Cell pellet was harvested by centrifugation and lysed in PBS buffer with a microfluidizer. After centrifugation at 50,000 g, cell lysate was subjected to Ni-NTA SUPERFLOW™ affinity purification (Qiagen) according to manufacturer's protocol followed by size exclusion chromatography on a SUPERDEX™ 200 column (GE Healthcare Life Sciences) in 20 mM Tris pH 8 and 150 mM NaCl at 30 cm/h flow rate. Fractions containing GST-fused chagasin variants were concentrated and cleaved with TEV protease (25 μg TEV per mg GST-chagasin) overnight at room temperature, supplemented with 1 mM DTT. Cleaved chagasin variants were isolated using SUPERDEX™ 75 size exclusion chromatography (GE Healthcare Life Sciences) in 20 mM Tris pH 8 and 150 mM NaCl at 30 cm/h flow rate and concentrated.

Small scale expression of chagasin variants with STREP-TAG® II (IBA GmbH). We introduced DNA sequence encoding for a STREP-TAG® II (SAWSHPQFEK) at the C-terminus of chagasin in phagemid containing chagasin variants. The Ser-Ala residues incorporated improve the affinity for STREPMAB-IMMO™. Transformed *E. coli* strain 33D3 (Genentech, Inc.) containing these phagemid variants were grown to log-phase and induced with 0.5 mM IPTG and grown at 30° C. overnight. Cells were removed by centrifugation at 10,000 g and supernatant medium contained secreted chagasin variants with STREP-TAG® II that were then used for binding studies on the OCTET® RED384 kinetic analysis system.

Small Scale Expression of Chagasin Variants Using the EXIPROGEN™ Automated Protein Synthesis System DNA encoding chagasin variants were amplified with C-terminal $His_6$-tag and Avi-tag using the EXIPROGEN™ ProXpress template kit according to manufacturer's protocol (Bioneer). Proteins were produced using the EXIPROGEN™ EC1 protein synthesis kit (Bioneer) on the EXIPROGEN™ instrument (Bioneer) with the addition of BirA and d-biotin (Avidity, LLC) to obtain 20-40 μg of purified biotinylated protein from Ni-affinity chromatography.

Wnt1 Cell-Based Assay

The luciferase reporter assay in HEK293S cells transfected by WNT1 was performed as described (Y Zhang et al., *Nat Chem Biol* 5, 217-219, 2009; Y Gong et al., *PLoS One* 5, e12682, 2010). Purified chagasin LRP6 variants and inhibitors were serially diluted 2-fold and added as indicated.

VEGFR1-VEGF Competition Binding ELISA

This assay was conducted as described previously (J Bostrom et al., *Science* 323, 1610-1614, 2009). MAX-ISORP™ immunoplates were coated with VEGFR1-Fc (5 pg/ml) in PBS overnight. 0.4 nM of biotinylated VEGF165 (labeling performed with NHS-PEG4-biotin from PIERCE™ according to their protocol) was mixed 1:1 with serial titration of VEGF binders for 2 hours prior to incubating it with VEGFR1-Fc coated plates for 15 min. After washing with PBS containing 0.05% TWEEN™ 20, binding was detected with HRP-conjugated NEUTRAVIDIN™ and TMB substrate (PIERCE™) with a spectrophotometer at 450 nm. VEGF109, 165 and VEGFR1-Fc were generously provided by Germaine Fuh (Genentech, Inc.).

Cellular VEGF Receptor Inhibition Assay

Inhibition of VEGF signaling on cells through the receptor KDR was measured essentially as described (MD Sadick et al., *J Pharm Biomed Anal* 19, 883-891, 1999; H Gille et al., *J Biol Chem* 276, 3222-3230, 2001). A constant amount of either 25 or 50 ng/mL of human, mouse or rat VEGF were mixed with various concentrations of chagasin variants or inhibitors prior to stimulating KDR-expressing CHO cells.

Kinetic Binding Measurements Using the OCTET® RED384 Kinetic Analysis System

Binding affinities of chagasin variants for the targets LRP6 and VEGF109 were measured using the OCTET® RED384 kinetic analysis system (FORTEBIO™). All washes, dilutions and measurements were performed in PBS-based kinetics buffer (FORTEBIO™) with the plate shaking at 1000 rpm. Streptavidin biosensors (FORTEBIO™) were equilibrated in kinetics buffer for 5 min and then loaded with either biotinylated LRP6-E1E2 or biotinylated VEGF109 (20 μg/ml) to a density of 2 nm signal difference, followed by a 3 min washing step. For the association phase, the ligand coated streptavidin biosensors were in chagasin variant containing solutions (7 serial 2-fold dilutions, starting at 1000 or 250 nM). Dissociation of the chagasin variant-target complex was measured in wells containing kinetics buffer alone for up to 30 min. Sensorgrams with ligand-loaded streptavidin biosensors going through wells containing only buffer in both association and dissociation measurement were used as reference for background subtraction. Kd, $k_a$ and $k_d$ were determined using the OCTET® evaluation software v7.0.1.3. using a 1:1 binding model with global fitting. Alternatively, AMC-biosensors (Fortebio) were loaded with STREPMAB-IMMO™ (IBA GmbH) to saturation and subsequently used to capture STREP-TAG® II containing chagasin variants to saturation. After 5 min of washing in kinetics buffer, binding kinetics to unlabeled LRP6-E1E2 fragment was determined essentially as described above.

Figure 2:
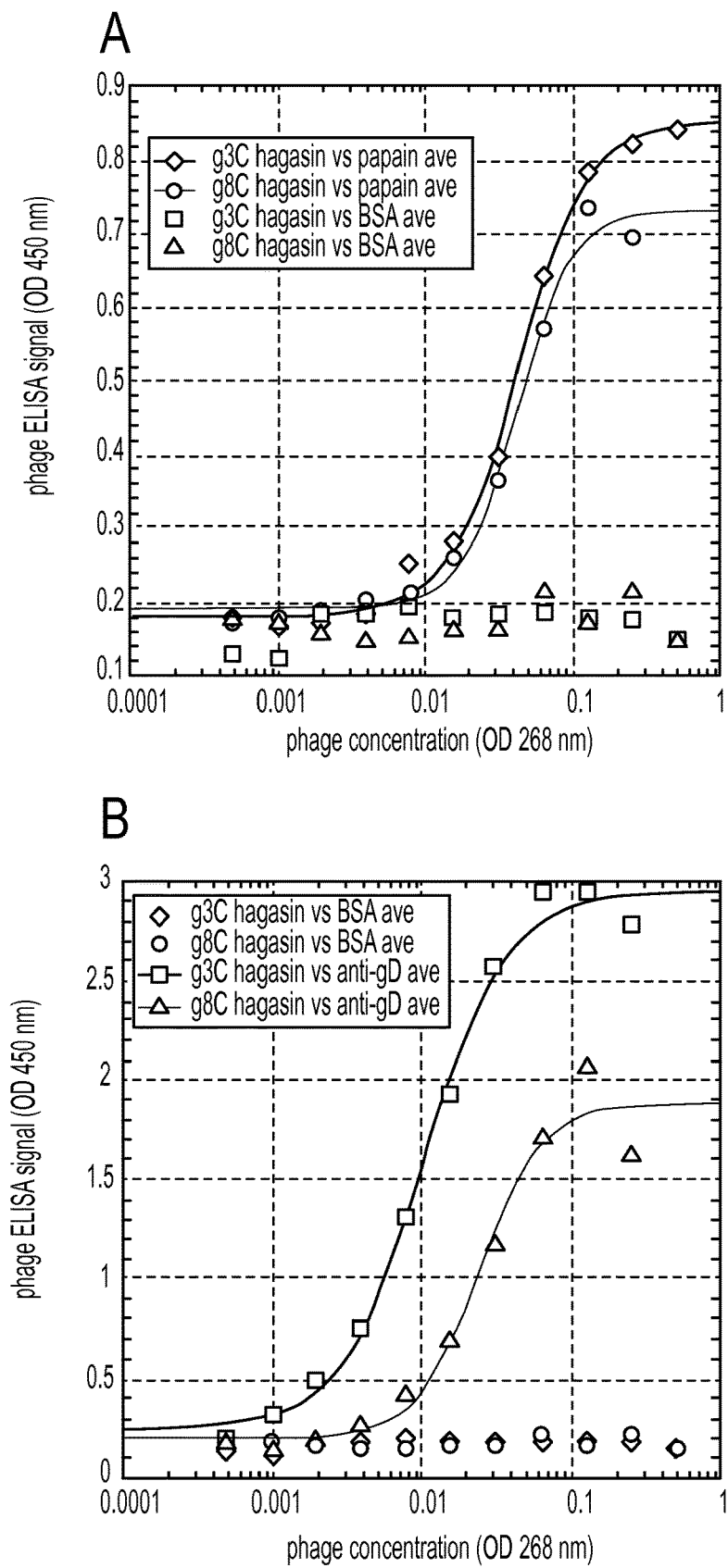
FIG. 2A shows the results of an ELISA performed to measure binding of phage-displayed chagasin to papain.
FIG. 2B shows the results of an ELISA performed to measure binding of phage-displayed chagasin to an antibody specific to the gD epitope tag fused to the N-terminus of chagasin.

Example 2: Determination of Amino Acid Positions for Randomization in Chagasin Loops In order verify compatibility of chagasin with phage, the chagasin wild-type (wt) gene was fused with an N-terminal epitope-tag (gD-tag) (NJ Skelton et al., *J Biol Chem* 278, 7645-7654, 2003) to the N-terminus of either g3 or g8 in a phagemid vector (SS Sidhu et al., *Methods Enzymol* 328, 333-363, 2000; R Tonikian et al., *Nat Protoc* 2, 1368-1386, 2007) and tested for its display and binding against papain or an anti-gD antibody. In both p3- and p8-fusion display modes, chagasin showed specific binding to papain in a phage titration ELISA and had no detectable binding to BSA (see FIG. 2). Phage concentration was determined by the OD at 268 nm and titrated against either anti-gD antibody or papain. Both binding events were specific when compared to binding to BSA as a control.

The positions in Loops 2, 4 and 6 that could be randomized for generating a naive chagasin protein library were then determined. Conformation-specific antibodies to chagasin to capture displayed chagasin variants are currently not available. Thus, in order to determine the tolerability of a given position, alanine scanning was performed to identify the amino acid position(s) at which either the wild-type residue or alanine was allowed to occur. In some case, due to the degeneration of the genetic code, two other amino acids were also possible instead of either wild-type or alanine (GA Weiss et al., *Proc Natl Acad Sci USA* 97, 8950-8954, 2000). Phage libraries displaying chagasin variants were captured via the N-terminal gD-tag on MAXI SORP™ immunoplates coated with anti-gD antibody, where only chagasin variants that were properly folded would be well displayed for capture. If a wild-type residue was essential for stability, it would be expected to dominate in this position over alanine, whereas a position with equal occurrence of alanine and wild-type residue would indicate tolerance for alanine and likely other residues. Positions with equal occurrence of alanine and wild-type residues were thus chosen as positions for randomization.

Three alanine scanning libraries with two loops scanned in pairs simultaneously (L2+L4, L2+L6, L4+L6) were made and subjected to two rounds of panning using a standard procedure (R Tonikian et al., *Nat Protoc* 2, 1368-1386, 2007). The DNA sequences of 96 individually picked clones from each library were obtained and the frequency/probability of the residues appearing at each randomized position was analyzed using a logo plot using WebLogo 3.3. Loop 2 contains the sequence SNPTT (SEQ ID NO: 4) and allowed for alanine substitution for the two threonines (positions 31 and 32) with some co-dependency of Thr32 with variations in L4. Either Asn or Asp was preferred at position 29, but all other positions showed high preference for wild-type residues. Loop 4 contains the wild-type sequence PPDSKLL-GAGG (SEQ ID NO: 149) and showed some preference for Pro59 and Ser62, but not as significant to exclude these positions from randomization. Gly66 and Gly69 were highly preferred residues in Loop 4. Loop 6 contains the sequence RPWTGPSHDS (SEQ ID NO: 84) and showed no strong preference for wild-type residues in any of the positions.

Example 3: Investigation of L2 Loop Elongation for Library Design

Next, tests were performed to determine whether Loop 2 could be extended without significantly affecting protein stability. Five libraries containing 1, 2, 3, 5 or 7 extra random residues in L2 between Asn30 and Gly33 were constructed and subjected them to two rounds of anti-gD antibody sorting to select for displayed chagasin variants. A total of 96 phage clones from each library were analyzed for chagasin display level by phage spot ELISA. Insertion of up to 3 residues in L2 resulted in clones with a very homogeneous display level binding to anti-gD antibody and a very low level of binding to BSA. Insertions of more than 3 residues showed reduced display level of chagasin variants with increased nonspecific binding, as measured by binding to BSA.

Example 4: Chagasin Library Design

Based on the positional alanine scanning of each loop as well as the loop length selection for L2, specific positions shown in Table 4 above were chosen for randomization. Eight naive chagasin protein libraries were designed and displayed on phage, i.e., 6 libraries on g3 and 2 libraries on g8 (Table 6 above). Since L4 can vary in length between 10-21 residues amongst chagasin homologs (D Salmon et al., *J Mol Biol* 357, 1511-1521, 2006), different length variations in this loop were not tested for their stability and sequence composition by panning a library against the anti-gD antibody.

Example 5: Generation of Chagasin Variants that Bind Target Proteins

In order to verify the utility of chagasin as a scaffold and its ability to yield variants that bind with high affinity, specificity and activity against other proteins than cysteine proteases, Wnt signaling co-receptor LRP6 (K I Pinson et al., *Nature* 407, 535-538, 2000; K Tamai et al., *Nature* 407, 530-535, 2000) and the growth factor VEGF (D W Leung et al., *Science* 246, 1306-1309, 1989) were chosen as target proteins for phage panning. Both LRP6 (V E Ahn et al., *Dev Cell* 21, 862-873, 2011; E Bourhis et al., *Structure* 19, 1433-1442, 2011; Z Cheng et al., *Nat Struct Mol Biol* 18, 1204-1210, 2011) and VEGF (Y A Muller et al., *Proc Natl Acad Sci USA* 94, 7192-7197, 1997; C Wiesmann et al., *Cell* 91, 695-704, 1997) and are structurally and functionally well characterized. VEGF used herein refers to VEGF-A, which has various forms (B A Keyt et al., *J Biol Chem* 271, 7788-7795, 1996). VEGF109 refers to the protein containing residues 8-109 (also referred to as VEGF109; VEGF8-109; $VEGF_{8-109}$) and VEGF165 refers the protein containing residues 1-165 (also referred to as VEGF165; VEGF1-165; $VEGF_{1-165}$; $VEGF_{165}$.

Generation of Chagasin Variants that Bind LRP6

The 8 naive chagasin libraries were first subjected individually to 4 rounds of solution phage panning (Y Zhang et al., *J Biol Chem* 289, 942-955, 2014) against the C-terminally Avi-tagged LRP6 receptor fragment E1E2 (E Bourhis et al., *Structure* 19, 1433-1442, 2011). All libraries generated chagasin variants that specifically bound to LRP6-E1E2 as determined by phage spot ELISA with phage titer enrichments for target binding ranging from 0 to 100-fold in the last round of panning.

Figure 3:
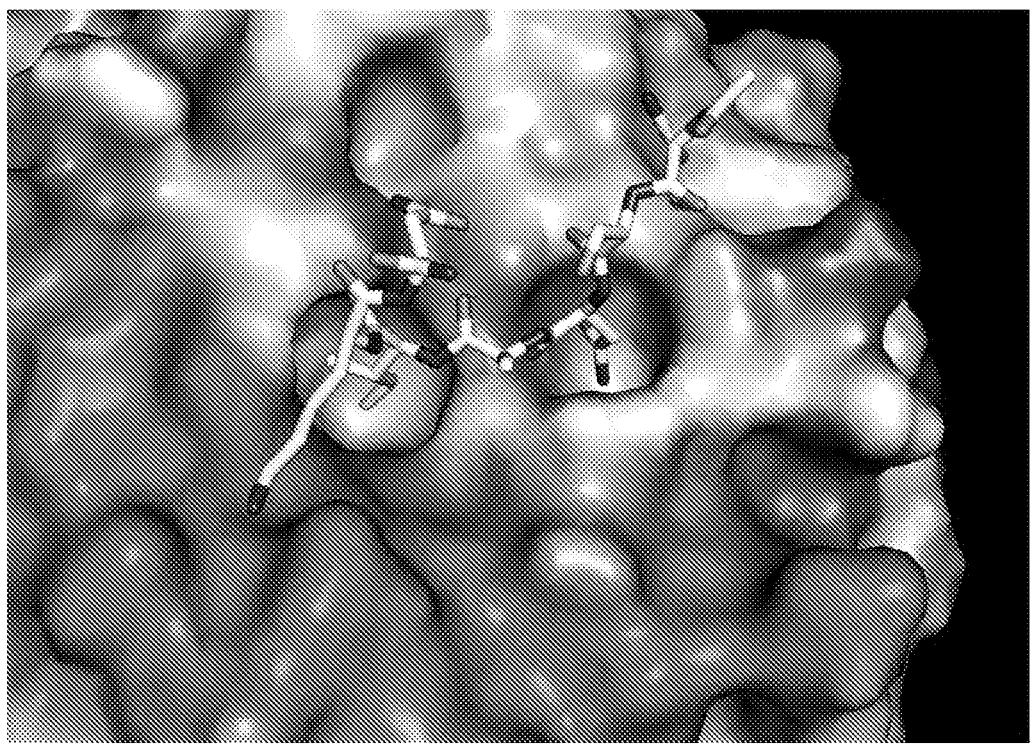
FIG. 3 shows a crystal structure of LRP6-E1 in complex with Dkk1 peptide Ac-NSNAIKN-NH$_2$ (SEQ ID NO: 109)

A functional protein-protein interaction site in the first β-propeller domain (E1) of LRP6 that selectively binds to a linear NXIK peptide motif has been described (E Bourhis et al., *Structure* 19, 1433-1442, 2011). The crystal structures of LRP6-E1 in complex with either the anti-LRP6 inhibitory antibody (YW210.09) or peptides from the natural inhibitor Dkk1, SOST or peptides derived phage display reveal a consistent interaction of these binding partners, exemplified by the Dkk1 peptide Ac-NSNAIKN-NH$_2$ (SEQ ID NO: 109), with the receptor fragment (FIG. 3).

Figure 4:
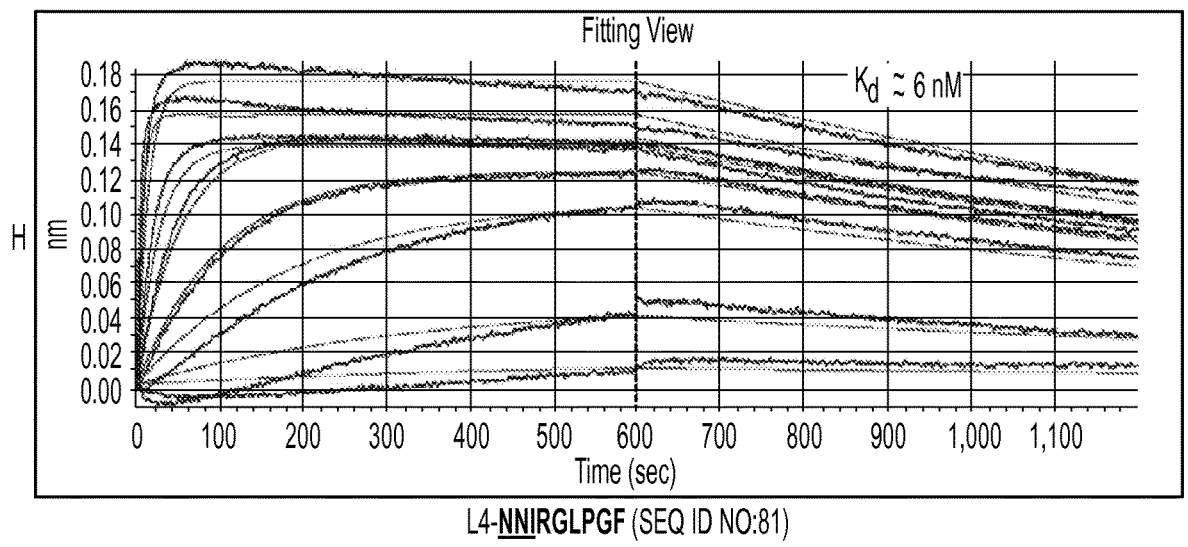
FIG. 4A shows the results of experiments performed to determine the binding kinetics of LRP6 binder H, the amino acid sequence of which is set forth in SEQ ID NO: 87.
FIG. 4B shows the results of experiments performed to determine the binding kinetics of LRP6 binder P, the amino acid sequence of which is set forth in SEQ ID NO: 88.
FIG. 4C shows the results of experiments performed to determine the binding kinetics of LRP6 binder S, the amino acid sequence of which is set forth in SEQ ID NO: 89.
Figure 4:
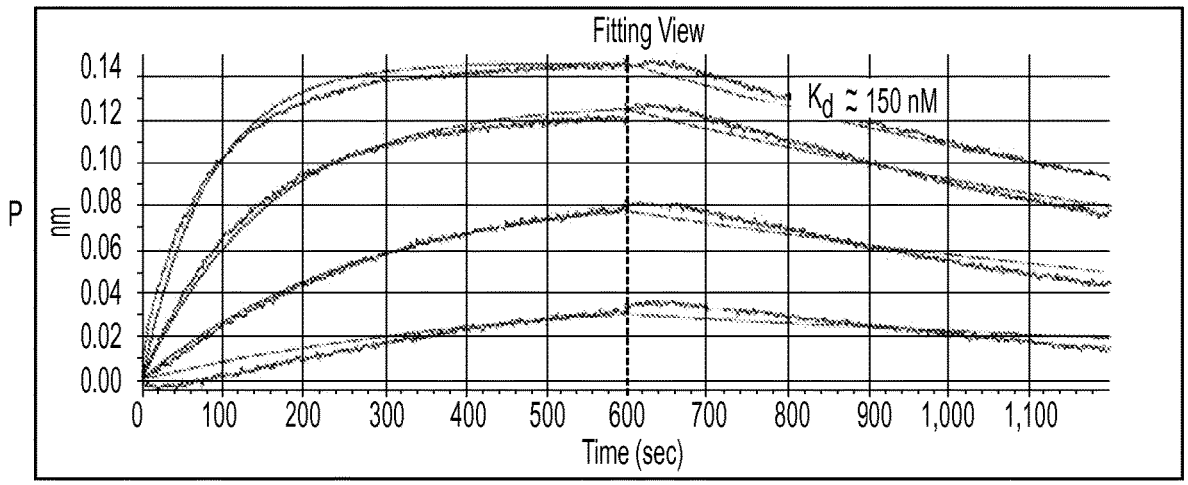
Figure 4:
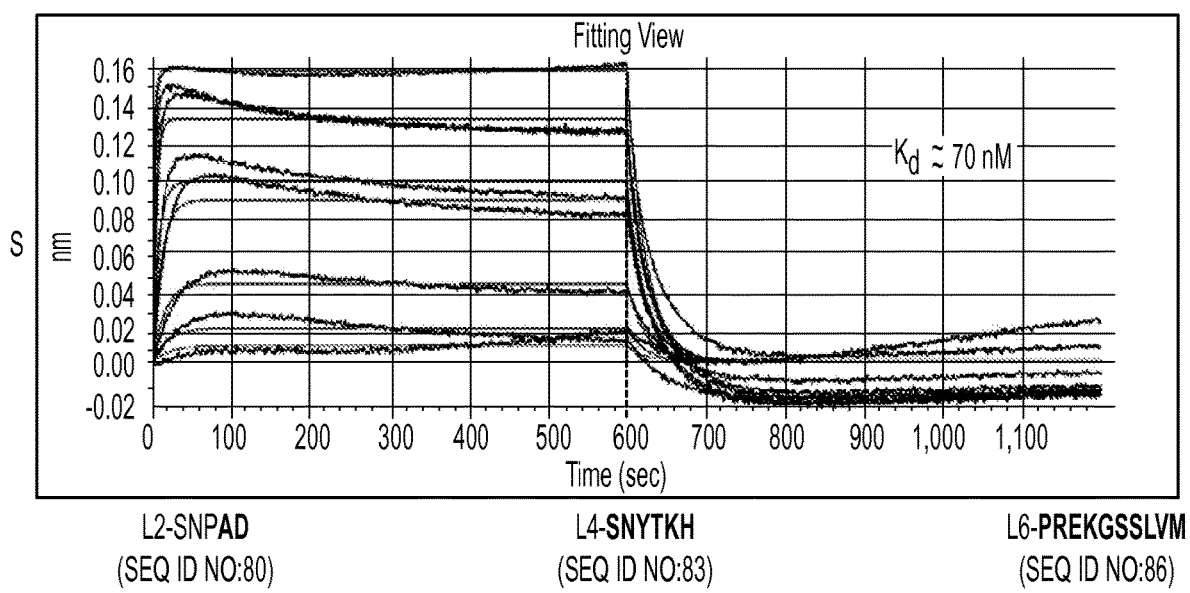

Sequence analysis of chagasin LRP6 variants (chagasin variants that specifically bound to LRP6) exhibited a strong preference for the NXIK sequence motif primarily in the randomized loop L4. Twenty-one variants that exhibited strong target binding and specificity in the phage spot ELISA were selected from libraries that were randomized in either L4 only, L2 and L4 or in all 3 loops. The variants were expressed in small scale as secreted proteins from *E. coli* with a C-terminal STREP-TAG® II (TG Schmidt and A Skerra, *Nat Protoc* 2, 1528-1535, 2007). Their binding kinetics were profiled and ranked by biolayer interferometry (BLI) measurements on an OCTET® RED384 kinetic analysis system, where AMC tips were loaded with STREPMAB-IMMO™ capture antibody to immobilize chagasin LRP6 variants and the LRP6-E1E2 receptor fragment was in solution. Three LRP6 binders, variants H, P and S, had slow off-rate kinetics and binding affinities in the nanomolar range (Kd=6, 150, 70 nM, respectively) (FIG. 4). Variant S contained 2 cysteines that can form an intramolecular disulfide bond, but also forms homodimers with itself as detected by SDS-PAGE under nonreducing conditions. Variant H and variant S were both subjected to affinity maturation by making libraries where all 3 loops were soft randomized simultaneously. The resulting libraries were subjected to 3 rounds of stringent solution phage panning with 3 different target concentrations (0.5, 0.1, 0.05 nM) in last step. 384 phage clones were expressed individually and analyzed by phage spot ELISA for specificity and improved affinity. From the many good binders, the top 16 clones with the highest target binding specificity from library H and from library S (i.e., 32 clones in total) were chosen for small scale expression with C-terminal Avi-tag using the Bioneer EXIPROGEN™ system and their kinetic binding profiles to LRP6-E1E2 were characterized by BLI measurements. The top 4 clones with best binding kinetic profiles (fast on-rate, slow off-rate) were chosen for large-scale expression as GST-fused proteins (see Table 7 below).

TABLE 7

Top 4 Variants out of 32 Screened on OctetRED384 for High Affinity Based on Their Binding Kinetics

| Library | Variant | L2 | L4 | L6 |
|---|---|---|---|---|
| H | H2 | SNPQT (SEQ ID NO: 3) | SNKVKGVPGF (SEQ ID NO: 7) | GPWTGASQEP (SEQ ID NO: 11) |
|   | H15 | SNPTT (SEQ ID NO: 4) | SNKIKGIPGF (SEQ ID NO: 8) | RPSTGPSDDS (SEQ ID NO: 12) |
| S | S11 | SNVD (SEQ ID NO: 5) | SNSTKR (SEQ ID NO: 9) | PRVKGAYLVM (SEQ ID NO: 13) |
|   | S15 | SNAD (SEQ ID NOL: 146) | SNSTKR (SEQ ID NO: 9) | RREKGSTLVV (SEQ ID NO: 147) |

Figure 5:
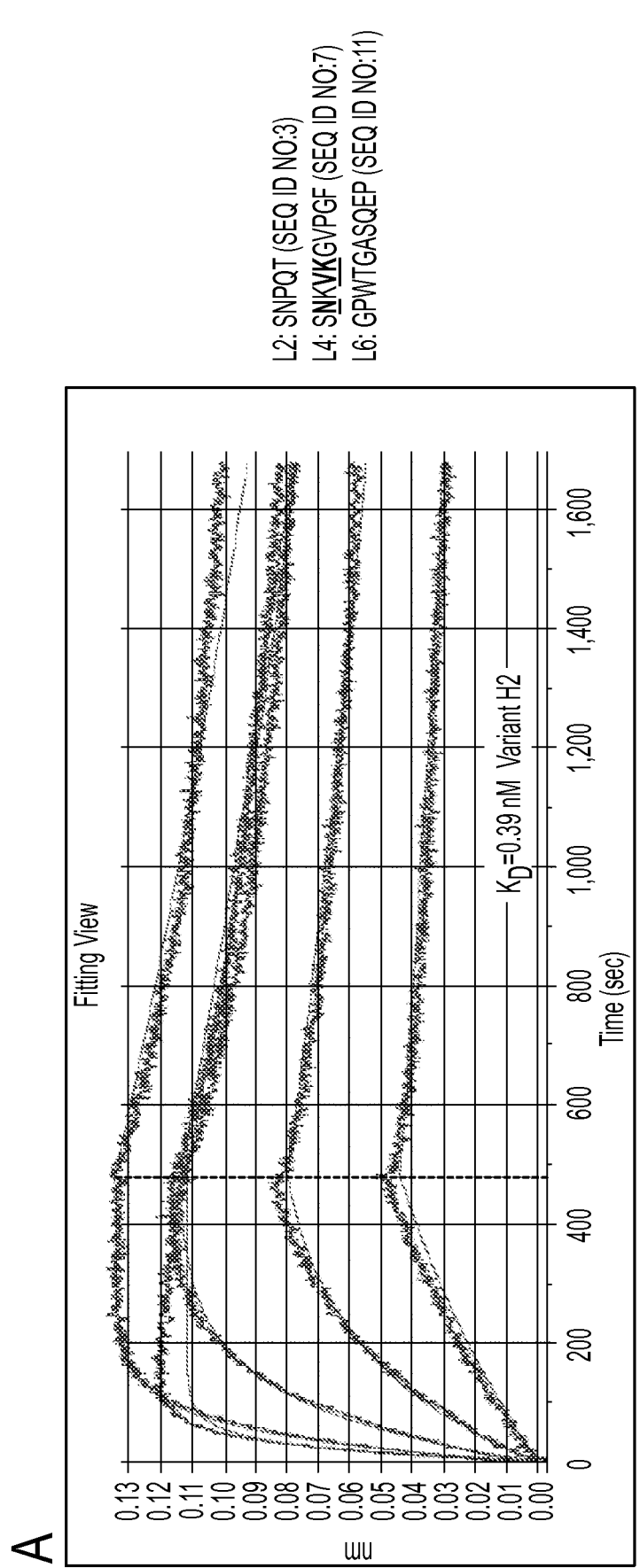
FIG. 5A shows the results of experiments performed to determine the binding kinetics of LRP6 binder H2, the amino acid sequence of which is set forth in SEQ ID NO: 15.
FIG. 5B shows the results of experiments performed to determine the binding kinetics of LRP6 binder H15, the amino acid sequence of which is set forth in SEQ ID NO: 16.
FIG. 5C shows the results of experiments performed to determine the binding kinetics of LRP6 binder S11, the amino acid sequence of which is set forth in SEQ ID NO: 17.
Figure 5:
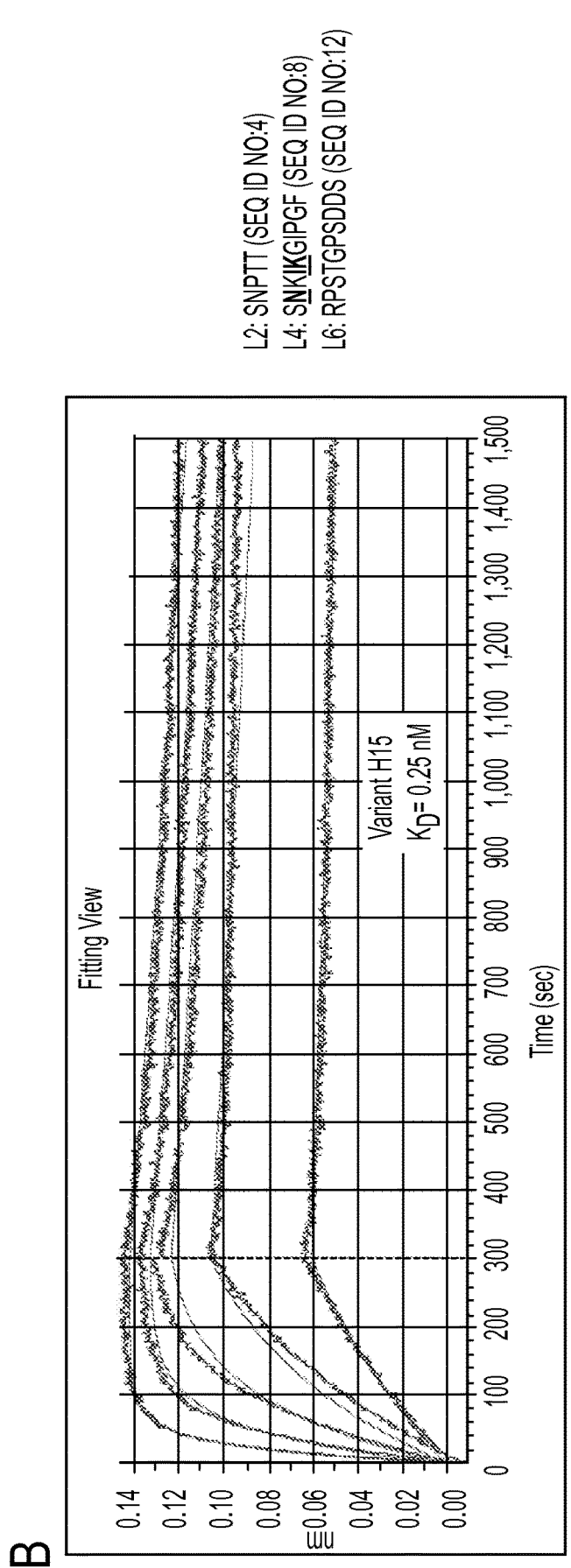
Figure 5:
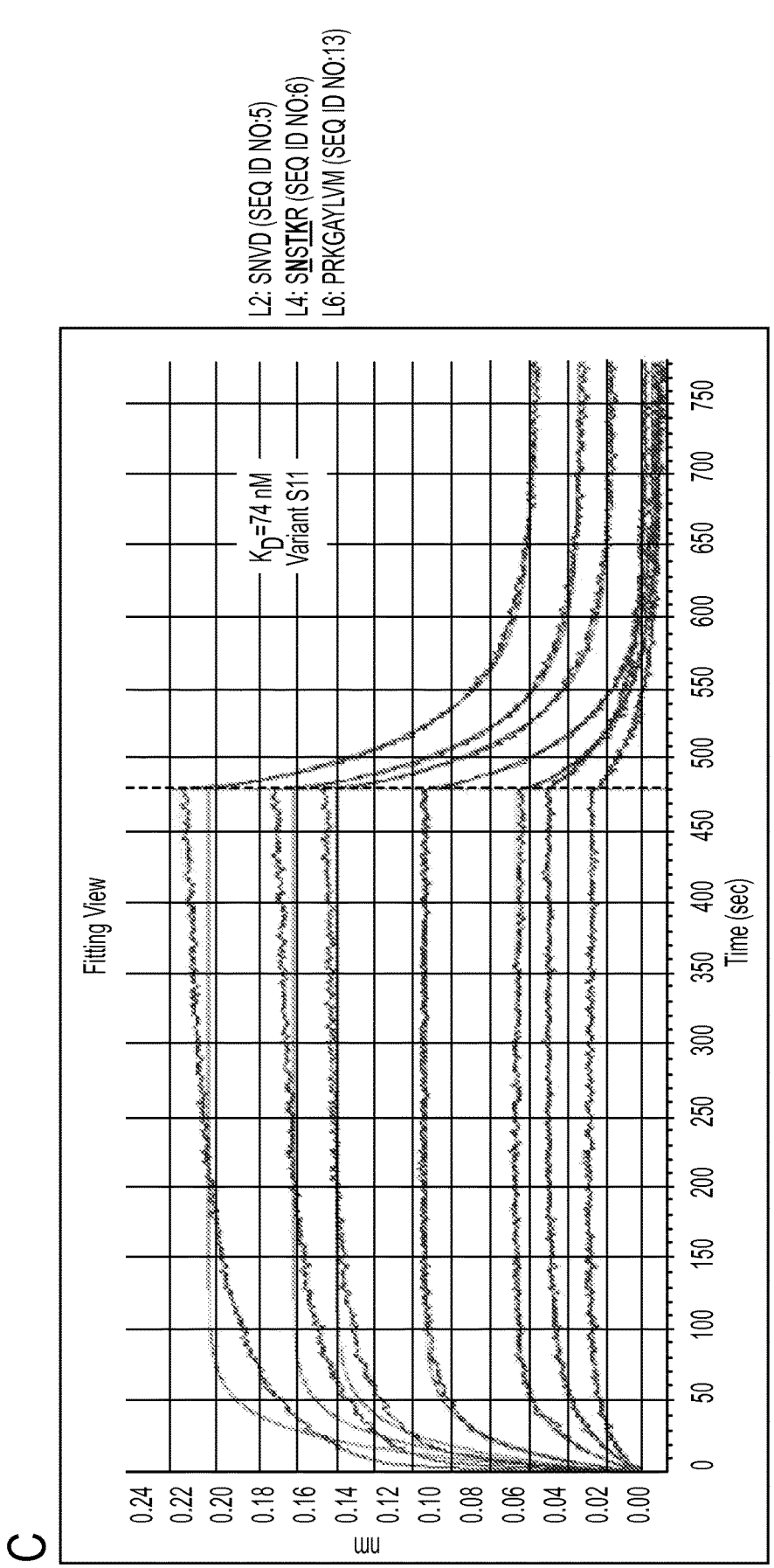

Clones H2, H15 and S11 all expressed well and resulted in monomeric chagasin LRP6 variants. Clone H2 and H15 had binding affinities (Kd) of 400 pM and 250 pM to LRP6-E1E2, respectively, whereas variant S11 had a binding affinity of 74 nM (FIG. 5).

High Affinity Chagasin LRP6 Variants Inhibit Wnt-Dependent Cellular Signaling

Figure 6:
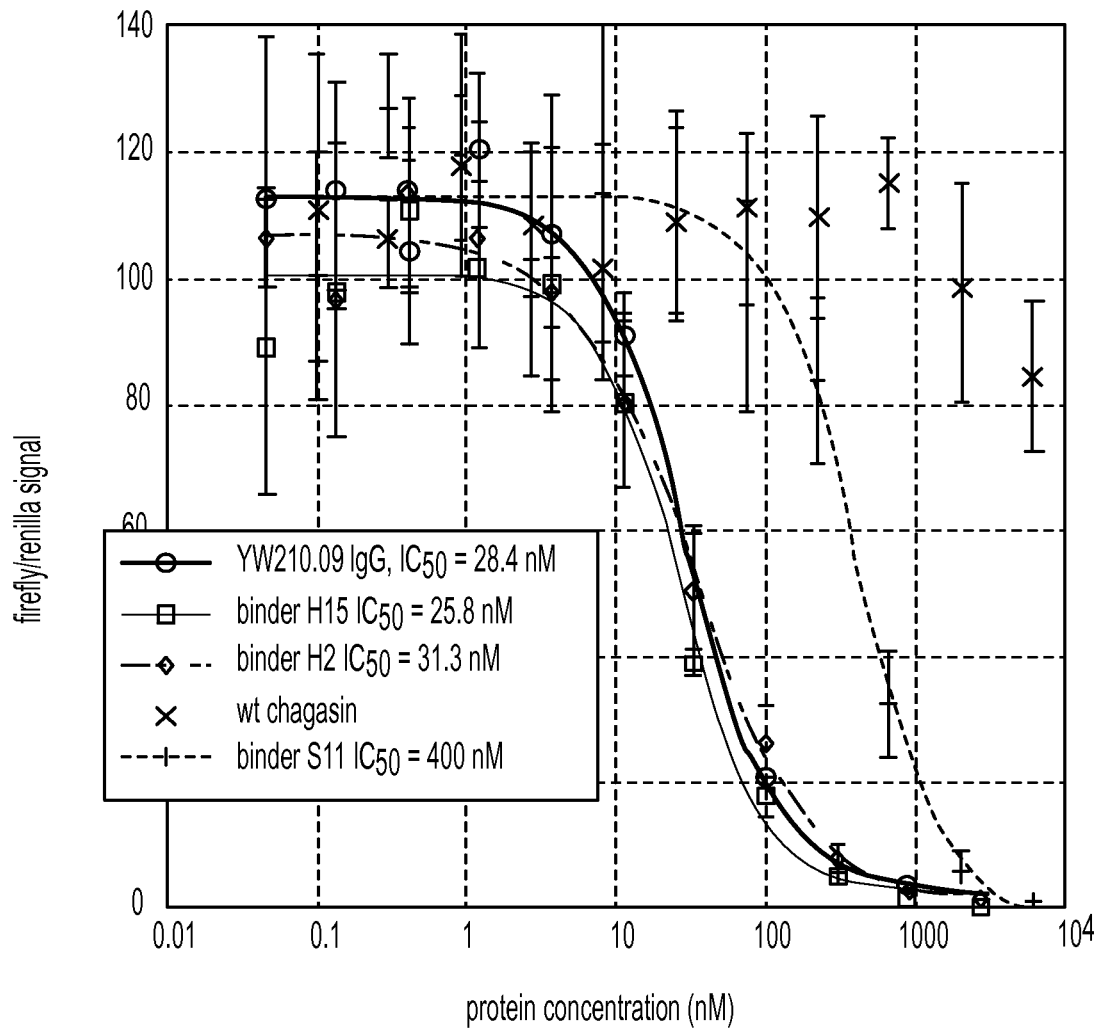
FIG. 6 shows the results of experiments performed to determine whether LRP6 binders H2, H15, and S11 are capable of inhibiting Wnt-dependent cellular signaling.
Figure 7:
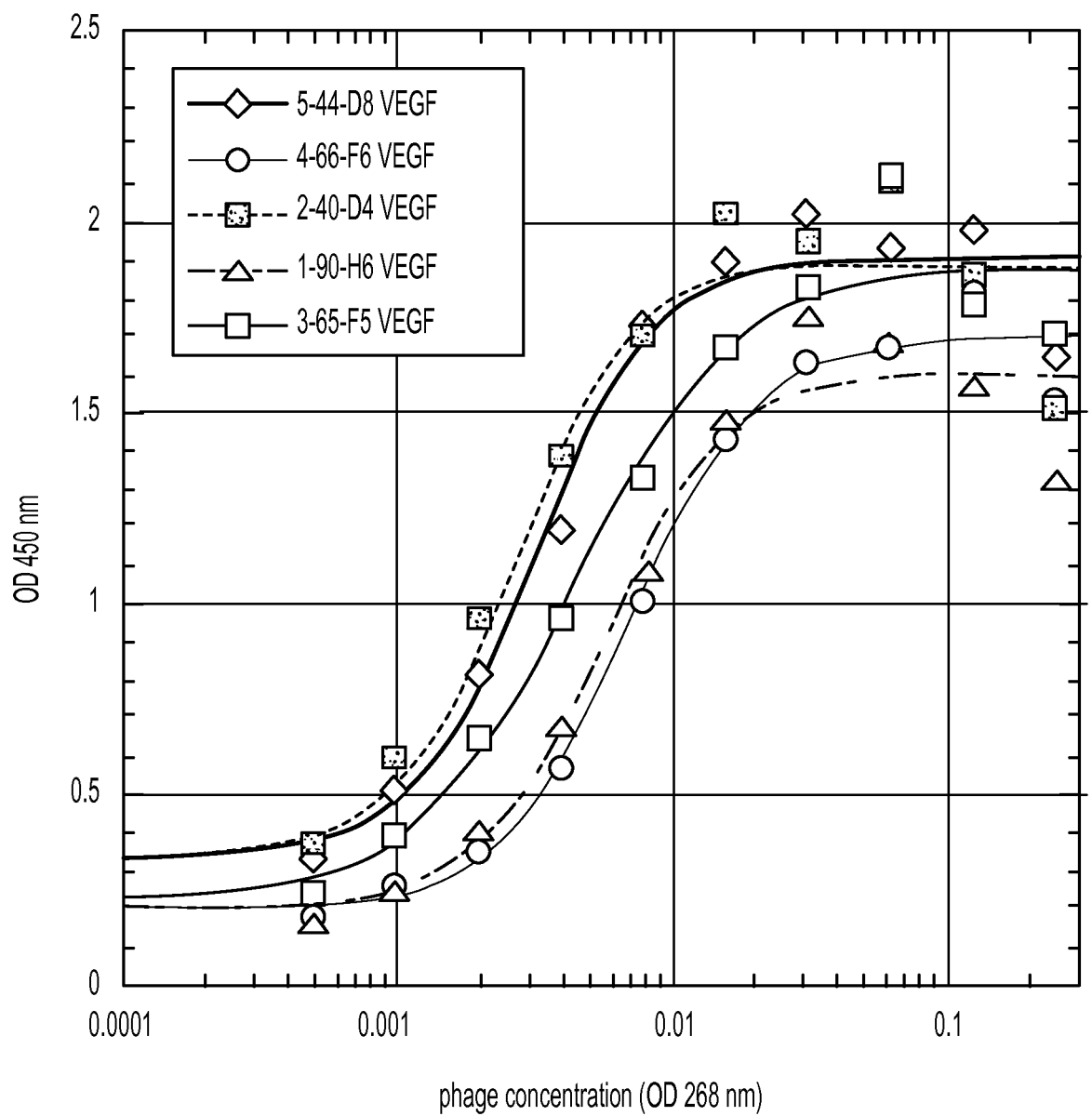
FIG. 7 shows phage binding titration of chagasin VEGF variants 5-44-D8 (SEQ ID NO: 36), 4-66-F6 (SEQ ID NO: 37), 2-40-D4 (SEQ ID NO: 38), 1-90-H6 (SEQ ID NO: 39), and 3-65-F5 (SEQ ID NO: 40) to VEGF coated onto ELISA plates (5 µg/ml VEGF coated on 384 well MAXISORP™ plates).
Figure 8:
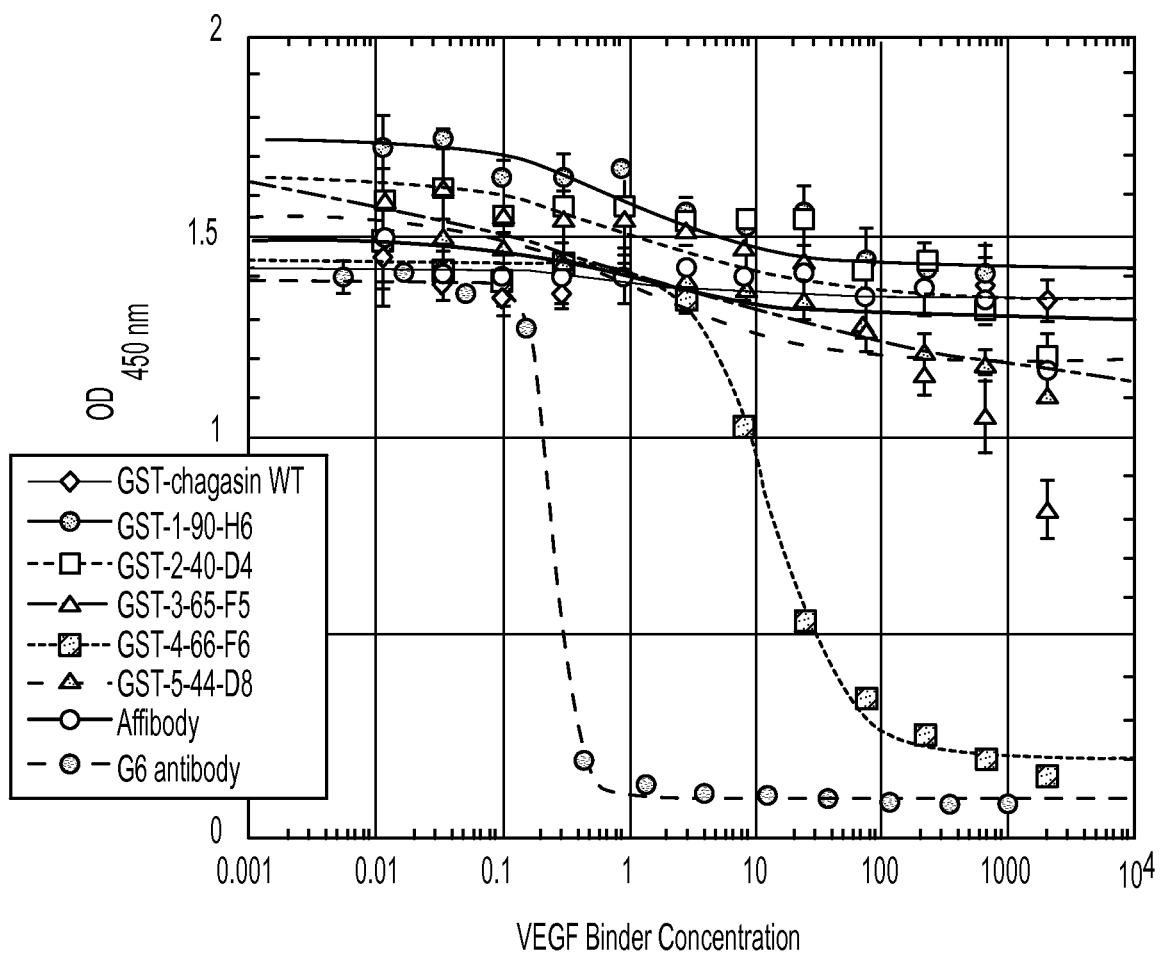
FIG. 8 shows the results of experiments performed to determine the ability of GST-fused chagasin VEGF variants 1-90-H6 (SEQ ID NO: 39), 2-40-D4 (SEQ ID NO: 38), 3-65-F5 (SEQ ID NO: 40), 4-66-F6 (SEQ ID NO: 37), and 5-44-D8 (SEQ ID NO: 36) to block VEGF binding to VEGFR1-ECD Fc fusion in a competition binding ELISA.
Figure 9:
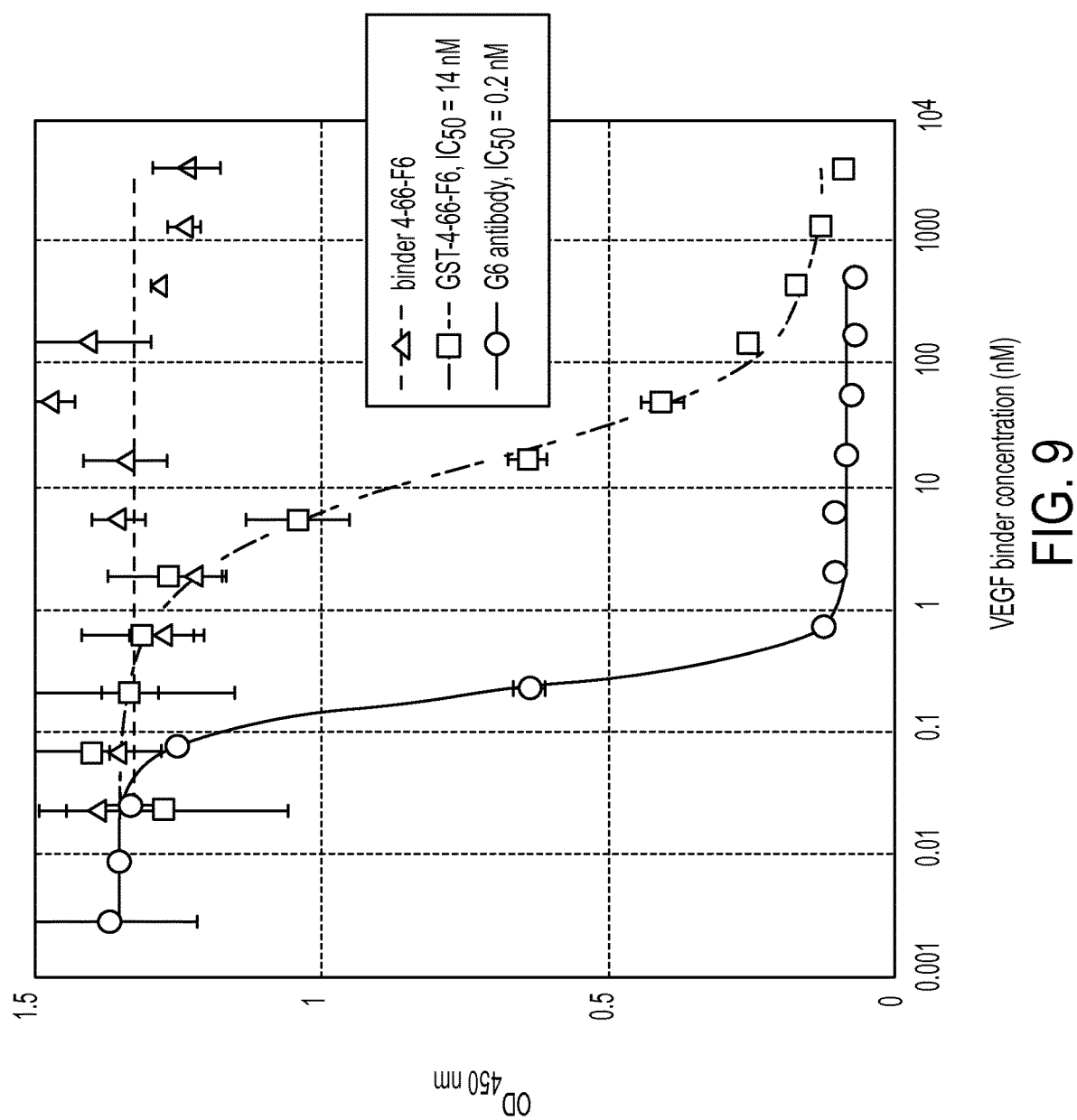
FIG. 9 shows the results of experiments performed to determine the ability of VEGF variant 4-66-F6 (SEQ ID NO: 37) alone and fused to GST to block VEGF binding to VEGFR1-ECD Fc fusion in a competition binding ELISA.
Figure 10:
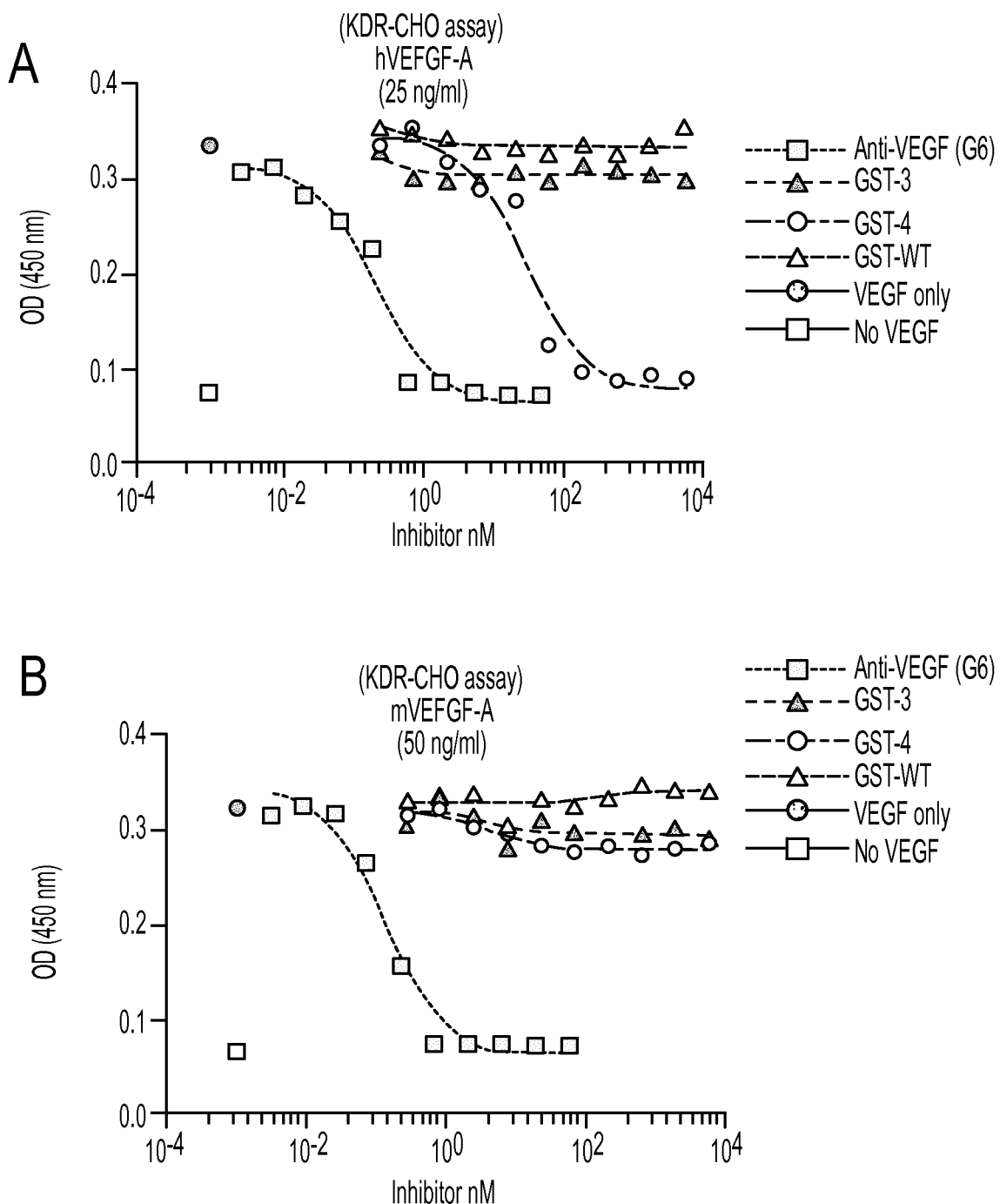
FIG. 10A shows the results of experiments performed to determine the inhibitory activity of GST-fused chagasin VEGF variants against human VEGF in a cell-based assay. (The amino acid sequence of Variant 3 is set forth in SEQ ID NO: 40; the amino acid sequence of Variant 4 is set forth in SEQ ID NO: 37; the amino acid sequence of WT is set forth in SEQ ID NO: 1.)
FIG. 10B shows the results of experiments performed to determine the inhibitory activity of GST-fused chagasin VEGF variants against mouse VEGF in a cell-based assay. (The amino acid sequence of Variant 3 is set forth in SEQ ID NO: 40; the amino acid sequence of Variant 4 is set forth in SEQ ID NO: 37; the amino acid sequence of WT is set forth in SEQ ID NO: 1.)
FIG. 10C shows the results of experiments performed to determine the inhibitory activity of GST-fused chagasin VEGF variants against rat VEGF in a cell-based assay. (The amino acid sequence of Variant 3 is set forth in SEQ ID NO: 40; the amino acid sequence of Variant 4 is set forth in SEQ ID NO: 37; the amino acid sequence of WT is set forth in SEQ ID NO: 1.)
Figure 10:
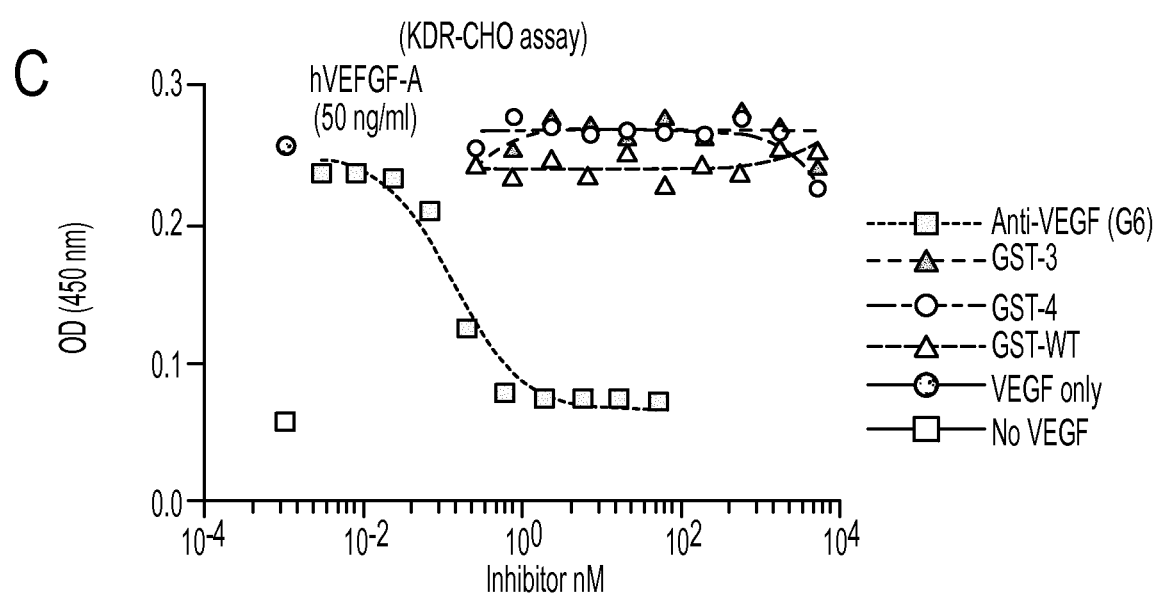
Figure 11:
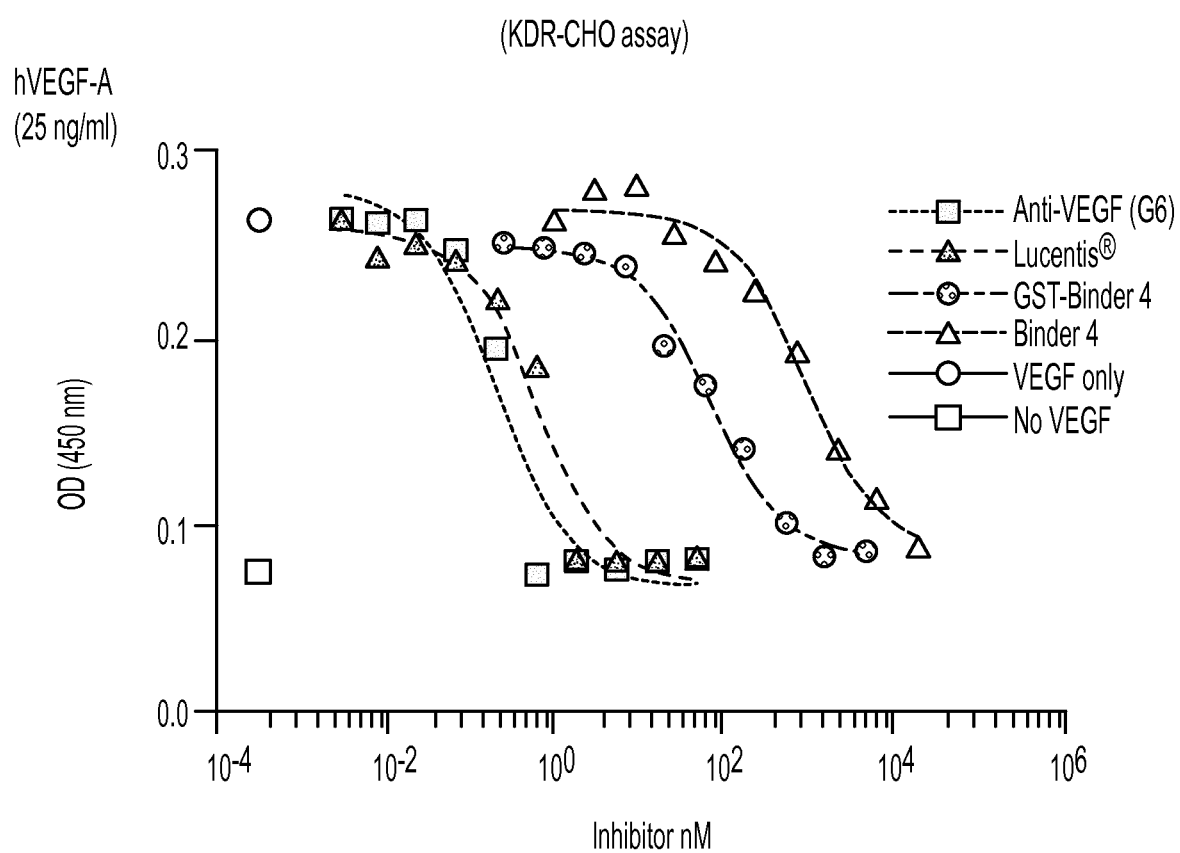
FIG. 11 shows the results of experiments performed to determine the inhibitory activity of GST-chagasin VEGF variant 4, variant 4 (SEQ ID NO: 37), and anti-VEGF antibodies against human VEGF in cell-based assays.

All three chagasin LRP6 variants were further characterization in a cell-based assay for their ability to block Wnt signaling (Y Zhang et al., *Nat Chem Biol* 5, 217-219, 2009; Y Gong et al., *PLoS One* 5, e12682, 2010). Different Wnt ligands bind to different parts of the LRP6 receptor (E Bourhis et al., *J Biol Chem* 285, 9172-9179, 2010). Wnt3a interacts with the E3 domain of LRP6, whereas Wnt1 interacts with the E1 domain, presumably at an overlapping site where the inhibitory antibody YW210.09 and Dkk1 bind (Y Gong et al., *PLoS One* 5, e12682, 2010). The monomeric chagasin LRP6 variants H2, H15 and S11 showed dose-dependent inhibition of Wnt1 signaling in this cell-based assay with $IC_{50}$ values of 31, 26 and 400 nM, respectively (FIG. 6). In comparison, the bivalent inhibitory antibody YW210.09 had an $IC_{50}$ of 28 nM, demonstrating that the monomeric variants H2 and H15 were equally potent reagents. All chagasin LRP6 variants resulted in complete inhibition at saturating concentrations in this assay. Wild-type chagasin does not inhibit Wnt1 signaling in this assay, nor does it interfere with normal cell growth. The high affinity chagasin LRP6 variants overlap with the YW210.09 binding epitope and utilize the same NXIK peptide binding site on E1 of LRP6.

Generation of Chagasin Variants that Bind VEGF

For generating chagasin VEGF variants (i.e., chagasin variants that specifically bind to VEGF), the 8 individual naive chagasin phage libraries were pooled into 3 groups (A, B, C), where pool A contained only libraries with different lengths of randomized Loop L4, pool B contained libraries with randomized L2 and L4 loops and pool C consisted of libraries where all 3 loops were randomized simultaneously (Table 6). These 3 library pools were subjected to 4 rounds of conventional plate sorting where VEGF was immobilized onto MAXISORP™ immunoplates (Y Chen et al., *J Mol Biol* 293, 865-881, 1999; R Tonikian et al., *Nat Protoc* 2, 1368-1386, 2007). A total of 96 individual phage clones from each library pool were grown and analyzed by phage spot ELISA for specific target binding. Only library pool C resulted in individual variants with high target binding and specificity, which was confirmed by phage titration against VEGF and BSA in an ELISA (FIG. 7). All 5 variants were produced as GST-fusion proteins and tested for their ability to block VEGF binding to VEGFR1-ECD Fc fusion in a competition binding ELISA (FIG. 8) (J Bostrom et al., *Science* 323, 1610-1614, 2009). Only variant 4 as a GST-fusion protein along with the G6 anti-VEGF antibody (G Fuh et al., *J Biol Chem* 281, 6625-6631, 2006; W C Liang et al., *J Biol Chem* 281, 951-961, 2006) were able to block VEGF binding to VEGFR1-ECD with $IC_{50}$ values of 13 nM and 0.25 nM, respectively. Variant 3 showed fairly weak inhibition at higher concentrations, but none of the other binders had inhibitory activity. Monomeric chagasin VEGF variant 4 did not block VEGF binding in the same assay (FIG. 9). Without being bound by theory, this may be due to the fact that GST forms dimers and could lead to increased avidity for chagasin variants binding to VEGF that enhance potency in this assay. In this assay, both binding sites of the homodimeric VEGF need to be blocked in this assay to abrogate the signal effectively.

Chagasin VEGF Variants Inhibit VEGF-Dependent Cellular Signaling

We tested variant 4 as a GST-fusion as well as monomeric chagasin VEGF variant 4 in cell-based assays to see whether they are capable of blocking VEGF-dependent cellular signaling through its receptor KDR, where intracellular receptor phosphorylation is the readout (FIGS. 10A-10C and 11 and Tables 7 and 8 below) (H Gille et al., *J Biol Chem* 276, 3222-3230, 2001). In this assay, both GST-fused and monomeric variant 4 had inhibitory activity with $IC_{50}$ values of 72 and 908 nM, respectively; none of the other GST-fused chagasin VEGF variants inhibited activity. Interestingly, variant 4 was specific to human VEGF, as it did not inhibit murine or rat VEGF-dependent signaling.

TABLE 8

Inhibitory activity ($IC_{50}$, nM) of VEGF-binding GST-chagasin variants against VEGF in cell-based assays

| Inhibitor | Anti-VEGF (G6) | GST-Variant 3 | GST-Variant 4 | GST-WT |
|---|---|---|---|---|
| hVEGF (25 ng/ml) | 0.21 | No blocking | 28 | No blocking |
| mVEGF (50 ng/ml) | 0.12 | No blocking | No blocking | No blocking |
| rVEGF (50 ng/ml) | 0.13 | No blocking | No blocking | No blocking |

TABLE 9

Inhibitory activity ($IC_{50}$, nM) of VEGF-binding GST-variant 4, variant 4, and anti-VEGF antibodies against VEGF in cell-based assays

| Inhibitor | Anti-VEGF (G6) | Lucentis ® | GST-Variant 4 | Variant 4 |
|---|---|---|---|---|
| hVEGF (25 ng/ml) | 0.21 | 0.63 | 73 | 910 |
| mVEGF (50 ng/ml) | 0.19 | No blocking | No blocking | No blocking |
| rVEGF (50 ng/ml) | 0.078 | No blocking | No blocking | No blocking |

Affinity Maturation of Chagasin VEGF Variant 4

In order to improve the affinity and potency of monomeric VEGF variant 4, we designed 4 new libraries where the sequence of L2 and L6 of this variant were soft randomized and L4 contained either 6, 8 or 10 randomized position with a YSGX composition (excluding cysteine) (F A Fellouse et al., *J Mol Biol* 373, 924-940, 2007) or a soft randomized parental sequence. All libraries were subjected to 4 rounds of stringent solution phage panning (Y Zhang et al., *J Biol Chem* 289, 942-955, 2014). A total of 96 clones from each library were expressed as individual clones and analyzed by phage ELISA. From the 384 phage clones analyzed, 34 individual clones with high target specificity were identified (FIG. 12) and 23 clones were expressed in small scale using the EXIPROGEN™ protein synthesis system from Bioneer. FIG. 12 shows partial sequence of 33 phage clones with high target affinity and specificity to VEGF determined by phage spot ELISA. Randomized positions in loops 2, 4, 6 are in bold type. 23 variants produced in small scale using the EXIPROGEN™ protein synthesis system are marked with asterisks. The six variants produced for tests in cell-based assays are E4B-10, E4B-5, E4B-7, 37, L4X6-3, L4X8-9, and L4X6-7, as noted on the right side of FIG. 12. Cysteines are underlined.

Figure 13:
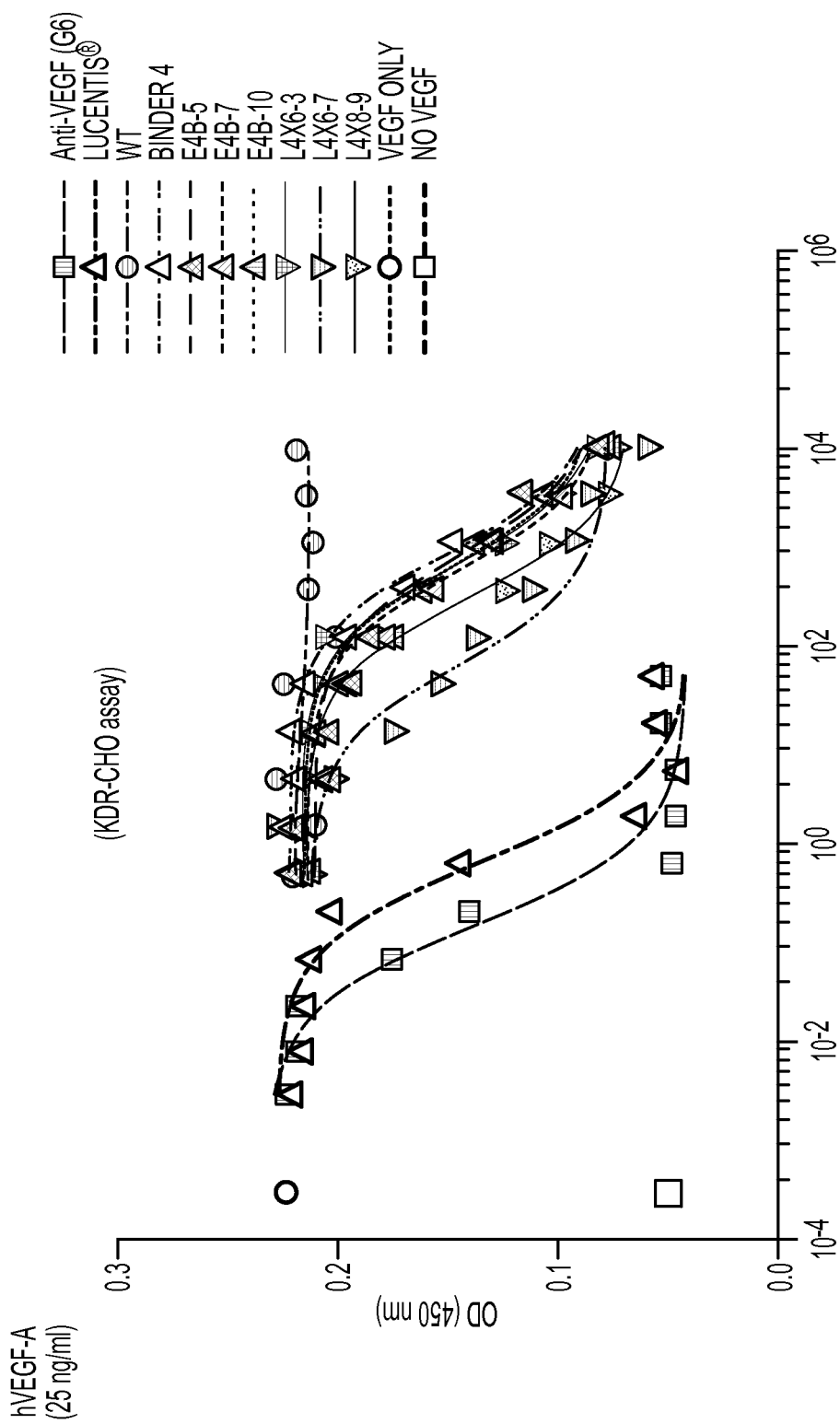
FIG. 13 shows the results of experiments performed to determine the inhibitory activity of affinity matured chagasin VEGF variants against human VEGF in cell-based assays. (The amino acid sequence of WT is set forth in SEQ ID NO: 1; the amino acid sequence of Binder 4 is set forth in SEQ ID NO: 37; the amino acid sequence of E4B-5 is set forth in SEQ ID NO: 70; the amino acid sequence of E4B-7 is set forth in SEQ ID NO: 71; the amino acid sequence of E4B-10 is set forth in SEQ ID NO: 69; the amino acid sequence of L4X6-3 is set forth in SEQ ID NO: 73; the amino acid sequence of L4X6-7 is set forth in SEQ ID NO: 75; and the amino acid sequence of L4X6-9 is set forth in SEQ ID NO: 74.)
Figure 14:
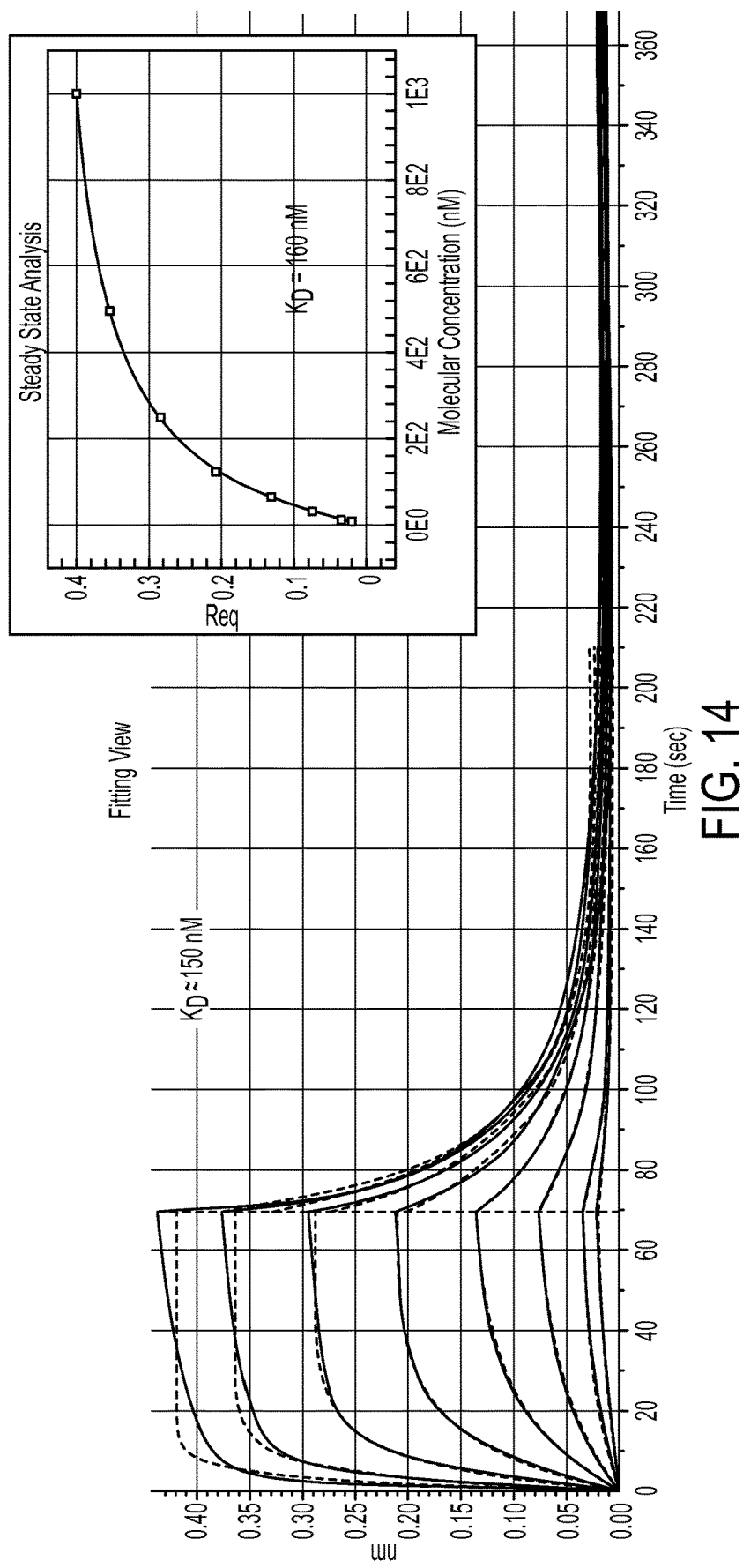
FIG. 14 shows the results of experiments performed to determine the binding kinetics of monomeric chagasin VEGF variant L4X6-7 (the amino acid sequence of which is set forth in SEQ ID NO: 75) in solution to biotinylated VEGF109.

The binding kinetics of these 23 variants were profiled by BLI on an OCTET® RED384 kinetic analysis system and the 6 best from these were expressed as GST-fusions in larger scale and purified as monomeric chagasin VEGF variants after cleavage by TEV protease. These 6 variants were tested for their ability to inhibit VEGF-dependent signaling through the KDR receptor on cells (H Gille et al., *J Biol Chem* 276, 3222-3230, 2001). Most of the variants showed relatively minor improvements in inhibition, but variants L4X6-7 and L4X8-9 had $IC_{50}$ values of 65 and 301 nM, respectively, which represent 13- and 2-fold improvements over the parental chagasin variant 4 (FIG. 13 and Table 9 below). The affinity of L4X6-7 binding to VEGF was Kd=150 nM based on kinetic binding measurements (FIG. 14), which is a 2.5-fold improvement over the parental variant 4.

Figure 15:
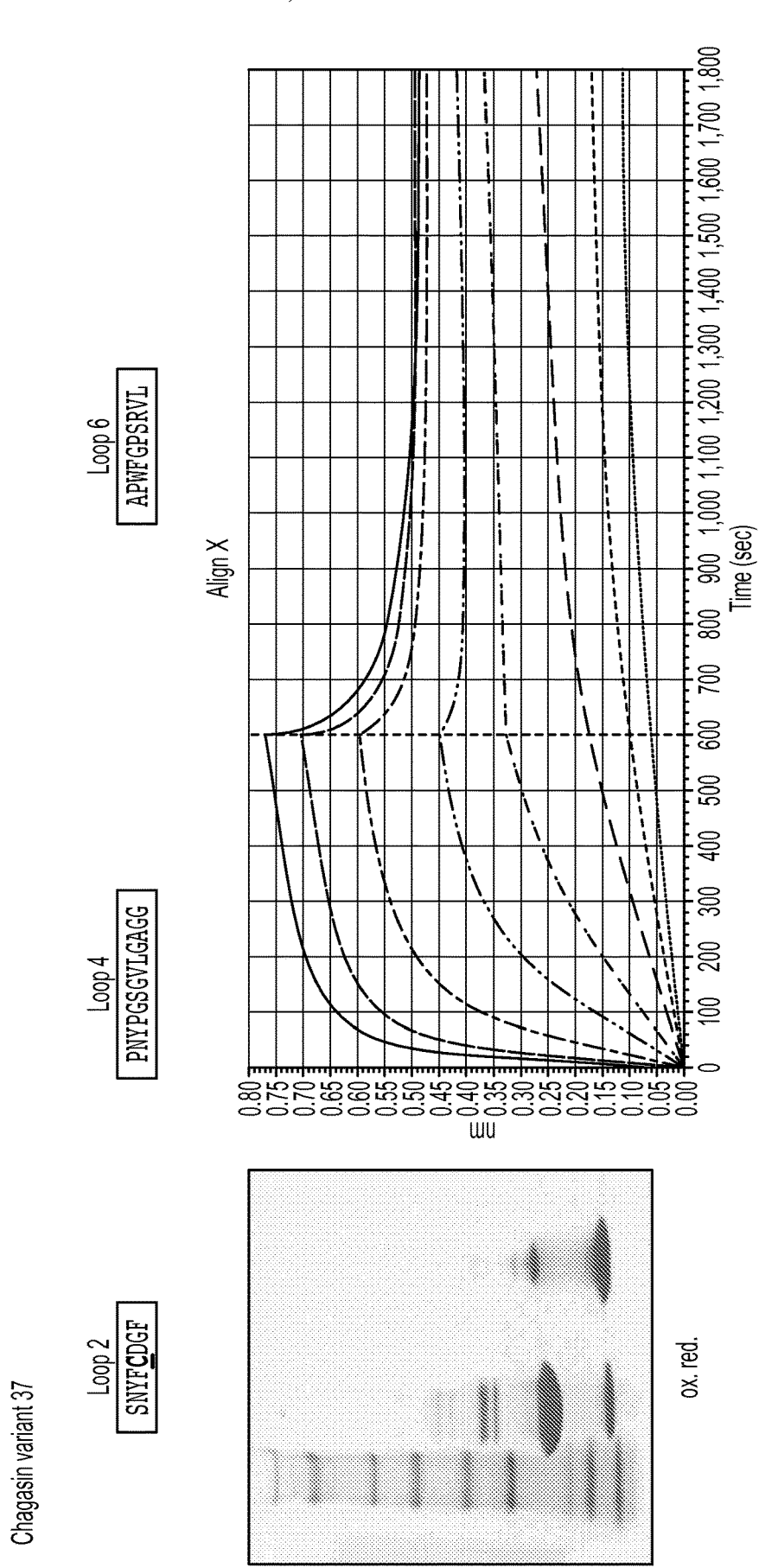
FIG. 15 shows SDS-PAGE analysis and binding kinetics of chagasin VEGF variants 37 (i.e., SEQ ID NO: 72) and 66 (SEQ ID NO: 76).
Figure 15:
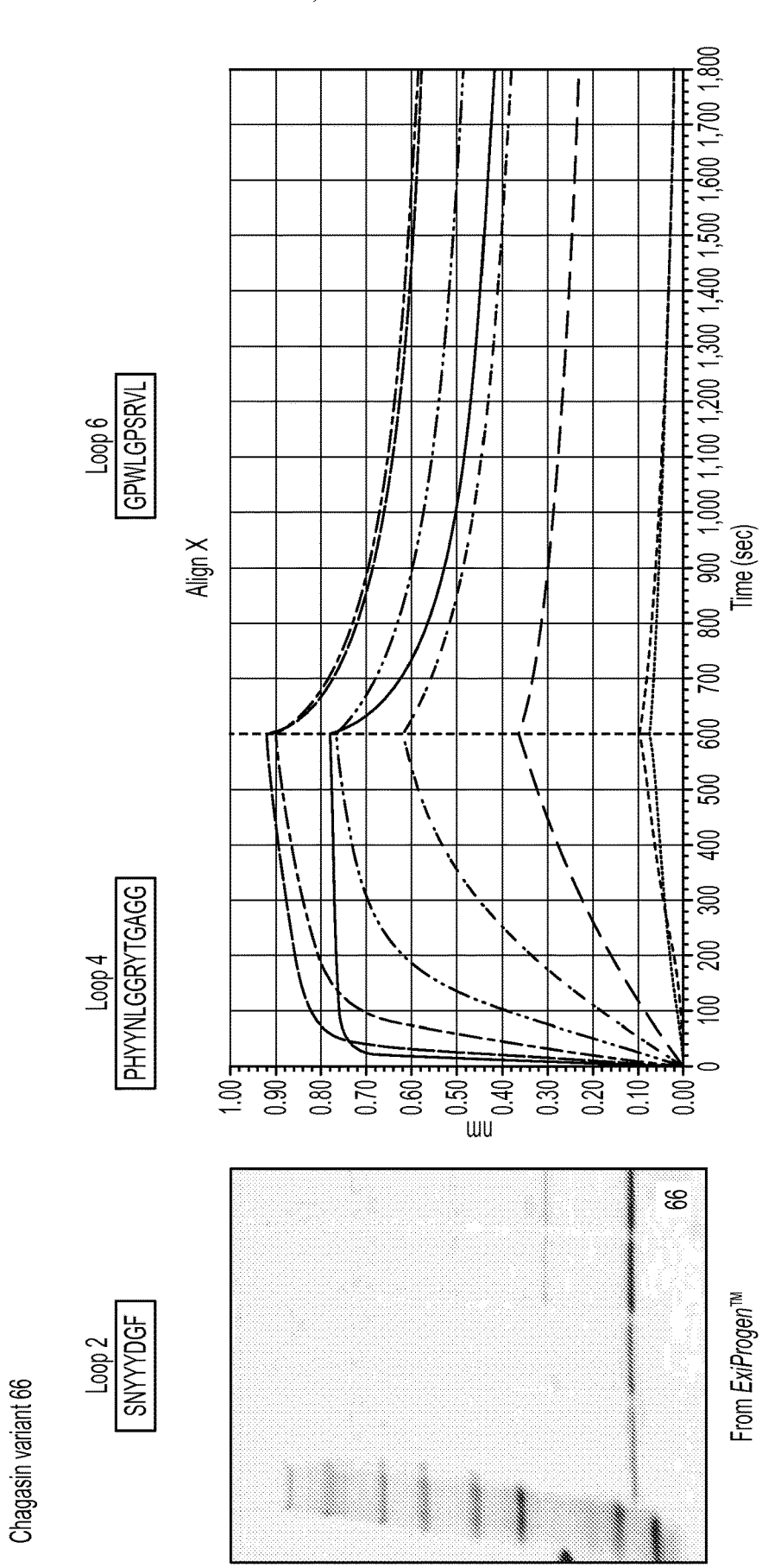

FIG. 15 shows SDS-PAGE analysis and binding kinetics of chagasin VEGF variants 37 and 66. Chagasin variant 37 forms dimers under oxidizing conditions that can be separated into monomers under reducing conditions. Binding kinetics of both binders were measured with biotinylated VEGF109 loaded on streptavidin biosensors on an OCTET® RED384 kinetic analysis system. Both binders showed slow dissociation rates, with dimeric chagasin variant 37 being biphasic.

Only a single clone (clone 66) that was displayed on g3 with an amber stop codon was found that did not contain any cysteines in any of the randomized loops. Chagasin variant 66 was produced on a small scale using the EXIPROGEN™ protein synthesis system and evaluated for binding to VEGF by BLI. This clone showed binding kinetic curves indicative of a double digit nanomolar binder (FIG. 15).

After a large-scale protein expression and purification, it was noticed that chagasin variant 66 had limited solubility and would precipitate at concentrations needed for cell-based experiments and affinity measurements. Two new phage libraries based on the sequence of clone 66 were designed, where each variant contained only a single randomized position in loops L2 and L4 at the time, allowing to incorporate any of the 20 amino acid ("NNK walk"). The libraries were panned for 2 rounds as previously described in the affinity maturation procedure and 200 random clones from the last sort were selected for DNA sequencing and analysis. Based on the sequence analysis, two Tyrosine residues in L2 and L4 were replaced individually with other residues that were chosen as second tier based on their abundance in the sequenced clones. Four new clones (66-L2-K, 66-L4-Q, 66-L4-T, 66-L4-S) were expressed and purified as GST-fusion and individual chagasin variants were obtained by TEV cleavage as described above. Their affinity to VEGF109 was measured using an OCTET® RED384 kinetic analysis system by Octet and their inhibitory activity was tested in the cell-based assay, as described above. The measured data of these variants is listed in Table 11, below:

TABLE 10

Inhibitory Activity ($IC_{50}$, nM) of affinity matured VEGF-binding variants derived from variant 4 against hVEGF in cell-based assays

| Inhibitor | Anti-VEGF (G6) | Lucentis ® | Variant 4 | E4B-5 | E4B-7 | E4B-10 | L4X6-3 | L4X6-7 | L4X8-7 |
|---|---|---|---|---|---|---|---|---|---|
| hVEGF (25 ng/ml) | 0.14 | 0.68 | 840 | 800 | 550 | 610 | 710 | 65 | 300 |

Identification of a Chagasin Homodimer Variant that Binds VEGF with Higher Affinity.

Nine out of the 34 individual clones that showed a high degree of target specificity detected by phage ELISA contained a single cysteine at the same position in L2 (YF<u>C</u>D). Since the L4 loop still carried a lot of sequence variability after affinity maturation of the parental sequence and loops L2 and L6 showed only very minor changes and mostly preferred the parental sequence, L4 is likely not significantly involved in VEGF binding. Clone 37 that was displayed on g3 with an amber stop containing a single cysteine in L2 (YFCD) was selected and expressed as a GST-fusion. After GST removal by TEV cleavage and SUPERDEX™ 75 size exclusion chromatography, variant 37 started to spontaneously form homodimers under oxidizing conditions (FIG.

TABLE 11

| Chagasin VEGF binder | L2 | L4 | L6 | $K_d$ (nM) | $IC_{50}$ Cell assay |
|---|---|---|---|---|---|
| Variant 66 | SNYYYD (SEQ ID NO: 48) | HYYNLGGRYT (SEQ ID NO: 57) | GPWLGPSRVL (SEQ ID NO: 66) | n.a. | n.a. |
| Variant 66-L2-K | SNYYKD (SEQ ID NO: 110) | HYYNLGGRYT (SEQ ID NO: 57) | GPWLGPSRVL (SEQ ID NO: 66) | 61 | 186 |
| Variant 66-L4-Q | SNYYYD (SEQ ID NO: 48) | HYQNLGGRYT (SEQ ID NO: 111) | GPWLGPSRVL (SEQ ID NO: 66) | 80 | 95 |

TABLE 11-continued

| Chagasin VEGF binder | L2 | L4 | L6 | $K_d$ (nM) | $IC_{50}$ Cell assay |
|---|---|---|---|---|---|
| Variant 66-L4-S | SNYYYD (SEQ ID NO: 48) | HYSNLGGRYT (SEQ ID NO: 112) | GPWLGPSRVL (SEQ ID NO: 66) | 50 | 216 |
| Variant 66-L4-T | SNYYYD (SEQ ID NO: 48) | HYTNLGGRYT (SEQ ID NO: 113) | GPWLGPSRVL (SEQ ID NO: 66) | 51 | 190 |

The preceding Examples are offered for illustrative purposes only, and are not intended to limit the scope of the present invention in any way. Various modifications of the invention in addition to those shown and described herein will become apparent to those skilled in the art from the foregoing description and fall within the scope of the appended claims.

List of Embodiments

1. A non-naturally occurring chagasin scaffold protein comprising at least one amino acid alteration in Loop 2 (L2), Loop 4 (L4), and/or Loop 6 (L6), with reference to a wild-type chagasin-like cysteine protease inhibitor.
2. The non-naturally occurring chagasin scaffold protein of embodiment 1, wherein the wild type chagasin-like cysteine protease inhibitor is from *T. cruzi* (Dm28c clone), *T. cruzi* (CL Brenner strain, isoform 1), *T. cruzi* (CL Brenner strain, isoform 2), *T. brucei, L. mexicana, L. major, E. hystolytica*, or *P. aeruginosa.*
3. The non-naturally occurring chagasin scaffold protein of embodiment 1, wherein the wild type chagasin-like cysteine protease inhibitor is from human CD8 T-cell surface glycoprotein, human interleukine-1 type 1 receptor (IL-1 R1), or human vascular cell adhesion molecule-1 (Vcam-1).
4. The non-naturally occurring chagasin scaffold protein of embodiment 2 or 3, wherein the wild type chagasin-like cysteine protease inhibitor is *T. cruzi* (CL Brenner strain, isoform 1) having the amino acid sequence set forth in SEQ ID NO: 1.
5. The non-naturally occurring chagasin scaffold protein of embodiment 4, wherein L2 comprises the amino acid sequence $X_{5-8}$-GF (SEQ ID NO: 151), wherein X represents any amino acid.
6. The non-naturally occurring chagasin scaffold protein of embodiment 5, wherein L2 comprises the amino acid sequence $SNX_{3-6}$-GF (SEQ ID NO: 152), wherein X represents any amino acid.
7. The non-naturally occurring chagasin scaffold protein of any one of embodiments 4-6, wherein L4 comprises the amino acid sequence $X_{7-15}$-GAGG (SEQ ID NO: 153) wherein X represents any amino acid.
8. The non-naturally occurring chagasin scaffold protein of any one of embodiments 4-7, wherein L6 comprises the amino acid sequence $X_{3-12}$ (SEQ ID NO: 154), wherein X represents any amino acid.
9. The non-naturally occurring chagasin scaffold protein of embodiment 8, wherein L6 comprises the amino acid sequence $X_{10}$ (SEQ ID NO: 106) wherein X represents any amino acid.
10. The non-naturally occurring chagasin scaffold protein of any one of embodiments 4-9, comprising the amino acid sequence set forth in SEQ ID NO: 2.
11. The non-naturally occurring chagasin scaffold protein of any one of embodiments 1-10, wherein the non-naturally occurring chagasin scaffold protein specifically binds a target ligand.
12. The non-naturally occurring chagasin scaffold protein of embodiment 11, wherein the target ligand is a protein, a nucleic acid, a polysaccharide, a lipopolysaccharide, a lipid, or a phospholipid.
13. The non-naturally occurring chagasin scaffold protein of embodiment 12, wherein the target ligand is a protein.
14. The non-naturally occurring chagasin scaffold protein of embodiment 13, wherein the protein is a cell surface protein, a soluble protein, a viral protein, a bacterial protein, a protein associated with ocular disease, a protein associated with cancer, a protein associated with bone disease, a protein associated with inflammation, or a therapeutic protein.
15. The non-naturally occurring chagasin scaffold protein of embodiment 13, wherein the protein is LRP6.
16. The non-naturally occurring chagasin scaffold protein of embodiment 13, wherein the protein is VEGF.
17. The non-naturally occurring chagasin scaffold protein of any one of embodiments 1-16 conjugated to a therapeutic agent.
18. The non-naturally occurring chagasin scaffold protein of any one of embodiments 1-16 conjugated to a label.
19. The non-naturally occurring chagasin scaffold protein according to embodiment 18, wherein the label is selected from the group consisting of a radioisotope, a fluorescent dye, and an enzyme.
20. An isolated nucleic acid encoding the non-naturally occurring chagasin scaffold protein according to any one of embodiments 1-16.
21. An expression vector encoding the nucleic acid molecule of embodiment 20.
22. A cell comprising the expression vector of embodiment 21.
23. A method of producing the non-naturally occurring chagasin scaffold protein of any one of embodiments 1-16 comprising culturing the cell of embodiment 22 and recovering the non-naturally occurring chagasin scaffold protein from the cell culture.
24. A method of producing the non-naturally occurring chagasin scaffold protein of any one of embodiments 1-16 comprising chemically synthesizing the non-naturally occurring chagasin scaffold protein.
25. A composition comprising the non-naturally occurring chagasin scaffold protein of any one of embodiments 1-16 and a pharmaceutically acceptable carrier.
26. A polypeptide display library comprising a plurality of the non-naturally occurring chagasin scaffold proteins of any one of embodiments 1-16.
27. The polypeptide display library of embodiment 26, wherein the non-naturally occurring chagasin scaffold proteins are displayed on the surfaces of ribosomes, bacteriophage, viruses, bacteria, or yeast cells.
28. The polypeptide display library of embodiment 27, wherein the non-naturally occurring chagasin scaffold proteins are displayed on bacteriophage.
29. The polypeptide display library of embodiment 28, wherein the bacteriophage is a filamentous bacteriophage.
30. The polypeptide display library of embodiment 29, wherein the filamentous bacteriophage are M13 phage.
31. The polypeptide display library of any one of embodiments 26-30, wherein the polypeptide library has a sequence diversity of between about $10^8$ and about $10^{14}$.
32. Nucleic acid molecules encoding the polypeptide display library of any one of embodiments 26-31.

33. An expression vector operably linked to the nucleic acid molecules of embodiment 32.

34. A method of obtaining a non-naturally occurring chagasin scaffold protein that specifically binds to a target ligand, comprising:
(a) contacting a target ligand with the library of any one of embodiments 26-31 under conditions that allow a non-naturally occurring chagasin scaffold protein: target ligand complex to form;
(b) detecting the formation of the non-naturally occurring chagasin scaffold protein: target ligand complex; and,
(c) obtaining from the complex the non-naturally occurring chagasin scaffold protein that specifically binds the target ligand.

35. The method of embodiment 34, further comprising randomizing L2, L4, and/or L6 of the non-naturally occurring chagasin scaffold protein obtained in step (c) to generate a further randomized non-naturally occurring chagasin scaffold protein and repeating steps (a) and (b) using said further randomized non-naturally occurring chagasin scaffold protein.

36. A non-naturally occurring chagasin scaffold protein that specifically binds to the same epitope as a second non-naturally occurring chagasin scaffold protein that binds human low density lipoprotein receptor-related protein 6 (LRP6), wherein the second non-naturally occurring chagasin scaffold protein that binds human LRP6 comprises an L2 that comprises the amino acid sequence SNP-T/S/A/Q-T/C/D (SEQ ID NO: 150) or SN-V/A-D (155), an L4 that comprises the amino acid sequence Y/S-N-N/K-I/V-R/K-G-L/V/I-PGF (SEQ ID NO: 156) or SN-Y/S-TK-H/R (SEQ ID NO: 157), or DSNEIWYC (SEQ ID NO: 77); and an L6 that comprises the amino acid sequence R/S/P/G-P/R-W/Y/E/S/V-T/Y/K/T-G-P/S/A-S/T/Y-H/K/L/Q/D-D/V/E-S/E/M/P/V (SEQ ID NO: 148), with reference to SEQ ID NO: 2.

37. A non-naturally occurring chagasin scaffold protein that specifically binds human low density lipoprotein receptor-related protein 6 (LRP6), wherein the non-naturally occurring chagasin scaffold protein competes for binding with a second non-naturally occurring chagasin scaffold protein that binds human LRP6, wherein the second non-naturally occurring chagasin scaffold protein that binds human LRP6 comprises an L2 that comprises the amino acid sequence SNP-T/S/A/Q-T/C/D (SEQ ID NO: 150) or SN-V/A-D (155), an L4 that comprises the amino acid sequence Y/S-N-N/K-I/V-R/K-G-L/V/I-PGF (SEQ ID NO: 156) or SN-Y/S-TK-H/R (SEQ ID NO: 157), or DSNEIWYC (SEQ ID NO: 77); and an L6 that comprises the amino acid sequence R/S/P/G-P/R-W/Y/E/S/V-T/Y/K/T-G-P/S/A-S/T/Y-H/K/L/Q/D-D/V/E-S/E/M/P/V (SEQ ID NO: 148), with reference to SEQ ID NO: 2.

38. The non-naturally occurring chagasin scaffold protein that specifically binds human LRP6 of any one of embodiments 36 or 37, wherein the non-naturally occurring chagasin scaffold protein that specifically binds human LRP6 comprises an L2 that comprises the amino acid sequence SNP-T/S/A/Q-T/C/D (SEQ ID NO: 150) or SN-V/A-D (155), an L4 that comprises the amino acid sequence Y/S-N-N/K-I/V-R/K-G-L/V/I-PGF (SEQ ID NO: 156) or SN-Y/S-TK-H/R (SEQ ID NO: 157), or DSNEIWYC (SEQ ID NO: 77); and an L6 that comprises the amino acid sequence R/S/P/G-P/R-W/Y/E/S/V-T/Y/K/T-G-P/S/A-S/T/Y-H/K/L/Q/D-D/V/E-S/E/M/P/V (SEQ ID NO: 148), with reference to SEQ ID NO: 2.

39. The non-naturally occurring chagasin scaffold protein of embodiment 38, wherein L2 comprises an amino acid sequence set forth in any one of SEQ ID NOs: 3-5, 78-80, and 146, L4 comprises an amino acid sequence set forth in any one of SEQ ID NOs: 7-9, 77, and 81-83; and L6 comprises an amino acid sequence set forth in any one of SEQ ID NOs: 11-13, 84-86, and 147, with reference to SEQ ID NO: 2.

40. The non-naturally occurring chagasin scaffold protein of embodiment 39, wherein L2 comprises the amino acid sequence SNPQT (SEQ ID NO: 3), wherein L4 comprises the amino acid sequence SNKVKGVPGF (SEQ ID NO: 7); and wherein L6 comprises the amino acid sequence GPWTGASQEP (SEQ ID NO: 11).

41. The non-naturally occurring chagasin scaffold protein of embodiment 39, wherein L2 comprises the amino acid sequence SNPTT (SEQ ID NO: 4), wherein L4 comprises the amino acid sequence SNKIKGIPGF (SEQ ID NO: 8); and wherein L6 comprises the amino acid sequence RPSTGPSDDS (SEQ ID NO: 12).

42. The non-naturally occurring chagasin scaffold protein of embodiment 39, wherein L2 comprises the amino acid sequence SNVD (SEQ ID NO: 5), wherein L4 comprises the amino acid sequence SNSTKR (SEQ ID NO: 9); and wherein L6 comprises the amino acid sequence PRVKGAYLVM (SEQ ID NO: 13).

43. The non-naturally occurring chagasin scaffold protein of embodiment 39, wherein L2 comprises the amino acid sequence SNPTT (SEQ ID NO: 4), L4 comprises the amino acid sequence YNNIRGLPGF (SEQ ID NO: 81); and L6 comprises the amino acid sequence RPWTGPSHDS (SEQ ID NO: 84), with reference to SEQ ID NO: 2.

44. The non-naturally occurring chagasin scaffold protein of embodiment 39, wherein L2 comprises the amino acid sequence SNPSC (SEQ ID NO: 79), L4 comprises the amino acid sequence DSNEIWYC (SEQ ID NO: 82); and L6 comprises the amino acid sequence SPYYGPTKVE (SEQ ID NO: 85), with reference to SEQ ID NO: 2.

45. The non-naturally occurring chagasin scaffold protein of embodiment 39, wherein L2 comprises the amino acid sequence SNPAD (SEQ ID NO: 80), L4 comprises the amino acid sequence SNYTKH (SEQ ID NO: 83); and L6 comprises the amino acid sequence PREKGSSLVM (SEQ ID NO: 86), with reference to SEQ ID NO: 2.

46. The non-naturally occurring chagasin scaffold protein of embodiment 39, wherein L2 comprises the amino acid sequence SNAD (SEQ ID NO: 146), L4 comprises the amino acid sequence SNSTKR (SEQ ID NO: 9); and an L6 that comprises the amino acid sequence RREKGSTLVV (SEQ ID NO: 147), with reference to SEQ ID NO: 2.

47. The non-naturally occurring chagasin scaffold protein of embodiment 39, comprising the amino acid sequence set forth in SEQ ID NO: 15.

48. The non-naturally occurring chagasin scaffold protein of embodiment 39, comprising the amino acid sequence set forth in SEQ ID NO: 16.

49. The non-naturally occurring chagasin scaffold protein of embodiment 39, comprising the amino acid sequence set forth in SEQ ID NO: 17.

50. The non-naturally occurring chagasin scaffold protein of embodiment 39, comprising the amino acid sequence set forth in SEQ ID NO: 87.

51. The non-naturally occurring chagasin scaffold protein of embodiment 39, comprising the amino acid sequence set forth in SEQ ID NO: 88.

52. The non-naturally occurring chagasin scaffold protein of embodiment 39, comprising the amino acid sequence set forth in SEQ ID NO: 89.

53. The non-naturally occurring chagasin scaffold protein of embodiment 39, comprising the amino acid sequence set forth in SEQ ID NO: 149.

54. The non-naturally occurring chagasin scaffold protein of any one of embodiments 36-53, wherein the non-naturally occurring chagasin scaffold protein binds a human LRP6 with a Kd between 500 nM and 1 pM.

55. The non-naturally occurring chagasin scaffold protein of any one of embodiments 36-54, wherein the chagasin-derived protein that specifically binds LRP6 inhibits Wnt1 signaling.

56. A non-naturally occurring chagasin scaffold protein that specifically binds to the same as a second non-naturally occurring chagasin scaffold protein that binds human vascular endothelial growth factor (VEGF), wherein the second non-naturally occurring chagasin scaffold protein that binds human VEGF comprises an L2 that comprises the amino acid sequence SN-L/Y-R/F/Q-S/Y/N/D-M/D/A/S (SEQ ID NO: 23), an L4 that comprises the amino acid sequence A/N/L/S/V-G/D/S/R-P/L/T/A-S/G/Y/T-A/S/G/Q-V/R/S/K/A-P/L/E/S/N-L/S/T/N/E (SEQ ID NO: 29); and an L6 that comprises the amino acid sequence A/N/F/S-P/K-W/N/S/V-R/L/W-G-P/L-A/S/D/M/R-N/R/Y/V/F-V/W/P-I/L (SEQ ID NO: 35), with reference to SEQ ID NO: 2.

57. A non-naturally occurring chagasin scaffold protein that specifically binds human vascular endothelial growth factor (VEGF), wherein the non-naturally occurring chagasin scaffold protein competes for binding with a second non-naturally occurring chagasin scaffold protein that binds human VEGF, wherein the second non-naturally occurring chagasin scaffold protein that binds human VEGF comprises an L2 that comprises the amino acid sequence SN-L/Y-R/F/Q-S/Y/N/D-M/D/A/S (SEQ ID NO: 23), an L4 that comprises the amino acid sequence A/N/L/S/V-G/D/S/R-P/L/T/A-S/G/Y/T-A/S/G/Q-V/R/S/K/A-P/L/E/S/N-L/S/T/N/E (SEQ ID NO: 29); and an L6 that comprises the amino acid sequence A/N/F/S-P/K-W/N/S/V-R/L/W-G-P/L-A/S/D/M/R-N/R/Y/V/F-V/W/P-I/L (SEQ ID NO: 35), with reference to SEQ ID NO: 2.

58. The non-naturally occurring chagasin scaffold protein embodiment 56 or 57, wherein the non-naturally occurring chagasin scaffold protein comprises an L2 that comprises the amino acid sequence SN-L/Y-R/F/Q-S/Y/N/D-M/D/A/S (SEQ ID NO: 23), an L4 that comprises the amino acid sequence A/N/L/S/V-G/D/S/R-P/L/T/A-S/G/Y/T-A/S/G/Q-V/R/S/K/A-P/L/E/S/N-L/S/T/N/E (SEQ ID NO: 29); and an L6 that comprises the amino acid sequence A/N/F/S-P/K-W/N/S/V-R/L/W-G-P/L-A/S/D/M/R-N/R/Y/V/F-V/W/P-I/L (SEQ ID NO: 35).

59. The non-naturally occurring chagasin scaffold protein of embodiment 58, wherein L2 comprises an amino acid sequence set forth in any one of SEQ ID NOs: 18-22, wherein L4 comprises an amino acid sequence set forth in any one of SEQ ID NOs: 24-28; and wherein L6 comprises an amino acid sequence set forth in any one of SEQ ID NOs: 30-34.

60. The non-naturally occurring chagasin scaffold protein of embodiment 58, wherein L2 comprises the amino acid sequence SNLRSM (SEQ ID NO: 18), wherein L4 comprises the amino acid sequence AGPSAVPL (SEQ ID NO: 24) and wherein L6 comprises the amino acid sequence APWRGPANVI (SEQ ID NO: 30).

61. The non-naturally occurring chagasin scaffold protein of embodiment 58, wherein L2 comprises the amino acid sequence SNYFYD (SEQ ID NO: 19), wherein L4 comprises the amino acid sequence NDPGSRLS (SEQ ID NO: 25) and wherein L6 comprises the amino acid sequence APWLGPSRVL (SEQ ID NO: 31).

62. The non-naturally occurring chagasin scaffold protein of embodiment 58, wherein L2 comprises the amino acid sequence SNLQNA (SEQ ID NO: 20), wherein L4 comprises the amino acid sequence LSLYASET (SEQ ID NO: 26) and wherein L6 comprises the amino acid sequence NPNWGPDYWI (SEQ ID NO: 32).

63. The non-naturally occurring chagasin scaffold protein of embodiment 58, wherein L2 comprises the amino acid sequence SNLQDS (SEQ ID NO: 21), wherein L4 comprises the amino acid sequence SGTTGKSN (SEQ ID NO: 27) and wherein L6 comprises the amino acid sequence FKSRGLMVPL (SEQ ID NO: 33).

64. The non-naturally occurring chagasin scaffold protein of embodiment 58, wherein L2 comprises the amino acid sequence SNYRDS (SEQ ID NO: 22), wherein L4 comprises the amino acid sequence VRAGQANE (SEQ ID NO: 28) and wherein L6 comprises the amino acid sequence SPVLGPRFWL (SEQ ID NO: 34).

65. The non-naturally occurring chagasin scaffold protein of embodiment 58, comprising the amino acid sequence set forth in SEQ ID NO: 36.

66. The non-naturally occurring chagasin scaffold protein of embodiment 58, comprising the amino acid sequence set forth in SEQ ID NO: 37.

67. The non-naturally occurring chagasin scaffold protein of embodiment 58, comprising the amino acid sequence set forth in SEQ ID NO: 38.

68. The non-naturally occurring chagasin scaffold protein of embodiment 58, comprising the amino acid sequence set forth in SEQ ID NO: 39.

69. The non-naturally occurring chagasin scaffold protein of embodiment 58, comprising the amino acid sequence set forth in SEQ ID NO: 40.

70. A non-naturally occurring chagasin scaffold protein that specifically binds to the same epitope as a second non-naturally occurring chagasin scaffold protein that binds human vascular endothelial growth factor (VEGF), wherein the second non-naturally occurring chagasin scaffold protein that binds human VEGF comprises an L2 that comprises the amino acid sequence SNY-F/Y-Y/C/N/R-D/E (SEQ ID NO: 49), an L4 that comprises the amino acid sequence HYYNLGGRYT (SEQ ID NO: 57), D/N/S-D/G/V/Y-P/N/S-G/Y-S/L/M-G/H/S-L/V/A/Y-W/Y/L/S (SEQ ID NO: 58), or G/H-S/V-S/Q-Y/W-W/G-G/W (SEQ ID NO: 68), and an L6 that comprises the amino acid sequence A/G-PW-S/Q/F/A/L/V-GPSR-Y/E/F/V/D-L (SEQ ID NO: 67), with reference to SEQ ID NO: 2.

71. A non-naturally occurring chagasin scaffold protein that specifically binds human vascular endothelial growth factor (VEGF), wherein the non-naturally occurring chagasin scaffold protein competes for binding with a second non-naturally occurring chagasin scaffold protein that binds human VEGF, wherein the second non-naturally occurring chagasin scaffold protein that binds human VEGF comprises an L2 that comprises the amino acid sequence SNY-F/Y-Y/C/N/R-D/E (SEQ ID NO: 49), an L4 that comprises the amino acid sequence HYYNLGGRYT (SEQ ID NO: 57), D/N/S-D/G/V/Y-P/N/S-G/Y-S/L/M-G/H/S-L/V/A/Y-W/Y/L/S (SEQ ID NO: 58), or G/H-S/V-S/Q-Y/W-W/G-G/W (SEQ ID NO: 68), and an L6 that comprises the amino acid sequence A/G-PW-S/Q/F/A/L/V-GPSR-Y/E/F/V/D-L (SEQ ID NO: 67), with reference to SEQ ID NO: 2.

72. The non-naturally occurring chagasin scaffold protein embodiment 70 or 71, wherein the non-naturally occurring chagasin scaffold protein comprises an L2 that comprises the amino acid sequence SNY-F/Y-Y/C/N/R-D/E (SEQ ID NO: 49), an L4 that comprises the amino acid sequence HYYN-LGGRYT (SEQ ID NO: 57), D/N/S-D/G/V/Y-P/N/S-G/Y-S/L/M-G/H/S-L/V/A/Y-W/Y/L/S (SEQ ID NO: 58), or G/H-S/V-S/Q-Y/W-W/G-G/W (SEQ ID NO: 68), and an L6 that comprises the amino acid sequence A/G-PW-S/Q/F/A/L/V-GPSR-Y/E/F/V/D-L (SEQ ID NO: 67), with reference to SEQ ID NO: 2.

73. The non-naturally occurring chagasin scaffold protein of embodiment 72, wherein L2 comprises an amino acid sequence set forth in any one of SEQ ID NOs: 19 and 42-48, wherein L4 comprises an amino acid sequence set forth in any one of SEQ ID NOs: 50-57; and wherein L6 comprises an amino acid sequence set forth in any one of SEQ ID NOs: 59-66.

74. The non-naturally occurring chagasin scaffold protein of embodiment 72, wherein L2 comprises the amino acid sequence SNYFYD (SEQ ID NO: 19), wherein L4 comprises the amino acid sequence DDPGSGLW (SEQ ID NO: 50) and wherein L6 comprises the amino acid sequence APWSGPSRYL (SEQ ID NO: 59).

75. The non-naturally occurring chagasin scaffold protein of embodiment 72, wherein L2 comprises the amino acid sequence SNYFYE (SEQ ID NO: 42), wherein L4 comprises the amino acid sequence NGPGLGVY (SEQ ID NO: 51) and wherein L6 comprises the amino acid sequence APWQGPSREL (SEQ ID NO: 60).

76. The non-naturally occurring chagasin scaffold protein of embodiment 72, wherein L2 comprises the amino acid sequence SNYYYD (SEQ ID NO: 48), wherein L4 comprises the amino acid sequence NVNGSHAW (SEQ ID NO: 52) and wherein L6 comprises the amino acid sequence APWSGPSRFL (SEQ ID NO: 61).

77. The non-naturally occurring chagasin scaffold protein of embodiment 72, wherein L2 comprises the amino acid sequence SNYFCD (SEQ ID NO: 44), wherein L4 comprises the amino acid sequence NYPGSGVL (SEQ ID NO: 53) and wherein L6 comprises the amino acid sequence APWFGPSRVL (SEQ ID NO: 62).

78. The non-naturally occurring chagasin scaffold protein of embodiment 72, wherein L2 comprises the amino acid sequence SNYFND (SEQ ID NO: 45), wherein L4 comprises the amino acid sequence GSSYWG (SEQ ID NO: 54) and wherein L6 comprises the amino acid sequence APWAGPSRVL (SEQ ID NO: 63).

79. The non-naturally occurring chagasin scaffold protein of embodiment 72, wherein L2 comprises the amino acid sequence SNYFYD (SEQ ID NO: 19), wherein L4 comprises the amino acid sequence SGSYMSYS (SEQ ID NO: 55) and wherein L6 comprises the amino acid sequence APWLGPSRDL (SEQ ID NO: 64).

80. The non-naturally occurring chagasin scaffold protein of embodiment 72, wherein L2 comprises the amino acid sequence SNYFRE (SEQ ID NO: 47), wherein L4 comprises the amino acid sequence HVQWGW (SEQ ID NO: 56) and wherein L6 comprises the amino acid sequence APWVGPSREL (SEQ ID NO: 65).

81. The non-naturally occurring chagasin scaffold protein of embodiment 72, wherein L2 comprises the amino acid sequence SNYYYD (SEQ ID NO: 48), wherein L4 comprises the amino acid sequence HYYNLGGRYT (SEQ ID NO: 57) and wherein L6 comprises the amino acid sequence GPWLGPSRVL (SEQ ID NO: 66).

82. The non-naturally occurring chagasin scaffold protein of embodiment 72, comprising the amino acid sequence set forth in SEQ ID NO: 69.

83. The non-naturally occurring chagasin scaffold protein of embodiment 72, comprising the amino acid sequence set forth in SEQ ID NO: 70.

84. The non-naturally occurring chagasin scaffold protein of embodiment 72, comprising the amino acid sequence set forth in SEQ ID NO: 71.

85. The non-naturally occurring chagasin scaffold protein of embodiment 72, comprising the amino acid sequence set forth in SEQ ID NO: 72.

86. The non-naturally occurring chagasin scaffold protein of embodiment 72, comprising the amino acid sequence set forth in SEQ ID NO: 73.

87. The non-naturally occurring chagasin scaffold protein of embodiment 72, comprising the amino acid sequence set forth in SEQ ID NO: 74.

88. The non-naturally occurring chagasin scaffold protein of embodiment 72, comprising the amino acid sequence set forth in SEQ ID NO: 75.

89. The non-naturally occurring chagasin scaffold protein of embodiment 72, comprising the amino acid sequence set forth in SEQ ID NO: 76.

90. A non-naturally occurring chagasin scaffold protein that specifically binds to the same epitope as a second non-naturally occurring chagasin scaffold protein that binds human vascular endothelial growth factor (VEGF), wherein the second non-naturally occurring chagasin scaffold protein that binds human VEGF comprises an L2 that comprises the amino acid sequence SNYY-Y/K-D (SEQ ID NO: 114), an L4 that comprises the amino acid sequence HY-Y/Q/S/T-NLGGRYT (SEQ ID NO: 115); and an L6 that comprises the amino acid sequence GPWLGPSRVL (SEQ ID NO: 66), with reference to SEQ ID NO: 2.

91. A non-naturally occurring chagasin scaffold protein that specifically binds human vascular endothelial growth factor (VEGF), wherein the non-naturally occurring chagasin scaffold protein competes for binding with a second non-naturally occurring chagasin scaffold protein that binds human VEGF, wherein the second non-naturally occurring chagasin scaffold protein that binds human VEGF comprises an L2 that comprises the amino acid sequence SNYY-Y/K-D (SEQ ID NO: 114), an L4 that comprises the amino acid sequence HY-Y/Q/S/T-NLGGRYT (SEQ ID NO: 115); and an L6 that comprises the amino acid sequence GPWL-GPSRVL (SEQ ID NO: 66), with reference to SEQ ID NO: 2.

92. The non-naturally occurring chagasin scaffold protein embodiment 90 or 91, wherein the non-naturally occurring chagasin scaffold protein comprises an L2 that comprises the amino acid sequence SNYY-Y/K-D (SEQ ID NO: 114), an L4 that comprises the amino acid sequence HY-Y/Q/S/T-NLGGRYT (SEQ ID NO: 115); and an L6 that comprises the amino acid sequence GPWLGPSRVL (SEQ ID NO: 66), with reference to SEQ ID NO: 2.

93. The non-naturally occurring chagasin scaffold protein of embodiment 92, wherein L2 comprises an amino acid sequence set forth in any one of SEQ ID NOs: 48 and 110, L4 comprises an amino acid sequence set forth in any one of SEQ ID NOs: 57 and 111-113; and L6 that comprises an amino acid sequence set forth in SEQ ID NO: 66, with reference to SEQ ID NO: 2.

94. The non-naturally occurring chagasin scaffold protein of embodiment 92, wherein L2 comprises the amino acid sequence SNYYKD (SEQ ID NO: 110), L4 comprises the amino acid sequence HYYNLGGRYT (SEQ ID NO: 57); and L6 comprises the amino acid sequence GPWLGPSRVL (SEQ ID NO: 66), with reference to SEQ ID NO: 2.

95. The non-naturally occurring chagasin scaffold protein of embodiment 92, wherein L2 comprises the amino acid sequence SNYYYD (SEQ ID NO: 48), L4 comprises the amino acid sequence HYQNLGGRYT (SEQ ID NO: 111); and L6 comprises the amino acid sequence GPWLGPSRVL (SEQ ID NO: 66), with reference to SEQ ID NO: 2.

96. The non-naturally occurring chagasin scaffold protein of embodiment 92, wherein L2 comprises the amino acid sequence SNYYYD (SEQ ID NO: 48), L4 comprises the amino acid sequence HYSNLGGRYT (SEQ ID NO: 112); and L6 comprises the amino acid sequence GPWLGPSRVL (SEQ ID NO: 66), with reference to SEQ ID NO: 2.

97. The non-naturally occurring chagasin scaffold protein of embodiment 92, wherein L2 comprises the amino acid sequence SNYYYD (SEQ ID NO: 48), L4 comprises the amino acid sequence HYTNLGGRYT (SEQ ID NO: 113); and L6 comprises the amino acid sequence GPWLGPSRVL (SEQ ID NO: 66), with reference to SEQ ID NO: 2.

98. The non-naturally occurring chagasin scaffold protein of embodiment 92, comprising the amino acid sequence set forth in SEQ ID NO: 116.

99. The non-naturally occurring chagasin scaffold protein of embodiment 92, comprising the amino acid sequence set forth in SEQ ID NO: 117.

100. The non-naturally occurring chagasin scaffold protein of embodiment 92, comprising the amino acid sequence set forth in SEQ ID NO: 118.

101. The non-naturally occurring chagasin scaffold protein of embodiment 92, comprising the amino acid sequence set forth in SEQ ID NO: 119.

102. The non-naturally occurring chagasin scaffold protein of any one of embodiments 56-101, wherein the non-naturally occurring chagasin scaffold protein binds a human VEGF with a Kd between 500 nM and 1 pM.

103. The non-naturally occurring chagasin scaffold protein of embodiment 77 or 85, wherein the non-naturally occurring chagasin scaffold protein forms a homodimer.

104. The non-naturally occurring chagasin scaffold protein that binds LRP6 of any one of embodiments 36-55 or the non-naturally occurring chagasin scaffold protein that binds VEGF of any one of embodiments 56-103 conjugated to a therapeutic agent.

105. The non-naturally occurring chagasin scaffold protein that binds LRP6 of any one of embodiments 36-55 or the non-naturally occurring chagasin scaffold protein that binds VEGF of any one of embodiments 56-103 conjugated to a label.

106. The non-naturally occurring chagasin scaffold protein that binds LRP6 or the non-naturally occurring chagasin scaffold protein that binds VEGF of embodiment 105, wherein the label is selected from the group consisting of a radioisotope, a fluorescent dye, and an enzyme.

107. An isolated nucleic acid molecule that encodes the non-naturally occurring chagasin scaffold protein that binds LRP6 of any one of embodiments 36-55 or the non-naturally occurring chagasin scaffold protein that binds VEGF of any one of embodiments 56-103.

108. An expression vector encoding the nucleic acid molecule of embodiment 107.

109. A cell comprising the expression vector of embodiment 108.

110. A method of producing the non-naturally occurring chagasin scaffold protein that binds LRP6 of any one of embodiments 36-55 or the non-naturally occurring chagasin scaffold protein that binds VEGF of any one of embodiments 56-103, comprising culturing the cell of embodiment 109 and recovering the non-naturally occurring chagasin scaffold protein from the cell culture.

111. A method of producing the non-naturally occurring chagasin scaffold protein that binds LRP6 of any one of embodiments 36-55 or the non-naturally occurring chagasin scaffold protein that binds VEGF of any one of embodiments 56-103 comprising chemically synthesizing the non-naturally occurring chagasin scaffold protein that binds LRP6 or the non-naturally occurring chagasin scaffold protein that binds VEGF.

112. A method of detecting an LRP6 protein in sample from a patient by contacting the non-naturally occurring chagasin scaffold protein that binds LRP6 of any one of embodiments 36-55, 105, and 106 to the sample and detecting the non-naturally occurring chagasin scaffold protein bound to the LRP6 protein.

113. A method of detecting a VEGF protein in sample from a patient by contacting the non-naturally occurring chagasin scaffold protein that binds VEGF of any one of embodiments 56-95, 105, and 105 to the sample and detecting the non-naturally occurring chagasin scaffold protein bound to the VEGF protein.

114. The method according to embodiment 112 or 113, wherein the non-naturally occurring chagasin scaffold protein is used an immunohistochemistry assay (IHC) or in an ELISA assay.

115. A composition comprising the non-naturally occurring chagasin scaffold protein that binds LRP6 of any one of embodiments 36-55 and 104 and a pharmaceutically acceptable carrier.

116. A composition comprising non-naturally occurring chagasin scaffold protein that binds VEGF according to any one of embodiments 56-95 and 104 and a pharmaceutically acceptable carrier.

117. A method of treating cancer, metastatic disease, osteoporosis, bone metabolism disease, neuronal disease, neurodegenerative disease, rheumatoid arthritis, or other inflammatory disease in a subject, comprising administering an effective amount of the non-naturally occurring chagasin scaffold protein that binds LRP6 of any one of embodiments 36-55 and 104 or the composition of embodiment 115 to the subject.

118. A composition comprising the non-naturally occurring chagasin scaffold protein that binds LRP6 of any one of embodiments 36-55 and 104 for use in treating cancer, metastatic disease, osteoporosis, bone metabolism disease, neuronal disease, neurodegenerative disease, rheumatoid arthritis, or other inflammatory disease.

119. The composition of embodiment 115 for use in treating cancer, metastatic disease, osteoporosis, bone metabolism disease, neuronal disease, neurodegenerative disease, rheumatoid arthritis, or other inflammatory disease.

120. Use of the non-naturally occurring chagasin scaffold protein that binds LRP6 of any one of embodiments 36-55 and 104 or the composition of embodiment 115 in the manufacture of a medicament for treating cancer, metastatic disease, osteoporosis, bone metabolism disease, neuronal disease, neurodegenerative disease, rheumatoid arthritis, or other inflammatory disease.

121. A method of inhibiting angiogenesis and/or vascular permeability or leakage in a subject, comprising administering an effective amount of the non-naturally occurring chagasin scaffold protein that binds VEGF according to any one of embodiments 56-95 and 116 or the composition of embodiment 108 to the subject.

122. A method of treating a disease characterized by angiogenesis and/or vascular permeability or leakage in a subject, comprising administering an effective amount of the non-naturally occurring chagasin scaffold protein that binds VEGF according to any one of embodiments 56-95 and 104 or the composition of embodiment 116 to the subject.

123. The method of embodiment 122, wherein the disease is cancer, ocular disease, or an inflammatory disease.

124. A composition comprising the non-naturally occurring chagasin scaffold protein that binds VEGF according to any one of embodiments 56-95 and 104 for use in treating a disease characterized by angiogenesis and/or vascular permeability or leakage in a subject.

125. The composition of embodiment 116 for use in treating a disease characterized by angiogenesis and/or vascular permeability or leakage in a subject.

126. Use of the non-naturally occurring chagasin scaffold protein that binds VEGF according to any one of embodiments 56-95 and 104 or the composition of embodiment 116 in the manufacture of a medicament for treating a disease characterized by angiogenesis and/or vascular permeability or leakage in a subject.

What is claimed is:

1. A peptide that comprises the amino acid sequence of SEQ ID NO: 117 and specifically binds vascular endothelial growth factor (VEGF).

2. The peptide of claim 1 conjugated to a therapeutic agent.

3. The peptide of claim 1 conjugated to a label.

4. The peptide according to claim 3, wherein the label is selected from the group consisting of a radioisotope, a fluorescent dye, and an enzyme.

5. A composition comprising the peptide of claim 1 and a pharmaceutically acceptable carrier.

* * * * *

SEQUENCE LISTING

```
<160> NUMBER OF SEQ ID NOS: 177

<210> SEQ ID NO 1
<211> LENGTH: 110
<212> TYPE: PRT
<213> ORGANISM: Trypanosoma cruzi

<400> SEQUENCE: 1

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Pro Thr Thr
            20                  25                  30

Gly Phe Ala Trp Tyr Phe Glu Gly Gly Thr Lys Glu Ser Pro Asn Glu
        35                  40                  45

Ser Met Phe Thr Val Glu Asn Lys Tyr Phe Pro Pro Asp Ser Lys Leu
    50                  55                  60

Leu Gly Ala Gly Gly Thr Glu His Phe Val Thr Val Lys Ala Ala
65                  70                  75                  80

Gly Thr His Ala Val Asn Leu Thr Tyr Met Arg Pro Trp Thr Gly Pro
                85                  90                  95

Ser His Asp Ser Glu Arg Phe Thr Val Tyr Leu Lys Ala Asn
            100                 105                 110

<210> SEQ ID NO 2
<211> LENGTH: 122
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 28, 29, 30, 31, 32, 33, 34, 35
<223> OTHER INFORMATION: Xaa = Any Amino Acid and up to 3 of them can be
      present or absent
<220> FEATURE:
<221> NAME/KEY: VARIANT
<222> LOCATION: 63, 64, 65, 66, 67, 68, 69,
      70, 71, 72, 73, 74, 75, 76, 77
<223> OTHER INFORMATION: Xaa = Any Amino Acid and up to 8 of them can be
      present or absent
<220> FEATURE:
<221> NAME/KEY: VARIANT
<222> LOCATION: 103, 104, 105, 106, 107
      108, 109, 110, 111, 112
<223> OTHER INFORMATION: Xaa = Any Amino Acid

<400> SEQUENCE: 2

Met Ser His Lys Val Thr Lys Ala His Asn Gly Ala Thr Leu Thr Val
1               5                   10                  15

Ala Val Gly Glu Leu Val Glu Ile Gln Leu Pro Xaa Xaa Xaa Xaa
            20                  25                  30

Xaa Xaa Xaa Gly Phe Ala Trp Tyr Phe Glu Gly Gly Thr Lys Glu Ser
        35                  40                  45
```

```
Pro Asn Glu Ser Met Phe Thr Val Glu Asn Lys Tyr Phe Pro Xaa Xaa
 50                  55                  60
Xaa Xaa Xaa Xaa Xaa Xaa Xaa Xaa Xaa Xaa Xaa Xaa Gly Ala Gly
 65                  70                  75                  80
Gly Thr Glu His Phe His Val Thr Val Lys Ala Ala Gly Thr His Ala
                 85                  90                  95
Val Asn Leu Thr Tyr Met Xaa Xaa Xaa Xaa Xaa Xaa Xaa Xaa Xaa
             100                 105                 110
Glu Arg Phe Thr Val Tyr Leu Lys Ala Asn
         115                 120

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct

<400> SEQUENCE: 3

Ser Asn Pro Gln Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Ser Asn Pro Thr Thr
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Construct

<400> SEQUENCE: 5

Ser Asn Val Asp
1

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = N or S
<220> FEATURE:
<221> NAME/KEY: VARIANT
<222> LOCATION: 3
<223> OTHER INFORMATION: Xaa = P or N
<220> FEATURE:
<221> NAME/KEY: VARIANT
<222> LOCATION: 4
<223> OTHER INFORMATION: Xaa = Q or T or V or S or A
<220> FEATURE:
<221> NAME/KEY: VARIANT
<222> LOCATION: 5
<223> OTHER INFORMATION: Xaa = T or D or C
```

```
<400> SEQUENCE: 6

Ser Xaa Xaa Xaa Xaa Gly Phe
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic Construct

<400> SEQUENCE: 7

Ser Asn Lys Val Lys Gly Val Pro Gly Phe
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Ser Asn Lys Ile Lys Gly Ile Pro Gly Phe
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct

<400> SEQUENCE: 9

Ser Asn Ser Thr Lys Arg
1               5

<210> SEQ ID NO 10
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = S or Y
<220> FEATURE:
<221> NAME/KEY: VARIANT
<222> LOCATION: 4
<223> OTHER INFORMATION: Xaa = N or K
<220> FEATURE:
<221> NAME/KEY: VARIANT
<222> LOCATION: 5
<223> OTHER INFORMATION: Xaa = V or I
<220> FEATURE:
<221> NAME/KEY: VARIANT
<222> LOCATION: 6
<223> OTHER INFORMATION: Xaa = K or R
<220> FEATURE:
<221> NAME/KEY: VARIANT
<222> LOCATION: 8
<223> OTHER INFORMATION: Xaa = V or I or L

<400> SEQUENCE: 10

Pro Xaa Asn Xaa Xaa Xaa Gly Xaa Pro Gly Phe Gly Ala Gly Gly
1               5                   10                  15
```

```
<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Gly Pro Trp Thr Gly Ala Ser Gln Glu Pro
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Arg Pro Ser Thr Gly Pro Ser Asp Asp Ser
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic Construct

<400> SEQUENCE: 13

Pro Arg Val Lys Gly Ala Tyr Leu Val Met
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = G or R or P or S
<220> FEATURE:
<221> NAME/KEY: VARIANT
<222> LOCATION: 2
<223> OTHER INFORMATION: Xaa = P or R
<220> FEATURE:
<221> NAME/KEY: VARIANT
<222> LOCATION: 3
<223> OTHER INFORMATION: Xaa = W or S or V or Y or E
<220> FEATURE:
<221> NAME/KEY: VARIANT
<222> LOCATION: 4
<223> OTHER INFORMATION: Xaa = T or K or Y
<220> FEATURE:
<221> NAME/KEY: VARIANT
<222> LOCATION: 6
<223> OTHER INFORMATION: Xaa = A or P or S
<220> FEATURE:
<221> NAME/KEY: VARIANT
<222> LOCATION: 7
<223> OTHER INFORMATION: Xaa = S or Y or T
<220> FEATURE:
<221> NAME/KEY: VARIANT
<222> LOCATION: 8
<223> OTHER INFORMATION: Xaa = Q or D or L or H or K
<220> FEATURE:
<221> NAME/KEY: VARIANT
<222> LOCATION: 9
<223> OTHER INFORMATION: Xaa = E or D or V
```

```
<220> FEATURE:
<221> NAME/KEY: VARIANT
<222> LOCATION: 10
<223> OTHER INFORMATION: Xaa = P or S or M or E

<400> SEQUENCE: 14

Xaa Xaa Xaa Xaa Gly Xaa Xaa Xaa Xaa Xaa
1               5                   10

<210> SEQ ID NO 15
<211> LENGTH: 114
<212> TYPE: PRT
<213> ORGANISM: Artificial Sequence
<220> FEATURE:
<223> OTHER INFORMATION: Synthetic Construct

<400> SEQUENCE: 15

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Pro Gln Thr
            20                  25                  30

Gly Phe Ala Trp Tyr Phe Glu Gly Gly Thr Lys Glu Ser Pro Asn Glu
        35                  40                  45

Ser Met Phe Thr Val Glu Asn Lys Tyr Phe Pro Ser Asn Lys Val Lys
    50                  55                  60

Gly Val Pro Gly Phe Gly Ala Gly Gly Thr Glu His Phe His Val Thr
65                  70                  75                  80

Val Lys Ala Ala Gly Thr His Ala Val Asn Leu Thr Tyr Met Gly Pro
                85                  90                  95

Trp Thr Gly Ala Ser Gln Glu Pro Glu Arg Phe Thr Val Tyr Leu Lys
            100                 105                 110

Ala Asn

<210> SEQ ID NO 16
<211> LENGTH: 114
<212> TYPE: PRT
<213> ORGANISM: Artificial Sequence
<220> FEATURE:
<223> OTHER INFORMATION: Synthetic Construct

<400> SEQUENCE: 16

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Pro Thr Thr
            20                  25                  30

Gly Phe Ala Trp Tyr Phe Glu Gly Gly Thr Lys Glu Ser Pro Asn Glu
        35                  40                  45

Ser Met Phe Thr Val Glu Asn Lys Tyr Phe Pro Ser Asn Lys Ile Lys
    50                  55                  60

Gly Ile Pro Gly Phe Gly Ala Gly Gly Thr Glu His Phe His Val Thr
65                  70                  75                  80

Val Lys Ala Ala Gly Thr His Ala Val Asn Leu Thr Tyr Met Arg Pro
                85                  90                  95

Ser Thr Gly Pro Ser Asp Asp Ser Glu Arg Phe Thr Val Tyr Leu Lys
            100                 105                 110

Ala Asn
```

```
<210> SEQ ID NO 17
<211> LENGTH: 109
<212> TYPE: PRT
<213> ORGANISM: Artificial Sequence
<220> FEATURE:
<223> OTHER INFORMATION: Synthetic Construct

<400> SEQUENCE: 17

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Val Asp Gly
            20                  25                  30

Phe Ala Trp Tyr Phe Glu Gly Gly Thr Lys Glu Ser Pro Asn Glu Ser
        35                  40                  45

Met Phe Thr Val Glu Asn Lys Tyr Phe Pro Ser Asn Ser Thr Lys Arg
    50                  55                  60

Gly Ala Gly Gly Thr Glu His Phe His Val Thr Val Lys Ala Ala Gly
65                  70                  75                  80

Thr His Ala Val Asn Leu Thr Tyr Met Pro Arg Val Lys Gly Ala Tyr
                85                  90                  95

Leu Val Met Glu Arg Phe Thr Val Tyr Leu Lys Ala Asn
            100                 105

<210> SEQ ID NO 18
<211> LENGTH: 6
<212> TYPE: PRT
<213> ORGANISM: Artificial Sequence
<220> FEATURE:
<223> OTHER INFORMATION: Synthetic Construct

<400> SEQUENCE: 18

Ser Asn Leu Arg Ser Met
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Construct

<400> SEQUENCE: 19

Ser Asn Tyr Phe Tyr Asp
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct

<400> SEQUENCE: 20

Ser Asn Leu Gln Asn Ala
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 21

Ser Asn Leu Gln Asp Ser
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Construct

<400> SEQUENCE: 22

Ser Asn Tyr Arg Asp Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = L or Y
<220> FEATURE:
<221> NAME/KEY: VARIANT
<222> LOCATION: 4
<223> OTHER INFORMATION: Xaa = R or F or Q
<220> FEATURE:
<221> NAME/KEY: VARIANT
<222> LOCATION: 5
<223> OTHER INFORMATION: Xaa = S or Y or N or D
<220> FEATURE:
<221> NAME/KEY: VARIANT
<222> LOCATION: 6
<223> OTHER INFORMATION: Xaa = M or D or A or S

<400> SEQUENCE: 23

Ser Asn Xaa Xaa Xaa Xaa
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Construct

<400> SEQUENCE: 24

Ala Gly Pro Ser Ala Val Pro Leu
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic Construct

<400> SEQUENCE: 25

Asn Asp Pro Gly Ser Arg Leu Ser
1               5

<210> SEQ ID NO 26
<211> LENGTH: 8
<212> TYPE: PRT
<213> ORGANISM: Artificial Sequence
```

```
<220> FEATURE:
<223> OTHER INFORMATION: Synthetic Construct

<400> SEQUENCE: 26

Leu Ser Leu Tyr Ala Ser Glu Thr
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic Construct

<400> SEQUENCE: 27

Ser Gly Thr Thr Gly Lys Ser Asn
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic Construct

<400> SEQUENCE: 28

Val Arg Ala Gly Gln Ala Asn Glu
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = A or N or L or S or V
<220> FEATURE:
<221> NAME/KEY: VARIANT
<222> LOCATION: 2
<223> OTHER INFORMATION: Xaa = G or D or S or R
<220> FEATURE:
<221> NAME/KEY: VARIANT
<222> LOCATION: 3
<223> OTHER INFORMATION: Xaa = P or L or T or A
<220> FEATURE:
<221> NAME/KEY: VARIANT
<222> LOCATION: 4
<223> OTHER INFORMATION: Xaa = S or G or Y or T
<220> FEATURE:
<221> NAME/KEY: VARIANT
<222> LOCATION: 5
<223> OTHER INFORMATION: Xaa = A or S or G or Q
<220> FEATURE:
<221> NAME/KEY: VARIANT
<222> LOCATION: 6
<223> OTHER INFORMATION: Xaa = V or R or S or K or A
<220> FEATURE:
<221> NAME/KEY: VARIANT
<222> LOCATION: 7
<223> OTHER INFORMATION: Xaa = P or L or E or S or N
<220> FEATURE:
<221> NAME/KEY: VARIANT
<222> LOCATION: 8
<223> OTHER INFORMATION: Xaa = L or S or T or N or E

<400> SEQUENCE: 29

Xaa Xaa Xaa Xaa Xaa Xaa Xaa Xaa
1               5
```

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct

<400> SEQUENCE: 30

Ala Pro Trp Arg Gly Pro Ala Asn Val Ile
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic Construct

<400> SEQUENCE: 31

Ala Pro Trp Leu Gly Pro Ser Arg Val Leu
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Asn Pro Asn Trp Gly Pro Asp Tyr Trp Ile
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Phe Lys Ser Arg Gly Leu Met Val Pro Leu
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct

<400> SEQUENCE: 34

Ser Pro Val Leu Gly Pro Arg Phe Trp Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = A or N or F or S
<220> FEATURE:
<221> NAME/KEY: VARIANT
<222> LOCATION: 2
<223> OTHER INFORMATION: Xaa = P or K

```
<220> FEATURE:
<221> NAME/KEY: VARIANT
<222> LOCATION: 3
<223> OTHER INFORMATION: Xaa = W or N or S or V
<220> FEATURE:
<221> NAME/KEY: VARIANT
<222> LOCATION: 4
<223> OTHER INFORMATION: Xaa = R or L or W
<220> FEATURE:
<221> NAME/KEY: VARIANT
<222> LOCATION: 6
<223> OTHER INFORMATION: Xaa = P or L
<220> FEATURE:
<221> NAME/KEY: VARIANT
<222> LOCATION: 7
<223> OTHER INFORMATION: Xaa = A or S or D or M or R
<220> FEATURE:
<221> NAME/KEY: VARIANT
<222> LOCATION: 8
<223> OTHER INFORMATION: Xaa = N or R or Y or V or F
<220> FEATURE:
<221> NAME/KEY: VARIANT
<222> LOCATION: 9
<223> OTHER INFORMATION: Xaa = V or W or P
<220> FEATURE:
<221> NAME/KEY: VARIANT
<222> LOCATION: 10
<223> OTHER INFORMATION: Xaa = I or L

<400> SEQUENCE: 35

Xaa Xaa Xaa Xaa Gly Xaa Xaa Xaa Xaa Xaa
1               5                   10

<210> SEQ ID NO 36
<211> LENGTH: 113
<212> TYPE: PRT
<213> ORGANISM: Artificial Sequence
<220> FEATURE:
<223> OTHER INFORMATION: Synthetic Construct

<400> SEQUENCE: 36

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Leu Arg Ser
            20                  25                  30

Met Gly Phe Ala Trp Tyr Phe Glu Gly Gly Thr Lys Glu Ser Pro Asn
        35                  40                  45

Glu Ser Met Phe Thr Val Glu Asn Lys Tyr Phe Pro Ala Gly Pro Ser
    50                  55                  60

Ala Val Pro Leu Gly Ala Gly Gly Thr Glu His Phe His Val Thr Val
65                  70                  75                  80

Lys Ala Ala Gly Thr His Ala Val Asn Leu Thr Tyr Met Ala Pro Trp
                85                  90                  95

Arg Gly Pro Ala Asn Val Ile Glu Arg Phe Thr Val Tyr Leu Lys Ala
            100                 105                 110

Asn

<210> SEQ ID NO 37
<211> LENGTH: 113
<212> TYPE: PRT
<213> ORGANISM: Artificial Sequence
<220> FEATURE:
<223> OTHER INFORMATION: Synthetic Construct
```

-continued

```
<400> SEQUENCE: 37

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Tyr Phe Tyr
            20                  25                  30

Asp Gly Phe Ala Trp Tyr Phe Glu Gly Gly Thr Lys Glu Ser Pro Asn
        35                  40                  45

Glu Ser Met Phe Thr Val Glu Asn Lys Tyr Phe Pro Asn Asp Pro Gly
    50                  55                  60

Ser Arg Leu Ser Gly Ala Gly Gly Thr Glu His Phe His Val Thr Val
65                  70                  75                  80

Lys Ala Ala Gly Thr His Ala Val Asn Leu Thr Tyr Met Ala Pro Trp
                85                  90                  95

Leu Gly Pro Ser Arg Val Leu Glu Arg Phe Thr Val Tyr Leu Lys Ala
            100                 105                 110

Asn

<210> SEQ ID NO 38
<211> LENGTH: 113
<212> TYPE: PRT
<213> ORGANISM: Artificial Sequence
<220> FEATURE:
<223> OTHER INFORMATION: Synthetic Construct

<400> SEQUENCE: 38

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Leu Gln Asn
            20                  25                  30

Ala Gly Phe Ala Trp Tyr Phe Glu Gly Gly Thr Lys Glu Ser Pro Asn
        35                  40                  45

Glu Ser Met Phe Thr Val Glu Asn Lys Tyr Phe Pro Leu Ser Leu Tyr
    50                  55                  60

Ala Ser Glu Thr Gly Ala Gly Gly Thr Glu His Phe His Val Thr Val
65                  70                  75                  80

Lys Ala Ala Gly Thr His Ala Val Asn Leu Thr Tyr Met Asn Pro Asn
                85                  90                  95

Trp Gly Pro Asp Tyr Trp Ile Glu Arg Phe Thr Val Tyr Leu Lys Ala
            100                 105                 110

Asn

<210> SEQ ID NO 39
<211> LENGTH: 113
<212> TYPE: PRT
<213> ORGANISM: Artificial Sequence
<220> FEATURE:
<223> OTHER INFORMATION: Synthetic Construct

<400> SEQUENCE: 39

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Leu Gln Asp
            20                  25                  30

Ser Gly Phe Ala Trp Tyr Phe Glu Gly Gly Thr Lys Glu Ser Pro Asn
        35                  40                  45

Glu Ser Met Phe Thr Val Glu Asn Lys Tyr Phe Pro Ser Gly Thr Thr
    50                  55                  60
```

```
Gly Lys Ser Asn Gly Ala Gly Gly Thr Glu His Phe His Val Thr Val
 65                  70                  75                  80

Lys Ala Ala Gly Thr His Ala Val Asn Leu Tyr Met Phe Lys Ser
                 85                  90                  95

Arg Gly Leu Met Val Pro Leu Glu Arg Phe Thr Val Tyr Leu Lys Ala
            100                 105                 110

Asn

<210> SEQ ID NO 40
<211> LENGTH: 113
<212> TYPE: PRT
<213> ORGANISM: Artificial Sequence
<220> FEATURE:
<223> OTHER INFORMATION: Synthetic Construct

<400> SEQUENCE: 40

Met Ser His Lys Val Thr Lys Ala His Asn Gly Ala Thr Leu Thr Val
 1               5                  10                  15

Ala Val Gly Glu Leu Val Glu Ile Gln Leu Pro Ser Asn Tyr Arg Asp
                20                  25                  30

Ser Gly Phe Ala Trp Tyr Phe Glu Gly Gly Thr Lys Glu Ser Pro Asn
             35                  40                  45

Glu Ser Met Phe Thr Val Glu Asn Lys Tyr Phe Pro Val Arg Ala Gly
 50                  55                  60

Gln Ala Asn Glu Gly Ala Gly Gly Thr Glu His Phe His Val Thr Val
 65                  70                  75                  80

Lys Ala Ala Gly Thr His Ala Val Asn Leu Tyr Met Ser Pro Val
                 85                  90                  95

Leu Gly Pro Arg Phe Trp Leu Glu Arg Phe Thr Val Tyr Leu Lys Ala
            100                 105                 110

Asn

<210> SEQ ID NO 41
<211> LENGTH: 6
<212> TYPE: PRT
<213> ORGANISM: Artificial Sequence
<220> FEATURE:
<223> OTHER INFORMATION: Synthetic Construct

<400> SEQUENCE: 41

Ser Asn Tyr Phe Tyr Asp
 1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic Construct

<400> SEQUENCE: 42

Ser Asn Tyr Phe Tyr Glu
 1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 43

Ser Asn Tyr Tyr Tyr Asp
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic Construct

<400> SEQUENCE: 44

Ser Asn Tyr Phe Cys Asp
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic Construct

<400> SEQUENCE: 45

Ser Asn Tyr Phe Asn Asp
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic Construct

<400> SEQUENCE: 46

Ser Asn Tyr Phe Tyr Asp
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic Construct

<400> SEQUENCE: 47

Ser Asn Tyr Phe Arg Glu
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic Construct

<400> SEQUENCE: 48

Ser Asn Tyr Tyr Tyr Asp
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: VARIANT
<222> LOCATION: 4
<223> OTHER INFORMATION: Xaa = F or Y
<220> FEATURE:
<221> NAME/KEY: VARIANT
<222> LOCATION: 5
<223> OTHER INFORMATION: Xaa = Y or C or N or R
<220> FEATURE:
<221> NAME/KEY: VARIANT
<222> LOCATION: 6
<223> OTHER INFORMATION: Xaa = D or E

<400> SEQUENCE: 49

Ser Asn Tyr Xaa Xaa Xaa
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic Construct

<400> SEQUENCE: 50

Asp Asp Pro Gly Ser Gly Leu Trp
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic Construct

<400> SEQUENCE: 51

Asn Gly Pro Gly Leu Gly Val Tyr
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic Construct

<400> SEQUENCE: 52

Asn Val Asn Gly Ser His Ala Trp
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic Construct

<400> SEQUENCE: 53

Asn Tyr Pro Gly Ser Gly Val Leu
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 54

Gly Ser Ser Tyr Trp Gly
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic Construct

<400> SEQUENCE: 55

Ser Gly Ser Tyr Met Ser Tyr Ser
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic Construct

<400> SEQUENCE: 56

His Val Gln Trp Gly Trp
1               5

<210> SEQ ID NO 57
<211> LENGTH: 10
<212> TYPE: PRT
<213> ORGANISM: Artificial Sequence
<220> FEATURE:
<223> OTHER INFORMATION: Synthetic Construct

<400> SEQUENCE: 57

His Tyr Tyr Asn Leu Gly Gly Arg Tyr Thr
1               5                   10

<210> SEQ ID NO 58
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = D or N or S
<220> FEATURE:
<221> NAME/KEY: VARIANT
<222> LOCATION: 2
<223> OTHER INFORMATION: Xaa = D or G or V or Y
<220> FEATURE:
<221> NAME/KEY: VARIANT
<222> LOCATION: 3
<223> OTHER INFORMATION: Xaa = P or N or S
<220> FEATURE:
<221> NAME/KEY: VARIANT
<222> LOCATION: 4
<223> OTHER INFORMATION: Xaa = G or Y
<220> FEATURE:
<221> NAME/KEY: VARIANT
<222> LOCATION: 5
<223> OTHER INFORMATION: Xaa = S or L or M
<220> FEATURE:
<221> NAME/KEY: VARIANT
<222> LOCATION: 6
<223> OTHER INFORMATION: Xaa = G or H or S
<220> FEATURE:
<221> NAME/KEY: VARIANT
<222> LOCATION: 7
<223> OTHER INFORMATION: Xaa = L or V or A or Y
```

```
<220> FEATURE:
<221> NAME/KEY: VARIANT
<222> LOCATION: 8
<223> OTHER INFORMATION: Xaa = W or Y or L or S

<400> SEQUENCE: 58

Xaa Xaa Xaa Xaa Xaa Xaa Xaa Xaa
1               5

<210> SEQ ID NO 59
<211> LENGTH: 10
<212> TYPE: PRT
<213> ORGANISM: Artificial Sequence
<220> FEATURE:
<223> OTHER INFORMATION: Synthetic Construct

<400> SEQUENCE: 59

Ala Pro Trp Ser Gly Pro Ser Arg Tyr Leu
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic Construct

<400> SEQUENCE: 60

Ala Pro Trp Gln Gly Pro Ser Arg Glu Leu
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic Construct

<400> SEQUENCE: 61

Ala Pro Trp Ser Gly Pro Ser Arg Phe Leu
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic Construct

<400> SEQUENCE: 62

Ala Pro Trp Phe Gly Pro Ser Arg Val Leu
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic Construct

<400> SEQUENCE: 63

Ala Pro Trp Ala Gly Pro Ser Arg Val Leu
1               5                   10
```

```
<210> SEQ ID NO 64
<211> LENGTH: 10
<212> TYPE: PRT
<213> ORGANISM: Artificial Sequence
<220> FEATURE:
<223> OTHER INFORMATION: Synthetic Construct

<400> SEQUENCE: 64

Ala Pro Trp Leu Gly Pro Ser Arg Asp Leu
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic Construct

<400> SEQUENCE: 65

Ala Pro Trp Val Gly Pro Ser Arg Glu Leu
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic Construct

<400> SEQUENCE: 66

Gly Pro Trp Leu Gly Pro Ser Arg Val Leu
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = A or G
<220> FEATURE:
<221> NAME/KEY: VARIANT
<222> LOCATION: 4
<223> OTHER INFORMATION: Xaa = S or Q or F or A or L or V
<220> FEATURE:
<221> NAME/KEY: VARIANT
<222> LOCATION: 9
<223> OTHER INFORMATION: Xaa = Y or E or F or V or D

<400> SEQUENCE: 67

Xaa Pro Trp Xaa Gly Pro Ser Arg Xaa Leu
1               5                   10

<210> SEQ ID NO 68
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = G or H
<220> FEATURE:
<221> NAME/KEY: VARIANT
<222> LOCATION: 2
<223> OTHER INFORMATION: Xaa = S or V
```

<220> FEATURE:
<221> NAME/KEY: VARIANT
<222> LOCATION: 3
<223> OTHER INFORMATION: Xaa = S or Q
<220> FEATURE:
<221> NAME/KEY: VARIANT
<222> LOCATION: 4
<223> OTHER INFORMATION: Xaa = Y or W
<220> FEATURE:
<221> NAME/KEY: VARIANT
<222> LOCATION: 5
<223> OTHER INFORMATION: Xaa = W or G
<220> FEATURE:
<221> NAME/KEY: VARIANT
<222> LOCATION: 6
<223> OTHER INFORMATION: Xaa = G or W

<400> SEQUENCE: 68

Xaa Xaa Xaa Xaa Xaa Xaa
1               5

<210> SEQ ID NO 69
<211> LENGTH: 113
<212> TYPE: PRT
<213> ORGANISM: Artificial Sequence
<220> FEATURE:
<223> OTHER INFORMATION: Synthetic Construct

<400> SEQUENCE: 69

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Tyr Phe Tyr
                20                  25                  30

Asp Gly Phe Ala Trp Tyr Phe Glu Gly Gly Thr Lys Glu Ser Pro Asn
            35                  40                  45

Glu Ser Met Phe Thr Val Glu Asn Lys Tyr Phe Pro Asp Asp Pro Gly
        50                  55                  60

Ser Gly Leu Trp Gly Ala Gly Thr Glu His Phe His Val Thr Val
65                  70                  75                  80

Lys Ala Ala Gly Thr His Ala Val Asn Leu Thr Tyr Met Ala Pro Trp
                85                  90                  95

Ser Gly Pro Ser Arg Tyr Leu Glu Arg Phe Thr Val Tyr Leu Lys Ala
            100                 105                 110

Asn

<210> SEQ ID NO 70
<211> LENGTH: 113
<212> TYPE: PRT
<213> ORGANISM: Artificial Sequence
<220> FEATURE:
<223> OTHER INFORMATION: Synthetic Construct

<400> SEQUENCE: 70

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Tyr Phe Tyr
                20                  25                  30

Glu Gly Phe Ala Trp Tyr Phe Glu Gly Gly Thr Lys Glu Ser Pro Asn
            35                  40                  45

Glu Ser Met Phe Thr Val Glu Asn Lys Tyr Phe Pro Asn Gly Pro Gly
        50                  55                  60

Leu Gly Val Tyr Gly Ala Gly Thr Glu His Phe His Val Thr Val
65                  70                  75                  80

Lys Ala Ala Gly Thr His Ala Val Asn Leu Thr Tyr Met Ala Pro Trp
                85                  90                  95

Gln Gly Pro Ser Arg Glu Leu Glu Arg Phe Thr Val Tyr Leu Lys Ala
            100                 105                 110

Asn

<210> SEQ ID NO 71
<211> LENGTH: 113
<212> TYPE: PRT
<213> ORGANISM: Artificial Sequence
<220> FEATURE:
<223> OTHER INFORMATION: Synthetic Construct

<400> SEQUENCE: 71

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Tyr Tyr Tyr
                20                  25                  30

Asp Gly Phe Ala Trp Tyr Phe Glu Gly Gly Thr Lys Glu Ser Pro Asn
            35                  40                  45

Glu Ser Met Phe Thr Val Glu Asn Lys Tyr Phe Pro Asn Val Asn Gly
50                  55                  60

Ser His Ala Trp Gly Ala Gly Gly Thr Glu His Phe His Val Thr Val
65                  70                  75                  80

Lys Ala Ala Gly Thr His Ala Val Asn Leu Thr Tyr Met Ala Pro Trp
                85                  90                  95

Ser Gly Pro Ser Arg Phe Leu Glu Arg Phe Thr Val Tyr Leu Lys Ala
            100                 105                 110

Asn

<210> SEQ ID NO 72
<211> LENGTH: 113
<212> TYPE: PRT
<213> ORGANISM: Artificial Sequence
<220> FEATURE:
<223> OTHER INFORMATION: Synthetic Construct

<400> SEQUENCE: 72

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Tyr Phe Cys
                20                  25                  30

Asp Gly Phe Ala Trp Tyr Phe Glu Gly Gly Thr Lys Glu Ser Pro Asn
            35                  40                  45

Glu Ser Met Phe Thr Val Glu Asn Lys Tyr Phe Pro Asn Tyr Pro Gly
50                  55                  60

Ser Gly Val Leu Gly Ala Gly Gly Thr Glu His Phe His Val Thr Val
65                  70                  75                  80

Lys Ala Ala Gly Thr His Ala Val Asn Leu Thr Tyr Met Ala Pro Trp
                85                  90                  95

Phe Gly Pro Ser Arg Val Leu Glu Arg Phe Thr Val Tyr Leu Lys Ala
            100                 105                 110

Asn

<210> SEQ ID NO 73
<211> LENGTH: 111
<212> TYPE: PRT
<213> ORGANISM: Artificial Sequence

```
<220> FEATURE:
<223> OTHER INFORMATION: Synthetic Construct

<400> SEQUENCE: 73

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Tyr Phe Asn
                20                  25                  30

Asp Gly Phe Ala Trp Tyr Phe Glu Gly Gly Thr Lys Glu Ser Pro Asn
            35                  40                  45

Glu Ser Met Phe Thr Val Glu Asn Lys Tyr Phe Pro Gly Ser Ser Tyr
        50                  55                  60

Trp Gly Gly Ala Gly Gly Thr Glu His Phe His Val Thr Val Lys Ala
65              70                  75                  80

Ala Gly Thr His Ala Val Asn Leu Thr Tyr Met Ala Pro Trp Ala Gly
                85                  90                  95

Pro Ser Arg Val Leu Glu Arg Phe Thr Val Tyr Leu Lys Ala Asn
            100                 105                 110

<210> SEQ ID NO 74
<211> LENGTH: 113
<212> TYPE: PRT
<213> ORGANISM: Artificial Sequence
<220> FEATURE:
<223> OTHER INFORMATION: Synthetic Construct

<400> SEQUENCE: 74

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Tyr Phe Tyr
                20                  25                  30

Asp Gly Phe Ala Trp Tyr Phe Glu Gly Gly Thr Lys Glu Ser Pro Asn
            35                  40                  45

Glu Ser Met Phe Thr Val Glu Asn Lys Tyr Phe Pro Ser Gly Ser Tyr
        50                  55                  60

Met Ser Tyr Ser Gly Ala Gly Gly Thr Glu His Phe His Val Thr Val
65              70                  75                  80

Lys Ala Ala Gly Thr His Ala Val Asn Leu Thr Tyr Met Ala Pro Trp
                85                  90                  95

Leu Gly Pro Ser Arg Asp Leu Glu Arg Phe Thr Val Tyr Leu Lys Ala
            100                 105                 110

Asn

<210> SEQ ID NO 75
<211> LENGTH: 111
<212> TYPE: PRT
<213> ORGANISM: Artificial Sequence
<220> FEATURE:
<223> OTHER INFORMATION: Synthetic Construct

<400> SEQUENCE: 75

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Tyr Phe Arg
                20                  25                  30

Glu Gly Phe Ala Trp Tyr Phe Glu Gly Gly Thr Lys Glu Ser Pro Asn
            35                  40                  45
```

```
Glu Ser Met Phe Thr Val Glu Asn Lys Tyr Phe Pro His Val Gln Trp
        50                  55                  60

Gly Trp Gly Ala Gly Thr Glu His Phe His Val Thr Val Lys Ala
65                  70                  75                  80

Ala Gly Thr His Ala Val Asn Leu Thr Tyr Met Ala Pro Trp Val Gly
                85                  90                  95

Pro Ser Arg Glu Leu Glu Arg Phe Thr Val Tyr Leu Lys Ala Asn
            100                 105                 110
```

<210> SEQ ID NO 76
<211> LENGTH: 115
<212> TYPE: PRT
<213> ORGANISM: Artificial Sequence
<220> FEATURE:
<223> OTHER INFORMATION: Synthetic Construct

<400> SEQUENCE: 76

```
Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Tyr Tyr Tyr
                20                  25                  30

Asp Gly Phe Ala Trp Tyr Phe Glu Gly Gly Thr Lys Glu Ser Pro Asn
            35                  40                  45

Glu Ser Met Phe Thr Val Glu Asn Lys Tyr Phe Pro His Tyr Tyr Asn
        50                  55                  60

Leu Gly Gly Arg Tyr Thr Gly Ala Gly Gly Thr Glu His Phe His Val
65                  70                  75                  80

Thr Val Lys Ala Ala Gly Thr His Ala Val Asn Leu Thr Tyr Met Gly
                85                  90                  95

Pro Trp Leu Gly Pro Ser Arg Val Leu Glu Arg Phe Thr Val Tyr Leu
            100                 105                 110

Lys Ala Asn
        115
```

<210> SEQ ID NO 77
<211> LENGTH: 8
<212> TYPE: PRT
<213> ORGANISM: Artificial Sequence
<220> FEATURE:
<223> OTHER INFORMATION: Synthetic Construct

<400> SEQUENCE: 77

```
Asp Ser Asn Glu Ile Trp Tyr Cys
1               5
```

<210> SEQ ID NO 78
<211> LENGTH: 5
<212> TYPE: PRT
<213> ORGANISM: Artificial Sequence
<220> FEATURE:
<223> OTHER INFORMATION: Synthetic Construct

<400> SEQUENCE: 78

```
Ser Asn Pro Thr Thr
1               5
```

<210> SEQ ID NO 79
<211> LENGTH: 5
<212> TYPE: PRT
<213> ORGANISM: Artificial Sequence
<220> FEATURE:
<223> OTHER INFORMATION: Synthetic Construct

```
<400> SEQUENCE: 79

Ser Asn Pro Ser Cys
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic Construct

<400> SEQUENCE: 80

Ser Asn Pro Ala Asp
1               5

<210> SEQ ID NO 81
<211> LENGTH: 10
<212> TYPE: PRT
<213> ORGANISM: Artificial Sequence
<220> FEATURE:
<223> OTHER INFORMATION: Synthetic Construct

<400> SEQUENCE: 81

Tyr Asn Asn Ile Arg Gly Leu Pro Gly Phe
1               5                   10

<210> SEQ ID NO 82
<211> LENGTH: 8
<212> TYPE: PRT
<213> ORGANISM: Artificial Sequence
<220> FEATURE:
<223> OTHER INFORMATION: Synthetic Construct

<400> SEQUENCE: 82

Asp Ser Asn Glu Ile Trp Tyr Cys
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic Construct

<400> SEQUENCE: 83

Ser Asn Tyr Thr Lys His
1               5

<210> SEQ ID NO 84
<211> LENGTH: 10
<212> TYPE: PRT
<213> ORGANISM: Artificial Sequence
<220> FEATURE:
<223> OTHER INFORMATION: Synthetic Construct

<400> SEQUENCE: 84

Arg Pro Trp Thr Gly Pro Ser His Asp Ser
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 85

Ser Pro Tyr Tyr Gly Pro Thr Lys Val Glu
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic Construct

<400> SEQUENCE: 86

Pro Arg Glu Lys Gly Ser Ser Leu Val Met
1               5                   10

<210> SEQ ID NO 87
<211> LENGTH: 114
<212> TYPE: PRT
<213> ORGANISM: Artificial Sequence
<220> FEATURE:
<223> OTHER INFORMATION: Synthetic Construct

<400> SEQUENCE: 87

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Pro Thr Thr
            20                  25                  30

Gly Phe Ala Trp Tyr Phe Glu Gly Gly Thr Lys Glu Ser Pro Asn Glu
        35                  40                  45

Ser Met Phe Thr Val Glu Asn Lys Tyr Phe Pro Tyr Asn Asn Ile Arg
    50                  55                  60

Gly Leu Pro Gly Phe Gly Ala Gly Gly Thr Glu His Phe His Val Thr
65                  70                  75                  80

Val Lys Ala Ala Gly Thr His Ala Val Asn Leu Thr Tyr Met Arg Pro
                85                  90                  95

Trp Thr Gly Pro Ser His Asp Ser Glu Arg Phe Thr Val Tyr Leu Lys
            100                 105                 110

Ala Asn

<210> SEQ ID NO 88
<211> LENGTH: 112
<212> TYPE: PRT
<213> ORGANISM: Artificial Sequence
<220> FEATURE:
<223> OTHER INFORMATION: Synthetic Construct

<400> SEQUENCE: 88

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Pro Ser Cys
            20                  25                  30

Gly Phe Ala Trp Tyr Phe Glu Gly Gly Thr Lys Glu Ser Pro Asn Glu
        35                  40                  45

Ser Met Phe Thr Val Glu Asn Lys Tyr Phe Pro Asp Ser Asn Glu Ile
    50                  55                  60

Trp Tyr Cys Gly Ala Gly Gly Thr Glu His Phe His Val Thr Val Lys
65                  70                  75                  80
```

Ala Ala Gly Thr His Ala Val Asn Leu Thr Tyr Met Ser Pro Tyr Tyr
                85                  90                  95

Gly Pro Thr Lys Val Glu Glu Arg Phe Thr Val Tyr Leu Lys Ala Asn
            100                 105                 110

<210> SEQ ID NO 89
<211> LENGTH: 110
<212> TYPE: PRT
<213> ORGANISM: Artificial Sequence
<220> FEATURE:
<223> OTHER INFORMATION: Synthetic Construct

<400> SEQUENCE: 89

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Pro Ala Asp
            20                  25                  30

Gly Phe Ala Trp Tyr Phe Glu Gly Gly Thr Lys Glu Ser Pro Asn Glu
        35                  40                  45

Ser Met Phe Thr Val Glu Asn Lys Tyr Phe Pro Ser Asn Tyr Thr Lys
    50                  55                  60

His Gly Ala Gly Gly Thr Glu His Phe His Val Thr Val Lys Ala Ala
65                  70                  75                  80

Gly Thr His Ala Val Asn Leu Thr Tyr Met Pro Arg Glu Lys Gly Ser
                85                  90                  95

Ser Leu Val Met Glu Arg Phe Thr Val Tyr Leu Lys Ala Asn
            100                 105                 110

<210> SEQ ID NO 90
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = S or Y
<220> FEATURE:
<221> NAME/KEY: VARIANT
<222> LOCATION: 7
<223> OTHER INFORMATION: Xaa = H or R

<400> SEQUENCE: 90

Pro Ser Asn Xaa Thr Lys Xaa Gly Ala Gly Gly
1               5                   10

<210> SEQ ID NO 91
<211> LENGTH: 330
<212> TYPE: DNA
<213> ORGANISM: Artificial Sequence
<220> FEATURE:
<223> OTHER INFORMATION: Synthetic Construct

<400> SEQUENCE: 91
atgtcccaca aggtgacgaa agcccataac ggtgcgacct tgacggtggc cgtcggcgag      60
ctggtggaga ttcagcttcc gagcaatccg accactgggt tcgcgtggta ttttgaaggt     120
ggtaccaaag aaagtccgaa tgaatccatg ttcaccgtcg agaataagta ctttccgccg     180
gacagtaaac tgttgggtgc tggcgggacg gagcactttc atgtgacagt gaaggcggcg     240
ggtacgcacg cagtaaatct cacttacatg cgcccgtgga caggcccgtc gcacgattcc     300
gagcgtttca ctgtatatct caaggcaaac                                       330

-continued

```
<210> SEQ ID NO 92
<211> LENGTH: 16
<212> TYPE: PRT
<213> ORGANISM: Artificial Sequence
<220> FEATURE:
<223> OTHER INFORMATION: Synthetic Construct

<400> SEQUENCE: 92

Met Ala Asp Pro Asn Arg Phe Arg Gly Lys Asp Leu Gly Ser Leu Glu
1               5                   10                  15

<210> SEQ ID NO 93
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4, 5
<223> OTHER INFORMATION: Xaa = Any Amino Acid

<400> SEQUENCE: 93

Ser Asn Pro Xaa Xaa Gly Phe
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3, 4, 5, 6
<223> OTHER INFORMATION: Xaa = Any Amino Acid

<400> SEQUENCE: 94

Ser Asn Xaa Xaa Xaa Xaa Gly Phe
1               5

<210> SEQ ID NO 95
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 3, 4, 5, 6, 7, 8, 9, 10, 11, 12, 13, 14, 15
<223> OTHER INFORMATION: Xaa = Any Amino Acid and up to 8 of them can be
      present or absent

<400> SEQUENCE: 95

Pro Xaa Xaa Xaa Xaa Xaa Xaa Xaa Xaa Xaa Xaa Xaa Xaa Xaa Xaa Gly
1               5                   10                  15

Ala Gly Gly

<210> SEQ ID NO 96
<211> LENGTH: 54
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 26, 27, 29, 30
<223> OTHER INFORMATION: n = A,T,C or G
```

<400> SEQUENCE: 96
ggagattcag cttccgagca atccgnnknn kgggttcgcg tggtatttg aagg          54

<210> SEQ ID NO 97
<211> LENGTH: 57
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 23, 24, 26, 27, 29, 30, 32, 33
<223> OTHER INFORMATION: n = A,T,C or G

<400> SEQUENCE: 97
ggagattcag cttccgagca atnnknnknn knnkgggttc gcgtggtatt ttgaagg       57

<210> SEQ ID NO 98
<211> LENGTH: 69
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 22, 23, 25, 26, 28, 29, 31, 32, 34, 35, 37, 38
<223> OTHER INFORMATION: n = A,T,C or G

<400> SEQUENCE: 98
gtcgagaata agtactttcc gnnknnknnk nnknnknnkg gtgctggcgg gacggagcac    60
tttcatgtg                                                           69

<210> SEQ ID NO 99
<211> LENGTH: 75
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 22, 23, 25, 26, 28, 29, 31, 32, 34, 35, 37, 38, 40, 41,
      43, 44
<223> OTHER INFORMATION: n = A,T,C or G

<400> SEQUENCE: 99
gtcgagaata agtactttcc gnnknnknnk nnknnknnkn nknnkggtgc tggcgggacg    60
gagcactttc atgtg                                                    75

<210> SEQ ID NO 100
<211> LENGTH: 81
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 22, 23, 25, 26, 28, 29, 31, 32, 34, 35, 37, 38, 40, 41,
      43, 44, 46, 47, 49, 50
<223> OTHER INFORMATION: n = A,T,C or G

<400> SEQUENCE: 100
gtcgagaata agtactttcc gnnknnknnk nnknnknnkn nknnknnknn kggtgctggc    60
gggacggagc actttcatgt g                                             81

```
<210> SEQ ID NO 101
<211> LENGTH: 67
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 19, 20, 22, 23, 25, 26, 28, 29, 34, 35, 37, 38, 40, 41,
      43, 44, 46, 47
<223> OTHER INFORMATION: n = A,T,C or G

<400> SEQUENCE: 101
gtaaatctca cttacatgnn knnknnknnk ggtnnknnkn nknnknnkga gcgtttcact    60
gtatatc                                                             67

<210> SEQ ID NO 102
<211> LENGTH: 67
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 19, 20, 25, 26, 28, 29, 37, 38, 40, 41, 43, 44, 46, 47
<223> OTHER INFORMATION: n = A,T,C or G

<400> SEQUENCE: 102
gtaaatctca cttacatgnn kccannknnk ggtccgnnkn nknnknnkga gcgtttcact    60
gtatatc                                                             67

<210> SEQ ID NO 103
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4
<223> OTHER INFORMATION: Xaa = Any Amino Acid

<400> SEQUENCE: 103

Xaa Xaa Xaa Xaa
1

<210> SEQ ID NO 104
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6
<223> OTHER INFORMATION: Xaa = Any Amino Acid

<400> SEQUENCE: 104

Xaa Xaa Xaa Xaa Xaa Xaa
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: VARIANT
<222> LOCATION: 1, 2, 3, 4, 5, 6, 7, 8
<223> OTHER INFORMATION: Xaa = Any Amino Acid

<400> SEQUENCE: 105

Xaa Xaa Xaa Xaa Xaa Xaa Xaa Xaa
1               5

<210> SEQ ID NO 106
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 7, 8, 9, 10
<223> OTHER INFORMATION: Xaa = Any Amino Acid

<400> SEQUENCE: 106

Xaa Xaa Xaa Xaa Xaa Xaa Xaa Xaa Xaa Xaa
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 6, 7, 8, 9, 10
<223> OTHER INFORMATION: Xaa = Any Amino Acid

<400> SEQUENCE: 107

Xaa Xaa Xaa Xaa Gly Xaa Xaa Xaa Xaa Xaa
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 3, 4, 7, 8, 9, 10
<223> OTHER INFORMATION: Xaa = Any Amino Acid

<400> SEQUENCE: 108

Xaa Pro Xaa Xaa Gly Pro Xaa Xaa Xaa Xaa
1               5                   10

<210> SEQ ID NO 109
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Acetylated Asparagine

<400> SEQUENCE: 109

Xaa Ser Asn Ala Ile Lys Asn
1               5
```

```
<210> SEQ ID NO 110
<211> LENGTH: 6
<212> TYPE: PRT
<213> ORGANISM: Artificial Sequence
<220> FEATURE:
<223> OTHER INFORMATION: Synthetic Construct

<400> SEQUENCE: 110

Ser Asn Tyr Tyr Lys Asp
1               5

<210> SEQ ID NO 111
<211> LENGTH: 10
<212> TYPE: PRT
<213> ORGANISM: Artificial Sequence
<220> FEATURE:
<223> OTHER INFORMATION: Synthetic Construct

<400> SEQUENCE: 111

His Tyr Gln Asn Leu Gly Gly Arg Tyr Thr
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Synthetic Construct

<400> SEQUENCE: 112

His Tyr Ser Asn Leu Gly Gly Arg Tyr Thr
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Synthetic Construct

<400> SEQUENCE: 113

His Tyr Thr Asn Leu Gly Gly Arg Tyr Thr
1               5                   10

<210> SEQ ID NO 114
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Y or K

<400> SEQUENCE: 114

Ser Asn Tyr Tyr Xaa Asp
1               5

<210> SEQ ID NO 115
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Y or Q or S or T
```

<400> SEQUENCE: 115

His Tyr Xaa Asn Leu Gly Gly Arg Tyr Thr
1               5                   10

<210> SEQ ID NO 116
<211> LENGTH: 115
<212> TYPE: PRT
<213> ORGANISM: Artificial Sequence
<220> FEATURE:
<223> OTHER INFORMATION: Synthetic Construct

<400> SEQUENCE: 116

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Tyr Tyr Lys
                20                  25                  30

Asp Gly Phe Ala Trp Tyr Phe Glu Gly Gly Thr Lys Glu Ser Pro Asn
            35                  40                  45

Glu Ser Met Phe Thr Val Glu Asn Lys Tyr Phe Pro His Tyr Tyr Asn
        50                  55                  60

Leu Gly Gly Arg Tyr Thr Gly Ala Gly Thr Glu His Phe His Val
65                  70                  75                  80

Thr Val Lys Ala Ala Gly Thr His Ala Val Asn Leu Thr Tyr Met Gly
                85                  90                  95

Pro Trp Leu Gly Pro Ser Arg Val Leu Glu Arg Phe Thr Val Tyr Leu
                100                 105                 110

Lys Ala Asn
        115

<210> SEQ ID NO 117
<211> LENGTH: 115
<212> TYPE: PRT
<213> ORGANISM: Artificial Sequence
<220> FEATURE:
<223> OTHER INFORMATION: Synthetic Construct

<400> SEQUENCE: 117

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Tyr Tyr Tyr
                20                  25                  30

Asp Gly Phe Ala Trp Tyr Phe Glu Gly Gly Thr Lys Glu Ser Pro Asn
            35                  40                  45

Glu Ser Met Phe Thr Val Glu Asn Lys Tyr Phe Pro His Tyr Gln Asn
        50                  55                  60

Leu Gly Gly Arg Tyr Thr Gly Ala Gly Thr Glu His Phe His Val
65                  70                  75                  80

Thr Val Lys Ala Ala Gly Thr His Ala Val Asn Leu Thr Tyr Met Gly
                85                  90                  95

Pro Trp Leu Gly Pro Ser Arg Val Leu Glu Arg Phe Thr Val Tyr Leu
                100                 105                 110

Lys Ala Asn
        115

<210> SEQ ID NO 118
<211> LENGTH: 115
<212> TYPE: PRT
<213> ORGANISM: Artificial Sequence

```
<220> FEATURE:
<223> OTHER INFORMATION: Synthetic Construct

<400> SEQUENCE: 118

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Tyr Tyr Tyr
                20                  25                  30

Asp Gly Phe Ala Trp Tyr Phe Glu Gly Gly Thr Lys Glu Ser Pro Asn
            35                  40                  45

Glu Ser Met Phe Thr Val Glu Asn Lys Tyr Phe Pro His Tyr Ser Asn
        50                  55                  60

Leu Gly Gly Arg Tyr Thr Gly Ala Gly Thr Glu His Phe His Val
65                  70                  75                  80

Thr Val Lys Ala Ala Gly Thr His Ala Val Asn Leu Thr Tyr Met Gly
                85                  90                  95

Pro Trp Leu Gly Pro Ser Arg Val Leu Glu Arg Phe Thr Val Tyr Leu
            100                 105                 110

Lys Ala Asn
        115

<210> SEQ ID NO 119
<211> LENGTH: 115
<212> TYPE: PRT
<213> ORGANISM: Artificial Sequence
<220> FEATURE:
<223> OTHER INFORMATION: Synthetic Construct

<400> SEQUENCE: 119

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Tyr Tyr Tyr
                20                  25                  30

Asp Gly Phe Ala Trp Tyr Phe Glu Gly Gly Thr Lys Glu Ser Pro Asn
            35                  40                  45

Glu Ser Met Phe Thr Val Glu Asn Lys Tyr Phe Pro His Tyr Thr Asn
        50                  55                  60

Leu Gly Gly Arg Tyr Thr Gly Ala Gly Thr Glu His Phe His Val
65                  70                  75                  80

Thr Val Lys Ala Ala Gly Thr His Ala Val Asn Leu Thr Tyr Met Gly
                85                  90                  95

Pro Trp Leu Gly Pro Ser Arg Val Leu Glu Arg Phe Thr Val Tyr Leu
            100                 105                 110

Lys Ala Asn
        115

<210> SEQ ID NO 120
<211> LENGTH: 80
<212> TYPE: PRT
<213> ORGANISM: Artificial Sequence
<220> FEATURE:
<223> OTHER INFORMATION: Synthetic Construct

<400> SEQUENCE: 120

Ser Asn Tyr Phe Tyr Glu Gly Phe Ala Trp Tyr Phe Glu Asp Gly Thr
1               5                   10                  15

Lys Glu Ser Pro Asn Glu Ser Met Phe Thr Val Glu Asn Lys Tyr Phe
                20                  25                  30
```

```
Pro Lys Val Ala Gly Ser Arg Thr Pro Gly Ala Gly Thr Glu His
         35                  40                  45

Phe His Val Thr Val Lys Ala Ala Gly Thr His Ala Val Asn Leu Thr
 50                      55                  60

Tyr Met Gly Pro Trp Leu Gly Pro Ser Arg Val Leu Glu Arg Phe Thr
 65                  70                  75                  80

<210> SEQ ID NO 121
<211> LENGTH: 80
<212> TYPE: PRT
<213> ORGANISM: Artificial Sequence
<220> FEATURE:
<223> OTHER INFORMATION: Synthetic Construct

<400> SEQUENCE: 121

Ser Asn Tyr Phe Tyr Asp Gly Phe Ala Trp Tyr Phe Glu Gly Gly Thr
 1               5                  10                  15

Lys Glu Ser Pro Asn Glu Ser Met Phe Thr Val Glu Asn Lys Tyr Phe
             20                  25                  30

Pro Asn Val Gly Gly Ser Gly Leu Ser Gly Ala Gly Thr Glu His
         35                  40                  45

Phe His Val Thr Val Lys Ala Ala Gly Thr His Ala Val Asn Leu Thr
 50                      55                  60

Tyr Met Ala Pro Trp Leu Gly Pro Ser Arg Val Leu Glu Arg Phe Thr
 65                  70                  75                  80

<210> SEQ ID NO 122
<211> LENGTH: 80
<212> TYPE: PRT
<213> ORGANISM: Artificial Sequence
<220> FEATURE:
<223> OTHER INFORMATION: Synthetic Construct

<400> SEQUENCE: 122

Ser Asn Tyr Tyr Tyr Asp Gly Phe Ala Trp Tyr Phe Glu Gly Gly Thr
 1               5                  10                  15

Lys Glu Ser Pro Asn Glu Ser Met Phe Thr Val Glu Asn Lys Tyr Phe
             20                  25                  30

Pro Asn Asp Pro Leu Ser Pro Phe Ser Gly Ala Gly Thr Glu His
         35                  40                  45

Phe His Val Thr Val Lys Ala Ala Gly Thr His Ala Val Asn Leu Thr
 50                      55                  60

Tyr Met Ala Pro Trp Leu Gly Pro Ser Arg Arg Leu Glu Arg Phe Thr
 65                  70                  75                  80

<210> SEQ ID NO 123
<211> LENGTH: 80
<212> TYPE: PRT
<213> ORGANISM: Artificial Sequence
<220> FEATURE:
<223> OTHER INFORMATION: Synthetic Construct

<400> SEQUENCE: 123

Ser Asn Tyr Phe Tyr Asp Gly Phe Ala Trp Tyr Phe Glu Gly Gly Thr
 1               5                  10                  15

Lys Glu Ser Pro Asn Glu Ser Met Phe Thr Val Glu Asn Lys Tyr Phe
             20                  25                  30

Pro Ala Asp Pro Gly Ser Gly His Trp Gly Ala Gly Gly Thr Glu His
         35                  40                  45
```

```
Phe His Val Thr Val Lys Ala Ala Gly Thr His Ala Val Asn Leu Thr
    50                  55                  60

Tyr Met Ala Pro Trp Ser Gly Pro Ser Arg Glu Leu Glu Arg Phe Thr
65                  70                  75                  80

<210> SEQ ID NO 124
<211> LENGTH: 80
<212> TYPE: PRT
<213> ORGANISM: Artificial Sequence
<220> FEATURE:
<223> OTHER INFORMATION: Synthetic Construct

<400> SEQUENCE: 124

Ser Asn Tyr Phe Ser Asp Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
            20                  25                  30

Pro Asn Asp Ser Gly Ser Arg Leu Ala Gly Ala Gly Thr Glu His
        35                  40                  45

Phe His Val Thr Val Lys Ala Ala Gly Thr His Ala Val Asn Leu Thr
    50                  55                  60

Tyr Met Ala Pro Trp Leu Gly Pro Ser Arg Met Leu Glu Arg Phe Thr
65                  70                  75                  80

<210> SEQ ID NO 125
<211> LENGTH: 80
<212> TYPE: PRT
<213> ORGANISM: Artificial Sequence
<220> FEATURE:
<223> OTHER INFORMATION: Synthetic Construct

<400> SEQUENCE: 125

Ser Asn Tyr Phe Val Asp Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
            20                  25                  30

Pro Asn Leu Thr Ala Ser Gly His Ser Gly Ala Gly Thr Glu His
        35                  40                  45

Phe His Val Thr Val Lys Ala Ala Gly Thr His Ala Val Asn Leu Thr
    50                  55                  60

Tyr Met Ala Pro Trp Arg Gly Pro Ser Arg Val Leu Glu Arg Phe Thr
65                  70                  75                  80

<210> SEQ ID NO 126
<211> LENGTH: 80
<212> TYPE: PRT
<213> ORGANISM: Artificial Sequence
<220> FEATURE:
<223> OTHER INFORMATION: Synthetic Construct

<400> SEQUENCE: 126

Ser Asn Tyr Phe Tyr Glu Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
            20                  25                  30

Pro Asn Glu Ser Gly Pro Arg Leu Leu Gly Ala Gly Thr Glu His
        35                  40                  45
```

```
Phe His Val Thr Val Lys Ala Ala Gly Thr His Ala Val Asn Leu Thr
    50                  55                  60

Tyr Met Ala Pro Trp Glu Gly Pro Ser Arg Met Leu Glu Arg Phe Thr
65                  70                  75                  80

<210> SEQ ID NO 127
<211> LENGTH: 80
<212> TYPE: PRT
<213> ORGANISM: Artificial Sequence
<220> FEATURE:
<223> OTHER INFORMATION: Synthetic Construct

<400> SEQUENCE: 127

Ser Asn Tyr Tyr Asp Glu Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
                20                  25                  30

Pro Asn Val Ser Glu Ser Gly Leu Lys Gly Ala Gly Gly Thr Glu His
            35                  40                  45

Phe His Val Thr Val Lys Ala Ala Gly Thr His Ala Val Asn Leu Thr
    50                  55                  60

Tyr Met Ala Pro Trp Ser Gly Pro Ser Arg Arg Leu Glu Arg Phe Thr
65                  70                  75                  80

<210> SEQ ID NO 128
<211> LENGTH: 80
<212> TYPE: PRT
<213> ORGANISM: Artificial Sequence
<220> FEATURE:
<223> OTHER INFORMATION: Synthetic Construct

<400> SEQUENCE: 128

Ser Asn Tyr Phe Tyr Glu Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
                20                  25                  30

Pro Asn Val Pro Gly Ala Gly His Ser Gly Ala Gly Gly Thr Glu His
            35                  40                  45

Phe His Val Thr Val Lys Ala Ala Gly Thr His Ala Val Asn Leu Thr
    50                  55                  60

Tyr Met Ala Pro Trp Leu Gly Pro Ser Arg Glu Leu Glu Arg Phe Thr
65                  70                  75                  80

<210> SEQ ID NO 129
<211> LENGTH: 80
<212> TYPE: PRT
<213> ORGANISM: Artificial Sequence
<220> FEATURE:
<223> OTHER INFORMATION: Synthetic Construct

<400> SEQUENCE: 129

Ser Asn Tyr Tyr Cys Asp Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
                20                  25                  30

Pro Asn Glu Pro Gly Leu Ile Leu Ser Gly Ala Gly Gly Thr Glu His
            35                  40                  45
```

```
Phe Tyr Val Thr Val Lys Ala Gly Thr His Ala Val Asn Leu Thr
 50                  55                  60

Tyr Met Ala Pro Trp Thr Gly Pro Ser Arg Asp Leu Glu Arg Phe Thr
 65                  70                  75                  80

<210> SEQ ID NO 130
<211> LENGTH: 80
<212> TYPE: PRT
<213> ORGANISM: Artificial Sequence
<220> FEATURE:
<223> OTHER INFORMATION: Synthetic Construct

<400> SEQUENCE: 130

Ser Asn Tyr Phe Cys Asp Gly Phe Ala Trp Tyr Phe Glu Gly Gly Thr
 1               5                  10                  15

Lys Glu Ser Pro Asn Glu Ser Met Phe Thr Val Glu Asn Lys Tyr Phe
                 20                  25                  30

Pro Asn Val Pro Gly Ser Pro Leu Ser Gly Ala Gly Gly Thr Glu His
             35                  40                  45

Phe His Val Thr Val Lys Ala Ala Gly Thr His Ala Val Asn Leu Thr
 50                  55                  60

Tyr Met Ala Pro Trp Leu Gly Pro Ser Arg Val Leu Glu Arg Phe Thr
 65                  70                  75                  80

<210> SEQ ID NO 131
<211> LENGTH: 80
<212> TYPE: PRT
<213> ORGANISM: Artificial Sequence
<220> FEATURE:
<223> OTHER INFORMATION: Synthetic Construct

<400> SEQUENCE: 131

Ser Asn Tyr Phe Cys Asp Gly Phe Ala Trp Tyr Phe Glu Gly Gly Thr
 1               5                  10                  15

Lys Glu Ser Pro Asn Glu Ser Met Phe Thr Val Glu Asn Lys Tyr Phe
                 20                  25                  30

Pro Asn Ala Pro Gly Ser Ile Leu Ser Gly Ala Gly Gly Thr Glu His
             35                  40                  45

Phe His Val Thr Val Lys Ala Ala Gly Thr His Ala Val Asn Leu Thr
 50                  55                  60

Tyr Met Ala Pro Trp Leu Gly Pro Ser Arg Glu Leu Glu Arg Phe Thr
 65                  70                  75                  80

<210> SEQ ID NO 132
<211> LENGTH: 80
<212> TYPE: PRT
<213> ORGANISM: Artificial Sequence
<220> FEATURE:
<223> OTHER INFORMATION: Synthetic Construct

<400> SEQUENCE: 132

Ser Asn Tyr Tyr Cys Asp Gly Phe Ala Trp Tyr Phe Glu Gly Gly Thr
 1               5                  10                  15

Lys Glu Ser Pro Asn Glu Ser Met Phe Thr Val Glu Asn Lys Tyr Phe
                 20                  25                  30

Pro Asn Asp Pro Gly Ser Ser Ser Ser Gly Ala Gly Gly Thr Glu His
             35                  40                  45
```

```
Phe His Val Thr Val Lys Ala Ala Gly Thr His Ala Val Asn Leu Thr
    50                  55                  60

Tyr Met Gly Pro Trp Ser Gly Pro Ser Arg Ala Ile Glu Arg Phe Thr
65                  70                  75                  80

<210> SEQ ID NO 133
<211> LENGTH: 80
<212> TYPE: PRT
<213> ORGANISM: Artificial Sequence
<220> FEATURE:
<223> OTHER INFORMATION: Synthetic Construct

<400> SEQUENCE: 133

Ser Asn Tyr Phe Cys Asp Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
            20                  25                  30

Pro Asn Asn Thr Glu Thr Leu Leu Met Gly Ala Gly Gly Thr Glu His
        35                  40                  45

Phe His Val Thr Val Lys Ala Ala Gly Thr His Ala Val Asn Leu Thr
    50                  55                  60

Tyr Met Ala Pro Trp Leu Gly Pro Ser Arg Val Leu Glu Arg Phe Thr
65                  70                  75                  80

<210> SEQ ID NO 134
<211> LENGTH: 80
<212> TYPE: PRT
<213> ORGANISM: Artificial Sequence
<220> FEATURE:
<223> OTHER INFORMATION: Synthetic Construct

<400> SEQUENCE: 134

Ser Asn Tyr Phe Cys Asp Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
            20                  25                  30

Pro Asn Glu Pro Ala Leu Gly Ala Phe Gly Ala Gly Gly Thr Glu His
        35                  40                  45

Phe His Val Thr Val Lys Ala Ala Gly Thr His Ala Val Asn Leu Thr
    50                  55                  60

Tyr Met Ala Pro Trp Ser Gly Pro Ser Arg Glu Leu Glu Arg Phe Thr
65                  70                  75                  80

<210> SEQ ID NO 135
<211> LENGTH: 80
<212> TYPE: PRT
<213> ORGANISM: Artificial Sequence
<220> FEATURE:
<223> OTHER INFORMATION: Synthetic Construct

<400> SEQUENCE: 135

Ser Asn Tyr Phe Cys Asp Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
            20                  25                  30

Pro Asn Glu Pro Gly Ser Leu Leu Ser Gly Ala Gly Gly Thr Glu His
        35                  40                  45
```

Phe His Val Thr Val Lys Ala Ala Gly Thr His Ala Val Asn Leu Thr
            50                  55                  60

Tyr Met Ala Pro Trp Ala Gly Pro Ser Arg Val Leu Glu Arg Phe Thr
65                  70                  75                  80

<210> SEQ ID NO 136
<211> LENGTH: 80
<212> TYPE: PRT
<213> ORGANISM: Artificial Sequence
<220> FEATURE:
<223> OTHER INFORMATION: Synthetic Construct

<400> SEQUENCE: 136

Ser Asn Tyr Phe Tyr Asp Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
            20                  25                  30

Pro Asn Asn Ser Gln Pro Gly Asp Leu Gly Ala Gly Gly Thr Glu His
        35                  40                  45

Phe His Val Thr Val Lys Ala Ala Gly Thr His Ala Val Asn Leu Thr
            50                  55                  60

Tyr Met Ala Pro Trp Leu Gly Pro Ser Arg Phe Leu Glu Arg Phe Thr
65                  70                  75                  80

<210> SEQ ID NO 137
<211> LENGTH: 80
<212> TYPE: PRT
<213> ORGANISM: Artificial Sequence
<220> FEATURE:
<223> OTHER INFORMATION: Synthetic Construct

<400> SEQUENCE: 137

Ser Asn Tyr Phe Tyr Asp Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
            20                  25                  30

Pro Asn Asp Pro Gly Met His Phe Ser Gly Ala Gly Gly Thr Glu His
        35                  40                  45

Phe His Val Thr Val Lys Ala Ala Gly Thr His Ala Val Asn Leu Thr
            50                  55                  60

Tyr Met Ala Pro Trp Tyr Gly Pro Ser Arg Phe Leu Glu Arg Phe Thr
65                  70                  75                  80

<210> SEQ ID NO 138
<211> LENGTH: 80
<212> TYPE: PRT
<213> ORGANISM: Artificial Sequence
<220> FEATURE:
<223> OTHER INFORMATION: Synthetic Construct

<400> SEQUENCE: 138

Ser Asn Tyr Phe Cys Asp Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
            20                  25                  30

Pro Asn Glu Pro Gly Ser Ile Leu Ser Gly Ala Gly Gly Thr Glu His
        35                  40                  45

```
Phe His Val Thr Val Lys Ala Ala Gly Thr His Ala Val Asn Leu Thr
        50                  55                  60

Tyr Met Ala Pro Trp Ser Gly Pro Ser Arg Val Leu Glu Arg Phe Thr
65                  70                  75                  80

<210> SEQ ID NO 139
<211> LENGTH: 80
<212> TYPE: PRT
<213> ORGANISM: Artificial Sequence
<220> FEATURE:
<223> OTHER INFORMATION: Synthetic Construct

<400> SEQUENCE: 139

Ser Asn Tyr Phe Tyr Asp Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
            20                  25                  30

Pro Asn Asp Pro Gly Ser Val Leu Trp Gly Ala Gly Thr Glu His
        35                  40                  45

Phe His Val Thr Val Lys Ala Ala Gly Thr His Ala Val Asn Leu Thr
        50                  55                  60

Tyr Met Ala Pro Trp Leu Gly Pro Ser Arg Met Leu Glu Arg Phe Thr
65                  70                  75                  80

<210> SEQ ID NO 140
<211> LENGTH: 80
<212> TYPE: PRT
<213> ORGANISM: Artificial Sequence
<220> FEATURE:
<223> OTHER INFORMATION: Synthetic Construct

<400> SEQUENCE: 140

Ser Asn Tyr Phe Phe Asp Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
            20                  25                  30

Pro Tyr Gly His Tyr Lys Pro Gly Ala Gly Thr Glu His Phe His
        35                  40                  45

Val Thr Val Lys Ala Ala Gly Thr His Ala Val Asn Leu Thr Tyr Met
        50                  55                  60

Ala Pro Trp Ser Gly Pro Ser Arg Glu Leu Glu Arg Phe Thr Val Tyr
65                  70                  75                  80

<210> SEQ ID NO 141
<211> LENGTH: 80
<212> TYPE: PRT
<213> ORGANISM: Artificial Sequence
<220> FEATURE:
<223> OTHER INFORMATION: Synthetic Construct

<400> SEQUENCE: 141

Ser Asn Tyr Tyr Gly Asp Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
            20                  25                  30

Pro Gly Asp Tyr Asn Ser Tyr Gly Tyr Gly Ala Gly Thr Glu His
        35                  40                  45
```

```
Phe His Val Thr Val Lys Ala Ala Gly Thr His Ala Val Asn Leu Thr
        50                  55                  60

Tyr Met Ala Pro Trp Leu Gly Pro Ser Arg Arg Leu Glu Arg Phe Thr
 65                  70                  75                  80
```

<210> SEQ ID NO 142
<211> LENGTH: 80
<212> TYPE: PRT
<213> ORGANISM: Artificial Sequence
<220> FEATURE:
<223> OTHER INFORMATION: Synthetic Construct

<400> SEQUENCE: 142

```
Ser Asn Tyr Phe Phe Asp Gly Phe Ala Trp Tyr Phe Glu Gly Gly Thr
 1               5                  10                  15

Lys Glu Ser Pro Asn Glu Ser Met Phe Thr Val Glu Asn Lys Tyr Phe
                20                  25                  30

Pro Met Asn Ser Ser Arg Pro Gly Ala Gly Gly Thr Glu His Phe His
                35                  40                  45

Val Thr Val Lys Ala Ala Gly Thr His Ala Val Asn Leu Thr Tyr Met
        50                  55                  60

Ala Pro Trp Val Gly Pro Ser Arg Lys Leu Glu Arg Phe Thr Val Tyr
 65                  70                  75                  80
```

<210> SEQ ID NO 143
<211> LENGTH: 80
<212> TYPE: PRT
<213> ORGANISM: Artificial Sequence
<220> FEATURE:
<223> OTHER INFORMATION: Synthetic Construct

<400> SEQUENCE: 143

```
Ser Asn Tyr Phe Tyr Asp Gly Phe Ala Trp Tyr Phe Glu Gly Gly Thr
 1               5                  10                  15

Lys Glu Ser Pro Asn Glu Ser Met Phe Thr Val Glu Asn Lys Tyr Phe
                20                  25                  30

Pro Ser Tyr Tyr Gln Ala Tyr Gly Ala Gly Gly Thr Glu His Phe His
                35                  40                  45

Val Thr Val Lys Ala Ala Gly Thr His Ala Val Asn Leu Thr Tyr Met
        50                  55                  60

Ala Pro Trp Leu Gly Pro Ser Arg Val Ile Glu Arg Phe Thr Val Tyr
 65                  70                  75                  80
```

<210> SEQ ID NO 144
<211> LENGTH: 80
<212> TYPE: PRT
<213> ORGANISM: Artificial Sequence
<220> FEATURE:
<223> OTHER INFORMATION: Synthetic Construct

<400> SEQUENCE: 144

```
Ser Asn Tyr Phe Asp Asp Gly Phe Ala Trp Tyr Phe Glu Gly Gly Thr
 1               5                  10                  15

Lys Glu Ser Pro Asn Glu Ser Met Phe Thr Val Glu Asn Lys Tyr Phe
                20                  25                  30

Pro Tyr Gln Ala Glu Leu Tyr Ser Ser Gly Ile Gly Ala Gly Gly Thr
                35                  40                  45
```

```
Glu His Phe His Val Thr Val Lys Ala Ala Gly Thr His Ala Val Asn
    50                  55                  60

Leu Thr Tyr Met Ala Pro Trp Ser Gly Pro Ser Arg Val Leu Glu Arg
65                  70                  75                  80

<210> SEQ ID NO 145
<211> LENGTH: 80
<212> TYPE: PRT
<213> ORGANISM: Artificial Sequence
<220> FEATURE:
<223> OTHER INFORMATION: Synthetic Construct

<400> SEQUENCE: 145

Ser Asn Tyr Phe Tyr Glu Gly Phe Ala Trp Tyr Phe Glu Gly Gly Thr
1               5                   10                  15

Lys Glu Ser Pro Asn Glu Ser Met Phe Thr Val Glu Asn Lys Tyr Phe
                20                  25                  30

Pro Arg Gly Tyr Gly Tyr Pro Pro Tyr Ala Arg Gly Ala Gly Gly Thr
            35                  40                  45

Glu His Phe His Val Thr Val Lys Ala Ala Gly Thr His Ala Val Asn
    50                  55                  60

Leu Thr Tyr Met Ala Pro Trp Ser Gly Pro Ser Arg Ala Ile Glu Arg
65                  70                  75                  80

<210> SEQ ID NO 146
<211> LENGTH: 4
<212> TYPE: PRT
<213> ORGANISM: Artificial Sequence
<220> FEATURE:
<223> OTHER INFORMATION: Synthetic Construct

<400> SEQUENCE: 146

Ser Asn Ala Asp
1

<210> SEQ ID NO 147
<211> LENGTH: 10
<212> TYPE: PRT
<213> ORGANISM: Artificial Sequence
<220> FEATURE:
<223> OTHER INFORMATION: Synthetic Construct

<400> SEQUENCE: 147

Arg Arg Glu Lys Gly Ser Thr Leu Val Val
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = R or S or P or G
<220> FEATURE:
<221> NAME/KEY: VARIANT
<222> LOCATION: 2
<223> OTHER INFORMATION: Xaa = P or R
<220> FEATURE:
<221> NAME/KEY: VARIANT
<222> LOCATION: 3
<223> OTHER INFORMATION: Xaa = W or Y or E or S or V
```

```
<220> FEATURE:
<221> NAME/KEY: VARIANT
<222> LOCATION: 4
<223> OTHER INFORMATION: Xaa = T or Y or K or T
<220> FEATURE:
<221> NAME/KEY: VARIANT
<222> LOCATION: 6
<223> OTHER INFORMATION: Xaa = P or S or A
<220> FEATURE:
<221> NAME/KEY: VARIANT
<222> LOCATION: 7
<223> OTHER INFORMATION: Xaa = S or T or Y
<220> FEATURE:
<221> NAME/KEY: VARIANT
<222> LOCATION: 8
<223> OTHER INFORMATION: Xaa = H or K or L or Q or D
<220> FEATURE:
<221> NAME/KEY: VARIANT
<222> LOCATION: 9
<223> OTHER INFORMATION: Xaa = D or V or E
<220> FEATURE:
<221> NAME/KEY: VARIANT
<222> LOCATION: 10
<223> OTHER INFORMATION: Xaa = S or E or M or P or V

<400> SEQUENCE: 148

Xaa Xaa Xaa Xaa Gly Xaa Xaa Xaa Xaa Xaa
1               5                   10

<210> SEQ ID NO 149
<211> LENGTH: 109
<212> TYPE: PRT
<213> ORGANISM: Artificial Sequence
<220> FEATURE:
<223> OTHER INFORMATION: Synthetic Construct

<400> SEQUENCE: 149

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Ala Asp Gly
            20                  25                  30

Phe Ala Trp Tyr Phe Glu Gly Gly Thr Lys Glu Ser Pro Asn Glu Ser
        35                  40                  45

Met Phe Thr Val Glu Asn Lys Tyr Phe Pro Ser Asn Ser Thr Lys Arg
    50                  55                  60

Gly Ala Gly Gly Thr Glu His Phe His Val Thr Val Lys Ala Ala Gly
65                  70                  75                  80

Thr His Ala Val Asn Leu Thr Tyr Met Arg Arg Glu Lys Gly Ser Thr
                85                  90                  95

Leu Val Val Glu Arg Phe Thr Val Tyr Leu Lys Ala Asn
            100                 105

<210> SEQ ID NO 150
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = T or S or A or Q
<220> FEATURE:
<221> NAME/KEY: VARIANT
<222> LOCATION: 5
<223> OTHER INFORMATION: Xaa = T or C or D
```

```
<400> SEQUENCE: 150

Ser Asn Pro Xaa Xaa
1               5

<210> SEQ ID NO 151
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 7, 8
<223> OTHER INFORMATION: Xaa = Any Amino Acid and up to 3 of them can be
      present or absent

<400> SEQUENCE: 151

Xaa Xaa Xaa Xaa Xaa Xaa Xaa Xaa Gly Phe
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3, 4, 5, 6, 7, 8
<223> OTHER INFORMATION: Xaa = Any Amino Acid and up to 3 of them can be
      present or absent

<400> SEQUENCE: 152

Ser Asn Xaa Xaa Xaa Xaa Xaa Xaa Gly Phe
1               5                   10

<210> SEQ ID NO 153
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 7, 8, 9, 10, 11, 12, 13, 14, 15
<223> OTHER INFORMATION: Xaa = Any Amino Acid and up to 8 of them can be
      present or absent

<400> SEQUENCE: 153

Xaa Xaa Xaa Xaa Xaa Xaa Xaa Xaa Xaa Xaa Xaa Xaa Xaa Xaa Xaa Gly
1               5                   10                  15

Ala Gly Gly

<210> SEQ ID NO 154
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 7, 8, 9, 10, 11, 12
<223> OTHER INFORMATION: Xaa = Any Amino Acid and up to 9 of them can be
      present or absent

<400> SEQUENCE: 154

Xaa Xaa Xaa Xaa Xaa Xaa Xaa Xaa Xaa Xaa Xaa Xaa
1               5                   10
```

```
<210> SEQ ID NO 155
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = V or A

<400> SEQUENCE: 155

Ser Asn Xaa Asp
1

<210> SEQ ID NO 156
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Y or S
<220> FEATURE:
<221> NAME/KEY: VARIANT
<222> LOCATION: 3
<223> OTHER INFORMATION: Xaa = N or K
<220> FEATURE:
<221> NAME/KEY: VARIANT
<222> LOCATION: 4
<223> OTHER INFORMATION: Xaa = I or V
<220> FEATURE:
<221> NAME/KEY: VARIANT
<222> LOCATION: 5
<223> OTHER INFORMATION: Xaa = R or K
<220> FEATURE:
<221> NAME/KEY: VARIANT
<222> LOCATION: 7
<223> OTHER INFORMATION: Xaa = L or V or I

<400> SEQUENCE: 156

Xaa Asn Xaa Xaa Xaa Gly Xaa Pro Gly Phe
1               5                   10

<210> SEQ ID NO 157
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Y or S
<220> FEATURE:
<221> NAME/KEY: VARIANT
<222> LOCATION: 6
<223> OTHER INFORMATION: Xaa = H or R

<400> SEQUENCE: 157

Ser Asn Xaa Thr Lys Xaa
1               5

<210> SEQ ID NO 158
<211> LENGTH: 11
<212> TYPE: PRT
<213> ORGANISM: Artificial Sequence
<220> FEATURE:
<223> OTHER INFORMATION: Synthetic Construct
```

```
<400> SEQUENCE: 158

Pro Pro Asp Ser Lys Leu Leu Gly Ala Gly Gly
1               5                   10

<210> SEQ ID NO 159
<211> LENGTH: 111
<212> TYPE: PRT
<213> ORGANISM: Artificial Sequence
<220> FEATURE:
<223> OTHER INFORMATION: Synthetic Construct

<400> SEQUENCE: 159

Gly Ser Ser His Lys Val Thr Lys Ala His Asn Gly Ala Thr Leu Thr
1               5                   10                  15

Val Ala Val Gly Glu Leu Val Glu Ile Gln Leu Pro Ser Asn Pro Thr
            20                  25                  30

Thr Gly Phe Ala Trp Tyr Phe Glu Gly Gly Thr Lys Glu Ser Pro Asn
        35                  40                  45

Glu Ser Met Phe Thr Val Glu Asn Lys Tyr Phe Pro Pro Asp Ser Lys
    50                  55                  60

Leu Leu Gly Ala Gly Gly Thr Glu His Phe His Val Thr Val Lys Ala
65                  70                  75                  80

Ala Gly Thr His Ala Val Asn Leu Thr Tyr Met Arg Pro Trp Thr Gly
                85                  90                  95

Pro Ser His Asp Ser Glu Arg Phe Thr Val Tyr Leu Lys Ala Asn
            100                 105                 110

<210> SEQ ID NO 160
<211> LENGTH: 110
<212> TYPE: PRT
<213> ORGANISM: Trypanosoma cruzi

<400> SEQUENCE: 160

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Pro Thr Thr
            20                  25                  30

Gly Phe Ala Trp Tyr Phe Glu Gly Gly Thr Lys Glu Ser Pro Asn Glu
        35                  40                  45

Ser Met Phe Thr Val Glu Asn Lys Tyr Phe Pro Pro Asp Ser Lys Leu
    50                  55                  60

Leu Gly Ala Gly Gly Thr Glu His Phe His Val Thr Val Lys Ala Ala
65                  70                  75                  80

Gly Thr His Ala Val Asn Leu Thr Tyr Met Arg Pro Trp Thr Gly Pro
                85                  90                  95

Ser His Asp Ser Glu Arg Phe Thr Val Tyr Leu Lys Ala Asn
            100                 105                 110

<210> SEQ ID NO 161
<211> LENGTH: 110
<212> TYPE: PRT
<213> ORGANISM: Trypanosoma cruzi

<400> SEQUENCE: 161

Met Ser His Lys Val Thr Lys Ala His Asn Gly Ala Thr Leu Thr Val
1               5                   10                  15

Ala Val Gly Glu Leu Val Glu Ile Gln Leu Pro Ser Asn Pro Thr Thr
            20                  25                  30
```

```
Gly Phe Ala Trp Phe Phe Glu Gly Gly Thr Lys Glu Ser Pro Asn Glu
            35                  40                  45

Ser Met Phe Thr Val Glu Asn Lys Tyr Phe Pro Pro Asp Ser Lys Leu
 50                  55                  60

Leu Gly Ala Gly Gly Thr Glu His Phe His Val Thr Val Lys Val Ala
65                  70                  75                  80

Gly Thr His Ala Val Asn Leu Thr Tyr Met Arg Pro Trp Ala Gly Pro
                85                  90                  95

Ser His Asp Ser Glu Arg Phe Ile Val Tyr Leu Lys Ala Asn
            100                 105                 110

<210> SEQ ID NO 162
<211> LENGTH: 110
<212> TYPE: PRT
<213> ORGANISM: Trypanosoma cruzi

<400> SEQUENCE: 162

Met Ser His Lys Val Thr Lys Ala His Asn Gly Ala Thr Leu Thr Val
 1               5                  10                  15

Ala Val Gly Glu Leu Val Glu Ile Gln Leu Pro Ser Asn Pro Thr Thr
                20                  25                  30

Gly Phe Ala Trp Tyr Phe Glu Gly Gly Thr Lys Glu Ser Pro Asn Glu
            35                  40                  45

Ser Met Phe Thr Val Glu Asn Lys Tyr Phe Pro Pro Asp Ser Lys Leu
 50                  55                  60

Leu Gly Ala Gly Gly Thr Glu His Phe His Val Thr Val Arg Val Ala
65                  70                  75                  80

Gly Thr His Pro Ile Asn Leu Ile Tyr Met Arg Pro Trp Thr Gly Ala
                85                  90                  95

Ser His Asp Ser Glu Arg Phe Thr Val Tyr Leu Lys Ala Asn
            100                 105                 110

<210> SEQ ID NO 163
<211> LENGTH: 121
<212> TYPE: PRT
<213> ORGANISM: Trypanosoma brucei

<400> SEQUENCE: 163

Met Ser His Asn Leu Phe Thr Glu Glu Asp Asn Asn Lys Thr Ile Arg
 1               5                  10                  15

Met Val Ile Gly Glu Thr Phe Thr Ile Glu Leu Glu Ser Asn Pro Thr
                20                  25                  30

Thr Gly Tyr Thr Trp Leu Arg Ser Gly Leu Ala Gly Thr Glu Leu Ser
            35                  40                  45

Asp Cys Thr Phe Ala Ile Gln Ser Lys Phe Asn Asn Arg Ala Pro His
 50                  55                  60

Asp Asn His Lys Asn His Arg Arg Leu Leu Val Gly Ala Gly Gly Thr
65                  70                  75                  80

Met Val Leu Glu Val Lys Ala Leu Lys Ala Gly Lys His Thr Leu Ser
                85                  90                  95

Leu Ala Tyr Gly Arg Pro Trp Val Gly Phe Asn Ala Ala Ala Lys Arg
            100                 105                 110

Tyr Asn Ile His Val Glu Ala Thr Ala
            115                 120
```

-continued

```
<210> SEQ ID NO 164
<211> LENGTH: 116
<212> TYPE: PRT
<213> ORGANISM: Leishmania mexicana

<400> SEQUENCE: 164
```

Gly Ser His Met Ile Ala Pro Leu Ser Val Lys Asp Asn Asp Lys Trp
1               5                   10                  15

Val Asp Thr His Val Gly Lys Thr Thr Glu Ile His Leu Lys Gly Asn
            20                  25                  30

Pro Thr Thr Gly Tyr Met Trp Thr Arg Val Gly Phe Val Gly Lys Asp
        35                  40                  45

Val Leu Ser Asp Glu Ile Leu Glu Val Val Cys Lys Tyr Thr Pro Thr
    50                  55                  60

Pro Ser Ser Thr Pro Met Val Gly Val Gly Ile Tyr Val Val Leu
65                  70                  75                  80

Val Lys Pro Arg Lys Arg Gly His His Thr Leu Glu Leu Val Tyr Thr
                85                  90                  95

Arg Pro Phe Glu Gly Ile Lys Pro Glu Asn Glu Arg Tyr Thr Leu His
            100                 105                 110

Leu Asn Val Lys
        115

```
<210> SEQ ID NO 165
<211> LENGTH: 117
<212> TYPE: PRT
<213> ORGANISM: Leishmania major

<400> SEQUENCE: 165
```

Met Gln Pro Lys Met Thr Ala Pro Leu Thr Met Lys Asp Asn Asn Lys
1               5                   10                  15

Cys Leu Ser Val Arg Val Gly Ser Thr Leu Glu Ile His Leu Glu Gly
            20                  25                  30

Asn Pro Thr Thr Gly Tyr Thr Trp Thr Arg Val Gly Phe Val Gly Lys
        35                  40                  45

Glu Met Leu Ser Asp Glu His Leu Glu Val Thr Ser Lys Tyr Thr Pro
    50                  55                  60

Lys Pro Val Ser Gly Ser Met Val Gly Ala Gly Ser Tyr Thr Val
65                  70                  75                  80

Phe Val Lys Pro Leu Arg Lys Gly Gln His Ala Val Gln Leu Val Tyr
                85                  90                  95

Ala Arg Pro Phe Glu Gly Pro Lys Pro Asp Asn Glu Arg Tyr Thr Leu
            100                 105                 110

His Leu Asn Val Glu
        115

```
<210> SEQ ID NO 166
<211> LENGTH: 102
<212> TYPE: PRT
<213> ORGANISM: Entamoeba histolytica

<400> SEQUENCE: 166
```

Met Ser Leu Thr Glu Asp Asn Asn Thr Thr Ile Thr Ile Ala Lys
1               5                   10                  15

Gly Glu Asn Lys Glu Ile Ile Leu His Gly Asn Pro Thr Thr Gly Tyr
            20                  25                  30

Ser Trp Val Val Asp Ser Cys Glu Gly Leu Ser Asn Thr Val Glu Tyr
        35                  40                  45

-continued

Val Ala Asp Gln His Ala Pro Gly Ile Cys Gly Cys Gly Gly Lys Tyr
        50                  55                  60

His Ile Lys Ile Thr Gly Thr Gln Thr Gly Glu Gly Lys Ile Val Leu
 65                  70                  75                  80

Val Tyr Arg Arg Pro Trp Ala Pro Asn Ala Asn Asp Arg Thr Phe Thr
                85                  90                  95

Leu Lys Val Asn Val Gln
                100

<210> SEQ ID NO 167
<211> LENGTH: 134
<212> TYPE: PRT
<213> ORGANISM: Pseudomonas aeruginosa

<400> SEQUENCE: 167

Met Ser Phe Ser Pro Ser Arg Leu Leu Leu Pro Leu Ser Ile Val Val
 1               5                  10                  15

Leu Ala Gly Cys Ala Gly Gln Gln Lys Pro Val Val Thr Leu Asp Asp
                20                  25                  30

Ala Asp Asp Cys Ser Pro Leu Lys Leu Thr Gln Gly Gln Glu Leu Val
            35                  40                  45

Leu Thr Leu Pro Ser Asn Pro Thr Thr Gly Phe Arg Trp Glu Leu Arg
 50                  55                  60

Asn Pro Ala Ala Ser Val Leu Lys Arg Leu Gly Pro Glu Val Tyr Ser
 65                  70                  75                  80

Asn Ser Glu Glu Asp Ser Gly Leu Val Gly Ser Gly Gly Ser Thr
                85                  90                  95

Trp Arg Phe Arg Val Ala Ala Ser Gly Asn Asp Arg Leu Glu Leu Val
                100                 105                 110

Tyr Arg Arg Pro Trp Glu Lys Asp Ala Glu Pro Ala Glu Ser Phe Ser
            115                 120                 125

Cys Ala Ile Arg Val Arg
        130

<210> SEQ ID NO 168
<211> LENGTH: 114
<212> TYPE: PRT
<213> ORGANISM: Homo sapiens

<400> SEQUENCE: 168

Ser Gln Phe Arg Val Ser Pro Leu Asp Arg Thr Trp Asn Leu Gly Glu
 1               5                  10                  15

Thr Val Glu Leu Lys Cys Gln Val Leu Leu Ser Asn Pro Thr Ser Gly
                20                  25                  30

Cys Ser Trp Leu Phe Gln Pro Arg Gly Ala Ala Ser Pro Thr Phe
            35                  40                  45

Leu Leu Tyr Leu Ser Gln Asn Lys Pro Lys Ala Ala Glu Gly Leu Asp
 50                  55                  60

Thr Gln Arg Phe Ser Gly Lys Arg Leu Gly Asp Thr Phe Val Leu Thr
 65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
                100                 105                 110

Pro Ala

<210> SEQ ID NO 169
<211> LENGTH: 315
<212> TYPE: PRT
<213> ORGANISM: Homo sapiens

<400> SEQUENCE: 169

```
Leu Glu Ala Asp Lys Cys Lys Glu Arg Glu Glu Lys Ile Ile Leu Val
1               5                   10                  15

Ser Ser Ala Asn Glu Ile Asp Val Arg Pro Cys Pro Leu Asn Pro Asn
            20                  25                  30

Glu His Lys Gly Thr Ile Thr Trp Tyr Lys Asp Asp Ser Lys Thr Pro
        35                  40                  45

Val Ser Thr Glu Gln Ala Ser Arg Ile His Gln His Lys Glu Lys Leu
    50                  55                  60

Trp Phe Val Pro Ala Lys Val Glu Asp Ser Gly His Tyr Tyr Cys Val
65                  70                  75                  80

Val Arg Asn Ser Ser Tyr Cys Leu Arg Ile Lys Ile Ser Ala Lys Phe
                85                  90                  95

Val Glu Asn Glu Pro Asn Leu Cys Tyr Asn Ala Gln Ala Ile Phe Lys
            100                 105                 110

Gln Lys Leu Pro Val Ala Gly Asp Gly Gly Leu Val Cys Pro Tyr Met
        115                 120                 125

Glu Phe Phe Lys Asn Glu Asn Asn Glu Leu Pro Lys Leu Gln Trp Tyr
130                 135                 140

Lys Asp Cys Lys Pro Leu Leu Leu Asp Asn Ile His Phe Ser Gly Val
145                 150                 155                 160

Lys Asp Arg Leu Ile Val Met Asn Val Ala Glu Lys His Arg Gly Asn
                165                 170                 175

Tyr Thr Cys His Ala Ser Tyr Thr Tyr Leu Gly Lys Gln Tyr Pro Ile
            180                 185                 190

Thr Arg Val Ile Glu Phe Ile Thr Leu Glu Glu Asn Lys Pro Thr Arg
        195                 200                 205

Pro Val Ile Val Ser Pro Ala Asn Glu Thr Met Glu Val Asp Leu Gly
    210                 215                 220

Ser Gln Ile Gln Leu Ile Cys Asn Val Thr Gly Gln Leu Ser Asp Ile
225                 230                 235                 240

Ala Tyr Trp Lys Trp Asn Gly Ser Val Ile Asp Glu Asp Pro Val
                245                 250                 255

Leu Gly Glu Asp Tyr Tyr Ser Val Glu Asn Pro Ala Asn Lys Arg Arg
            260                 265                 270

Ser Thr Leu Ile Thr Val Leu Asn Ile Ser Glu Ile Glu Ser Arg Phe
        275                 280                 285

Tyr Lys His Pro Phe Thr Cys Phe Ala Lys Asn Thr His Gly Ile Asp
    290                 295                 300

Ala Ala Tyr Ile Gln Leu Ile Tyr Pro Val Thr
305                 310                 315
```

<210> SEQ ID NO 170
<211> LENGTH: 198
<212> TYPE: PRT
<213> ORGANISM: Homo sapiens

<400> SEQUENCE: 170

Gln Ala Phe Lys Ile Glu Thr Thr Pro Glu Ser Arg Tyr Leu Ala Gln
1               5                   10                  15

Ile Gly Asp Ser Val Ser Leu Thr Cys Ser Thr Thr Gly Cys Glu Ser
            20                  25                  30

Pro Phe Phe Ser Trp Arg Thr Gln Ile Asp Ser Pro Leu Asn Gly Lys
        35                  40                  45

Val Thr Asn Glu Gly Thr Thr Ser Thr Leu Thr Met Asn Pro Val Ser
50                  55                  60

Phe Gly Asn Glu His Ser Tyr Leu Cys Thr Ala Thr Cys Glu Ser Arg
65                  70                  75                  80

Lys Leu Glu Lys Gly Ile Gln Val Glu Ile Tyr Ser Phe Pro Lys Asp
                85                  90                  95

Pro Glu Ile His Leu Ser Gly Pro Leu Glu Ala Gly Lys Pro Ile Thr
            100                 105                 110

Val Lys Cys Ser Val Ala Asp Val Tyr Pro Phe Asp Arg Leu Glu Ile
        115                 120                 125

Asp Leu Leu Lys Gly Asp His Leu Met Lys Ser Gln Glu Phe Leu Glu
130                 135                 140

Asp Ala Asp Arg Lys Ser Leu Glu Thr Lys Ser Leu Glu Val Thr Phe
145                 150                 155                 160

Thr Pro Val Ile Glu Asp Ile Gly Lys Val Leu Val Cys Arg Ala Lys
                165                 170                 175

Leu His Ile Asp Glu Met Asp Ser Val Pro Thr Val Arg Gln Ala Val
            180                 185                 190

Lys Glu Leu Gln Val Tyr
        195

<210> SEQ ID NO 171
<211> LENGTH: 107
<212> TYPE: PRT
<213> ORGANISM: Trypanosoma brucei

<400> SEQUENCE: 171

Ser His Asn Leu Phe Thr Glu Glu Asp Asn Asn Lys Thr Ile Arg Met
1               5                   10                  15

Val Ile Gly Glu Thr Phe Thr Ile Glu Leu Lys Ser Asn Pro Thr Thr
            20                  25                  30

Gly Tyr Thr Trp Leu Arg Ser Gly Leu Ala Gly Thr Glu Leu Ser Asp
        35                  40                  45

Cys Thr Phe Ala Ile Gln Ser Lys Phe Asn Asn Arg Leu Val Gly Ala
50                  55                  60

Gly Gly Thr Met Val Leu Glu Val Lys Ala Leu Lys Pro Gly Lys His
65                  70                  75                  80

Thr Leu Ser Leu Ala Tyr Gly Arg Pro Trp Val Gly Phe Asn Ala Ala
                85                  90                  95

Ala Lys Arg Tyr Asn Ile His Val Glu Ala Thr
            100                 105

<210> SEQ ID NO 172
<211> LENGTH: 106
<212> TYPE: PRT
<213> ORGANISM: Leishmania mexicana -continued

```
<400> SEQUENCE: 172

Met Ile Ala Pro Leu Ser Val Lys Asp Asn Asp Lys Trp Val Asp Thr
1               5                   10                  15

His Val Gly Lys Thr Thr Glu Ile His Leu Lys Gly Asn Pro Thr Thr
            20                  25                  30

Gly Tyr Met Trp Thr Arg Val Gly Lys Asp Val Leu Ser Asp Glu
        35                  40                  45

Ile Leu Glu Val Val Cys Lys Tyr Thr Pro Thr Met Val Gly Val Gly
50                  55                  60

Gly Ile Tyr Val Val Leu Val Lys Pro Arg Lys Arg Gly His His Thr
65                  70                  75                  80

Leu Glu Leu Val Tyr Thr Arg Pro Phe Glu Gly Ile Lys Pro Glu Asn
            85                  90                  95

Glu Arg Tyr Thr Leu His Leu Asn Val Lys
        100                 105

<210> SEQ ID NO 173
<211> LENGTH: 106
<212> TYPE: PRT
<213> ORGANISM: Leishmania major

<400> SEQUENCE: 173

Met Thr Ala Pro Leu Thr Met Lys Asp Asn Asn Lys Cys Leu Ser Val
1               5                   10                  15

Arg Val Gly Ser Thr Leu Glu Ile His Leu Glu Gly Asn Pro Thr Thr
            20                  25                  30

Gly Tyr Thr Trp Thr Arg Val Gly Gly Lys Glu Met Leu Ser Asp Glu
        35                  40                  45

His Leu Glu Val Thr Ser Lys Tyr Thr Pro Lys Met Val Gly Ala Gly
50                  55                  60

Gly Ser Tyr Thr Val Phe Val Lys Pro Leu Arg Lys Gly Gln His Ala
65                  70                  75                  80

Val Gln Leu Val Tyr Ala Arg Pro Phe Glu Gly Pro Lys Pro Asp Asn
            85                  90                  95

Glu Arg Tyr Thr Leu His Leu Asn Val Glu
        100                 105

<210> SEQ ID NO 174
<211> LENGTH: 105
<212> TYPE: PRT
<213> ORGANISM: Pseudomonas aeruginosa

<400> SEQUENCE: 174

Pro Val Val Thr Leu Asp Asp Ala Asp Cys Ser Pro Leu Lys Leu
1               5                   10                  15

Thr Gln Gly Gln Glu Leu Val Leu Thr Leu Pro Ser Asn Pro Thr Thr
            20                  25                  30

Gly Phe Arg Trp Glu Leu Arg Asn Pro Ala Ala Ser Val Leu Lys Arg
        35                  40                  45

Leu Gly Pro Glu Val Tyr Ser Asn Ser Glu Leu Val Gly Ser Gly Gly
50                  55                  60

Glu Ser Thr Trp Arg Phe Arg Val Ala Ala Ser Gly Asp Asp Arg Leu
65                  70                  75                  80
```

```
Glu Leu Val Tyr Arg Arg Pro Trp Glu Lys Asp Ala Glu Pro Ala Glu
                85                  90                  95

Ser Phe Ser Cys Ala Ile Gln Val Arg
            100                 105

<210> SEQ ID NO 175
<211> LENGTH: 84
<212> TYPE: PRT
<213> ORGANISM: Homo sapiens

<400> SEQUENCE: 175

Arg Val Ser Pro Leu Asp Arg Thr Trp Asn Leu Gly Glu Thr Val Glu
1               5                   10                  15

Leu Lys Cys Ser Asn Pro Thr Ser Gly Cys Ser Trp Leu Phe Gln Pro
            20                  25                  30

Arg Gly Ala Leu Asp Thr Gln Arg Phe Ser Gly Lys Arg Leu Gly Asp
        35                  40                  45

Thr Phe Val Leu Thr Leu Ser Arg Arg Glu Asn Glu Gly Tyr Tyr Phe
    50                  55                  60

Cys Ser Ala Leu Ser Asn Ser Ile Met Tyr Phe Ser His Phe Val Pro
65                  70                  75                  80

Val Phe Leu Pro

<210> SEQ ID NO 176
<211> LENGTH: 91
<212> TYPE: PRT
<213> ORGANISM: Homo sapiens

<400> SEQUENCE: 176

Val Ser Pro Ala Asn Glu Thr Met Glu Val Asp Leu Gly Ser Gln Ile
1               5                   10                  15

Gln Leu Ile Cys Asn Val Thr Gly Ser Asp Ile Ala Tyr Trp Lys Ser
            20                  25                  30

Val Ile Asp Glu Asp Asp Pro Val Leu Gly Glu Asp Tyr Tyr Ser Val
        35                  40                  45

Glu Asn Pro Arg Arg Ser Thr Leu Ile Thr Val Leu Asn Ile Ser Glu
    50                  55                  60

Ile Glu Ser Lys His Pro Phe Thr Cys Phe Ala Lys Asn Thr His Gly
65                  70                  75                  80

Ile Asp Ala Ala Tyr Ile Gln Leu Ile Tyr Pro
                85                  90

<210> SEQ ID NO 177
<211> LENGTH: 81
<212> TYPE: PRT
<213> ORGANISM: Homo sapiens

<400> SEQUENCE: 177

Thr Thr Pro Glu Ser Arg Tyr Leu Ala Gln Ile Gly Asp Ser Val Ser
1               5                   10                  15

Leu Thr Cys Ser Thr Thr Gly Ser Pro Phe Pro Ser Trp Arg Thr Gln
            20                  25                  30

Ile Asp Ser Pro Leu Asn Gly Lys Val Thr Asn Glu Gly Thr Thr Ser
        35                  40                  45

Thr Leu Thr Met Asn Ser Phe Gly Asn Glu His Ser Tyr Leu Cys Thr
    50                  55                  60
```

```
Ala Thr Cys Glu Ser Arg Lys Leu Glu Lys Gly Ile Gln Val Glu Ile
 65                  70                  75                  80
Tyr
```